US012698523B2

(12) United States Patent
Chandrasekar et al.

(10) Patent No.: US 12,698,523 B2
(45) **Date of Patent: *Aug. 4, 2026**

(54) ENHANCEMENT OF NUCLEIC ACID POLYMERIZATION BY AROMATIC COMPOUNDS

(71) Applicant: Roche Sequencing Solutions, Inc., Pleasanton, CA (US)

(72) Inventors: Jagadeeswaran Chandrasekar, Seattle, WA (US); Drew Goodman, Seattle, WA (US); Aaron Jacobs, Seattle, WA (US); Mark Stamatios Kokoris, Bothell, WA (US); Lacey Merrill, Seattle, WA (US); Melud Nabavi, Seattle, WA (US); Dylan O'Connell, Seattle, WA (US); John Tabone, Kirkland, WA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 1109 days.

This patent is subject to a terminal disclaimer.

(21) Appl. No.: 17/645,381

(22) Filed: Dec. 21, 2021

(65) Prior Publication Data

US 2022/0112548 A1 Apr. 14, 2022

Related U.S. Application Data

(63) Continuation of application No. PCT/US2020/038682, filed on Jun. 19, 2020.

(60) Provisional application No. 62/867,049, filed on Jun. 26, 2019.

(51) Int. Cl.
*C12Q 1/68* (2018.01)
*C12Q 1/6848* (2018.01)

(52) U.S. Cl.
CPC .................................. *C12Q 1/6848* (2013.01)

(58) Field of Classification Search
CPC .................................................... C12Q 1/6848
See application file for complete search history.

(56) References Cited

U.S. PATENT DOCUMENTS

| | | | | |
|---|---|---|---|---|
| 6,183,997 | B1 | 2/2001 | Hogrefe | |
| 7,939,259 | B2 | 5/2011 | Kokoris et al. | |
| 11,970,731 | B2 * | 4/2024 | Kokoris | C07D 249/06 |
| 2013/0139686 | A1 | 6/2013 | Wilmer et al. | |
| 2013/0143768 | A1 | 6/2013 | Wilmer et al. | |
| 2015/0284787 | A1 | 10/2015 | Kokoris et al. | |
| 2016/0145292 | A1 | 5/2016 | Kokoris et al. | |
| 2017/0268052 | A1 | 9/2017 | Ayer et al. | |
| 2021/0062251 | A1 * | 3/2021 | Kokoris | C12Q 1/6848 |

FOREIGN PATENT DOCUMENTS

| | | | |
|---|---|---|---|
| CN | 1299419 | A | 9/1999 |
| CN | 109072291 | A | 12/2018 |
| JP | 2002505572 | A | 2/2002 |
| JP | 2011041572 | A | 3/2011 |
| JP | 2011041573 | A | 3/2011 |
| WO | 9842860 | A1 | 10/1998 |
| WO | 9946400 | A1 | 9/1999 |
| WO | 0102559 | A1 | 1/2001 |
| WO | 2004/081225 | A2 | 9/2004 |
| WO | 2008157696 | A2 | 12/2008 |
| WO | 2016081871 | A1 | 5/2016 |
| WO | 2017050751 | A1 | 3/2017 |
| WO | 2017087281 | A1 | 5/2017 |
| WO | 2017148860 | A1 | 9/2017 |
| WO | 2017/177025 | A1 | 10/2017 |
| WO | 2018204717 | A1 | 11/2018 |
| WO | 2019118372 | A1 | 6/2019 |
| WO | 2019135975 | A1 | 7/2019 |

OTHER PUBLICATIONS

Donald M et al., The Polymerase Chain Reaction, Curr Prot Mol Biol, vol. 88 Suppl. Chapter 15, pp. 4, (2009).
Panda, D. et al, A Nucleus-Imaging Probe That Selectively Stabilizes a Minor Conformation of c-MYC G-quadruplex and Down-regulates c-MYC Transcription in Human Cancer Cells, Scientific Reports, vol. 5, No. 13183, pp. 1-16, (2015).
Tepper R et al., Preorganization in a Cleft-Type Anion Receptor Featuring Iodo-1,2,3-Triazoles As Halogen Bond Donors, Org Letters, vol. 17 Issue 23, pp. 5740-5743, (2015).
International Search Report and Written Opinion mailed Nov. 18, 2020 in connection with PCT/US20/38682 filed Jun. 19, 2020, 12 pages.
Kasianowicz et al, Characterization of individual polynucleotide molecules using a membrane channel, Proceedings of the National Academy of Sciences USA, Nov. 1996, pp. 13770-13773, vol. 93.
PubChem-CID-82369680, Create Date: Oct. 20, 2014 (Oct. 20, 2014). p. 2, Fig.
Kwon, Hyukin et al., DNA as an environmental sensor: detection and identification of pesticide contaminants in water with fluorescent nucleobases, Organic & Biomolecular Chemistry, vol. 15, pp. 1801-1809, 2017.
Pala N et al., Inhibitory Effect of 2,3,5,6-Tetrafluoro-4-[4-(aryl)-1H-1,2,3-triazol-1-yl]benzenesulfonamide Derivatives on HIV Reverse Transcriptase Associated RNase H Activities, Int J Mol Sci, (2016), pp. 1371, vol. 17 Issue 8.

* cited by examiner

*Primary Examiner* — Jezia Riley
(74) *Attorney, Agent, or Firm* — Kristen K. Walker

(57) ABSTRACT

The invention relates to compounds, methods and compositions for improving on nucleic acid polymerization, including DNA replication by in vitro primer extension to generate, for example, polymers for nanopore-based single molecule sequencing of a DNA template. A nucleic acid polymerase reaction composition is provided with polymerization enhancement moieties, which allows enhanced DNA polymerase activity with nucleotide analogs, resulting in improved length of primer extension products for sequencing applications.

34 Claims, 16 Drawing Sheets

Specification includes a Sequence Listing.

SEQUENCE LISTING

```
<160> NUMBER OF SEQ ID NOS: 5

<210> SEQ ID NO 1
<211> LENGTH: 340
<212> TYPE: PRT
<213> ORGANISM: Sulfolobus solfataricus

<400> SEQUENCE: 1

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Glu Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Ala Val Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Gln Gly Ile Pro Tyr Phe Thr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
```

```
        275                 280                 285

Trp Lys Ser Tyr Trp Asn Ser Gln Tyr Arg Trp Ser Trp Phe Pro His
    290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                325                 330                 335

Phe Ser Lys Phe
            340


<210> SEQ ID NO 2
<211> LENGTH: 340
<212> TYPE: PRT
<213> ORGANISM: Sulfolobus solfataricus

<400> SEQUENCE: 2

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Arg Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Ala Val Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Gln Gly Ile Pro Tyr Phe Thr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
    290                 295                 300
```

-continued

Gly Ile Ser Lys Glu Thr Ala Tyr Ser Glu Ser Val Gln Leu Leu Gln
305 310 315 320

Gln Ile Leu Lys Lys Asp Lys Arg Lys Ile Arg Arg Ile Gly Val Arg
325 330 335

Phe Ser Lys Phe
340

<210> SEQ ID NO 3
<211> LENGTH: 340
<212> TYPE: PRT
<213> ORGANISM: Sulfolobus solfataricus

<400> SEQUENCE: 3

Met Ile Val Leu Phe Val Asp Phe Asp Tyr Phe Tyr Ala Gln Val Glu
1 5 10 15

Glu Val Leu Asn Pro Ser Leu Lys Gly Lys Pro Val Val Val Cys Val
20 25 30

Phe Ser Gly Arg Phe Glu Asp Ser Gly Val Val Ala Thr Ala Asn Tyr
35 40 45

Glu Ala Arg Lys Phe Gly Val Tyr Ala Gly Ile Pro Ile Val Arg Ala
50 55 60

Lys Lys Ile Leu Pro Asn Ala Val Tyr Leu Pro Trp Arg Asp Leu Val
65 70 75 80

Tyr Trp Gly Val Ser Glu Arg Ile Met Asn Leu Leu Arg Glu Tyr Ser
85 90 95

Glu Lys Ile Glu Ile Ala Ser Ile Asp Glu Ala Tyr Leu Asp Ile Ser
100 105 110

Asp Lys Val Arg Asp Tyr Arg Glu Ala Tyr Asn Leu Gly Leu Glu Ile
115 120 125

Lys Asn Lys Ile Leu Glu Lys Glu Lys Ile Thr Val Thr Val Gly Ile
130 135 140

Ser Lys Asn Lys Val Phe Ala Ala Val Ala Gly Arg Met Ala Lys Pro
145 150 155 160

Asn Gly Ile Lys Val Ile Asp Asp Glu Glu Val Lys Arg Leu Ile Arg
165 170 175

Glu Leu Asp Ile Ala Asp Val Gln Gly Ile Pro Tyr Phe Thr Ala Glu
180 185 190

Lys Leu Lys Lys Leu Gly Ile Asn Lys Leu Val Asp Thr Leu Ser Ile
195 200 205

Glu Phe Asp Lys Leu Lys Gly Met Ile Gly Glu Ala Lys Ala Lys Tyr
210 215 220

Leu Ile Ser Leu Ala Arg Asp Glu Tyr Asn Glu Pro Ile Arg Thr Arg
225 230 235 240

Val Arg Arg Ser Ile Gly Arg Thr Val Thr Met Lys Arg Asn Ser Arg
245 250 255

Asn Leu Glu Glu Ile Lys Pro Tyr Leu Phe Arg Ala Ile Glu Glu Ser
260 265 270

Tyr Tyr Lys Leu Asp Lys Arg Ile Pro Lys Ala Ile His Val Val Ala
275 280 285

Trp Lys Ser Tyr Trp Asn Ser Gln Tyr Arg Trp Ser Trp Phe Pro His
290 295 300

Gly Ile Ser Lys Glu Thr Ala Tyr Ser Glu Ser Val Gln Leu Leu Gln
305 310 315 320

Gln Ile Leu Lys Lys Asp Lys Arg Lys Ile Arg Arg Ile Gly Val Arg
325 330 335

```
Phe Ser Lys Phe
            340


<210> SEQ ID NO 4
<211> LENGTH: 340
<212> TYPE: PRT
<213> ORGANISM: Sulfolobus solfataricus

<400> SEQUENCE: 4

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Val Arg Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Ala Val Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Gln Gly Ile Pro Tyr Phe Thr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asp Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
    290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                325                 330                 335

Phe Ser Lys Phe
            340
```

-continued

```
<210> SEQ ID NO 5
<211> LENGTH: 340
<212> TYPE: PRT
<213> ORGANISM: Sulfolobus solfataricus

<400> SEQUENCE: 5

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Val Val Ala Thr Ala Asn Tyr
        35                  40                  45

Glu Ala Arg Lys Phe Gly Val Tyr Ala Gly Ile Pro Ile Lys Arg Ala
    50                  55                  60

Lys Lys Ile Leu Pro Asn Ala Val Tyr Leu Pro Trp Arg Asp Leu Val
65                  70                  75                  80

Tyr Trp Gly Val Ser Glu Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Ala Val Ala Gly Arg Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Gln Gly Ile Pro Tyr Phe Thr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Thr Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Trp Lys Ser Tyr Trp Asn Ser Gln Tyr Arg Trp Ser Trp Phe Pro His
    290                 295                 300

Gly Ile Ser Lys Glu Thr Ala Tyr Ser Glu Ser Val Gln Leu Leu Gln
305                 310                 315                 320

Gln Ile Leu Lys Lys Asp Lys Arg Lys Ile Arg Arg Ile Gly Val Arg
                325                 330                 335

Phe Ser Lys Phe
            340
```

ENHANCEMENT OF NUCLEIC ACID POLYMERIZATION BY AROMATIC COMPOUNDS

CROSS REFERENCE TO RELATED APPLICATIONS

This patent application is a continuation of International Patent application PCT/US2020/038682, filed Jun. 19, 2020, which claims priority to and benefit of U.S. Provisional Patent Application No. 62/867,049, filed Jun. 26, 2019. Each of the above patent applications is incorporated herein by reference as setforth in its entirety.

FIELD OF THE INVENTION

The present invention relates generally to new chemical entities, more specifically to new organic molecules optionally having inorganic components, including compositions thereof, and methods for the manufacture and utilization thereof, particularly in influencing enzyme performance.

STATEMENT REGARDING SEQUENCE LISTING

The Sequence Listing associated with this application is provided in xml format in lieu of a paper copy, and is hereby incorporated by reference into the specification. The name of the text file containing the Sequence Listing is P36237-US-1.xml. The xml file is 10240 bytes, was created on Jan. 27, 2026, and is being submitted electronically via Patent Center.

BACKGROUND

Measurement of biomolecules is a foundation of modern medicine and is broadly used in medical research, and more specifically in diagnostics and therapy, as well in drug development. Nucleic acids encode the necessary information for living things to function and reproduce, and are essentially a blueprint for life. Determining such blueprints is useful in pure research as well as in applied sciences. In medicine, sequencing can be used for diagnosis and to develop treatments for a variety of pathologies, including cancer, heart disease, autoimmune disorders, multiple sclerosis, and obesity. In industry, sequencing can be used to design improved enzymatic processes or synthetic organisms. In biology, this tool can be used to study the health of ecosystems, for example, and thus have a broad range of utility. Similarly, measurement of proteins and other biomolecules has provided markers and understanding of disease and pathogenic propagation.

An individual's unique DNA sequence provides valuable information concerning their susceptibility to certain diseases. It also provides patients with the opportunity to screen for early detection and/or to receive preventative treatment. Furthermore, given a patient's individual blueprint, clinicians will be able to administer personalized therapy to maximize drug efficacy and/or to minimize the risk of an adverse drug response. Similarly, determining the blueprint of pathogenic organisms can lead to new treatments for infectious diseases and more robust pathogen surveillance. Low cost, whole genome DNA sequencing will provide the foundation for modern medicine. To achieve this goal, sequencing technologies must continue to advance with respect to throughput, accuracy, and read length.

Over the last decade, a multitude of next generation DNA sequencing technologies have become commercially available and have dramatically reduced the cost of sequencing whole genomes. These include sequencing by synthesis ("SBS") platforms (Illumina, Inc., 454 Life Sciences, Ion Torrent, Pacific Biosciences) and analogous ligation based platforms (Complete Genomics, Life Technologies Corporation). A number of other technologies are being developed that utilize a wide variety of sample processing and detection methods. For example, GnuBio, Inc. (Cambridge, Mass.) uses picoliter reaction vessels to control millions of discreet probe sequencing reactions, whereas Halcyon Molecular (Redwood City, Calif.) was attempting to develop technology for direct DNA measurement using a transmission electron microscope.

Nanopore based nucleic acid sequencing is a compelling approach that has been widely studied. Kasianowicz et al. (Proc. Natl. Acad. Sci. USA 93: 13770-13773, 1996) characterized single-stranded polynucleotides as they were electrically translocated through an alpha hemolysin nanopore embedded in a lipid bilayer. It was demonstrated that during polynucleotide translocation partial blockage of the nanopore aperture could be measured as a decrease in ionic current. Polynucleotide sequencing in nanopores, however, is burdened by having to resolve tightly spaced bases (0.34 nm) with small signal differences immersed in significant background noise. The measurement challenge of single base resolution in a nanopore is made more demanding due to the rapid translocation rates observed for polynucleotides, which are typically on the order of 1 base per microsecond. Translocation speed can be reduced by adjusting run parameters such as voltage, salt composition, pH, temperature, and viscosity, to name a few. However, such adjustments have been unable to reduce translocation speed to a level that allows for single base resolution.

Stratos Genomics has developed a method called Sequencing by Expansion ("SBX") that uses a biochemical process to transcribe the sequence of DNA onto a measurable polymer called an "Xpandomer" (Kokoris et al., U.S. Pat. No. 7,939,259, "High Throughput Nucleic Acid Sequencing by Expansion"). The transcribed sequence is encoded along the Xpandomer backbone in high signal-to-noise reporters that are separated by ~10 nm and are designed for high-signal-to-noise, well-differentiated responses. These differences provide significant performance enhancements in sequence read efficiency and accuracy of Xpandomers relative to native DNA. Xpandomers can enable several next generation DNA sequencing detection technologies and are well suited to nanopore sequencing.

Xpandomers are generated from non-natural nucleotide analogs, termed XNTPs, characterized by lengthy substituents that enable the Xpandomer backbone to be expanded following synthesis (see Published PCT Appl. No. WO2016/081871 to Kokoris et al., herein incorporated by reference in its entirety). Because of their atypical structures, XNTPs, as well as other nucleotide analogs (e.g., nucleotide analogs modified with detectable label moieties) introduce novel challenges as substrates for currently available DNA polymerases. Published PCT Appl. Nos. WO2017/087281 and WO2018/204717 to Kokoris et al., herein incorporated by reference in their entirety, describes engineered DP04 polymerase variants with enhanced primer extension activity utilizing non-natural, bulky nucleotide analogues as substrates.

Within the DNA template itself, certain nucleotide sequence motifs are known to present additional replication challenges to DNA polymerases. Of particular consequence are runs of homopolymers, or short repeated DNA sequences, which can trigger slipped-strand mispairing, or "replication slippage". Replication slippage is thought to encompass the following steps: (i) copying of the first repeat by the replication machinery, (ii) replication pausing and dissociation of the polymerase from the newly synthesized end, (iii) unpairing of the newly synthesized strand and its pairing with the second repeat, and (iv) resumption of DNA synthesis. Arrest of the replication machinery within a repeated region thus results in misalignment of primer and template. In vivo, misalignment of two DNA strands during replication can lead to DNA rearrangements such as deletions or duplications of varying lengths. In vitro, replication slippage results in replication errors at the site of the slippage event. Such reduction in polymerase processivity, or accuracy, significantly impairs the particular application or desired genetic manipulation.

Thus, new methods and compositions for enhancing polymerase reactions under conditions including one or more reagents with atypical structures are necessary (e.g., in sequencing by expansion (SBX) and other applications in biotechnology and biomedicine, such as DNA amplification, conventional sequencing, labeling, detection, cloning, etc.), and would find value in the art. The present invention fulfills these needs and provides further related advantages.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY

In brief, the present disclosure provides compounds, compositions and uses thereof that enhance nucleic acid polymerase activity. In certain embodiments polymerase activity is enhanced in polymerization reactions under conditions that introduce one or more challenges to the polymerase, e.g., conditions that include non-natural nucleotide analog substrates or template motifs that impair polymerase processivity. Such enhancement is achieved by supplementing a polymerization reaction with one or more compounds of the present disclosure, which may optionally be referred to herein as Polymerase Enhancing Molecules, or PEMs.

In one aspect, the PEM is a compound of formula (I)

(I)

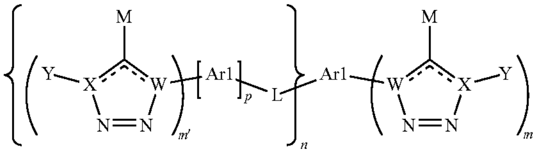

or a solvate, hydrate, tautomer, chelate or salt thereof, wherein:

m is 1, 2 or 3;

m' is 1, 2 or 3;

n is 0, 1 or 2;

p is 0, 1 or 2;

W is N when X is C or W is C when X is N;

--- is a single or double bond, wherein the double bond begins at whichever of W or X is carbon;

L is a linking group;

M is, at each occurrence, independently selected from hydrogen, halogen and $C_1$-$C_4$alkyl;

Ar1 is, at each occurrence, independently selected from optionally substituted pyridine, pyrazine, pyridazine, furan, thiophene, naphthalene, fluorene, phenanthrene, cinnoline, phthalazine, quinazoline, quinoxaline, naphthyridine, phenanthroline, purine, and carbazole, wherein substituents for Ar1 are, at each occurrence, independently selected from halogen, —OH, —CN, —$NO_2$, $C_1$-$C_6$alkyl, $C_1$-$C_6$haloalkyl, $C_1$-$C_6$heteroalkyl, $C_1$-$C_6$cycloloalkyl, —$OR^0$, —$CONH_2$, —C(O)$NR^1R^{1'}$, —$NR^1R^{1'}$, —$NR^1C(O)R^3$, —$C(O)SR^3$, —$COR^3$, —$OC(O)R^3$, —$C(O)OR^3$, mercaptan, —$R^4$—H, —$SOR^1$, —$S(O)_2R^1$, —$S(O)_2NR^1R^{1'}$, and —$NS(O)_2R^3$;

$R^0$ is, at each occurrence, independently selected from $C_1$-$C_6$alkyl, $C_1$-$C_6$haloalkyl, $C_2$-$C_6$alkenyl, $C_2$-$C_6$alkynyl, substituted or unsubstituted cycloalkyl, substituted or unsubstituted heterocyclyl, substituted or unsubstituted aryl, and substituted or unsubstituted heteroaryl;

$R^1$ and $R^{1'}$ are, at each occurrence, independently selected from H, hydroxyl, $C_1$-$C_6$alkyl, $C_1$-$C_6$haloalkyl, $C_1$-$C_6$heteroalkyl, $C_2$-$C_6$alkenyl, $C_2$-$C_6$alkynyl, substituted or unsubstituted cycloalkyl, substituted or unsubstituted heterocyclyl, substituted or unsubstituted aryl, substituted or unsubstituted arylalkyl, and substituted or unsubstituted heteroaryl, —C(=NH)$NH_2$, —$CH_2CO_2R^0$, —$CH_2C(O)NHCH_2CO_2H$, —$CH_2CH_2OH$, —$CH_2CH_2NHC(O)R^3$, —$CH_2C(O)NHCH_2CO_2H$,

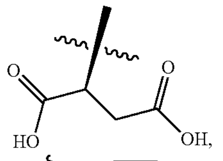

and

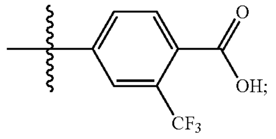

and wherein $R^1$ and $R^{1'}$ can come together to form a heterocyclic ring, including, but not limited to, azetidine, pyrrolidine, piperidine, piperazine, morpholine,

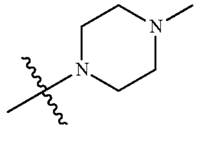

, or

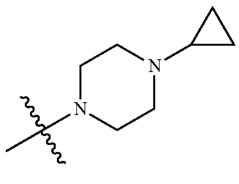

;

$R^2$ is, at each occurrence, independently selected from $C_2$-$C_6$alkyl, $C_1$-$C_6$haloalkyl, $C_1$-$C_6$heteroalkyl, or substituted or unsubstituted cycloalkyl, substituted or unsubstituted heterocyclyl, substituted or unsubstituted aryl, substituted or unsubstituted heteroaryl, and substituted or unsubstituted haloalkoxy;

$R^3$ is, at each occurrence, independently selected from H, $C_1$-$C_6$alkyl, $C_1$-$C_6$haloalkyl, $C_1$-$C_6$heteroalkyl, or substituted or unsubstituted cycloalkyl, substituted or unsubstituted heterocyclyl, substituted or unsubstituted aryl, and substituted or unsubstituted heteroaryl, substituted or unsubstituted haloalkoxy, and guanidine;

$R^4$ is, at each occurrence, independently selected from one or more heteroatom interrupted alkylene wherein the heteroatom is O, S, NH or a combination thereof, Y is, at each occurrence, independently selected from Ar2, —$(CH_2)_3PO(OEt)_2$, or —CH2$CO_2$Me;

Ar2 is, at each occurrence, independently selected from substituted 5- and 6-membered monocyclic aromatic rings and 9- and 10-membered fused bicyclic rings comprising two monocyclic rings together, where at least one of the two monocyclic rings is an aromatic ring, wherein: Ar2 is substituted with $G^1$, $G^2$, $G^3$, $G^4$ and $G^5$, wherein: when Ar2 is monosubstituted, $G^1$ is, at each occurrence, independently selected from oxo, —$NH_2$, —$COR^3$, -E-$CO_2$H, —C(O)$NR^1R^{1'}$, -E-PO$(OR^1)_2$ and aryl substituted with $G^2$, $G^3$, $G^4$ and $G^5$; $G^2$, $G^3$, $G^4$ and $G^5$ are, at each occurrence, independently selected from absent or selected from the groups comprising, halogen, —CN, $C_1$-$C_6$alkyl, $C_1$-$C_6$haloalkyl, -E-$CO_2$H, -E-CHO, -E-C(O)$R^3$, -E-C(O)NH(OH), -E-C(O)$NHR^1$, -E-$CONR^1R^{1'}$, -E-$NR^1R^{1'}$, and -E-$OR^2$, wherein E is, at each occurrence, independently selected from a direct bond, and $C_1$-$C_6$alkylene.

In one aspect, the present disclosure provides a method of enhancing a nucleic acid polymerase reaction, the method including the steps of forming a nucleic acid polymerase reaction composition including a template nucleic acid, a nucleic acid polymerase, a mixture of nucleotides and/or nucleotide analogs, at least one PEM; and incubating the nucleic acid polymerase reaction composition under conditions allowing a nucleic acid polymerization reaction. The PEM increases the processivity, rate, and/or fidelity of the nucleic acid polymerase reaction. In one embodiment, the at least one PEM increases the length of a resulting nucleic acid product compared to a nucleic acid polymerase reaction lacking the PEM.

In additional embodiments, the nucleic acid polymerase is a DNA polymerase. In certain embodiments, the DNA polymerase is $DPO_4$ or a variant thereof. In other embodiments, the mixture of nucleotides or nucleotide analogs is a mixture of nucleotide analogs comprising nucleoside triphosphoramidates, wherein each of the nucleoside triphosphoramidates includes a nucleobase selected from the group consisting of adenine, guanine, thymine, and cytosine and a polymeric tether moiety, wherein a first end of the polymeric tether moiety is attached to the nucleobase and a second end of the polymeric tether moiety is attached to the alpha phosphate of the nucleoside triphosphoramidate to provide for expansion of the nucleotide analogs by cleavage of the phosphoramidate bond. In some embodiments, the nucleic acid polymerization reaction produces an expandable polymer of nucleotide analogs, wherein the expandable polymer encodes the nucleobase sequence information of the template nucleic acid. In other embodiments, the conditions for allowing a nucleic acid polymerization reaction includes a suitable polymerization buffer and an oligonucleotide primer. In further embodiments, the suitable buffer includes one or more of, e.g., each of, Tris OAc, $NH_4OAc$, PEG, a water-miscible organic solvent such as DMF, NMP and acetone, polyphosphate 60, and $MnCl_2$. In other embodiments, the reaction mixture further includes a nucleic acid intercalating agent. In other embodiments, the reaction mixture further includes a polyanion recognition moiety. In further embodiments, the mixture of nucleotides or nucleotide analogs includes nucleotide analogs comprising a detectable label. In yet other embodiments, the detectable label is an optically detectable label selected from the group consisting of luminescent, chemiluminescent, fluorescent, fluorogenic, chromophoric or chromogenic labels.

In another aspect, the present disclosure provides a composition including at least one PEM and a mixture of nucleotide analogs. This composition is useful, e.g., when combined with a polymerase, wherein the at least one PEM increases the number and accuracy of nucleotide analogs incorporated into a daughter strand during a template-dependent polymerization reaction relative to an identical polymerization reaction absent the at least PEM. In other embodiments, the at least one PEM comprises a plurality of PEMs.

Optionally, the mixture of nucleotide analogs comprises nucleoside triphosphoramidates, wherein each of the nucleoside triphosphoramidates comprises a nucleobase selected from the group consisting of adenine, guanine, thymine, and cytosine and a polymeric tether moiety, wherein a first end of the polymeric tether moiety is attached to the nucleobase and a second end of the polymeric ether moiety is attached to the alpha phosphate of the nucleoside triphosphoramidate to provide for expansion of the nucleotide analogs by cleavage of the phosphoramidate bond. In other embodiments, the composition further includes a buffer including at least one of, e.g., two of, three of, four of, etc., or each of, Tris OAc, $NH_4OAc$, PEG, water-miscible organic solvent such as DMF and NMP, polyphosphate 60, N-methyl succinimide (NMS), and $MnCl_2$. In other embodiments, the composition further includes a single-strand binding protein (SSB). In other embodiments, the composition further includes urea. In certain embodiments, the mixture of nucleotide analogs includes nucleotide analogs including a detectable label. In some embodiments, the detectable label is an optically detectable label selected from the group consisting of luminescent, chemiluminescent, fluorescent, fluorogenic, chromophoric or chromogenic labels.

In another aspect, the invention provides a method of sequencing a DNA or RNA template, the method including the steps of forming a DNA polymerase reaction composition including the DNA or RNA template, a replication primer that complexes with the template, a DNA polymerase, a mixture of nucleotides or nucleotide analogs, and at least one PEM, incubating the DNA polymerase reaction composition under conditions allowing a DNA polymerization reaction, wherein the at least one PEM increases the rate, fidelity or processivity of the DNA polymerase reaction. The method may further include determining the sequence of the nucleotides or nucleotide analogs in the resulting polymer of nucleotides or nucleotide analogs. The PEM may be described as a compound of formula (I). In some embodiments, the at least one PEM is selected from compounds of formula (II). In other embodiments, the mixture of nucleotide analogs comprises nucleoside triphosphoramidates, wherein each of the nucleoside triphosphoramidates comprises a nucleobase selected from the group consisting of adenine, guanine, thymine, and cytosine and a polymeric tether moiety, wherein a first end of the polymeric tether moiety is attached to the nucleobase and a second end of the polymeric ether moiety is attached to the alpha phosphate of the nucleoside triphosphoramidate to provide for expansion of the nucleotide analogs by cleavage of the phosphoramidate bond. In other embodiments, the DNA polymerase is DPO4 or a variant thereof. In other embodiments, the resulting polymer of nucleotide analogs is an expandable polymer. In other embodiments, the method further includes the step of contacting the expandable polymer with a phosphoramidate cleavage agent to produce an expanded polymer of nucleotide analogs. In certain embodiments, the polymeric tether moiety of each of the nucleotide analogs comprises a reporter moiety unique to the nucleobase of the analog. In other embodiments, the reporter moieties produce a characteristic electronic signal. In yet other embodiments, the step of determining the sequence of the nucleotide analogs includes the step of translocating the expanded polymer of nucleotide analogs through a nanopore.

Thus, in one embodiment the present disclosure provides a composition comprising a PEM and a polynucleotide. In another embodiment the present disclosure provides a composition comprising a PEM and a polypeptide, e.g., a polypeptide such as an enzyme, where the enzyme may be a nucleic acid polymerase.

The following are some exemplary specific and numbered embodiments of the present disclosure. Also, unless otherwise specifically mentioned, each atom identified in a chemical formula may be any of the isotopes of that atom. For example, the designation C (carbon) includes $^{12}C$, $^{13}C$, or $^{14}C$ and mixtures thereof, particularly natural abundance isotope mixtures, while H (hydrogen) includes $^{1}H$, $^{2}H$ and $^{3}H$ and mixtures thereof, and O (oxygen) includes $^{16}O$ and $^{18}O$ and mixtures thereof, and N (nitrogen) includes $^{14}N$ and $^{15}N$ and mixtures thereof, etc. for other atoms:

1) A compound of formula (I)

(I)

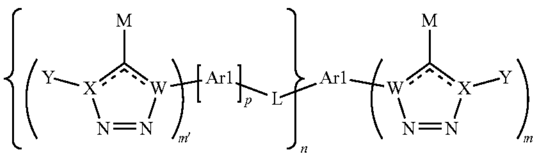

or a solvate, hydrate, tautomer, chelate or salt thereof, wherein:

m is 1, 2 or 3;

m' is 1, 2 or 3;

n is 0, 1 or 2;

p is 0, 1 or 2;

W is N when X is C or W is C when X is N;

--- is a single or double bond, wherein the double bond begins at whichever of W or X is carbon;

L is a linking group;

M is, at each occurrence, independently selected from hydrogen, halogen and $C_1$-$C_4$alkyl;

Ar1 is, at each occurrence, independently selected from optionally substituted pyridine, pyrazine, pyridazine, furan, thiophene, naphthalene, fluorene, phenanthrene, cinnoline, phthalazine, quinazoline, quinoxaline, naphthyridine, phenanthroline, purine, and carbazole, wherein: substituents for Ar1 are, at each occurrence, independently selected from halogen, —OH, —CN, —$NO_2$, $C_1$-$C_6$alkyl, $C_1$-$C_6$haloalkyl, $C_1$-$C_6$heteroalkyl, $C_1$-$C_6$cycloloalkyl, —$OR^0$, —$CONH_2$, —C(O)$NR^1R^{1'}$, —$NR^1R^{1'}$, —$NR^1C(O)R^3$, —C(O)$SR^3$, —$COR^3$, —OC(O)$R^3$, —C(O)O$R^3$, mercaptan, —$R^4$—H, —$SOR^1$, —$S(O)_2R^1$, —$S(O)_2NR^1R^{1'}$, and —$NS(O)_2R^3$;

$R^0$ is, at each occurrence, independently selected from $C_1$-$C_6$alkyl, $C_1$-$C_6$haloalkyl, $C_2$-$C_6$alkenyl, $C_2$-$C_6$alkynyl, substituted or unsubstituted cycloalkyl, substituted or unsubstituted heterocyclyl, substituted or unsubstituted aryl, and substituted or unsubstituted heteroaryl;

$R^1$ and $R^{1'}$ are, at each occurrence, independently selected from H, hydroxyl, $C_1$-$C_6$alkyl, $C_1$-$C_6$haloalkyl, $C_1$-$C_6$heteroalkyl, $C_2$-$C_6$alkenyl, $C_2$-$C_6$alkynyl, substituted or unsubstituted cycloalkyl, substituted or unsubstituted heterocyclyl, substituted or unsubstituted aryl, substituted or unsubstituted arylalkyl, and substituted or unsubstituted heteroaryl, —C(=NH)$NH_2$, —$CH_2CO_2R^0$, —$CH_2C(O)NHCH_2CO_2H$, —$CH_2CH_2OH$, —$CH_2CH_2NHC(O)R^3$, —$CH_2C(O)NHCH_2CO_2H$,

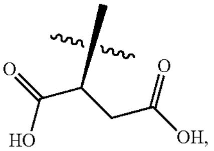
and
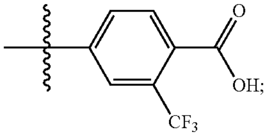

wherein $R^1$ and $R^{1'}$ can come together to form a heterocyclic ring, including, but not limited to, azetidine, pyrrolidine, piperidine, piperazine, morpholine,

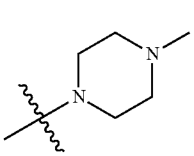
, or
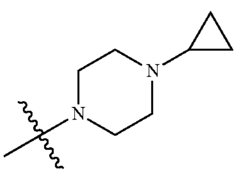
;

$R^2$ is, at each occurrence, independently selected from $C_2$-$C_6$alkyl, $C_1$-$C_6$haloalkyl, $C_1$-$C_6$heteroalkyl, or substituted or unsubstituted cycloalkyl, substituted or unsubstituted heterocyclyl, substituted or unsubstituted aryl, substituted or unsubstituted heteroaryl, and substituted or unsubstituted haloalkoxy;

$R^3$ is, at each occurrence, independently selected from H, $C_1$-$C_6$alkyl, $C_1$-$C_6$haloalkyl, $C_1$-$C_6$heteroalkyl, or substituted or unsubstituted cycloalkyl, substituted or unsubstituted heterocyclyl, substituted or unsubstituted aryl, and substituted or unsubstituted heteroaryl, substituted or unsubstituted haloalkoxy, and guanidine;

$R^4$ is, at each occurrence, independently selected from one or more heteroatom interrupted alkylene wherein the heteroatom is O, S, NH or a combination thereof, Y is, at each occurrence, independently selected from Ar2, —$(CH_2)_3PO(OEt)_2$, or —CH2$CO_2$Me;

Ar2 is, at each occurrence, independently selected from substituted 5- and 6-membered monocyclic aromatic rings and 9- and 10-membered fused bicyclic rings comprising two monocyclic rings together, where at least one of the two monocyclic rings is an aromatic ring, wherein: Ar2 is substituted with $G^1$, $G^2$, $G^3$, $G^4$ and $G^5$, wherein: when Ar2 is monosubstituted, $G^1$ is, at each occurrence, independently selected from oxo, —$NH_2$, —$COR^3$, -E-$CO_2H$, —C(O)$NR^1R^{1'}$, -E-PO$(OR^1)_2$ and aryl substituted with $G^2$, $G^3$, $G^4$ and $G^5$; $G^2$, $G^3$, $G^4$ and $G^5$ are, at each occurrence, independently selected from absent or selected from the groups comprising, halogen, —CN, $C_1$-$C_6$alkyl, $C_1$-$C_6$haloalkyl, -E-$CO_2H$, -E-CHO, -E-C(O)$R^3$, -E-C(O)NH(OH), -E-C(O)$NHR^1$, -E-$CONR^1R^{1'}$, -E-$NR^1R^{1'}$, and -E-$OR^2$, wherein E is, at each occurrence, independently selected from a direct bond and $C_1$-$C_6$alkylene.

2) The compound of embodiment 1, wherein Ar1 is monocyclic heterocyclic aryl.

3) The compound of embodiment 2, wherein Ar1 is selected from:

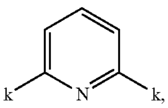 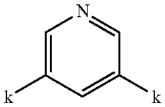 and

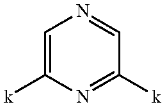

wherein triazole rings are located at positions k on Ar1.

4) The compound of embodiment 1, wherein Ar1 is bicyclic aryl.

5) The compound of embodiment 4, wherein Ar1 is a bicyclic carbocyclic aryl selected from:

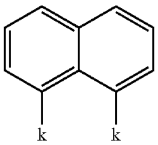, 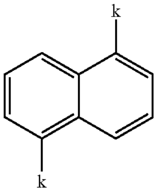, 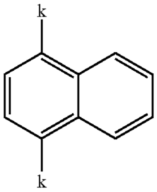,

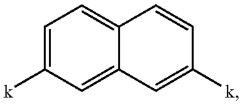

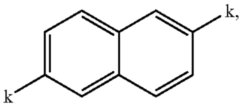 and 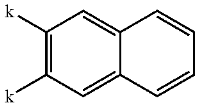

wherein triazole rings are located at positions k on Ar1.

6) The compound of embodiment 4, wherein Ar1 is a bicyclic heterocyclic aryl selected from:

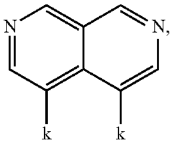 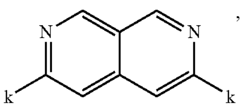,

-continued

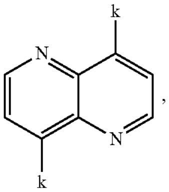, 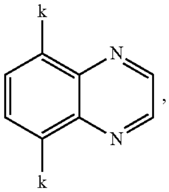,

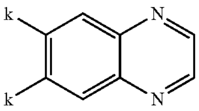 and 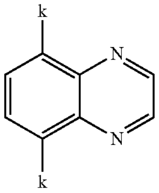

wherein triazole rings are located at positions k on Ar1.

7) The compound of embodiment 1, wherein Ar1 is tricyclic aryl.

8) The compound of embodiment 7, wherein Ar1 is a tricyclic carbocyclic aryl selected from:

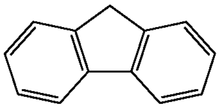 and 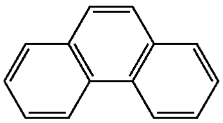.

9) The compound of embodiment 7, wherein Ar1 is tricyclic heteroaryl selected from:

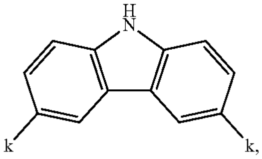

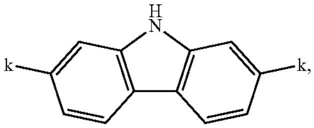 and

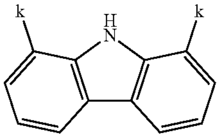

wherein triazole rings are located at positions k on Ar1.

10) The compound of embodiment 7, wherein Ar1 is a tricyclic heteroaryl selected from

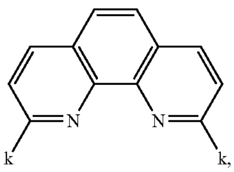

-continued

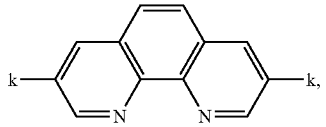

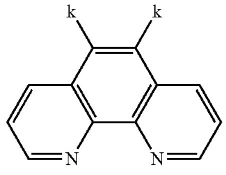
, and
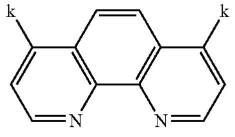

wherein the triazole rings are located at positions k on Ar1.

11) The compound of embodiment 1, wherein Ar2 is a substituted 5-membered monocyclic aromatic ring selected from the group consisting of thiophene, 1,2-thiazole, 1,3-thiazole, furan, 1,2-oxazole, 1,3-oxazole, 1H-pyrrole, 1H-pyrazole, oxadiazole, thiadiazole, 1,2,4-triazole, 1,2,3-triazole and 1H-imidazole.

12) The compound of embodiment 1, wherein Ar2 is a 6-membered monocyclic aromatic ring selected from the group consisting of benzene, pyridine, pyridazine, pyrimidine and pyrazine.

13) The compound of embodiment 1, wherein Ar2 is a 9-membered fused bicyclic aromatic ring system selected from the group consisting of benzofuran, 1,3-benzoxazole, furo[3,2-b]pyridine, furo[3,2-c]pyridine, furo[2,3-c]pyridine, furo[2,3-b]pyridine, indole, 1H-benzimidazole, 1H-pyrrolo[3,2-b]pyridine, 1H-pyrrolo[3,2-c]pyridine, 1H-pyrrolo[2,3-c]pyridine, 1H-pyrrolo[2,3-b]pyridine, benzothiophene, 1,3-benzothiazole, thienol[3,2-b]pyridine, thieno[3,2-c]pyridine, thieno[2,3-c]pyridine, benzoxadiazole, benzothiadiazole, benzisoxazole, benzotriazole and thieno[2,3-b]pyridine.

14) The compound of embodiment 1, wherein Ar2 is a 10-membered fused bicyclic aromatic ring system selected from the group consisting of naphthylene, quinoline, quinazoline, quinoxaline, 1,5-naphthyridine, 1,6-naphthyridine, 1,7-naphthyridine, 1,8-naphthyridine, isoquinoline, phthalazine, 2,6-naphthyridine and 2,7-naphthyridine.

15) The compound of embodiment 1, wherein Ar2 is a pyridinyl ring selected from

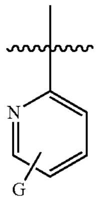
,
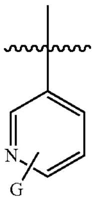
and
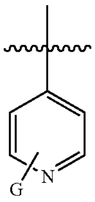
;

wherein the substituent G ($G^1$, $G^2$, $G^3$, $G^4$ and $G^5$ as defined above) is present 0, 1 or 2 times on the pyridinyl ring.

16) The compound of embodiment 1, wherein Ar2 is a phenyl ring of the formula

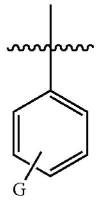

wherein the substituent G ($G^1$, $G^2$, $G^3$, $G^4$ and $G^5$ as defined above) is present 0, 1 or 2 times on the phenyl ring. In one embodiment, G is aryl (such as phenyl) substituted with $G^2$, $G^3$, $G^4$ and $G^5$.

17) The compound of embodiment 1, wherein Ar2 is a phenyl ring selected from

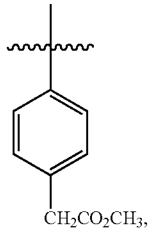
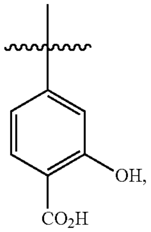
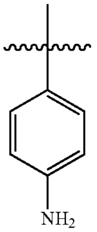
,
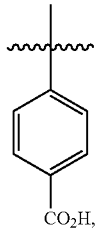
and
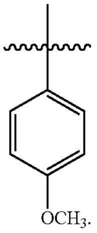

18) The compound of embodiment 1, wherein the substitution on Ar2 includes amino.

19) The compound of embodiment 1, wherein the substitution on Ar2 includes methoxy.

20) The compound of embodiment 1, wherein the substitution on Ar2 includes carboxylic acid.

21) The compound of embodiment 1, wherein the substitution on Ar2 includes $-CH_2-CO_2-CH_3$.

22) The compound of embodiment 1, wherein substitution on Ar2 includes trifluormethyl.

23) The compound of embodiment 1, wherein substitution on Ar2 includes hydroxyl.

24) The compound of embodiment 1, wherein substitution on Ar2 is one carboxylic acid and one hydroxyl.

25) The compound of embodiment 1, wherein substitution on Ar2 is one carboxylic acid and one trifluoromethyl.

26) The compound of embodiment 1, in a form of a chelate.

27) The compound of embodiment 26, wherein the chelate is a copper chelate.

28) The compound of embodiment 1, having a log P of at least 4.9.

29) The compound of embodiment 1, wherein n is 0 and m is 2, having one of the following structures (III) or (IV):

(III)

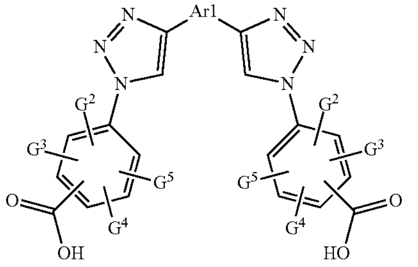

or (IV)

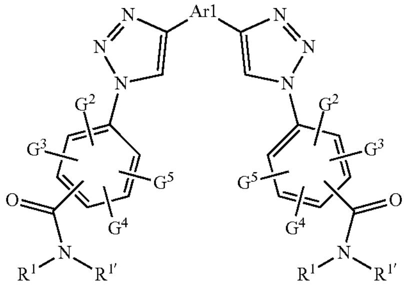

30) The compound of embodiment 1, having substitution on Ar2 including at least two of hydroxyl, carboxylic acid carboxamide and trifluoromethyl.

31) The compound of embodiment 1, wherein the compound has one of the following structures (V), (VI), (VII), (VIII), or (IX):

(V)

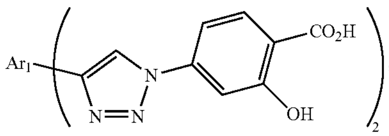

;

(VI)

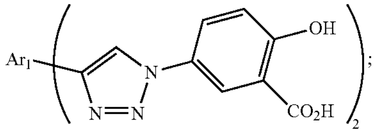

;

(VII)

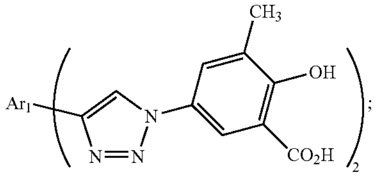

;

(VIII)

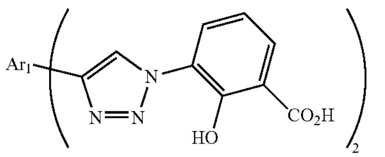

or (IX)

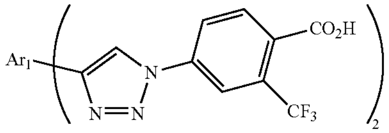

.

32) The compound of embodiment 1, wherein the compound has one of the following structures (X), (XI) or (XII):

(X)

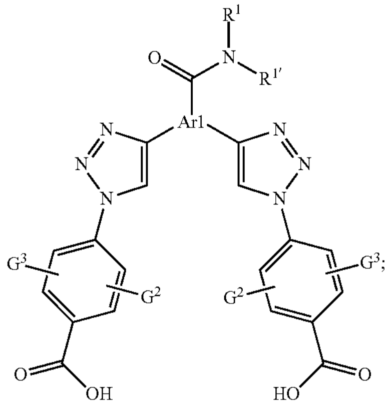

;

(XI)

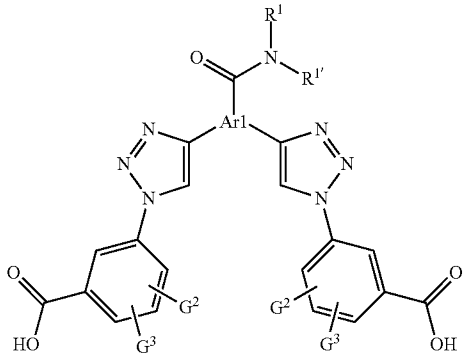

or (XII)

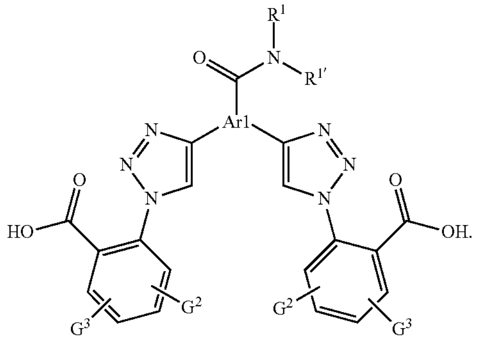

.

33) The compound of embodiment 1, wherein the compound has one of the following structures (XIII), (XIV) or (XV):

(XIII)
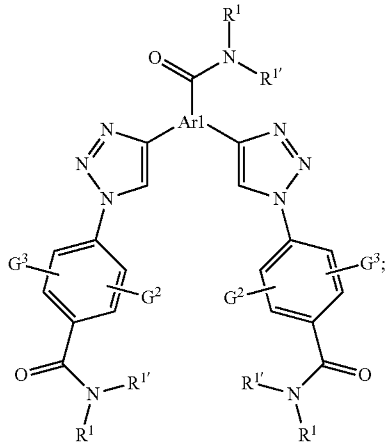
(XIV)
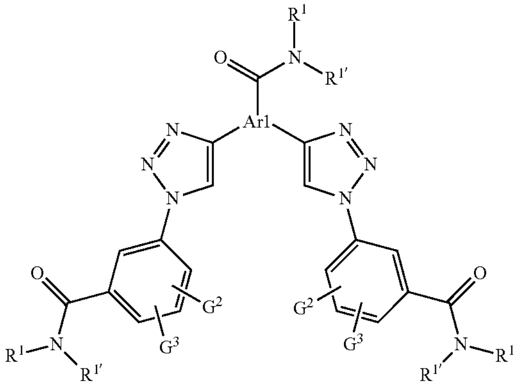
or
(XV)
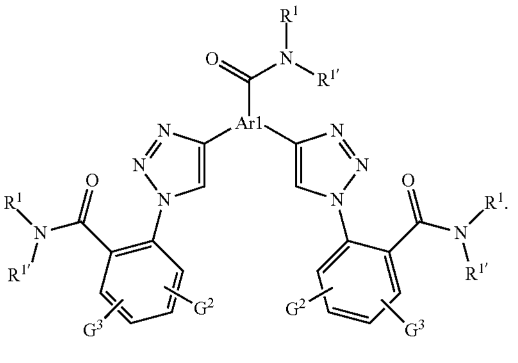
34) The compound of embodiment 1, wherein the compound has one of the following structures (XVI), (XVII), (XVIII), (XIX), (XX), (XXI) or (XXII):
(XVI)
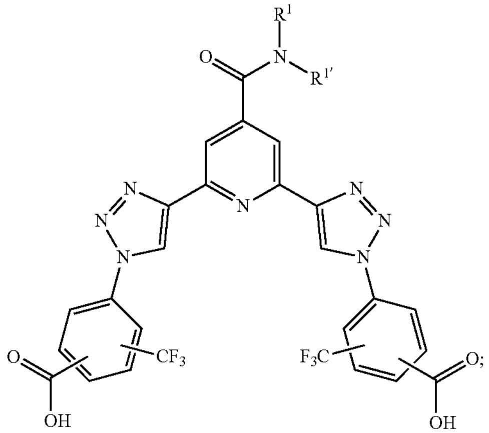
(XVII)
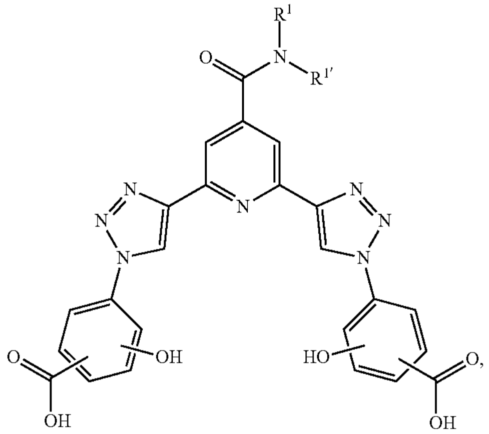
(XVIII)
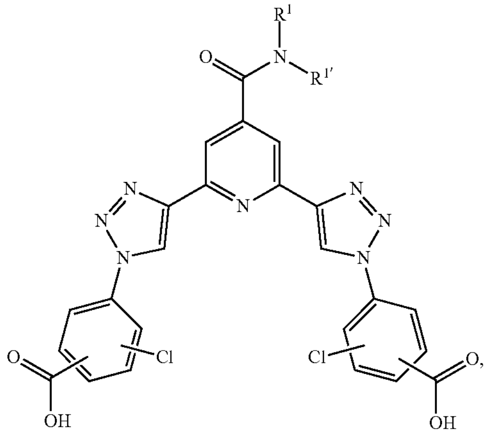

-continued
(XIX)
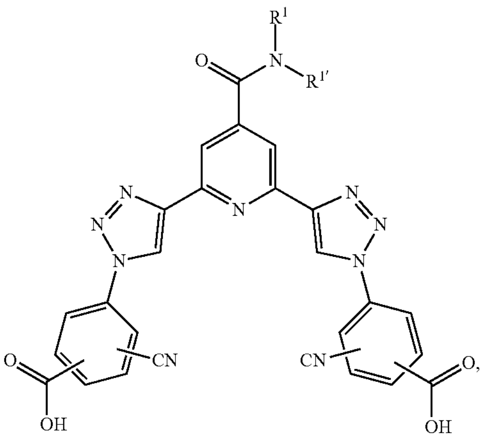
(XX)
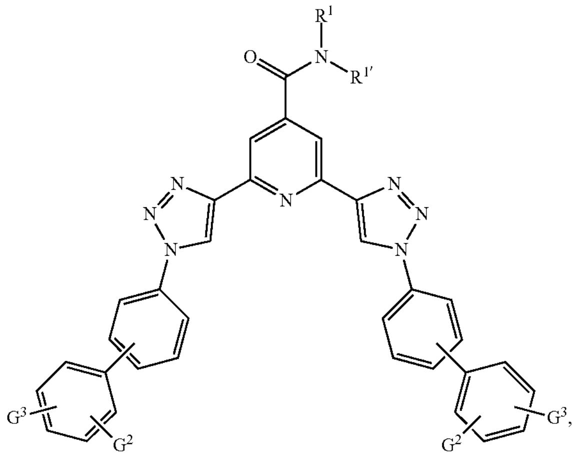
(XXI)
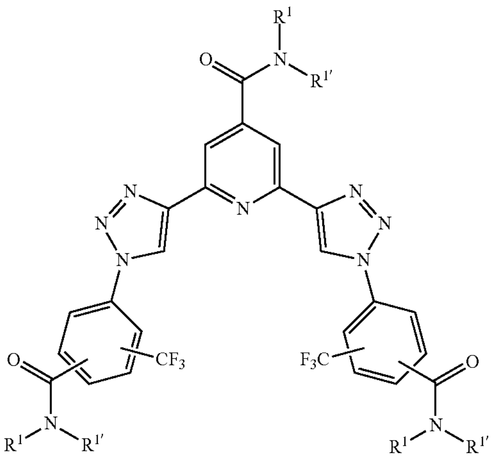
or
-continued
(XXII)
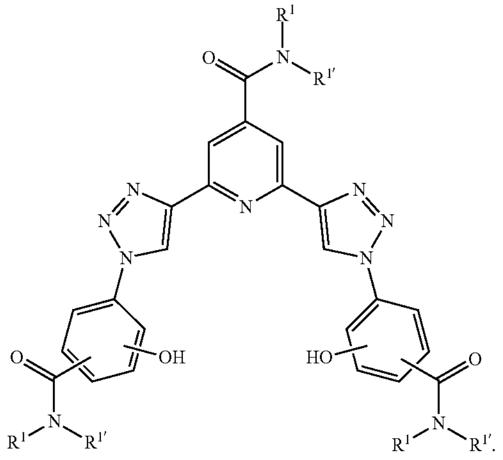
35) The compound of embodiment 1, wherein the compound has one of the following structures (XXIII), (XXIV) or (XXV):
(XXIII)
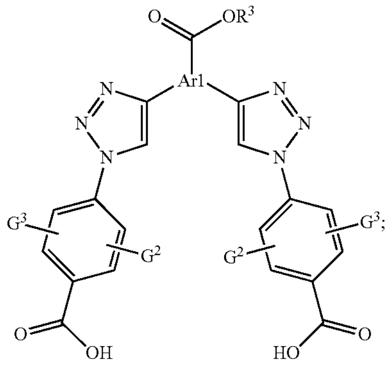
(XXIV)
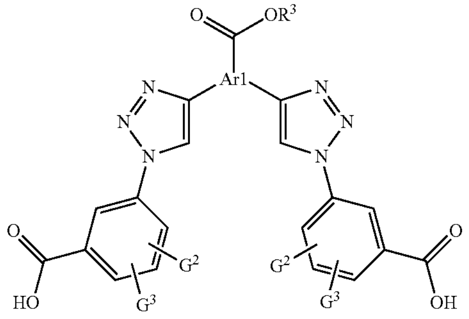
or -continued
(XXV)
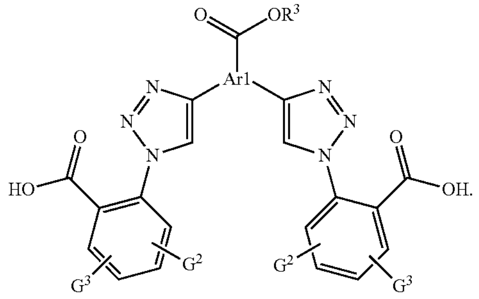
36) The compound of embodiment 1, wherein the compound has one of the following structures (XXVI), (XXVII) or (XXVIII):
(XXVI)
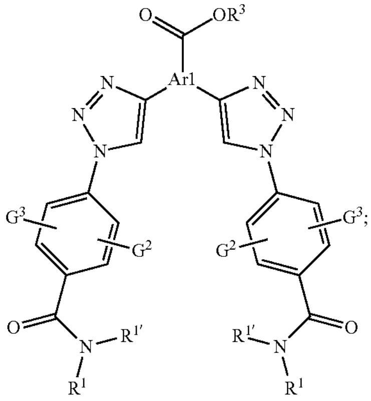
(XXVII)
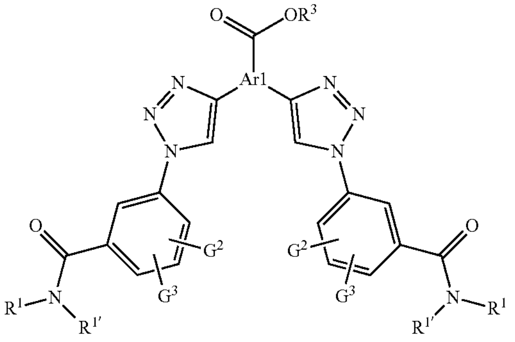
or
(XXVIII)
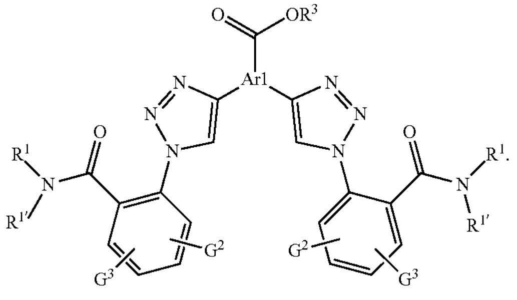
37) The compound of embodiment 1, wherein the compound has one of the following structures (XXIX), (XXX), (XXXI) or (XXXII):
(XXIX)
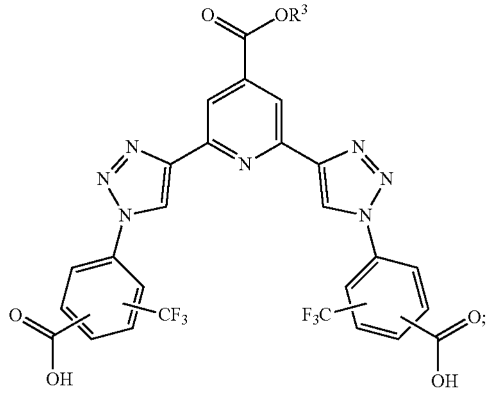
(XXX)
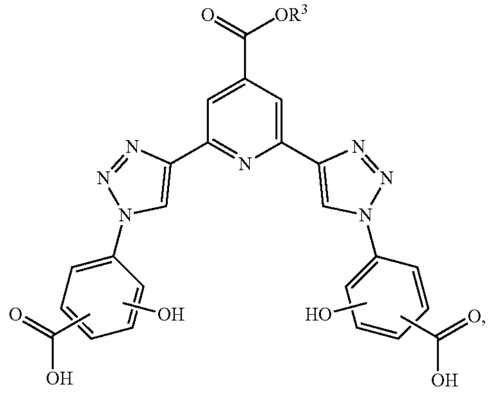
(XXXI)
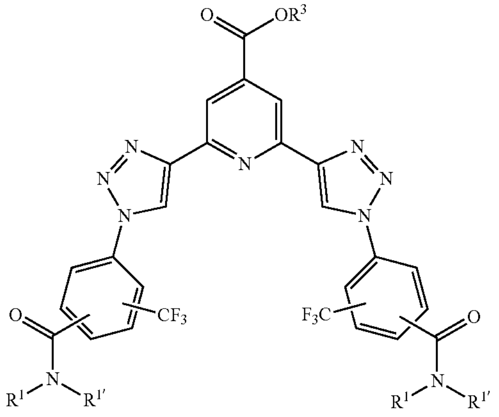
or -continued (XXXII)

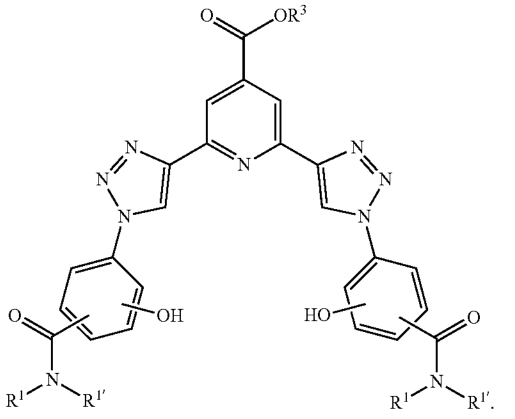

38) The compound of embodiment 1, selected from any one of:

4,4'-(pyridine-2,6-diylbis(1H-1,2,3-triazole-4,1-diyl))bis(2-hydroxybenzoic acid);
4,4'-(pyridine-3,5-diylbis(1H-1,2,3-triazole-4,1-diyl))bis(2-hydroxybenzoic acid);
4,4'-((9H-carbazole-3,6-diyl)bis(1H-1,2,3-triazole-4,1-diyl))bis(2-hydroxybenzoic acid);
4,4'-((9H-carbazole-3,6-diyl)bis(1H-1,2,3-triazole-4,1-diyl))dibenzoic acid;
4,4'-((4-methoxypyridine-2,6-diyl)bis(1H-1,2,3-triazole-4,1-diyl))bis(2-hydroxybenzoic acid);
4,4'-((4-carboxypyridine-2,6-diyl)bis(1H-1,2,3-triazole-4,1-diyl))bis(2-hydroxybenzoic acid);
4,4'-((4-nitropyridine-2,6-diyl)bis(1H-1,2,3-triazole-4,1-diyl))bis(2-hydroxybenzoic acid);
5,5'-((4-cyanopyridine-2,6-diyl)bis(1H-1,2,3-triazole-4,1-diyl))bis(2-hydroxybenzoic acid);
4,4'-((4-methylpyridine-2,6-diyl)bis(1H-1,2,3-triazole-4,1-diyl))bis(2-hydroxybenzoic acid);
4,4'-((4-(ethoxycarbonyl)pyridine-2,6-diyl)bis(1H-1,2,3-triazole-4,1-diyl))bis(2-hydroxybenzoic acid);
5,5'-((4-(ethoxycarbonyl)pyridine-2,6-diyl)bis(1H-1,2,3-triazole-4,1-diyl))bis(2-hydroxybenzoic acid);
4,4'-((4-(methoxycarbonyl)pyridine-2,6-diyl)bis(1H-1,2,3-triazole-4,1-diyl))bis(2-hydroxybenzoic acid);
4,4'-((4-(ethylcarbamoyl)pyridine-2,6-diyl)bis(1H-1,2,3-triazole-4,1-diyl))bis(2-hydroxybenzoic acid);
4,4'-((4-(methylcarbamoyl)pyridine-2,6-diyl)bis(1H-1,2,3-triazole-4,1-diyl))bis(2-hydroxybenzoic acid);
4,4'-((4-carbamoylpyridine-2,6-diyl)bis(1H-1,2,3-triazole-4,1-diyl))bis(2-hydroxybenzoic acid);
4,4'-(pyrazine-2,6-diylbis(1H-1,2,3-triazole-4,1-diyl))bis(2-hydroxybenzoic acid);
4,4'-(1,3-phenylenebis(1H-1,2,3-triazole-4,1-diyl))dianiline;
4,4'-(1,3-phenylenebis(1H-1,2,3-triazole-4,1-diyl))dibenzoic acid;
4-(4-(3-(1-(4-methoxyphenyl)-1H-1,2,3-triazol-4-yl)phenyl)-1H-1,2,3-triazol-1-yl)benzoic acid;
4,4'-(pyridine-2,6-diylbis(1H-1,2,3-triazole-4,1-diyl))dibenzoic acid;
4-(4-(3-(1-(4-methoxyphenyl)-1H-1,2,3-triazol-4-yl)phenyl)-1H-1,2,3-triazol-1-yl)benzoic acid;
4,4'-((3,5-dimethylpyridine-2,6-diyl)bis(1H-1,2,3-triazole-4,1-diyl))bis(2-hydroxybenzoic acid);
4,4'-((413-pyridine-2,6-diyl)bis(5-iodo-1H-1,2,3-triazole-4,1-diyl))bis(2-hydroxybenzoic acid);
4,4'-((4-acetamidopyridine-2,6-diyl)bis(1H-1,2,3-triazole-4,1-diyl))bis(2-hydroxybenzoic acid);
4,4'-((9-acetyl-9H-carbazole-3,6-diyl)bis(1H-1,2,3-triazole-4,1-diyl))bis(2-hydroxybenzoic acid);
4,4'-(pyridine-2,6-diylbis(1H-1,2,3-triazole-4,1-diyl))bis(N,2-dihydroxybenzamide);
4,4'-(pyridine-2,6-diylbis(1H-1,2,3-triazole-4,1-diyl))bis(2-hydroxybenzamide);
4,4'-((4-carboxypyridine-2,6-diyl)bis(1H-1,2,3-triazole-4,1-diyl))bis(2-hydroxybenzoic acid);
4,4'-((1,10-phenanthroline-2,9-diyl)bis(1H-1,2,3-triazole-4,1-diyl))bis(2-hydroxybenzoic acid);
4,4'-((4-(trifluoromethyl)pyridine-2,6-diyl)bis(1H-1,2,3-triazole-4,1-diyl))bis(2-hydroxybenzoic acid);
4,4'-((3-cyanopyridine-2,6-diyl)bis(1H-1,2,3-triazole-4,1-diyl))bis(2-hydroxybenzoic acid);
4,4'-((3-nitropyridine-2,6-diyl)bis(1H-1,2,3-triazole-4,1-diyl))bis(2-hydroxybenzoic acid);
3,3'-((4-cyanopyridine-2,6-diyl)bis(1H-1,2,3-triazole-4,1-diyl))bis(2-hydroxybenzoic acid);
4,4'-((4-(tert-butoxycarbonyl)pyridine-2,6-diyl)bis(1H-1,2,3-triazole-4,1-diyl))bis(2-hydroxybenzoic acid);
4-(4-(4-cyanopyridin-2-yl)-1H-1,2,3-triazol-1-yl)-2-hydroxybenzoic acid;
5-(4-(6-(4-(3-carboxy-4-hydroxy-5-methylphenyl)-1H-1,2,3-triazol-1-yl)-4-(methoxycarbonyl)pyridin-2-yl)-1H-1,2,3-triazol-1-yl)-2-hydroxy-3-methylbenzoic acid;
4,4'-((4-(dimethylcarbamoyl)pyridine-2,6-diyl)bis(1H-1,2,3-triazole-4,1-diyl))bis(2-hydroxybenzoic acid);
4,4'-((4-(cyclopropylcarbamoyl)pyridine-2,6-diyl)bis(1H-1,2,3-triazole-4,1-diyl))bis(2-hydroxybenzoic acid);
4,4'-((4-(but-3-yn-1-ylcarbamoyl)pyridine-2,6-diyl)bis(1H-1,2,3-triazole-4,1-diyl))bis(2-hydroxybenzoic acid);
4,4'-((4-(butylcarbamoyl)pyridine-2,6-diyl)bis(1H-1,2,3-triazole-4,1-diyl))bis(2-hydroxybenzoic acid);
4,4'-((4-(diethylcarbamoyl)pyridine-2,6-diyl)bis(1H-1,2,3-triazole-4,1-diyl))bis(2-hydroxybenzoic acid);
4,4'-((4-(tert-butylcarbamoyl)pyridine-2,6-diyl)bis(1H-1,2,3-triazole-4,1-diyl))bis(2-hydroxybenzoic acid);
4,4'-((4-(morpholine-4-carbonyl)pyridine-2,6-diyl)bis(1H-1,2,3-triazole-4,1-diyl))bis(2-hydroxybenzoic acid);
4,4'-((4-(propylcarbamoyl)pyridine-2,6-diyl)bis(1H-1,2,3-triazole-4,1-diyl))bis(2-hydroxybenzoic acid);
4,4'-((4-(phenylcarbamoyl)pyridine-2,6-diyl)bis(1H-1,2,3-triazole-4,1-diyl))bis(2-hydroxybenzoic acid);
4,4'-((4-((2-acetamidoethyl)carbamoyl)pyridine-2,6-diyl)bis(1H-1,2,3-triazole-4,1-diyl))bis(2-hydroxybenzoic acid);
4,4'-((4-(4-cyclopropylpiperazine-1-carbonyl)pyridine-2,6-diyl)bis(1H-1,2,3-triazole-4,1-diyl))bis(2-hydroxybenzoic acid);
4,4'-((4-(carbamimidoylcarbamoyl)pyridine-2,6-diyl)bis(1H-1,2,3-triazole-4,1-diyl))bis(2-hydroxybenzoic acid);
4,4'-((4-(piperidine-1-carbonyl)pyridine-2,6-diyl)bis(1H-1,2,3-triazole-4,1-diyl))bis(2-hydroxybenzoic acid);
4,4'-((4-(cyclobutylcarbamoyl)pyridine-2,6-diyl)bis(1H-1,2,3-triazole-4,1-diyl))bis(2-hydroxybenzoic acid);
4,4'-((1,10-phenanthroline-3,8-diyl)bis(1H-1,2,3-triazole-4,1-diyl))bis(2-hydroxybenzoic acid);
4,4'-((4-(cyclopentylcarbamoyl)pyridine-2,6-diyl)bis(1H-1,2,3-triazole-4,1-diyl))bis(2-hydroxybenzoic acid);
4,4'-((4-(dipropylcarbamoyl)pyridine-2,6-diyl)bis(1H-1,2,3-triazole-4,1-diyl))bis(2-hydroxybenzoic acid);
4,4'-((4-(di-sec-butylcarbamoyl)pyridine-2,6-diyl)bis(1H-1,2,3-triazole-4,1-diyl))bis(2-hydroxybenzoic acid);

4,4'-(naphthalene-2,7-diylbis(1H-1,2,3-triazole-4,1-diyl))bis(2-hydroxybenzoic acid);
4,4'-(naphthalene-2,3-diylbis(1H-1,2,3-triazole-4,1-diyl))bis(2-hydroxybenzoic acid);
4,4'-((4-(dibutylcarbamoyl)pyridine-2,6-diyl)bis(1H-1,2,3-triazole-4,1-diyl))bis(2-hydroxybenzoic acid);
4,4'-((4-((2-hydroxyethyl)carbamoyl)pyridine-2,6-diyl)bis(1H-1,2,3-triazole-4,1-diyl))bis(2-hydroxybenzoic acid);
4,4'-((4-(cyclohexylcarbamoyl)pyridine-2,6-diyl)bis(1H-1,2,3-triazole-4,1-diyl))bis(2-hydroxybenzoic acid);
4,4'-((4-(benzylcarbamoyl)pyridine-2,6-diyl)bis(1H-1,2,3-triazole-4,1-diyl))bis(2-hydroxybenzoic acid);
4,4'-((4-(4-methylpiperazine-1-carbonyl)pyridine-2,6-diyl)bis(1H-1,2,3-triazole-4,1-diyl))bis(2-hydroxybenzoic acid);
4-(4-(3-(1-(4-methoxyphenyl)-1H-1,2,3-triazol-4-yl)phenyl)-1H-1,2,3-triazol-1-yl)benzoic acid;
4,4',4'',4'''-((((butane-1,4-diylbis(azanediyl))bis(carbonyl))bis(pyridine-4,2,6-triyl))tetrakis(1H-1,2,3-triazole-4,1-diyl))tetrakis(2-hydroxybenzoic acid);
4,4'-((4-(ethylcarbamoyl)pyridine-2,6-diyl)bis(1H-1,2,3-triazole-4,1-diyl))bis(3,5,6-trichloropicolinic acid);
4,4'-((4-(ethylcarbamoyl)pyridine-2,6-diyl)bis(1H-1,2,3-triazole-4,1-diyl))bis(2-(trifluoromethyl)benzoic acid);
7,7'-((4-(ethylcarbamoyl)pyridine-2,6-diyl)bis(1H-1,2,3-triazole-4,1-diyl))bis(2-hydroxy-1,8-naphthyridine-4-carboxylic acid);
5,5'-((4-(ethylcarbamoyl)pyridine-2,6-diyl)bis(1H-1,2,3-triazole-4,1-diyl))bis(2-(trifluoromethyl)benzoic acid);
4,4'-((4-(ethylcarbamoyl)pyridine-2,6-diyl)bis(1H-1,2,3-triazole-4,1-diyl))bis(2-fluorobenzoic acid);
5,5'-((4-(ethylcarbamoyl)pyridine-2,6-diyl)bis(1H-1,2,3-triazole-4,1-diyl))bis(3-fluorobenzoic acid);
4,4'-((4-(methylcarbamoyl)pyridine-2,6-diyl)bis(1H-1,2,3-triazole-4,1-diyl))bis(2-(trifluoromethyl)benzoic acid);
4,4'-((4-(morpholine-4-carbonyl)pyridine-2,6-diyl)bis(1H-1,2,3-triazole-4,1-diyl))bis(2-(trifluoromethyl)benzoic acid);
4,4'-((4-(diethylcarbamoyl)pyridine-2,6-diyl)bis(1H-1,2,3-triazole-4,1-diyl))bis(2-(trifluoromethyl)benzoic acid);
4,4'-((4-carbamoylpyridine-2,6-diyl)bis(1H-1,2,3-triazole-4,1-diyl))bis(2-(trifluoromethyl)benzoic acid);
4,4'-((4-(ethoxycarbonyl)pyridine-2,6-diyl)bis(1H-1,2,3-triazole-4,1-diyl))bis(2-(trifluoromethyl)benzoic acid);
4,4'-((4-(azetidine-1-carbonyl)pyridine-2,6-diyl)bis(1H-1,2,3-triazole-4,1-diyl))bis(2-hydroxybenzoic acid);
4,4'-((4-(ethyl(methyl)carbamoyl)pyridine-2,6-diyl)bis(1H-1,2,3-triazole-4,1-diyl))bis(2-hydroxybenzoic acid);
N-ethyl-2,6-bis(1-(4-(2,2,2-trifluoroacetyl)phenyl)-1H-1,2,3-triazol-4-yl)isonicotinamide;
4,4'-(pyridine-2,6-diylbis(1H-1,2,3-triazole-4,1-diyl))bis(2-(trifluoromethyl)benzoic acid);
4,4'-((4-(cyclopropylcarbamoyl)pyridine-2,6-diyl)bis(1H-1,2,3-triazole-4,1-diyl))bis(2-(trifluoromethyl)benzoic acid);
4,4'-((4-(butylcarbamoyl)pyridine-2,6-diyl)bis(1H-1,2,3-triazole-4,1-diyl))bis(2-(trifluoromethyl)benzoic acid);
5,5'-((4-(diethylcarbamoyl)pyridine-2,6-diyl)bis(1H-1,2,3-triazole-4,1-diyl))bis(2-(trifluoromethyl)benzoic acid);
5,5'-((4-(morpholine-4-carbonyl)pyridine-2,6-diyl)bis(1H-1,2,3-triazole-4,1-diyl))bis(2-(trifluoromethyl)benzoic acid);
4,4'-(pyridazine-3,6-diylbis(1H-1,2,3-triazole-4,1-diyl))bis(2-hydroxybenzoic acid);
5,5'-((4-(ethylcarbamoyl)pyridine-2,6-diyl)bis(1H-1,2,3-triazole-4,1-diyl))bis(3-(trifluoromethyl)benzoic acid);
3,3'-(((4-(ethylcarbamoyl)pyridine-2,6-diyl)bis(1H-1,2,3-triazole-4,1-diyl))bis(4,1-phenylene))dipropionic acid;
4,4'-(((4-(ethylcarbamoyl)pyridine-2,6-diyl)bis(1H-1,2,3-triazole-4,1-diyl))bis(4,1-phenylene))dibutyric acid;
4,4'-((4-(ethylcarbamoyl)pyridine-2,6-diyl)bis(1H-1,2,3-triazole-4,1-diyl))diphthalic acid;
4,4'-((4-(ethylcarbamoyl)pyridine-2,6-diyl)bis(1H-1,2,3-triazole-4,1-diyl))bis(2-methoxybenzoic acid);
5,5'-((4-(ethylcarbamoyl)pyridine-2,6-diyl)bis(1H-1,2,3-triazole-4,1-diyl))diisophthalic acid;
4,4'-((4-(ethylcarbamoyl)pyridine-2,6-diyl)bis(1H-1,2,3-triazole-4,1-diyl))bis(3-hydroxybenzoic acid);
diethyl (3-(4-(6-(1-(3-(diethoxyphosphoryl)propyl)-1H-1,2,3-triazol-4-yl)-4-(ethylcarbamoyl) pyridin-2-yl)-1H-1,2,3-triazol-1-yl)propyl) phosphonate;
4,4'-((4-(ethylcarbamoyl)pyridine-2,6-diyl)bis(1H-1,2,3-triazole-4,1-diyl))bis(2-methylbenzoic acid);
2,2'-((4-(ethylcarbamoyl)pyridine-2,6-diyl)bis(1H-1,2,3-triazole-4,1-diyl))bis(3-(trifluoromethyl)benzoic acid);
4,4'-((4-((2-hydroxyethyl)carbamoyl)pyridine-2,6-diyl)bis(1H-1,2,3-triazole-4,1-diyl))bis(2-(trifluoromethyl)benzoic acid);
4,4'-((4-(ethylcarbamoyl)pyridine-2,6-diyl)bis(1H-1,2,3-triazole-4,1-diyl))bis(2-nitrobenzoic acid);
4,4'-((4-((3,3,3-trifluoropropyl)carbamoyl)pyridine-2,6-diyl)bis(1H-1,2,3-triazole-4,1-diyl))bis(2-(trifluoromethyl)benzoic acid);
(4-(4-(4-(ethylcarbamoyl)-6-(1-(4-phosphonophenyl)-1H-1,2,3-triazol-4-yl)pyridin-2-yl)-1H-1,2,3-triazol-1-yl)phenyl)phosphonic acid;
4,4',4'',4'''-((((butane-1,4-diylbis(azanediyl))bis(carbonyl))bis(pyridine-4,2,6-triyl))tetrakis(1H-1,2,3-triazole-4,1-diyl))tetrakis(2-(trifluoromethyl)benzoic acid);
2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))diacetic acid;
dimethyl 2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))diacetate;
(2S,2'S)-2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))disuccinic acid;
2,2'-((2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))bis(acetyl))bis(azanediyl))diaceti c acid;
2,6-bis(1-(4-cyano-3-(trifluoromethyl)phenyl)-1H-1,2,3-triazol-4-yl)-N-ethylisonicotinamide;
4,4'-(thiophene-2,5-diylbis(1H-1,2,3-triazole-4,1-diyl))bis(2-(trifluoromethyl)benzoic acid); and
4,4'-(furan-2,5-diylbis(1H-1,2,3-triazole-4,1-diyl))bis(2-(trifluoromethyl)benzoic acid).

39) A compound selected from any one of the following:
4,4'-(1,3-phenylenebis(1H-1,2,3-triazole-4,1-diyl))bis(2-hydroxybenzoic acid);
4,4'-((9H-carbazole-3,6-diyl)bis(1H-1,2,3-triazole-4,1-diyl))dianiline;
3,6-bis(1-(4-methoxyphenyl)-1H-1,2,3-triazol-4-yl)-9H-carbazole;
4,4'-(1,4-phenylenebis(1H-1,2,3-triazole-4,1-diyl))bis(2-hydroxybenzoic acid);
4,4'-(1,3-phenylenebis(1H-1,2,3-triazole-4,1-diyl))dianiline;
4,4'-(1,3-phenylenebis(1H-1,2,3-triazole-4,1-diyl))dibenzoic acid; 1,3-bis(1-(4-methoxyphenyl)-1H-1,2,3-triazol-4-yl)benzene;

4,4'-(pyridine-2,6-diylbis(1H-1,2,3-triazole-4,1-diyl))dianiline;

4-(4-(3-(1-(4-carboxyphenyl)-1H-1,2,3-triazol-4-yl)phenyl)-1H-1,2,3-triazol-1-yl)-2-hydroxybenzoic acid;

4-(4-(3-(1-(4-methoxyphenyl)-1H-1,2,3-triazol-4-yl)phenyl)-1H-1,2,3-triazol-1-yl)benzoic acid;

4,4'-((4-carboxypyridine-2,6-diyl)bis(1H-1,2,3-triazole-4,1-diyl))bis(2-hydroxybenzoic acid);

2-(1-(1H-benzo[d]imidazol-4-yl)-1H-1,2,3-triazol-4-yl)-6-(1-(1H-benzo[d]imidazol-7-yl)-1H-1,2,3-triazol-4-yl)-N-ethylisonicotinamide;

4,4'-((4-carboxypyridine-2,6-diyl)bis(1H-1,2,3-triazole-4,1-diyl))bis(2-(trifluoromethyl)benzoic acid);

4,4'-((5-carboxy-1,3-phenylene)bis(1H-1,2,3-triazole-4,1-diyl))bis(2-(trifluoromethyl)benzoic acid);

4,4'-((5-carboxy-1,3-phenylene)bis(1H-1,2,3-triazole-1,4-diyl))bis(2-(trifluoromethyl)benzoic acid);

4,4'-((5-(ethylcarbamoyl)-1,3-phenylene)bis(1H-1,2,3-triazole-1,4-diyl))bis(2-(trifluoromethyl)benzoic acid);

3'-(4-(4-(ethylcarbamoyl)-6-(1-(3'-(trifluoromethyl)-[1,1'-biphenyl]-3-yl)-1H-1,2,3-triazol-4-yl)pyridin-2-yl)-1H-1,2,3-triazol-1-yl)-3-(trifluoromethyl)-[1,1'-biphenyl]-4-carboxylic acid;

4,4'-((4-(ethylcarbamoyl)pyridine-2,6-diyl)bis(1H-1,2,3-triazole-4,1-diyl))bis(2-cyanobenzoic acid); and 4,4'-((4-(ethylcarbamoyl)pyridine-2,6-diyl)bis(1H-1,2,3-triazole-4,1-diyl))bis(2-chlorobenzoic acid).

40) A composition comprising a compound of any one of embodiments 1-39 and a molecular crowding agent.

41) The composition of embodiment 41, wherein the molecular crowding agent is a polyalkylene glycol.

42) A composition comprising a compound of any one of embodiments 1-39, and an aqueous buffer.

43) The composition of embodiment 43, wherein the aqueous buffer is Tris HCl.

44) A composition comprising a compound of any one of embodiments 1-39, and a polynucleotide.

45) The composition of embodiment 44, wherein the polynucleotide is a 20-60 mer oligonucleotide.

46) A composition comprising a compound of any one of embodiments 1-39, and a protein.

47) The composition of embodiment 46, wherein the protein is a DNA polymerase.

48) A composition comprising a compound of any one of embodiments 1-39 and a mixture of nucleotides or nucleotide analogs.

49) A composition for enhancing the processivity, fidelity, or rate of a DNA polymerase reaction comprising at least one compound of any one of embodiments 1-39 and a mixture of nucleotide analogs.

50) A composition comprising at least one compound of any one of embodiments 1-39 and a mixture of nucleotide analogs wherein the at least one compound of any of embodiments 1-39 increases the number and accuracy of nucleotide analogs incorporated into a daughter strand during a template-dependent polymerization reaction relative to an identical polymerization reaction absent the at least one compound of any of embodiments 1-39.

51) The composition of embodiment 50, wherein the mixture of nucleotide analogs comprises nucleoside triphosphoramidates, wherein each of the nucleoside triphosphoramidates comprises a nucleobase selected from the group consisting of adenine, guanine, thymine, and cytosine and a polymeric tether moiety, wherein a first end of the polymeric tether moiety is attached to the nucleobase and a second end of the polymeric ether moiety is attached to the alpha phosphate of the nucleoside triphosphoramidate to provide for expansion of the nucleotide analogs by cleavage of the phosphoramidate bond.

52) The composition of embodiment 51, further comprising a buffer component selected from at least one of Tris OAc, $NH_4OAc$, PEG, a water-miscible organic solvent, polyphosphate 60, NMS, and $MnCl_2$.

53) The composition of embodiment 51, further comprising a single-strand binding protein.

54) The composition of embodiment 51, further comprising urea.

55) The composition of embodiment 51, wherein the mixture of nucleotide analogs comprises nucleotide analogs comprising a detectable label.

56) The composition of embodiment 55, wherein the detectable label is an optically detectable label selected from the group consisting of luminescent, chemiluminescent, fluorescent, fluorogenic, chromophoric or chromogenic labels.

57) A kit for sequencing a nucleic acid template comprising at least one composition of any of embodiments 40-56.

58) A method of enhancing a nucleic acid polymerase reaction, the method comprising:

a. forming a nucleic acid polymerase reaction composition comprising:

i. a template nucleic acid, ii. a nucleic acid polymerase, iii. a mixture of nucleotides or nucleotide analogs, and iv. at least one compound of any of embodiments 1-39; and b. incubating the nucleic acid polymerase reaction composition under conditions allowing a nucleic acid polymerization reaction, wherein the at least one compound of any one of embodiments 1-39 increases the processivity, rate, or fidelity of the nucleic acid polymerase reaction.

59) The method of embodiment 58, wherein the compound of any one of embodiments 1-39 increases the length of a resulting nucleic acid product compared to a nucleic acid polymerase reaction lacking the compound of any one of embodiments 1-39.

60) The method of embodiment 58 wherein the at least one compound of any one of embodiments 1-39 comprises a plurality of compounds of any one of embodiments 1-39.

61) The method of embodiment 58, wherein the nucleic acid polymerase is a DNA polymerase.

62) The method of embodiment 61, wherein the DNA polymerase is DPO4 or a variant thereof.

63) The method of embodiment 58, wherein the mixture of nucleotides or nucleotide analogs is a mixture of nucleotide analogs comprising nucleoside triphosphoramidates, wherein each of the nucleoside triphosphoramidates comprises a nucleobase selected from the group consisting of adenine, guanine, thymine, and cytosine and a polymeric tether moiety, wherein a first end of the polymeric tether moiety is attached to the nucleobase and a second end of the polymeric tether moiety is attached to the alpha phosphate of the nucleoside triphosphoramidate to provide for expansion of the nucleotide analogs by cleavage of the phosphoramidate bond.

64) The method of embodiment 58, wherein the nucleic acid polymerization reaction produces an expandable polymer of nucleotide analogs, wherein the expandable polymer encodes the nucleobase sequence information of the template nucleic acid.

65) The method of embodiment 58, wherein the conditions for allowing a nucleic acid polymerization reaction comprise a suitable polymerization buffer and an oligonucleotide primer.

66) The method of embodiment 58, wherein the suitable buffer comprises a component selected from the group Tris OAc, $NH_4OAc$, PEG, a water-miscible organic solvent, polyphosphate 60, NMS and $MnCl_2$.

67) The method of embodiment 58, wherein the reaction mixture further comprises a single-strand binding protein.

68) The method of embodiment 58, wherein the reaction mixture further comprises urea.

69) The method of embodiment 58, wherein the mixture of nucleotides or nucleotide analogs comprises nucleotide analogs comprising a detectable label.

70) The method of embodiment 69, wherein the detectable label is an optically detectable label selected from the group consisting of luminescent, chemiluminescent, fluorescent, fluorogenic, chromophoric or chromogenic labels.

71) A method of sequencing a DNA or RNA template, the method comprising the steps of:

a. forming a DNA polymerase reaction composition comprising:

i. a DNA or RNA template, ii. a replication primer that complexes with the template, iii. a DNA polymerase, iv. a mixture of nucleotides or nucleotide analogs, v. at least one compound of any of embodiments 1-39, b. incubating the DNA polymerase reaction composition under conditions allowing a DNA polymerization reaction, wherein the at least one compound of any of embodiments 1-39 increases the rate, fidelity or processivity of the DNA polymerase reaction; and c. determining the sequence of the nucleotides or nucleotide analogs in the resulting polymer of nucleotides or nucleotide analogs.

72) The method of embodiment 71, wherein the mixture of nucleotide analogs comprises nucleoside triphosphoramidates, wherein each of the nucleoside triphosphoramidates comprises a nucleobase selected from the group consisting of adenine, guanine, thymine, and cytosine and a polymeric tether moiety, wherein a first end of the polymeric tether moiety is attached to the nucleobase and a second end of the polymeric ether moiety is attached to the alpha phosphate of the nucleoside triphosphoramidate to provide for expansion of the nucleotide analogs by cleavage of the phosphoramidate bond.

73) The method of embodiments 71 or 72, wherein the DNA polymerase is DPO4 or a variant thereof.

74) The method of embodiments 71 or 72, wherein the resulting polymer of nucleotide analogs is an expandable polymer.

75) The method of embodiment 74, further including the step of contacting the expandable polymer with a phosphoramidate cleavage agent to produce an expanded polymer of nucleotide analogs.

76) The method of embodiments 71 or 72, wherein the polymeric tether moiety of each of the nucleotide analogs comprises a reporter moiety unique to the nucleobase of the analog.

77) The method of embodiment 72, wherein the reporter moieties produce a characteristic electronic signal.

78) The method of embodiment 72, wherein the step of determining the sequence of the nucleotide analogs comprises the step of translocating the expanded polymer of nucleotide analogs through a nanopore.

The above-mentioned and additional features of the present invention and the manner of obtaining them will become apparent, and the invention will be best understood by reference to the following more detailed description. All references disclosed herein are hereby incorporated by reference in their entirety as if each was incorporated individually.

This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, the drawings, and the claims.

BRIEF DESCRIPTION OF THE DRAWINGS

Exemplary features of the present disclosure, its nature and various advantages will be apparent from the accompanying drawings and the following detailed description of various embodiments. Non-limiting and non-exhaustive embodiments are described with reference to the accompanying drawings, wherein like labels or reference numbers refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings.

DETAILED DESCRIPTION OF THE INVENTION

Figure 1A:
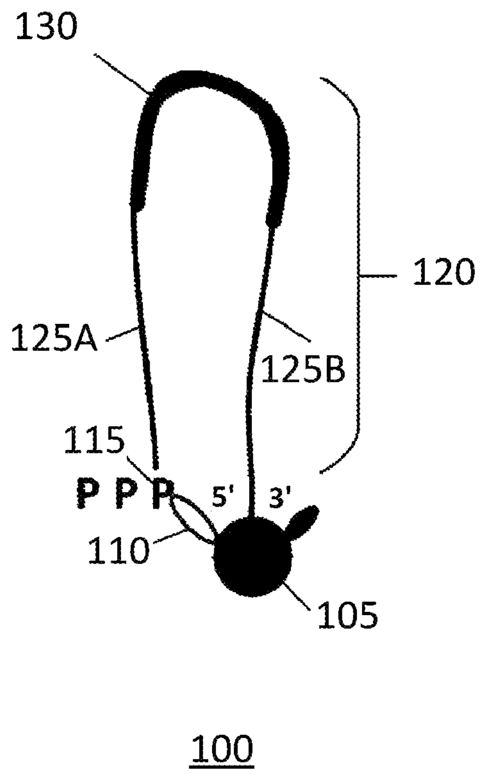
FIGS. 1A, 1B, 1C and 1D are condensed schematics illustrating the main features of a generalized XNTP and their use in Sequencing by Expansion (SBX).

The present invention may be understood more readily by reference to the following detailed description of preferred embodiments of the invention and the Examples included herein. Unless otherwise explained, all technical and scientific terms used herein have the same meaning as commonly understood by one of ordinary skill in the art to which this disclosure belongs.

In one aspect, the PEMs of the present disclosure are compounds of formula (I)

(I)

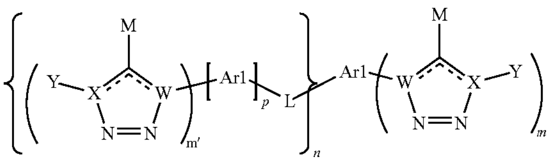

or a solvate, hydrate, tautomer, chelate or salt thereof, wherein:

m is 1, 2 or 3;

m' is 1, 2 or 3;

n is 0, 1 or 2;

p is 0, 1 or 2;

W is N when X is C or W is C when X is N;

--- is a single or double bond, wherein the double bond begins at whichever of W or X is carbon;

L is a linking group;

M is, at each occurrence, independently selected from hydrogen, halogen and $C_1$-$C_4$alkyl; Ar1 is, at each occurrence, independently selected from optionally substituted pyridine, pyrazine, pyridazine, furan, thiophene, naphthalene, fluorene, phenanthrene, cinnoline, phthalazine, quinazoline, quinoxaline, naphthyridine, phenanthroline, purine, and carbazole, wherein:

substituents for Ar1 are, at each occurrence, independently selected from halogen, —OH, —CN, —$NO_2$, $C_1$-$C_6$alkyl, $C_1$-$C_6$haloalkyl, $C_1$-$C_6$heteroalkyl, $C_1$-$C_6$cycloloalkyl, —$OR^0$, —$CONH_2$, —C(O)$NR^1R^{1'}$, —$NR^1R^{1'}$, —$NR^1C(O)R^3$, —C(O)$SR^3$, —$COR^3$, —OC(O)$R^3$, —C(O)$OR^3$, mercaptan, —$R^4$—H, —$SOR^1$, —$S(O)_2R^1$, —$S(O)_2NR^1R^{1'}$, and —$NS(O)_2R^3$; and wherein $R^0$ is, at each occurrence, independently selected from $C_1$-$C_6$alkyl, $C_1$-$C_6$haloalkyl, $C_2$-$C_6$alkenyl, $C_2$-$C_6$alkynyl, substituted or unsubstituted cycloalkyl, substituted or unsubstituted heterocyclyl, substituted or unsubstituted aryl, and substituted or unsubstituted heteroaryl;

$R^1$ and $R^{1'}$ are, at each occurrence, independently selected from H, hydroxyl, $C_1$-$C_6$alkyl, $C_1$-$C_6$haloalkyl, $C_1$-$C_6$heteroalkyl, $C_2$-$C_6$alkenyl, $C_2$-$C_6$alkynyl, arylalkyl, substituted or unsubstituted cycloalkyl, substituted or unsubstituted heterocyclyl, substituted or unsubstituted aryl, substituted or unsubstituted arylalkyl, and substituted or unsubstituted heteroaryl, —C(=NH)$NH_2$, —$CH_2CO_2R^0$, —$CH_2C(O)NHCH_2CO_2H$, —$CH_2CH_2OH$, —$CH_2CH_2NHC(O)R^3$, —$CH_2C(O)NHCH_2CO_2H$,

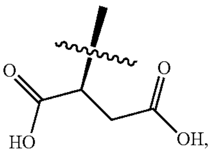

and

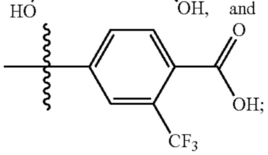

wherein $R^1$ and $R^{1'}$ can come together to form a heterocyclic ring, including, but not limited to, azetidine, pyrrolidine, piperidine, piperazine, morpholine,

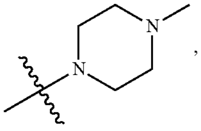

, or

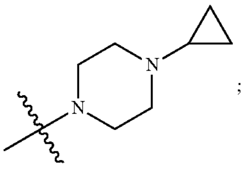

;

$R^2$ is, at each occurrence, independently selected from $C_2$-$C_6$alkyl, $C_1$-$C_6$haloalkyl, $C_1$-$C_6$heteroalkyl, or substituted or unsubstituted cycloalkyl, substituted or unsubstituted heterocyclyl, substituted or unsubstituted aryl, substituted or unsubstituted heteroaryl, and substituted or unsubstituted haloalkoxy;

$R^3$ is, at each occurrence, independently selected from H, $C_1$-$C_6$alkyl, $C_1$-$C_6$haloalkyl, $C_1$-$C_6$heteroalkyl, or substituted or unsubstituted cycloalkyl, substituted or unsubstituted heterocyclyl, substituted or unsubstituted aryl, and substituted or unsubstituted heteroaryl, substituted or unsubstituted haloalkoxy, and guanidine;

$R^4$ is, at each occurrence, independently selected from one or more heteroatom interrupted alkylene wherein the heteroatom is O, S, NH or a combination thereof, Y is, at each occurrence, independently selected from Ar2, —$(CH_2)_3PO(OEt)_2$, or —$CH2CO_2Me$;

Ar2 is, at each occurrence, independently selected from substituted 5- and 6-membered monocyclic aromatic rings and 9- and 10-membered fused bicyclic rings comprising two monocyclic rings together, where at least one of the two monocyclic rings is an aromatic ring, wherein:

Ar2 is substituted with $G^1$, $G^2$, $G^3$, $G^4$ and $G^5$, wherein:

when Ar2 is monosubstituted, $G^1$ is, at each occurrence, independently selected from oxo, —$NH_2$, —$COR^3$, -E-$CO_2$H, —C(O)$NR^1R^{1'}$, -E-$PO(OR^1)_2$, and aryl substituted with $G^2$, $G^3$, $G^4$ and $G^5$; and $G^2$, $G^3$, $G^4$ and $G^5$ are, at each occurrence, independently selected from absent or selected from the groups comprising, halogen, —CN, $C_1$-$C_6$alkyl, $C_1$-$C_6$haloalkyl, -E-$CO_2$H, -E-CHO, -E-C(O)$R^3$, -E-C(O)NH(OH), -E-C(O)$NHR^1$, -E-$CONR^1R^{1'}$, -E-$NR^1R^{1'}$, and -E-$OR^2$;

wherein E is, at each occurrence, independently selected from a direct bond and $C_1$-$C_6$alkylene.

As used in the specification and appended claims, unless specified to the contrary, the following terms have the meaning indicated.

Certain chemical groups named herein are preceded by a shorthand notation indicating the total number of carbon atoms that are to be found in the indicated chemical group. For example; $C_1$-$C_4$alkyl, which may alternatively be written as $C_{1-4}$alkyl, describes an alkyl group having at least one and up to as many as 4 carbon atoms, while $C_4$-$C_{12}$cycloalkylalkyl (which likewise may be written as $C_{4-12}$cycloalkylalkyl) describes a cycloalkylalkyl group having a total of 4 to 12 carbon atoms. The total number of carbons in the shorthand notation does not include carbons that may exist in substituents of the group described. As examples, $C_1$-$C_6$alkyl refers to an alkyl radical containing one to six carbon atoms; $C_1$-$C_6$haloalkyl refers to a haloalkyl radical containing one to six carbon atoms; $C_1$-$C_6$alkylene refers to an alkylene diradical containing one to six carbon atoms.

In addition to the foregoing, as used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, and optionally having an indicated number of carbon atoms, e.g., having from one to twelve carbon atoms, one to eight carbon atoms, or one to six carbon atoms, or one to four carbon atoms, and which is attached to the rest of the molecule by a single bond. Examples are methyl, ethyl, n-propyl, 1-methylethyl (iso-propyl), n-butyl, n-pentyl, 1,1-dimethylethyl (t-butyl), 3-methylhexyl, 2-methylhexyl, and the like. When unsaturation is introduced into an alkyl group, the resulting group may be referred to as an unsaturated alkyl group, where unsaturated alkyl groups are commonly known as alkenyl groups (having at least one carbon-carbon double bond) and alkynyl groups (having at least one carbon-carbon triple bond). In one embodiment, and when specified, the alkyl groups in compounds of the present disclosure may be, or include, unsaturated alkyl groups.

"Alkenyl" refers to a straight or branched hydrocarbon chain radical group consisting solely of carbon and hydrogen atoms, containing at least one double bond, optionally having an indicted number of carbons, e.g., from two to twelve carbon atoms, or two to eight carbon atoms, or two to six carbon atoms, or two to four carbon atoms, and which is attached to the rest of the molecule by a single bond, e.g., ethenyl, prop-1-enyl, but-1-enyl, pent-1-enyl, penta-1,4-dienyl, and the like.

"Alkynyl" refers to a straight or branched hydrocarbon chain radical group consisting solely of carbon and hydrogen atoms, containing at least one triple bond, optionally having an indicated number of carbons, e.g., having from two to twelve carbon atoms, or two to eight carbon atoms, or two to six carbon atoms, or two to four carbon atoms, and which is attached to the rest of the molecule by a single bond, e.g., ethenyl, prop-1-enyl, but-1-enyl, pent-1-enyl, penta-1,4-dienyl, and the like.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. Likewise, "haloalkenyl" refers to an alkenyl radical, as defined herein, that is substituted by one or more halo radicals, as defined herein, and "haloalkynyl" refers to an alkynyl radical, as defined herein, which is substituted by one or more halo radicals, as defined herein.

"Alkylene" or "alkylene chain" refers to a straight or branched divalent hydrocarbon chain linking the rest of the molecule to a radical group, consisting solely of carbon and hydrogen, containing no unsaturation and optionally having an indicated number of carbon atoms. Examples are methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. In analogy to alkyl groups, unsaturation may be introduced into an alkylene chain, to provide an unsaturated alkylene chain. If unsaturation is introduced into an alkylene chain, the resulting group may be referred to as an unsaturated alkylene group or chain, where unsaturated alkylene chains are commonly known as alkenylene groups (having at least one carbon-carbon double bond) and alkynylene groups (having at least one carbon-carbon triple bond). In one embodiment, and when specified, the alkylene chains in compounds of the present disclosure may be, or include, unsaturated alkylene chains.

"Alkenylene" or "alkenylene chain" refers to a straight or branched divalent hydrocarbon chain linking the rest of the molecule to a radical group, consisting solely of carbon and hydrogen, containing at least one double bond and optionally having an indicated number of carbon atoms, e.g., from two to twelve carbon atoms. Examples of alkenylene groups are ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain.

"Aryl" refers to a ring system radical comprising at least 5 ring atoms, optionally comprising 1-6 hetero ring atoms selected from O, S and N, and at least one aromatic ring. A 5-membered monocyclic aromatic ring contains 5 ring atoms selected from carbon and heteroatoms, while a 6-membered monocyclic aromatic ring contains 6 ring atoms selected from carbon and heteroatoms. Exemplary monocyclic aromatic rings having 5 members is pyrrole and having six-members is pyridine. The aryl radical may be, e.g., a monocyclic, bicyclic, tricyclic or tetracyclic ring system, which may include fused or bridged ring systems. Carbocyclic aryl radicals contain only carbon at the ring atoms, where examples include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In one embodiment, aryl is phenyl or naphthyl, and in another embodiment is phenyl. When the aryl radical includes non-carbon ring atoms, e.g., oxygen, sulfur, and nitrogen, the aryl group may be referred to as a heteroaryl group. The heteroaryl radical may be, e.g., a monocyclic, bicyclic, tricyclic or tetracyclic ring system, which may include fused or bridged ring systems. The nitrogen, carbon or sulfur atoms in the heteroaryl radical may be optionally oxidized; the nitrogen atom may be optionally quaternized.

"Arylalkyl" groups are alkyl, alkenyl or alkynyl groups as defined above in which a hydrogen atom thereof is replaced with an aryl group as defined above. Representative aralkyl groups include benzyl ($-CH_2$phenyl), phenylethyl ($-CH_2CH_2$phenyl) and phenylethylene (—CH═CHphenyl) groups and fused (cycloalkylaryl)alkyl groups such as 4-ethyl-indanyl. Aralkyl groups can be substituted on the aryl moiety, the alkyl, alkenyl or alkynyl moiety, or both.

"Fused" refers to a ring system which contains fusion between rings, where fusion refers to the rings sharing two adjacent ring atoms. Fused rings that contain two 5- and/or 6-membered monocyclic rings fused together refers to bicyclic ring systems where each ring is monocyclic and independently has either 5 or 6 ring atoms, and the two rings are fused in that they share two ring atoms. For example, naphthalene is a 10-membered fused ring system formed from two 6-membered monocyclic rings (benzene) fused together. Naphthalene is bicyclic in that it contains two (bi=2) rings. As another example, 1,3-benzothiazole which is a 9-membered fused ring system formed from one 6-membered ring (benzene) and one 5-membered ring (1,3-thiazole) fused together. 1,3-benzothiazole is bicyclic in that it contains two rings.

"Carbocyclyl" refers to a stable 3- to 18-membered aromatic or non-aromatic ring radical which consists of 3 to 18 carbon atoms. Unless stated otherwise specifically in the specification, the carbocyclyl radical may be a monocyclic, bicyclic, tricyclic or tetracyclic ring system, which may include fused or bridged ring systems, and may be partially or fully saturated. Non-aromatic carbocyclyl radicals include cycloalkyl, while aromatic carbocyclyl radicals include aryl.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl and cyclooctyl. Polycyclic radicals include, for example, adamantyl, norbornyl, decalinyl, 7,7-dimethyl-bicyclo-[2.2.1]heptanyl, and the like.

"Heterocyclyl" refers to a stable 3- to 18-membered aromatic or non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of non-aromatic heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, pyrazolopyrimidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl.

Optionally, although only when specified, each of alkyl, alkenyl, alkylene, alkenylene, carbocyclyl, cycloalkyl, aryl, heterocyclyl and heteroaryl in PEM compounds of the present disclosure may be substituted by one or more unsubstituted (e.g., an alkyl substituent on an alkyl group is not further substituted, i.e., the alkyl substituent is unsubstituted alkyl) substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, $—R_b—OR_a$, $—R_b—OC(O)—R_a$, $—R_b—N(R_a)_2$, $—R_b—C(O)R_a$, $—R_b—C(O)OR_a$, $—R_b—C(O)N(R_a)_2$, $—R_b—N(R_a)C(O)OR_c$, $—R_b—N(R_a)C(O)R_c$, $—R_b—N(R_a)S(O)_tR_c$ (where t is 1 to 2), $—R_b$ $N═C(OR_a)R_a$, $—R_b—S(O)_tOR_c$ (where t is 1 to 2), $—R_b—S(O)_sR_c$ (where s is 0 to 2), and $—R_b—S(O)_tN(R_a)_2$ (where t is 1 to 2) where each $R_a$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R_b$ is independently a direct bond or a straight or branched alkylene or alkenylene chain; and each $R_c$ is alkyl, alkenyl, haloalkyl, cycloalkyl, cycloalkylalkyl, aryl, aralkyl, heterocyclyl, heterocyclylalkyl, heteroaryl or heteroarylalkyl.

"Amino" refers to the $—NH_2$ radical. "Cyano" refers to the —CN radical. "Hydroxy" refers to the —OH radical. "Nitro" refers to the $—NO_2$ radical. "Oxo" refers to the ═O substituent. "Thioxo" refers to the ═S substituent. "Trifluoromethyl" refers to the $—CF_3$ radical. "Trifluoromethoxy" refers to the $—OCF_3$ radical. Mercaptan, also known as thiol, refers to the —SH radical.

"Acyl" refers to a radical —C(O)R, which may also be written as —C(═O)R, wherein R is alkyl, aralkyl, carbocyclyl, aryl, heteroaryl, or heterocyclyl. For example, when R is methyl, the acyl group may be referred to as acetyl.

"Alkoxy" refers to a radical of the formula —OR where R is an alkyl or haloalkyl radical. In one embodiment, the alkoxy radical contains up to six carbon atoms. Representative alkoxy groups include methoxy and ethoxy. An alkoxy that is substituted with halo may be called herein a haloalkoxy, which includes for example trifluoromethoxy, trichloromethoxy and the like.

"Heteroalkenylene" or "heteroalkenylene chain" refers to a straight or branched divalent hydrocarbon chain linking the rest of the molecule to a radical group, consisting of carbon and hydrogen and at least one heteroatom selected from N, O, and S.

"Haloalkoxy" refers to an alkoxy radical that is substituted by one or more halo radicals, as defined above, e.g., trifluoromethoxy, difluoromethoxy, trichloromethoxy, 2,2,2-trifluoroethoxy, 3-bromo-2-fluoropropyloxy, and the like. The alkoxy part of the haloalkoxy radical may be optionally substituted as defined above for an alkoxy group.

"N-heterocyclyl" refers to a heterocyclyl radical containing at least one nitrogen. An N-heterocyclyl radical may be optionally substituted as described above for heterocyclyl radicals.

"Heterocyclylalkyl" refers to a radical of the formula $—R_bR_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. The alkylene chain of the heterocyclylalkyl radical may be optionally substituted as defined above for an alkylene chain. The heterocyclyl part of the heterocyclylalkyl radical may be optionally substituted as defined above for a heterocyclyl group.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical may be optionally substituted as described above for heteroaryl radicals.

"Heteroarylalkyl" refers to a radical of the formula —$R_bR_i$ where $R_b$ is an alkylene chain as defined above and $R_i$ is a heteroaryl radical as defined herein. The heteroaryl part of the heteroarylalkyl radical may be optionally substituted as defined herein for a heteroaryl group. The alkylene chain part of the heteroarylalkyl radical may be optionally substituted as defined herein for an alkylene chain. Likewise, an arylalkyl group refers to a heteroarylalkyl group wherein the heteroaryl portion is replaced with the corresponding carbocyclic aryl group, i.e., heteroatoms are replaced with carbon, with adjustment as necessary for hydrogen substitution.

"Hydroxyalkyl" refers to a radical of the formula —$R_bOH$ where $R_b$ is an alkylene chain as defined herein. The —OH (hydroxyl a.k.a. hydroxy) group can be attached to any carbon in the alkylene chain. The alkylene chain part of the heteroarylalkyl radical may additionally be optionally substituted as defined above for an alkylene chain.

The PEM compounds described herein having acidic or basic groups may generally be used as the free acid or free base. Alternatively, the PEM compounds having acidic or basic groups may be used in the form of salts, e.g., acid or base addition salts. Acid addition salts of the free amino compounds may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "salt" of the PEM compounds described herein is intended to encompass any and all salt forms.

The PEM compounds of the present disclosure may be in the form of a chelate. A chelate refers to a compound containing an organic ligand (such as a triazole-Ar group) bonded to a central metal atom at two or more points.

With regard to stereoisomers, the PEM compounds described herein may have one or more chiral (or asymmetric) centers and may thus give rise to enantiomers, diastereomers, and other stereoisomeric forms that may be defined, in terms of absolute stereochemistry, as (R)- or (S)-. When the compounds described herein contain olefinic double bonds or other centers of geometric asymmetry, and unless specified otherwise, it is intended that the compounds include both E and Z geometric isomers (e.g., cis or trans). Likewise, unless otherwise indicated, all possible isomers, as well as their racemic and optically pure forms, and all tautomeric forms are also intended to be included. It is therefore contemplated that various stereoisomers and mixtures thereof include "enantiomers," which refers to two stereoisomers whose molecules are nonsuperimposeable mirror images of one another. Thus, the compounds may occur in any isomeric form, including racemates, racemic mixtures, and as individual enantiomers or diastereomers.

Furthermore, some of the crystalline forms of the PEM compounds may exist as polymorphs, which are contemplated herein. In addition, some of the PEM compounds may also form solvates with water or other organic solvents. Such solvates are similarly included within the scope of the compounds described herein.

As one of skill in the art would appreciate, any of the aforementioned compounds may incorporate radioactive isotopes. Accordingly, also contemplated is use of isotopically-labeled compounds identical to those described herein, wherein one or more atoms are replaced by an atom having an atomic mass or mass number different from the atomic mass or mass number usually found in nature. Examples of isotopes that can be incorporated into these compounds include isotopes of hydrogen, carbon, nitrogen, oxygen, phosphorous, fluorine and chlorine. Thus, reference to an element, such as hydrogen (H) or carbon (C), is intended to encompass all isotopes of the same. For example, the designation C (carbon) includes $^{12}C$, $^{13}C$, or $^{14}C$ and mixtures thereof, while H (hydrogen) includes $^{1}H$, $^{2}H$ and $^{3}H$ and mixtures thereof, and O (oxygen) includes $^{16}O$ and $^{18}O$ and mixtures thereof, and N (nitrogen) includes $^{14}N$ and $^{15}N$ and mixtures thereof, etc. for other atoms. Isotopically labeled PEM compounds may be useful in tracking PEM compounds or portions thereof during their use in assays etc.

In PEM compounds of Formula (I), Ar1 is an aryl group, also referred to as an aromatic moiety. The aromatic moiety may be a carbocyclic or heterocyclic aromatic moiety, where each of the aromatic ring atoms is carbon in a carbocyclic aromatic moiety, while at least one of the aromatic ring atoms is nitrogen, oxygen or sulfur in a heterocyclic aromatic moiety.

In one embodiment, Ar1 may comprise 1-6 rings, where up to six of the ring atoms may be selected from oxygen, sulfur and nitrogen, with the remainder being carbon atoms. Optionally, the Ar1 moiety may comprise 1-5 rings, where up to five of the ring atoms may be selected from oxygen, sulfur and nitrogen. As another option, the Ar1 group may comprise 1-4 rings, where up to four of the ring atoms may be selected from oxygen, sulfur and nitrogen. As yet another option, the Ar1 moiety may comprise 1-3 rings, where up to three of the ring atoms may be selected from oxygen, sulfur and nitrogen. As a further example, Ar1 may comprise 1-2 rings, where up to three of the ring atoms may be selected from oxygen, sulfur and nitrogen. In any event, each ring may independently be a five-membered ring, i.e., five ring atoms form the ring, or a six-membered ring, or a seven-membered ring, while in one option each of the rings is either a five- or six-membered ring.

An exemplary aromatic moiety is a carbocyclic aromatic moiety. The carbocyclic moiety may contain one (e.g., benzene) or two (e.g., naphthalene, azulene) or three (e.g., acenaphthylene, fluorene) or four (e.g., fluoranthene, aceanthrylene) or five (e.g., pentacene, picene) or six (e.g., hexacene) aromatic rings, where for convenience the Ar1 group may be exemplified herein by naming the unsubstituted version thereof (e.g., benzene) although in compounds of the present disclosure the Ar1 group is the corresponding radical, e.g., when m is 2 and Ar1 is otherwise unsubstituted, two ring hydrogens replaced with triazole groups. For example, the aromatic moiety may be a monocyclic carbocyclic moiety, i.e., phenyl, also referred to as a $C_6$ aromatic moiety. As another example, the aromatic moiety may be a bicyclic carbocyclic moiety, e.g., naphthyl, which is a $C_{10}$ aromatic moiety.

An exemplary Ar1 aromatic moiety is a heterocyclic aromatic moiety, which may also be referred to as a heteroaryl group. The heterocyclic moiety may contain one or two or three or four or five or six aromatic rings, in addition to containing 1 or 2 or 3 or 4 or 5 or 6 heteroatoms, i.e., atoms other than carbon, selected from nitrogen, sulfur and oxygen atoms. Optionally, the heteroatom, if present, is nitrogen. For example, the aromatic moiety may be a monocyclic heterocyclic moiety, e.g., pyridinyl, which is a six-membered $C_5$ aromatic moiety, or pyrazinyl, which is a six-membered $C_4$ aromatic moiety. As another example, the aromatic moiety may be a bicyclic heterocyclic moiety, e.g., quinolinyl or isoquinolinyl, which are ten-membered $C_9$ aromatic moieties, or 1,5-naphthylidinyl, 2,6-naphthylidinyl or 2,7-naphthylidinyl, which are exemplary ten-membered $C_8$ aromatic moieties.

Thus, the heteroaryl groups are aromatic ring compounds containing 5 or more ring members, of which, one or more is a heteroatom such as, but not limited to, N, O, and S. A heteroaryl group designated as a $C_2$-heteroaryl can be a 5-membered ring with two carbon atoms and three heteroatoms, a 6-membered ring with two carbon atoms and four heteroatoms and so forth. Likewise a $C_4$-heteroaryl can be a 5-membered ring with one heteroatom, a 6-membered ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, iso quinolinyl, tetrahydroquinolinyl, tetrahydroisoquinolinyl, quinoxalinyl, and quinazolinyl groups. Thus, the terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl.

When m is 2, such that Ar1 is necessarily substituted with two triazole-Ar2 moiety, any two carbons of the Ar1 aromatic moiety may be substituted with one of these two triazole-Ar2 moieties. For example, when Ar1 is substituted benzene, Ar1 may be substituted in the ortho, meta or para positions, as shown below, where k designates where the substitution may occur on the aromatic moiety:

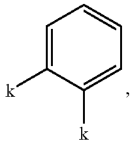

(ortho)

, 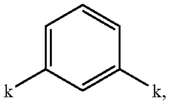, and (meta)

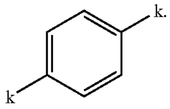.

(para)

As another example, when Ar1 is substituted naphthalene and m is 2, Ar1 may be substituted at any two naphthyl carbon atoms, where the following structures show the substitution options, with k showing where triazole substitution provided by (triazole-Ar2) may occur on the aromatic moiety:

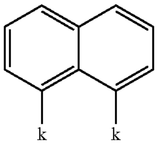, 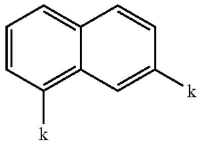,

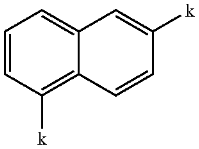, 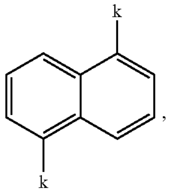,

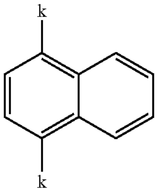, 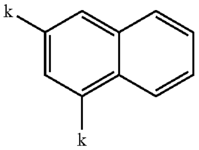,

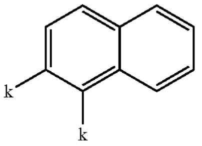, 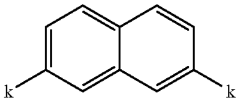,

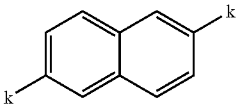, and

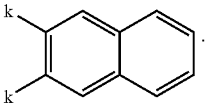.

The preceding examples illustrated triazole substitution on Ar1 using carbocyclic aromatic Ar1 groups as an illustrative Ar1 moiety. However, the same principle applies to triazole substitution on heterocyclic aromatic Ar1 groups. For example, when Ar1 is substituted pyridine and m is 2, the two triazole groups of (triazole-Ar2) may be located at any of the following locations on the pyridine ring, where k is used to designate the positions where triazole groups may be located:

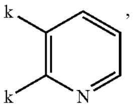, 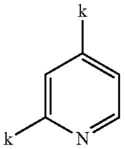, 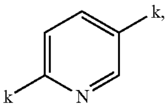,

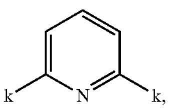, 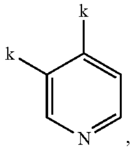, and

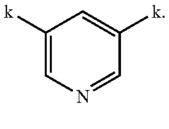.

Thus, in one exemplary embodiment, Ar1 is a monocyclic heteroaromatic structure selected from

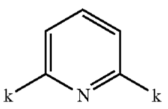 and 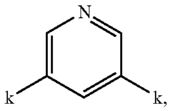

wherein the triazole rings are substituted at positions k on Ar1. In another exemplary embodiment, Ar1 is a monocyclic carbocyclic structure selected from

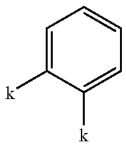, 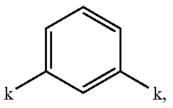 and 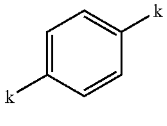

wherein the triazole rings are substituted at positions k on Ar1. In another exemplary embodiment, Ar1 is a bicyclic carbocyclic structure selected from

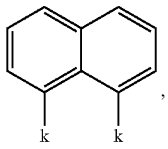, 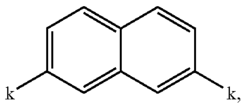

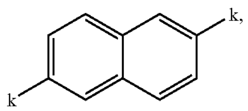 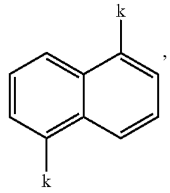,

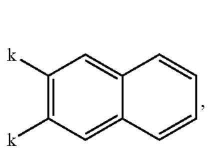, and 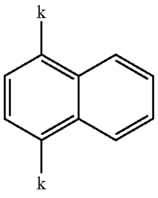

wherein the triazole rings are substituted at positions k on Ar1. In another embodiment, Ar1 is a polycyclic heterocyclic structure having two six-membered rings and one five-membered ring, and one nitrogen ring atom and selected from

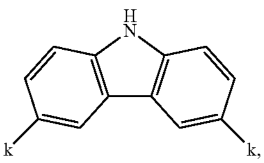

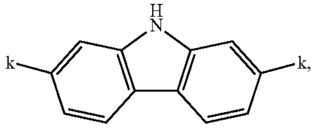 and

-continued

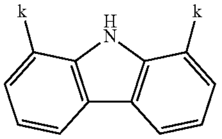

wherein the triazole rings are substituted at positions k on Ar1. In yet another exemplary embodiment, Ar1 is a polycyclic heterocyclic structure having three six-membered rings and two nitrogen ring atoms and being selected from

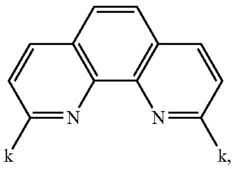

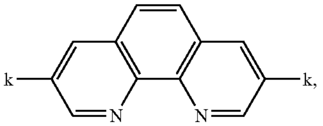

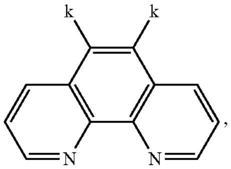, and 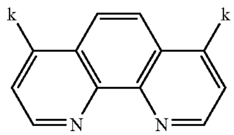

wherein the triazole rings are substituted at positions k on Ar1.

Ar1 includes both substituted and nonsubstituted aromatic moieties as described herein. In one embodiment, Ar1 is a substituted aromatic moiety. In one embodiment, Ar1 is a non-substituted aromatic moiety, which may also be referred to as an unsubstituted aromatic moiety. In a substituted aromatic moiety, one or more hydrogen atoms that would have been bonded to a ring atom has been replaced with a substituent, for example, optionally 1, or 2, or 3, or 4, or 5, or 6 of the hydrogen atoms may be replaced with a substituent. A substituent on Ar1 does not refer to the triazole-Ar2 moiety that is necessarily present when m equals 1, or the two triazole-Ar2 moieties that are necessarily present when m equals 2, or the three triazole Ar2 moieties that are necessarily present when m equals 3.

In one embodiment, a substituent on Ar1 will consist of atoms selected from deuterium, halogen (F, Cl, Br, I), carbon, nitrogen, oxygen and sulfur, and optionally will also contain hydrogen, and also will contain additional atoms that form a counterion, if present. Deuterium and halide are considered monovalent atoms, while carbon, nitrogen, oxygen and sulfur, because they are capable of simultaneously forming more than one covalent bond, are considered multivalent atoms. In addition to monovalent atoms, a substituent on Ar1 may have multiple multivalent atoms, e.g., 1-25 multivalent atoms, or 1-22 multivalent atoms, or 1-15 multivalent atoms, or 1-10 multivalent atoms, or 1-5 multivalent atoms, the atoms being optionally selected from carbon, nitrogen, oxygen and sulfur. Illustrations of substituents with up to 10 multivalent atoms are provided below. Other substituents, including substituents with up to 25 multivalent atoms, are known by analogy to one of ordinary skill in the art.

In one embodiment, a substituent on Ar1 contains 0 multivalent atoms. In this embodiment, a hydrogen bonded to a ring atom is replaced with another monovalent atom, such as deuterium, fluorine, chlorine, bromine or iodine.

In one embodiment, a substituent on Ar1 contains 1 multivalent atom. In this embodiment, one or more hydrogen atoms bonded to a ring atom of Ar1 are replaced with a single multivalent atom, where open valencies on the multivalent atom are filled with one or more monovalent atoms, examples being hydroxyl (OH), thiol (SH), amino ($NH_2$), methyl ($CH_3$) and methylene ($=CH_2$) including fully or partially halogenated and deuterated version thereof, e.g., $CF_3$.

In one embodiment, a substituent on Ar1 contains 2 multivalent atoms. In this embodiment, one or more hydrogen atoms bonded to a ring atom of Ar1 are replaced with a first multivalent atom which, in turn, is bonded to a second multivalent atom, thus providing a substituent formed from two multivalent atoms, where open valencies on the multivalent atoms are filled with one or more monovalent atoms. Examples of these substituents are well known to one of ordinary skill in the art. Specific examples include ethyl ($CH_2CH_3$), ethylene ($CH=CH_2$), ethynyl ($C\equiv CH$), ethylidene ($=CHCH_3$), aminomethyl ($CH_2NH_2$), aminomethylene ($=CHNH_2$), thiomethylene ($=CHSH$), hydroxymethylene ($=CHOH$), hydroxymethyl ($CH_2OH$), thiomethyl ($CH_2SH$), N-methylamine ($NHCH_3$), methylsulfide ($SCH_3$), methoxy ($OCH_3$), nitrile (CN), formyl (C(O)H), thioformyl (C(S)H), N-hydroxy (N—OH), hydroxylamine ($ONH_2$), hydrazine ($NH_2NH_2$), diazine (N=NH), diazonium ($N\equiv N$), including fully or partially halogenated and deuterated versions thereof, e.g., $OCF_3$ and $CH_2CD_3$.

In one embodiment, a substituent on Ar1 contains 3 multivalent atoms. In this embodiment, one or more hydrogen atoms bonded to a ring atom of Ar1 are replaced with a first multivalent atom which, in turn, is bonded directly or indirectly to each of a second and third multivalent atom; thus, the first multivalent atom is bonded to a second multivalent atom, and a third multivalent atom is bonded to either or both of the first and second multivalent atoms, thus providing a substituent formed from three multivalent atoms, where open valencies on the multivalent atoms are filled with one or more monovalent atoms. Examples of these substituents are well known to one of ordinary skill in the art and are provided herein, e.g., nitro, methylketone, carboxyl.

In one embodiment, a substituent on Ar1 contains 4 multivalent atoms. In this embodiment, one or more hydrogen atoms bonded to a ring atom of Ar1 are replaced with a first multivalent atom which, in turn, is bonded directly or indirectly to each of a second, third and fourth multivalent atom, thus providing a substituent formed from four multivalent atoms, where open valencies on the multivalent atoms are filled with one or more monovalent atoms. Examples of these substituents are well known to one of ordinary skill in the art and are provided herein, e.g., methylester ($CO_2CH_3$), N-methylcarboxamide ($C(O)NHCH_3$) and acetamide ($NHC(O)CH_3$).

In one embodiment, a substituent on Ar1 contains 5 multivalent atoms. In this embodiment, one or more hydrogen atoms bonded to a ring atom of Ar1 are replaced with a first multivalent atom which, in turn, is bonded directly or indirectly to each of a second, third, fourth and fifth multivalent atom, thus providing a substituent formed from five multivalent atoms, where open valencies on the multivalent atoms are filled with one or more monovalent atoms. Examples of these substituents are well known to one of ordinary skill in the art and are provided herein, e.g., ethylester ($CO_2CH_2CH_3$), S-ethylcarbothioate ($C(O)SCH_2CH_3$), N-ethylcarboxamide ($C(O)NHCH_2CH_3$) and N,N-dimethylcarboxamide ($C(O)N(CH_3)_2$).

In one embodiment, a substituent on Ar1 contains 6 multivalent atoms. In this embodiment, one or more hydrogen atoms bonded to a ring atom of Ar1 are replaced with a first multivalent atom which, in turn, is bonded directly or indirectly to each of a second, third, fourth, fifth and sixth multivalent atom, thus providing a substituent formed from six multivalent atoms, where open valencies on the multivalent atoms are filled with one or more monovalent atoms. Examples of these substituents are well known to one of ordinary skill in the art and are provided herein, e.g., N-cyclopropylcarboxamide (C(O)NH-cyclopropyl), N-propylcarboxamide ($C(O)NHCH_2CH_2CH_3$), N-(2-hydroxyethyl)carboxamide ($C(O)NHCH_2CH_2OH$) and N-carbamimidocarboxamide ($C(O)NHC(=NH)NH_2$).

In one embodiment, a substituent on Ar1 contains 7 multivalent atoms. In this embodiment, one or more hydrogen atoms bonded to a ring atom of Ar1 are replaced with a first multivalent atom which, in turn, is bonded directly or indirectly to each of a second, third, fourth, fifth sixth and seventh multivalent atom, thus providing a substituent formed from seven multivalent atoms, where open valencies on the multivalent atoms are filled with one or more monovalent atoms. Examples of these substituents are well known to one of ordinary skill in the art and are provided herein, e.g., N-(n-butyl)carboxamide ($C(O)NHCH_2CH_2CH_2CH_3$), N-(t-butyl)carboxamide ($C(O)NHC(CH_3)_3$), NN-diethylcarboxamide ($C(O)N(CH_2CH_3)_2$), and N-cyclobutylcarboxamide (C(O)NH(cyclobutyl)).

In one embodiment, a substituent on Ar1 contains 8 multivalent atoms. In this embodiment, one or more hydrogen atoms bonded to a ring atom of Ar1 are replaced with a first multivalent atom which, in turn, is bonded directly or indirectly to each of a second, third, fourth, fifth sixth, seventh and eighth multivalent atom, thus providing a substituent formed from eight multivalent atoms, where open valencies on the multivalent atoms are filled with one or more monovalent atoms. Examples of these substituents are well known to one of ordinary skill in the art and are provided herein, e.g., N-cyclopentylcarboxamide (C(O)NH(cyclopentyl)), (piperidin-1-yl)methanone (C(O)-piperidin-1-yl) and (morpholin-4-yl)methanone (C(O)-morpholin-4-yl).

In one embodiment, a substituent on Ar1 contains 9 multivalent atoms. In this embodiment, one or more hydrogen atoms bonded to a ring atom of Ar1 are replaced with a first multivalent atom which, in turn, is bonded directly or indirectly to each of a second, third, fourth, fifth sixth, seventh, eighth and ninth multivalent atom, thus providing a substituent formed from nine multivalent atoms, where open valencies on the multivalent atoms are filled with one or more monovalent atoms. Examples of these substituents are well known to one of ordinary skill in the art and are provided herein, e.g., di-(iso-propyl)ester ($C(O)O(CH(CH_3)_2)_2$, di-(n-propyl)ester ($C(O)O(CH_2CH_2CH_3)_2$), N-cyclohexylcarboxamide (C(O)NH(cyclohexyl)), (4-methylpiperazin-1-yl)methanone (C(O)(4-methylpiperazin-1-yl), 2-(acetylamino)ethylcarboxamide ($C(O)NHCH_2CH_2NHC(O)CH_3$) and N-phenylcarboxamide (C(O)NH(phenyl)).

In one embodiment, a substituent on Ar1 contains 10 multivalent atoms. In this embodiment, one or more hydrogen atoms bonded to a ring atom of Ar1 are replaced with a first multivalent atom which, in turn, is bonded directly or indirectly to each of a second, third, fourth, fifth sixth, seventh, eighth, ninth and tenth multivalent atom, thus providing a substituent formed from ten multivalent atoms, where open valencies on the multivalent atoms are filled with one or more monovalent atoms. Examples of these substituents are well known to one of ordinary skill in the art and are provided herein, e.g., N-benzylcarboxamide (C(O) $NHCH_2$(phenyl)).

In one embodiment, Ar1 is substituted aryl wherein at least one substituent on Ar1 is selected from the group consisting of halogen, hydroxyl, mercaptan, nitro, and nitrile.

In one embodiment, Ar1 is substituted aryl wherein at least one substituent on Ar1 is selected from halogen, —OH, —CN, —$NO_2$, $C_1$-$C_6$alkyl, $C_1$-$C_6$haloalkyl, $C_1$-$C_6$heteroalkyl, $C_1$-$C_6$cycloloalkyl, —$OR^0$, —$CONH_2$, —C(O)$NR^1R^{1'}$, —$NR^1R^{1'}$, —$NR^1C(O)R^3$, —$C(O)SR^3$, —$COR^3$, —$OC(O)R^3$, —$C(O)OR^3$, mercaptan, —$R^4$—H, —$SOR^1$, —$S(O)_2R^1$, —$S(O)_2NR^1R^{1'}$, and —$NS(O)_2R^3$; and wherein (a) $R^0$ is, at each occurrence, independently selected from $C_1$-$C_6$alkyl, $C_1$-$C_6$haloalkyl, $C_2$-$C_6$alkenyl, $C_2$-$C_6$alkynyl, substituted or unsubstituted cycloalkyl, substituted or unsubstituted heterocyclyl, substituted or unsubstituted aryl, and substituted or unsubstituted heteroaryl; (b) $R^1$ and $R^{1'}$ are, at each occurrence, independently selected from H, hydroxyl, $C_1$-$C_6$alkyl, $C_1$-$C_6$haloalkyl, $C_1$-$C_6$heteroalkyl, $C_2$-$C_6$alkenyl, $C_2$-$C_6$alkynyl, substituted or unsubstituted cycloalkyl, substituted or unsubstituted heterocyclyl, substituted or unsubstituted aryl, substituted or unsubstituted arylalkyl, and substituted or unsubstituted heteroaryl, —C(=NH)$NH_2$, —$CH_2CO_2R^0$, —$CH_2C(O)NHCH_2CO_2H$, —$CH_2CH_2OH$, —$CH_2CH_2NHC(O)R^3$, —$CH_2C(O)NHCH_2CO_2H$,

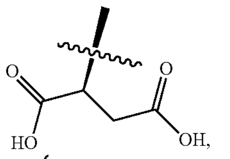

and

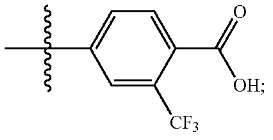

and (c) wherein $R^1$ and $R^{1'}$ can come together to form a heterocyclic ring, including, but not limited to, azetidine, pyrrolidine, piperidine, piperazine, morpholine,

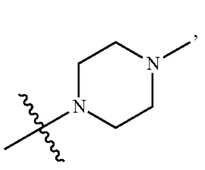

, or

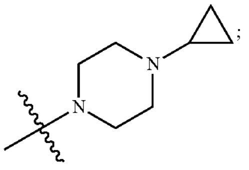

;

(d) $R^2$ is, at each occurrence, independently selected from $C_2$-$C_6$alkyl, $C_1$-$C_6$haloalkyl, $C_1$-$C_6$heteroalkyl, or substituted or unsubstituted cycloalkyl, substituted or unsubstituted heterocyclyl, substituted or unsubstituted aryl, substituted or unsubstituted heteroaryl, and substituted or unsubstituted haloalkoxy; and (e) $R^3$ is, at each occurrence, independently selected from H, $C_1$-$C_6$alkyl, $C_1$-$C_6$haloalkyl, $C_1$-$C_6$heteroalkyl, or substituted or unsubstituted cycloalkyl, substituted or unsubstituted heterocyclyl, substituted or unsubstituted aryl, and substituted or unsubstituted heteroaryl, substituted or unsubstituted haloalkoxy, and guanidine; and (f) $R^4$ is, at each occurrence, independently selected from one or more heteroatom interrupted alkylene wherein the heteroatom is O, S, NH or a combination thereof.

In one embodiment, Ar1 is substituted aryl wherein at least one substituent on Ar1 is selected from the group consisting of substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted haloalkyl, and substituted or unsubstituted haloalkoxy.

The Ar1 group will include an aromatic moiety as explained herein, where that aromatic moiety may optionally be substituted as also described herein, which substitution is in addition to being substituted with (triazole-Ar2)$_m$ groups. In one embodiment, exemplary substituents of Ar1 are halide such as fluoride, chloride and bromide, alkyl groups having 1-6 carbon atoms such as methyl and ethyl, haloalkyl groups having 1-6 carbon atoms such as trifluoromethyl, cyano, formyl, and carboxamide. In another embodiment, exemplary substituents of Ar1 are nitro (—$NO_2$), cyano (—CN), carboxylic acid (—COOH, or salts thereof), carboxamide (—C(O)$NH_2$), $C_1$-$C_6$alkoxy including methoxy, $C_1$-$C_6$alkyl including methyl, $C_1$-$C_6$haloalkyl such as trifluoromethyl, $C_1$-$C_6$heteroalkyl including amides such as —NHC(O)($C_1$-$C_6$alkyl), —NHC(O)($C_1$-$C_6$heteroalkyl), —C(O)NH($C_1$-$C_6$alkyl), —C(O)NH($C_1$-$C_6$heteroalkyl), —C(O)N($C_1$-$C_6$alkyl)($C_1$-$C_6$alkyl), —C(O)N($C_1$-$C_6$alkyl)($C_1$-$C_6$heteroalkyl) and —C(O)N($C_1$-$C_6$heteroalkyl)($C_1$-$C_6$heteroalkyl) including —NHC(O)$CH_3$, C(O)$NHCH_3$, —C(O)$N(CH_3)_2$, —NHC(O)$CH_2CH_3$, C(O)$NHCH_2CH_3$, —C(O)N($CH_3$)$CH_2CH_3$, —C(O)N($CH_2CH_3$)$_2$, —C(O)NH($C_1$-$C_6$cycloalkyl) and —NHC(O)($C_1$-$C_6$cycloalkyl) (e.g., C(O)NH(cyclopropyl), —NHC(O)-cyclopropyl, C(O)NH(cyclohexyl), NHC(O)-cyclohexyl), C(O)$NHCH_2CH_2CH_2CH_3$, —C(O)NH(C(CH3)$_3$), —C(O)NH($CH_2CH_2OH$), ketones such as —C(O)($C_1$-$C_6$alkyl) including —C(O)$CH_3$, —C(O)(cycloalkyl) including —C(O)-cyclohexyl, and C(O)-(heterocycloalkyl) where the heterocycloalkyl may be, e.g., morpholinyl, piperidinyl, piperazinyl, N-methylpiperazinyl, esters such as —$CO_2$—($C_1$-$C_6$alkyl) including —$CO_2CH_3$, —$CO_2CH_2CH_3$, —$CO_2CH_2CH_2CH_3$, —$CO_2CH_2(CH_3)_2$, and thioesters such as C(O)—S—($C_1$-$C_6$alkyl) including —C(O)—S—$CH_3$ and —C(O)—S—$CH_2CH_3$.

In one embodiment, Ar1 is substituted aryl wherein at least one substituent on Ar1 is selected from the group consisting of —O—($C_{1-6}$ alkyl), $C_{1-6}$ alkyl, $C_{1-6}$ haloalkyl, —$CO_2$—$C_{1-6}$ alkyl, —CONH—$C_{1-6}$ alkyl, —$CONH_2$, CN; and —$NO_2$.

When n is 1 or 2, compounds of Formula (I) will include a linker, L. In one embodiment, the linker L may be a direct bond. In another embodiment, the linker is not a direct bond, but is instead one or more atoms, particularly atoms selected from carbon, nitrogen, oxygen, sulfur. In another embodiment, the linker may be an alkylene group (e.g., $C_1$-$C_6$ alkylene), or a substituted alkylene. The linker may be a heteroalkylene linker, which refers to a substituted or non-substituted alkylene which further includes at least one heteroatom (e.g., 1, 2, 3, or 4 heteroatoms) selected from oxygen, nitrogen, or sulfur within and/or placed at one or more terminal position(s) of the parent chain. In one embodiment, L is a heteroalkylene group of 2 to 10 carbon atoms in length, wherein one or more carbon atoms is replaced with at least one heteroatom selected from oxygen, nitrogen and sulfur. In one embodiment, L may be a heteroalkylene linker having at least one N, O or S heteroatom, wherein the heteroalkylene may be a straight chain or cyclized and optionally substituted, where exemplary substituents include oxo, —OH, $C_{1-4}$alkyl and $C_{1-4}$alkoxy. Examples of heteroalkylene linker groups include amide-containing heteroalkylene groups such as —C(O)NH—alkylene- and —C(O)NH-alkylene-NHC(O)—, where alkylene is optionally $C_1$-$C_6$alkylene. Other examples of heteroalkylene groups include ester-containing heteroalkylene groups such as —C(O)O-alkylene- and —C(O)O-alkylene-OC(O)—, where in one embodiment alkylene is unsubstituted $C_1$-$C_6$alkylene, and in another embodiment alkylene is substituted $C_1$-$C_6$alkylene. In one embodiment, the linker is hydrolytically stable, so that it does not decompose or degrade or otherwise break when the PEM is placed into water.

The linker L typically does not need to be too long; in one embodiment it contains 1 to about 25 atoms excluding hydrogen and halogen from that atomic count, where the linker may optionally be composed of atoms selected from carbon, nitrogen, oxygen and sulfur, in addition to hydrogen and halogen. In various other embodiments, the linker has fewer than 25 atoms (excluding hydrogen and halogen), e.g., it contains 1 to about 20 atoms, or 1 to about 15 atoms, or 1 to about 10 atoms, or 1 to about 5 atoms, in each case excluding hydrogen and halogen from that atomic count, where the counted atoms may optionally be selected from carbon, oxygen, nitrogen and sulfur.

In one embodiment, a triazole ring in a compound of Formula (I) may be substituted in addition to being directly bonded to Ar1 and Ar2. In general, compounds of the present disclosure may optionally be described as including the chemical formula

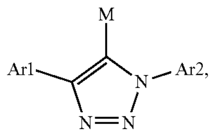

where Ar1 and Ar2 are defined elsewhere herein, and M may be hydrogen (in which case the triazole ring is only substituted by Ar1 and Ar2), $C_1$-$C_4$alkyl, or M may be a halide substituent, e.g., fluoride, chloride, bromide or iodide. In one embodiment, compounds of the present disclosure have a triazole ring substituted only by Ar1 and Ar2, i.e., M is hydrogen. In yet another embodiment, compounds of the present disclosure have a triazole ring substituted by Ar1, Ar2 and $C_1$-$C_4$alkyl. In another embodiment, compounds of the present disclosure have a triazole ring substituted by Ar1, Ar2 and a halide. In another embodiment, compounds of the present disclosure include an iodide-substituted triazole ring, i.e., M is iodide. In another embodiment, compounds of the present disclosure have an M-substituent on a triazole ring, where M is selected from hydrogen and iodide.

Thus, in one embodiment, the present disclosure provides compounds of the formula

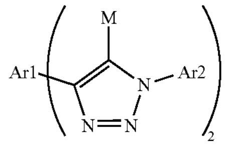

where Ar1 and Ar2 are defined elsewhere herein, and M is selected from hydrogen, $C_1$-$C_4$alkyl, and halide. Optionally, as stated above, M may be hydrogen, or in another option, M may be, e.g., a halide such as iodide, as illustrated with the compound 4,4'-((pyridine-2,6-diyl)bis(5-iodo-1H-1,2,3-triazole-4,1-diyl))bis(2-hydroxybenzoic acid). When, as in the above structure, a compound of the present disclosure has more than one M-substituted triazole ring, M is independently selected at each occurrence. However, in one embodiment, M is the same atom at each occurrence in a compound of the present disclosure. For example, the present disclosure provides compounds wherein M is hydrogen at each occurrence of M. In another example, the present disclosure provides compounds wherein M is iodide at each occurrence of M.

Compounds of Formula (I) include at least one triazole-Ar2 moiety. In one embodiment, compounds of the present disclosure include two or more triazole-Ar2 moieties, such as compounds of the formula

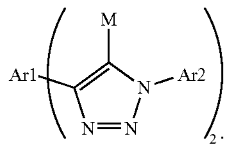

When a compound of the present disclosure includes two, or more than two, triazole-Ar2 moieties, the Ar2 moieties may optionally have the same chemical structure at each occurrence. However, when a PEM compound of the present disclosure contains multiple triazole-Ar2 moieties, in one embodiment those Ar2 moieties are not necessarily identical to one another, and in fact they may be non-identical. The Ar2 moieties may differ from one another in terms of the Ar2 ring atoms and/or in terms of the substitution on the Ar2 ring atoms. For example, if one Ar2 group is phenyl and the other Ar2 group is pyridinyl, then the two Ar2 groups differ in terms of the ring atoms that compose the Ar2 group. As another example, if both Ar2 groups are phenyl, but one phenyl is substituted with carboxyl while the other phenyl is substituted with methoxy, as in, e.g., 4-(4-(3-(1-(4-methoxyphenyl)-1H-1, 2,3-triazol-4-yl)phenyl)-1H-1,2,3-triazol-1-yl)benzoic acid, then the compound is considered to have two different Ar2 groups. An yet another example, the two Ar2 groups may be positional isomers of one another, as in when both Ar2 groups are phenyl, and both phenyl rings are substituted with hydroxyl and carboxyl, but the locations of the hydroxyl and/or carboxyl groups are different on the two phenyl rings, e.g., if on one phenyl ring the triazole is located at the 3 position (meta) relative to the carboxyl group while on the other phenyl ring the triazole is located at the 4 position (para) relative to the carboxyl group, then the two Ar2 groups are considered to be positional isomers and non-identical. In one embodiment, the Ar2 rings are identical in all respects at each occurrence in a compound of the present disclosure. In one embodiment, the Ar2 ring atoms are identical at each occurrence of Ar2, but the substitution on the Ar2 rings is non-identical at each occurrence of Ar2. In another embodiment, the Ar2 ring atoms are non-identical at each occurrence of Ar2, and the substitution on the Ar2 rings may or may not be identical.

Compounds of Formula (I) include at least one Ar2 moiety, where in one embodiment Ar2 is a monocyclic aromatic ring selected from phenyl and pyridinyl, which may optionally be substituted. In one embodiment, Ar2 is a monocyclic 6-membered aromatic ring, where examples are phenyl, pyridinyl and pyrazinyl, where again the Ar2 group optionally includes substituents on the ring atoms. In another embodiment, Ar2 is a 5-membered monocyclic aromatic ring, which may optionally be substituted. In another embodiment, Ar2 is a 5- or 6-membered aromatic ring, which may optionally be substituted. In another embodiment, Ar2 is a 9- or 10-membered fused bicyclic ring comprising two 5- and/or 6-membered monocyclic rings fused together, where at least one of the two monocyclic rings is an aromatic ring. In another embodiment, Ar2 is a 9- or 10-membered fused bicyclic ring comprising two 5- and/or 6-membered monocyclic rings fused together, where both of the two monocyclic rings is an aromatic ring. In one embodiment, Ar2 may be any of these options, that is, Ar2 is selected from (a) 5-membered monocyclic aromatic rings, (b) 6-membered monocyclic aromatic rings, (c) 9-membered fused bicyclic rings comprising one 5-membered and one 6-membered monocyclic ring fused together, where at least one of the two monocyclic rings, and optionally both of the monocyclic rings, is an aromatic ring, and (d) 10-membered fused bicyclic rings comprising two 6-membered monocyclic rings fused together, where at least one of the two monocyclic rings, and optionally both of the monocyclic rings, is an aromatic ring, In compounds of Formula (I), optionally, Ar2 is a 5-membered monocyclic aromatic ring selected from the group consisting of thiophene, 1,2-thiazole, 1,3-thiazole, furan, 1,2-oxazole, 1,3-oxazole, 1H-pyrrole, 1H-pyrazole, oxadiazole, thiadiazole, 1,2,4-triazole, 1,2,3-triazole and 1H-imidazole.

In compounds of Formula (I), optionally, Ar2 is a 6-membered monocyclic aromatic ring selected from the group consisting of benzene, pyridine, pyridazine, pyrimidine and pyrazine.

In compounds of Formula (I), optionally, Ar2 is a 9-membered fused bicyclic aromatic ring system selected from the group consisting of benzofuran, 1,3-benzoxazole, furo[3,2-b]pyridine, furo[3,2-c]pyridine, furo[2,3-c]pyridine, furo[2,3-b]pyridine, indole, 1H-benzimidazole, 1H-pyrrolo[3,2-b]pyridine, 1H-pyrrolo[3,2-c]pyridine, 1H-pyrrolo[2,3-c]pyridine, 1H-pyrrolo[2,3-b]pyridine, benzothiophene, 1,3-benzothiazole, thienol[3,2-b]pyridine, thieno[3,2-c]pyridine, thieno[2,3-c]pyridine, benzoxadiazole, benzothiadiazole, benzisoxazole, benzotriazole and thieno[2,3-b]pyridine.

In compounds of Formula (I), optionally, Ar2 is a 10-membered fused bicyclic aromatic ring system selected from the group consisting of naphthalene, quinoline, quinazoline, quinoxaline, 1,5-naphthyridine, 1,6-naphthyridine, 1,7-naphthyridine, 1,8-naphthyridine, isoquinoline, phthalazine, 2,6-naphthyridine and 2,7-naphthyridine.

As mentioned above, a compound of the present disclosure includes at least one Ar2 group, where the Ar2 group includes at least one aromatic ring and optionally includes one or more substituents on the aromatic ring. In one embodiment, Ar2 includes at least one, i.e., one or more, substituent on the aromatic ring, such as 1-5, or 1-4, or 1-3, or 1-2 substituents. Optionally, Ar2 includes exactly one substituent on the aromatic ring. In another option, Ar2 includes exactly two substituents on the aromatic ring. In yet another option, Ar2 includes exactly three substituents on the aromatic ring. In a further option, Ar2 includes exactly four substituents on the aromatic ring. In one optional embodiment, Ar2 includes two or more substituents on the aromatic ring.

In one embodiment, the one or more substituents on the ring atoms of Ar2 are selected from substituents optionally named "G", where the substituents are selected from, halogen, $C_1$-$C_6$alkyl, $C_1$-$C_6$haloalkyl, -E-$CO_2$H, -E-CHO, -E-C(O)$R^3$, -E-C(O)NH(OH), -E-C(O)NH$R^1$, -E-CON$R^1R^{1'}$, -E-N$R^1R^{1'}$, and -E-O$R^2$; wherein (a) E is selected from a direct bond and $C_1$-$C_6$alkylene; (b) $R^0$ is, at each occurrence, independently selected from $C_1$-$C_6$alkyl, $C_1$-$C_6$haloalkyl, $C_2$-$C_6$alkenyl, $C_2$-$C_6$alkynyl, substituted or unsubstituted cycloalkyl, substituted or unsubstituted heterocyclyl, substituted or unsubstituted aryl, and substituted or unsubstituted heteroaryl; (c) $R^1$ and $R^{1'}$ are, at each occurrence, independently selected from H, hydroxyl, $C_1$-$C_6$alkyl, $C_1$-$C_6$haloalkyl, $C_1$-$C_6$heteroalkyl, $C_2$-$C_6$alkenyl, $C_2$-$C_6$alkynyl, substituted or unsubstituted cycloalkyl, substituted or unsubstituted heterocyclyl, substituted or unsubstituted aryl, substituted or unsubstituted arylalkyl, and substituted or unsubstituted heteroaryl, —C(═NH)$NH_2$, —$CH_2CO_2R^0$, —$CH_2$C(O)NH$CH_2CO_2$H, —$CH_2CH_2$OH, —$CH_2CH_2$NHC(O)$R^3$, —$CH_2$C(O)NH$CH_2CO_2$H,

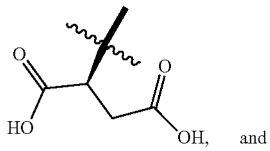

and

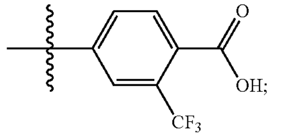

and (d) wherein $R^1$ and $R^{1'}$ can come together to form a heterocyclic ring, including, but not limited to, azetidine, pyrrolidine, piperidine, piperazine, morpholine,

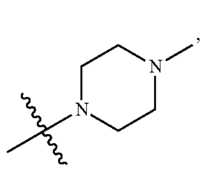

, or

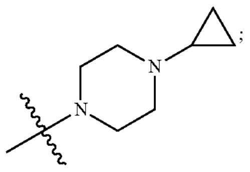

(e) $R^2$ is, at each occurrence, independently selected from $C_2$-$C_6$alkyl, $C_1$-$C_6$haloalkyl, $C_1$-$C_6$heteroalkyl, or substituted or unsubstituted cycloalkyl, substituted or unsubstituted heterocyclyl, substituted or unsubstituted aryl, substituted or unsubstituted heteroaryl, and substituted or unsubstituted haloalkoxy; and (f) $R^3$ is, at each occurrence, independently selected from H, $C_1$-$C_6$alkyl, $C_1$-$C_6$haloalkyl, $C_1$-$C_6$heteroalkyl, or substituted or unsubstituted cycloalkyl, substituted or unsubstituted heterocyclyl, substituted or unsubstituted aryl, and substituted or unsubstituted heteroaryl, substituted or unsubstituted haloalkoxy, and guanidine.

In one embodiment, the substitution on Ar2 includes amino (—$NH_2$). In one embodiment, the substitution on Ar2 includes alkoxy, e.g., $C_1$-$C_6$alkoxy. For example, in one embodiment, the substitution on Ar2 includes methoxy. In one embodiment, the substitution on Ar2 includes carboxylic acid or alkylene-carboxylic acid. For example, in one embodiment, the substitution on Ar2 of PEM compounds of Formula (I) includes carboxylic acid. In one embodiment, the substitution on Ar2 includes carboxylic acid ester, or alkylene-carboxylic acid ester. For example, in one embodiment the substitution on Ar2 of PEM compounds of the Formula (I) includes —$CH_2$—$CO_2$—$CH_3$. In one embodiment, the substitution on Ar2 includes a haloalkyl group, e.g., a $C_1$-$C_6$haloalkyl group. For example, in one embodiment, the substitution on Ar2 of a PEM compounds of Formula (I) includes trifluoromethyl. In one embodiment, the substitution on Ar2 includes hydroxyl or hydroxyl-substituted alkyl, e.g., hydroxyl-substituted $C_1$-$C_6$alkyl. For example, in one embodiment, the substitution on Ar2 of a compound of Formula (I) includes hydroxyl (—OH).

In one embodiment, the substitution on Ar2 includes one group selected from carboxylic acid and alkylene-carboxylic acid, e.g., $C_1$-$C_6$alkylene-carboxylic acid, and another group selected from hydroxyl and hydroxyl-substituted alkyl, e.g., $C_1$-$C_6$alkyl substituted with one hydroxyl. For example, in one embodiment, the substitution on Ar2 is, or includes, one carboxylic acid and one hydroxyl.

In one embodiment, the substitution on Ar2 includes one group selected from carboxylic acid and alkylene-carboxylic acid, e.g., $C_1$-$C_6$alkylene-carboxylic acid, and one group selected from haloalkyl, e.g., $C_1$-$C_6$haloalkyl. For example, in one embodiment, the substitution on Ar2 is, or includes, one carboxylic acid group and one trifluoromethyl group.

In one embodiment, the substitution on Ar2 includes one group selected from hydroxyl and hydroxyl-substituted alkyl, e.g., $C_1$-$C_6$alkyl substituted with one hydroxyl, and another group selected from haloalkyl, e.g., $C_1$-$C_6$haloalkyl. For example, in one embodiment, the substitution on Ar2 is, or includes one hydroxyl group and one trifluoromethyl group.

In one embodiment, the substitution on the Ar2 ring of Formula (I) includes at least of one of a) carboxylic acid and alkylene-carboxylic acid, e.g., $C_1$-$C_6$alkylene-carboxylic acid; b) hydroxyl and hydroxyl-substituted alkyl, e.g., $C_1$-$C_6$alkyl substituted with one hydroxyl; and c) haloalkyl, e.g., $C_1$-$C_6$haloalkyl. For example, at least one of carboxylic acid, hydroxyl and trifluoromethyl.

In one embodiment, the substitution on the Ar2 ring of Formula (I) includes at least two of a) carboxylic acid and alkylene-carboxylic acid, e.g., $C_1$-$C_6$alkylene-carboxylic acid; b) hydroxyl and hydroxyl-substituted alkyl, e.g., $C_1$-$C_6$alkyl substituted with one hydroxyl; and c) haloalkyl, e.g., $C_1$-$C_6$haloalkyl. For example, at least two of carboxylic acid, hydroxyl and trifluoromethyl.

In one embodiment, the substitution on the Ar2 ring of Formula (I) includes all three of a) carboxylic acid and alkylene-carboxylic acid, e.g., $C_1$-$C_6$alkylene-carboxylic acid; b) hydroxyl and hydroxyl-substituted alkyl, e.g., $C_1$-$C_6$alkyl substituted with one hydroxyl; and c) haloalkyl, e.g., $C_1$-$C_6$haloalkyl. That is, Ar2 may be substituted with carboxylic acid, hydroxyl and trifluoromethyl.

For example, in one embodiment, the Ar2 group is a substituted phenyl group selected from

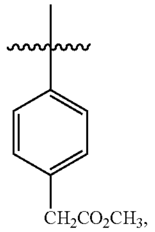 , 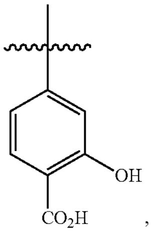 , 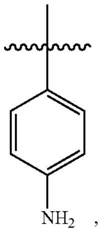 ,

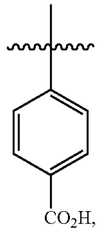 and 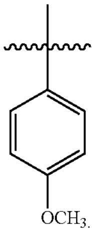

In one embodiment, the Ar2 group is a substituted phenyl group, wherein the substituent of the phenyl group is aryl further substituted with $G^2$, $G^3$, $G^4$ and $G^5$, and in a more specific embodiment the substituent of the phenyl group is phenyl further substituted with $G^2$, $G^3$, $G^4$ and $G^5$, such as phenyl further substituted with $G^2$ or with $G^2$ and $G^3$.

As mentioned, in one embodiment, the PEM compounds of the present disclosure may have hydroxyl and carboxylic acid substitution on $Ar_2$. These two groups may be located at various positions on the $Ar_2$ ring. For instance, in one embodiment, the present disclosure provides Formula (I) PEM compounds described by the formula:

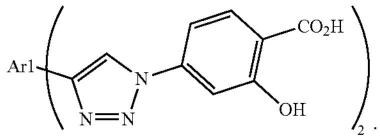

In another embodiment, the Formula (I) PEM compounds of the present disclosure have hydroxyl and carboxylic acid substitution on $Ar_2$ as provided in the formula:

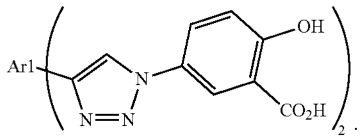

In yet another embodiment, the Formula (I) PEM compounds of the present disclosure have hydroxyl and carboxylic acid substitution on $Ar_2$ as shown in the formula:

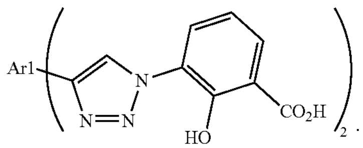

In one embodiment, the Formula (I) PEM compounds of the present disclosure have at least hydroxyl and carboxylic acid substitution on $Ar_2$, and may have other substitution on $Ar_2$.

For instance, $Ar_2$ may be substituted with hydroxyl, carboxylic acid and alkyl, e.g., $C_1$-$C_6$alkyl, to provide, e.g., a compound of the formula:

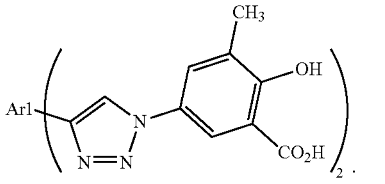

As mentioned previously, in one embodiment, the Formula (I) PEM compounds of the present disclosure may have haloalkyl and carboxylic acid substitution on Ar2 rather than hydroxyl and carboxylic acid as illustrated in the structures above. As one example, the PEM compounds of the present disclosure may be described by the formula:

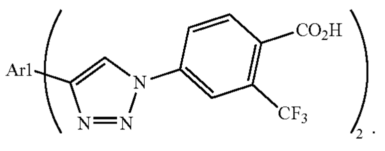

The PEM compounds of formula (I) include solvate including hydrate, chelate, and salt forms thereof. In some instances, the PEM compounds may be amorphous, while in other instances the PEM compounds may be crystalline. Furthermore, some of the crystalline forms of the compounds may exist as polymorphs, which are contemplated herein. In addition, some of the compounds may also form solvates with water or other organic solvents. Such solvates are similarly included within the scope of the compounds described herein.

The PEM compounds of formula (I) may be in the form of a chelate, such as a copper chelate. A copper chelate may be formed by combining a PEM compound of the present disclosure with copper sulfate. The PEM compounds of formula (I) may be in the form of a salt, either an acid addition salt or a base addition salt, depending on the substituents on the Ar1 and Ar2 groups.

The PEM structures include all stable stereoisomeric forms thereof. Thus, the PEM compounds described herein may have one or more chiral (or asymmetric) centers and may thus give rise to enantiomers, diastereomers, and other stereoisomeric forms that may be defined, in terms of absolute stereochemistry, as (R)- or (S)-. When the compounds described herein contain olefinic double bonds or other centers of geometric asymmetry, and unless specified otherwise, it is intended that the compounds include both E and Z geometric isomers (e.g., cis or trans). Likewise, unless otherwise indicated, all possible isomers, as well as their racemic and optically pure forms, and all tautomeric forms are also intended to be included. It is therefore contemplated that various stereoisomers and mixtures thereof include "enantiomers," which refers to two stereoisomers whose molecules are nonsuperimposeable mirror images of one another. Thus, the compounds may occur in any isomeric form, including racemates, racemic mixtures, and as individual enantiomers or diastereomers.

PEM compounds of the present disclosure generally are water soluble. One measure of water solubility is the log P value of a compound. Log P values may be calculated using commercial software, based on the chemical structure of the compound. For instance, the CHEMDRAW chemical drawing software (Cambridgesoft Limited, a subsidiary of PerkinElmer Holdings) can calculate a log P value for a drawn chemical structure. In one embodiment, a PEM compound of the present disclosure has a log P of at least 4.9.

Compounds of the present disclosure, for example, PEM compounds of the formula (I) as described above, may typically be synthesized by the reaction of diethynyl compounds of the formula $Ar1(C\equiv CH)_2$ with azide compounds of the formula $Ar2\text{-}N_3$ in the presence of Cu(I) catalyst. See also Crowley J. D., McMorran D. A. (2012) "Click-Triazole" Coordination Chemistry: Exploiting 1,4-Disubstituted-1,2,3-Triazoles as Ligands. In: Košmrlj J. (eds.) Click Triazoles. Topics in Heterocyclic Chemistry, vol. 28. Springer, Berlin, Heidelberg doi.org/10.1007/7081_2011_67.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Wermuth "Handbook of Pharmaceutical Salts," Verlag Helvetica Chimica Acta, Zurich, 2002.

Compounds of the formula $Ar1(C\equiv CH)$ are commercially available, e.g., from TCI America (Portland, Oregon, USA), which sells, e.g., 1,3-diethynylbenzene, 1,4-diethynylbenzene, 2,6-diethynylpyridine and 3,6-diethynylcarbazole.

In general, ethynyl aromatic compounds may be prepared via a Seyferth-Gilbert homologation from an aryl aldehyde using dimethyl (diazaomethyl) phosphonate available from MilliporeSigma Corp. (St. Louis, MO, USA). Alternatively, dimethyl (diazomethyl)phosphonate can be generated in situ from dimethyl-1-diazo-2-oxopropylphosphonate (Ohira-Bestmann reagent). See, e.g., Seyforth et al., J. Org. Chem. 36(10): 1379-1386 (1971). doi:10.1021/jo00809a014 and Bestman et al., Synlett. 1996 (06): 521-522 (1996). doi: 10.1055/s-1996-5474.

Another route to ethynyl aromatic compounds entails a Sonogashira coupling of halo aromatic compounds with (t-butyldimethylsilyl)acetylene in the presence of a palladium catalyst. The ethynyl aromatic forms upon subsequent deprotection the silyl group. See, e.g., Sonogashira, Organomet. Chem., 653: 46-49 (2002). doi:10.1016/s0022-328x(02)01158-0.

The following reactions (I), (II) and (III) illustrate exemplary preparations of diethynyl aromatic compounds. In reaction (I), 2,6-dibromopyridin-4-amine is converted to the corresponding 2,6-diethynylpyridin-4-amine compound. In reaction (II), 2,6-diiodo-4-nitroanilie is converted to the corresponding 2,6-diethynyl-4-nitroaniline. In reaction (III), 2-hydroxy-3,5-diiodobenzoic acid is converted to the corresponding 3,5-diethynyl-2-hydroxybenzoic acid. In each case, the conversion proceeds through the intermediate di-trimethylsilyl (TMS) compound as shown.

(I)

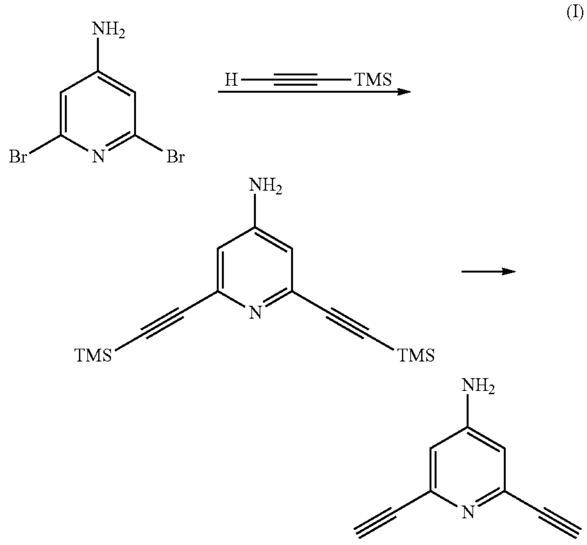

(II)

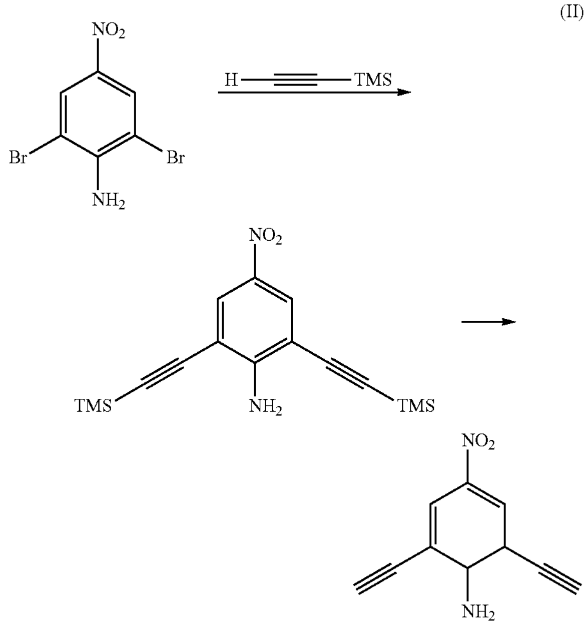 [SMILES: Nc1c(Br)cc([N+](=O)[O-])cc1Br ; C#C[Si](C)(C)C ; C[Si](C)(C)C#Cc1cc([N+](=O)[O-])cc(C#C[Si](C)(C)C)c1N ; C#CC1=CC([N+](=O)[O-])=CC(C#C)C1N]

(III)

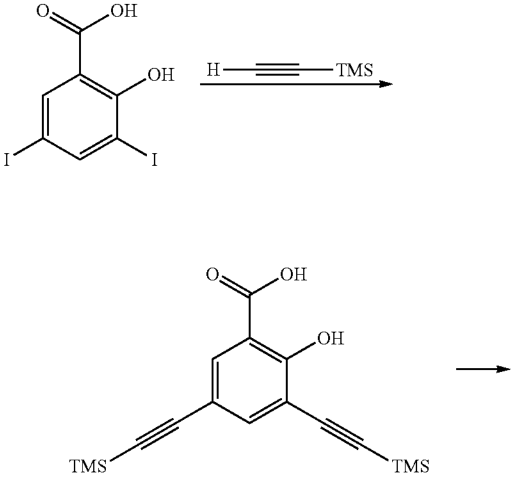

-continued

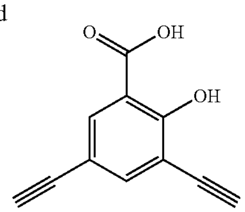

Each of these reaction products, namely 2,6-diethynylpyridin-4-amine, and 2,6-diethynyl-4-nitroaniline, and 3,5-diethynyl-2-hydroxybenzoic acid, may function as the precursor to Ar1 in preparing PEMs of the present disclosure. Thus, each of them represents an $Ar1(C{\equiv}CH)_2$ compound which may be reacted with an azide compound of the formula $Ar2\text{-}N_3$ in the presence of Cu(I) catalyst to provide a PEM. The reactions (I), (II) and (III) illustrate the preparation of a precursor to a substituted Ar1 moiety of the present disclosure.

Compounds of the formula $Ar2\text{-}N_3$ are likewise commercially available, e.g., from TCI America (Portland, Oregon, USA), Synthonix (Wake Forest, North Carolina, USA), SigmaAldrich (St. Louis, Missouri, USA), Toronto Research Chemicals (Toronto, Canada), and AnaSpec (Fremont, California, USA). In general, azides of the formula $Ar2\text{-}N_3$ may be prepared by nucleophilic displacement with sodium azide of electrophilic compounds such as an alkyl, benzylic or allylic iodide or bromide.

In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Across Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

In one embodiment, a PEM compound of the present disclosure, e.g., a PEM compound of formula (I) is present in a composition. For example, the PEM compounds of the present disclosure may be present in a composition also comprising an aqueous buffer. In one embodiment, the PEM compounds of the present disclosure are present in a composition comprising a biomolecule such as a polypeptide and/or a polynucleotide. The polypeptide may be an enzyme such as a DNA polymerase. The following definitions may be helpful to an understanding of these compositions and certain uses thereof.

As used herein, "nucleic acids", also called polynucleotides, are covalently linked series of nucleotides in which the 3' position of the pentose of one nucleotide is joined by a phosphodiester group to the 5' position of the next. A nucleic acid molecule can be deoxyribonucleic acid (DNA), ribonucleic acid (RNA), or a combination of both. DNA (deoxyribonucleic acid) and RNA (ribonucleic acid) are biologically occurring polynucleotides in which the nucleotide residues are linked in a specific sequence by phosphodiester linkages. As used herein, the terms “nucleic acid”, “polynucleotide” or “oligonucleotide” encompass any polymer compound having a linear backbone of nucleotides. Oligonucleotides, also termed oligomers, are generally shorter chained polynucleotides. Nucleic acids are generally referred to as “target nucleic acids” or “target sequence” if targeted for sequencing.

As used herein, the term “template dependent manner” is intended to refer to a process that involves the template dependent extension of a primer molecule (e.g., DNA synthesis by DNA polymerase). The term “template dependent manner” refers to polynucleotide synthesis of RNA or DNA wherein the sequence of the newly synthesized strand of polynucleotide is dictated by the well-known rules of complementary base pairing (see, for example, Watson, J. D. et al., In: Molecular Biology of the Gene, 4th Ed., W. A. Benjamin, Inc., Menlo Park, Calif. (1987)).

As used herein, “nucleic acid polymerase” is an enzyme generally for joining 3'-OH 5'-triphosphate nucleotides, oligomers, and their analogs. Polymerases include, but are not limited to, DNA-dependent DNA polymerases, DNA-dependent RNA polymerases, RNA-dependent DNA polymerases, RNA-dependent RNA polymerases, T7 DNA polymerase, T3 DNA polymerase, T4 DNA polymerase, T7 RNA polymerase, T3 RNA polymerase, SP6 RNA polymerase, DNA polymerase 1, Klenow fragment, *Thermophilus aquaticus* DNA polymerase, Tth DNA polymerase, VentR® DNA polymerase (New England Biolabs), Deep VentR® DNA polymerase (New England Biolabs), Bst DNA Polymerase Large Fragment, Stoeffel Fragment, 9° N DNA Polymerase, 9° N DNA polymerase, Pfu DNA Polymerase, Tfl DNA Polymerase, Tth DNA Polymerase, RepliPHI Phi29 Polymerase, Tli DNA polymerase, eukaryotic DNA polymerase beta, telomerase, Therminator™ polymerase (New England Biolabs), KOD HiFi™ DNA polymerase (Novagen), KOD1 DNA polymerase, Q-beta replicase, terminal transferase, AMV reverse transcriptase, M-MLV reverse transcriptase, Phi6 reverse transcriptase, HIV-1 reverse transcriptase. A polymerase according to the invention can be a variant, mutant, or chimeric polymerase.

As used herein, a “DP04-type DNA polymerase” is a DNA polymerase naturally expressed by the archaea, *Sulfolobus solfataricus*, or a related Y-family DNA polymerase, which generally function in the replication of damaged DNA by a process known as translesion synthesis (TLS). Y-family DNA polymerases are homologous to the DPO4 polymerase; examples include the prokaryotic enzymes, PolII, PolIV, PolV, the archaeal enzyme, Dbh, and the eukaryotic enzymes, Rev3p, Rev1p, Pol η, REV3, REV1, Pol 1, and Pol κ DNA polymerases, as well as chimeras thereof. A modified recombinant DPO4-type DNA polymerase includes one or more mutations relative to naturally-occurring wild-type DPO4-type DNA polymerases, for example, one or more mutations that increase the ability to utilize bulky nucleotide analogs as substrates or another polymerase property, and may include additional alterations or modifications over the wild-type DPO4-type DNA polymerase, such as one or more deletions, insertions, and/or fusions of additional peptide or protein sequences (e.g., for immobilizing the polymerase on a surface or otherwise tagging the polymerase enzyme). Examples of variant polymerase according to the invention are the variants of *Sulfolobus sulfataricus* DPO4 described in published PCT patent application WO2017/087281 A1 and PCT patent applications nos. PCTUS2018/030972 and PCTUS2018/64794 which are hereby incorporated by reference in their entirety.

As used herein, “nucleic acid polymerase reaction” refers to an in vitro method for making a new strand of nucleic acid or elongating an existing nucleic acid (e.g., DNA or RNA) in a template dependent manner. Nucleic acid polymerase reactions, according to the invention, includes primer extension reactions, which result in the incorporation of nucleotides or nucleotide analogs to a 3-end of the primer such that the incorporated nucleotide or nucleotide analog is complementary to the corresponding nucleotide of the target polynucleotide. The primer extension product of the nucleic acid polymerase reaction can further be used for single molecule sequencing or as templates to synthesize additional nucleic acid molecules.

Primer extension reaction reagents typically include (i) a polymerase enzyme; (ii) a buffer; and (iii) one or more extendible nucleotides or nucleotide analogs. Primer extension reactions can be used to measure the length of a resulting nucleic acid product under particular experimental conditions and to determine the effect of various polymerase reaction additives (e.g., PEMs) on polymerase activity by comparing the lengths of the extended primer products by, e.g., gel electrophoresis.

As used herein, “enhancing a nucleic acid polymerase reaction” refers to the ability of an additive, e.g., a PEM to enable a nucleic acid polymerase to synthesize a primer extension product at least one subunit longer in length than it would in the absence of the PEM.

The rate of a nucleic acid polymerase reaction as used herein refers to the average speed at which a nucleic acid polymerase extends a polymer chain. As used herein, the terms “speed” and “elongation rate” are used inter-changeably. The nucleotide incorporation assay of Hogrefe et al. (Methods in Enzymol. Vol. 334, pp. 91-116 (2001)) can be used to measure the rate of polymerization. Briefly, polymerase activity can be measured as the rate of incorporation of $^{32}P$-dCTP into activated salmon sperm DNA (purchased from Pharmacia; for activation protocol see C. C. Richardson, Procedures in Nucl. Acid Res. (Cantoni and Davies, eds.), p. 263-276 (1966) at p. 264). The reaction buffer can be, for example, 50 mM Tris-HCl (pH 8.0), 5 mM $MgCl_2$, 1 mM dithiothreitol (DTT), 50 μg/ml bovine serum albumin (BSA), and 4% (v/v) glycerol. Nucleotide substrates and DNA are used in large excess, typically at least 10 times the Km for the polymerase being assayed, e.g., 200 μM each of dATP, dTTP, and dGTP, 195 μM of dCTP plus 5 μIM of labeled dCTP, and 250 μg/ml of activated DNA. The reactions are quenched on ice, and aliquots of the reaction mixture are spotted onto ion exchange filters (e.g., Whatman DE81). Unincorporated nucleotide is washed through, followed by scintillation counting to measure incorporated radioactivity.

As used herein, “increasing the rate” refers to an increase of 5-10%, 10-50%, or 50-100% or more, as compared to a polymerization reaction that lacks a PEM that increases rate as defined herein.

As used herein, “processivity” refers to the extent of polymerization by a nucleic acid polymerase during a single contact between the polymerase and its template, i.e., its property to continue to act on a substrate instead of dissociating therefrom. The extent of polymerization refers to the number of nucleotides or nucleotide analogs added by the polymerase during a single contact between the polymerase and its template. Processivity can depend on the nature of the polymerase, the sequence of a template, the structure of the nucleotide or nucleotide analog substrates, and the reaction conditions, for example, salt concentration, temperature or the presence of specific additives.

As used herein, "increasing the processivity" refers to an increase of 5-10%, 10-50%, or 50-100% or more, as compared to a polymerization reaction that lacks a PEM that increases processivity as defined herein. Methods for measuring processivity of a nucleic acid polymerase are generally known in the art, e.g., as described in Sambrook et al. 1989, In Molecular Cloning, 2nd Edition, CSH Press, 7.79-7.83 and 13.8, as described in U.S. published patent application no. 2002/0119467, published PCT application no. WO01/92501 and in U.S. Pat. No. 5,972,603, the entireties of which are incorporated herein by reference.

The term "fidelity" as used herein refers to the accuracy of nucleic acid polymerization by template-dependent nucleic acid polymerase. The fidelity of a DNA polymerase is measured by the error rate (the frequency of incorporating an inaccurate nucleotide, i.e., a nucleotide that is not incorporated at a template-dependent manner). The fidelity or error rate of a DNA polymerase may be measured using assays known to the art (see for example, Lundburg et al., 1991 Gene, 108:1-6). As used herein, "increasing the fidelity" refers to an increase of 5-10%, 10-50%, or 50-100% or more, as compared to a polymerization reaction that lacks an additive that increases fidelity as defined herein.

The term "plurality" as used herein refers to "at least two."

"XNTP" is an expandable, 5' triphosphate modified nucleotide substrate compatible with template dependent enzymatic polymerization. An XNTP has two distinct functional components; namely, a nucleobase 5'-triphosphoramidate and a tether that is attached within each nucleoside triphosphoramidate at positions that allow for controlled expansion by intra-nucleotide cleavage of the phosphoramidate bond. XNTPs are exemplary "non-natural, highly substituted nucleotide analog substrates", as used herein. Exemplary XNTPs and methods of making the same are described, e.g., in Applicants' published PCT application no. WO2016/081871, herein incorporated by reference in its entirety.

"Xpandomer intermediate" is an intermediate product (also referred to herein as a "daughter strand") assembled from XNTPs, and is formed by polymerase-mediated template-directed assembly of XNTPs using a target nucleic acid template. The newly synthesized Xpandomer intermediate is a constrained Xpandomer. Under a process step in which the phosphoramidate bonds provided by the XNTPs are cleaved, the constrained Xpandomer is no longer constrained and is the Xpandomer product which is extended as the tethers are stretched out.

"Xpandomer" or "Xpandomer product" is a synthetic molecular construct produced by expansion of a constrained Xpandomer, which is itself synthesized by template-directed assembly of XNTP substrates. The Xpandomer is elongated relative to the target template it was produced from. It is composed of a concatenation of subunits, each subunit a motif, each motif a member of a library, comprising sequence information, a tether and optionally, a portion, or all of the substrate, all of which are derived from the formative substrate construct. The Xpandomer is designed to expand to be longer than the target template thereby lowering the linear density of the sequence information of the target template along its length. In addition, the Xpandomer optionally provides a platform for increasing the size and abundance of reporters which in turn improves signal to noise for detection. Lower linear information density and stronger signals increase the resolution and reduce sensitivity requirements to detect and decode the sequence of the template strand.

"Tether" or "tether member" refers to a polymer or molecular construct having a generally linear dimension and with an end moiety at each of two opposing ends. A tether is attached to a nucleoside triphosphoramidate with a linkage at end moiety to form an XNTP. The linkages serve to constrain the tether in a "constrained configuration". Tethers have a "constrained configuration" and an "expanded configuration". The constrained configuration is found in XNTPs and in the daughter strand, or Xpandomer intermediate. The constrained configuration of the tether is the precursor to the expanded configuration, as found in Xpandomer products. The transition from the constrained configuration to the expanded configuration results cleaving of selectively cleavable phosphoramidate bonds. Tethers comprise one or more reporters or reporter constructs along its length that can encode sequence information of substrates. The tether provides a means to expand the length of the Xpandomer and thereby lower the sequence information linear density.

"Tether element" or "tether segment" is a polymer having a generally linear dimension with two terminal ends, where the ends form end-linkages for concatenating the tether elements. Tether elements are segments of tether. Such polymers can include, but are not limited to: polyethylene glycols, polyglycols, polypyridines, polyisocyanides, polyisocyanates, poly(triarylmethyl)methacrylates, polyaldehydes, polypyrrolinones, polyureas, polyglycol phosphodiesters, polyacrylates, polymethacrylates, polyacrylamides, polyvinyl esters, polystyrenes, polyamides, polyurethanes, polycarbonates, polybutyrates, polybutadienes, polybutyrolactones, polypyrrolidinones, polyvinylphosphonates, polyacetamides, polysaccharides, polyhyaluranates, polyamides, polyimides, polyesters, polyethylenes, polypropylenes, polystyrenes, polycarbonates, polyterephthalates, polysilanes, polyurethanes, polyethers, polyamino acids, polyglycines, polyprolines, N-substituted polylysine, polypeptides, side-chain N-substituted peptides, poly-N-substituted glycine, peptoids, side-chain carboxyl-substituted peptides, homopeptides, oligonucleotides, ribonucleic acid oligonucleotides, deoxynucleic acid oligonucleotides, oligonucleotides modified to prevent Watson-Crick base pairing, oligonucleotide analogs, polycytidylic acid, polyadenylic acid, polyuridylic acid, polythymidine, polyphosphate, polynucleotides, polyribonucleotides, polyethylene glycol-phosphodiesters, peptide polynucleotide analogues, threosyl-polynucleotide analogues, glycol-polynucleotide analogues, morpholino-polynucleotide analogues, locked nucleotide oligomer analogues, polypeptide analogues, branched polymers, comb polymers, star polymers, dendritic polymers, random, gradient and block copolymers, anionic polymers, cationic polymers, polymers forming stem-loops, rigid segments and flexible segments.

A "reporter" is composed of one or more reporter elements. Reporters serve to parse the genetic information of the target nucleic acid.

"Reporter construct" comprises one or more reporters that can produce a detectable signal(s), wherein the detectable signal(s) generally contain sequence information. This signal information is termed the "reporter code" and is subsequently decoded into genetic sequence data. A reporter construct may also comprise tether segments or other architectural components including polymers, graft copolymers, block copolymers, affinity ligands, oligomers, haptens, aptamers, dendrimers, linkage groups or affinity binding group (e.g., biotin).

"Reporter Code" is the genetic information from a measured signal of a reporter construct. The reporter code is decoded to provide sequence-specific genetic information data.

Thus, in one embodiment the present disclosure provides a composition comprising a PEM as disclosed herein and a buffer. In another embodiment, the present disclosure provides a composition comprising a PEM as disclosed herein and a plurality of nucleotides and/or nucleotide analogs. In another embodiment, the present disclosure provides a composition comprising a PEM as disclosed herein and a polynucleotide. In another embodiment, the present disclosure provides a composition comprising a PEM as disclosed herein and a protein, where optionally the protein is a polymerase including any of the polymerases described above.

In one embodiment, the present disclosure provides a composition comprising a PEM compound of the present disclosure, e.g., a PEM compound of formula (I), and a molecular crowding agent. In general terms, molecular crowding agents include a range of large, neutral polymers. Examples of useful molecular crowding reagents include, but are not limited to, polyethylene glycol (PEG), ficoll, dextran, or polyvinyl alcohol. Exemplary molecular crowding reagents and formulations are set forth in U.S. Pat. No. 7,399,590, which is incorporated herein by reference. In one embodiment, the molecular crowding agent is a polyalkylene glycol, optionally having a number average molecular weight of 4,000-10,000. In one embodiment, the molecular crowing agent is a derivative of a polyalkylene glycol, e.g., one or both of the terminal hydroxyl groups of a polyalkylene glycol is in the form of an ester or ether group. In one embodiment, the molecular crowding agent is an inert, water soluble polymer.

In one embodiment, the present disclosure provides a composition comprising a PEM compound of the present disclosure and an aqueous buffer. In one embodiment the PEM compound has formula (I). In one option, the composition has a pH of about 6 to 8.5, and the buffer helps to stabilize the pH of the composition. An exemplary buffer is Tris HCl. Other suitable buffers include those known in there art, e.g., phosphate buffers, citric acid buffers, sodium acetate buffers, sodium carbonate buffers, and the like.

In one embodiment, the present disclosure provides a composition comprising a PEM compound of the present disclosure, e.g., a PEM compound of formula (I), and a polynucleotide. In one option, the polynucleotide is single stranded, e.g., single stranded DNA or a single stranded RNA. When the polynucleotide is intended to function as a primer, the polynucleotide is a single stranded DNA molecule. When intended to function as a primer, the polynucleotide may have a length of about 10-60 mer oligonucleotide, e.g., 20-30 oligonucleotides. The polynucleotide may alternatively function as a template, in which case it may be a single stranded DNA or a single stranded RNA, and may have a length of from 30 bases to kilobase and above values, e.g., 10 k bases and above.

In one embodiment, the present disclosure provides a composition comprising a PEM compound of the present disclosure, e.g., a PEM compound of formula (I), and a protein. For example, the protein may be an enzyme, a nucleic acid polymerase, a DNA polymerase. One example of a suitable DNA polymerase is a variant of DPO4 polymerase, as discussed herein.

In one embodiment, the present disclosure provides a composition comprising at least one PEM compound of the present disclosure, e.g., a PEM compound of formula (I), and a mixture of nucleotides or nucleotide analogs wherein the at least one compound increases the number and accuracy of nucleotide analogs incorporated into a daughter strand during a template-dependent polymerization reaction relative to an identical polymerization reaction absent the at least one compound. Optionally, the mixture of nucleotide analogs includes nucleoside triphosphoramidates, wherein each of the nucleoside triphosphoramidates has a nucleobase selected from adenine, guanine, thymine, and cytosine and a polymeric tether moiety, wherein a first end of the polymeric tether moiety is attached to the nucleobase and a second end of the polymeric ether moiety is attached to the alpha phosphate of the nucleoside triphosphoramidate to provide for expansion of the nucleotide analogs by cleavage of the phosphoramidate bond. Optionally, the composition further includes a buffer comprising one or more of Tris OAc, $NH_4OAc$, PEG, a water-miscible organic solvent such as dimethylformamide (DMF), N-methylpyrrolidone (NMP) or acetone, polyphosphate 60, NMS, and $MnCl_2$. Optionally, the composition also includes a single-strand binding protein. Optionally, the composition includes urea. Optionally, the mixture of nucleotide analogs includes nucleotide analogs that comprise a detectable label, where the detectable label is optionally one of luminescent, chemiluminescent, fluorescent, fluorogenic, chromophoric or chromogenic. In one embodiment, the composition includes two or more of these options, e.g., all, of these options.

In one aspect of the present disclosure, PEMs and compositions thereof as disclosed herein may be used to enhance a nucleic acid polymerization reaction or improve the properties of the resulting nucleic acid, e.g., the length or accuracy of the reaction product. Polymerization reactions include, e.g., primer extension reactions, PCR, mutagenesis, isothermal amplification, DNA sequencing, and probe labeling. Such methods are well known in the art. Enhancement may be provided by stimulating nucleotide incorporation through mechanisms such as increasing processivity of the polymerase (i.e., reducing dissociation of the polymerase from the template), increasing the rate of substrate binding or enzymatic catalysis, and increasing the accuracy or fidelity of nucleotide incorporation. In addition, enhancement may be provided by reducing impediments in the nucleic acid template, such as secondary structure and duplex DNA. Overcoming or improving such impediments through the addition of PEMs can allow polymerization reactions to occur more accurately or efficiently, or allow the use of lower denaturation/extension temperatures or isothermal temperatures.

In some embodiments, a PEM may be used in combination with another additive classes to enhance a polymerase reaction. One exemplary class of additives is minor groove binding proteins (MGBs). In one embodiment, the MGB is selected from the group consisting of distamycin A and synthetic analogs thereof, netropsin, (+)-CC-1065, duocarmycins, pyrrolobenzodiazepines, trabectin and analogs thereof, Hoechst dyes and derivatives thereof, lexitropsin, thiazotropsin A, diamidines, and polyamides. In certain embodiments, the at least one minor groove binding moiety is a Hoechst dye. More information about the use of MGBs to enhance a polymerase reaction may be found in applicants' co-filed application titled ENHANCEMENT OF NUCLEIC ACID POLYMERIZATION BY MGBS.

One exemplary polymerase reaction that can be enhanced with PEMs is the polymerization of the non-natural nucleotide analogs known as "XNTPs", which forms the basis of the "Sequencing by Expansion" (SBX) protocol, developed by Stratos Genomics (see, e.g., Kokoris et al., U.S. Pat. No. 7,939,259, "High Throughput Nucleic Acid Sequencing by Expansion"). In general terms, SBX uses this biochemical polymerization to transcribe the sequence of a DNA template onto a measurable polymer called an "Xpandomer". The transcribed sequence is encoded along the Xpandomer backbone in high signal-to-noise reporters that are separated by ~10 nm and are designed for high-signal-to-noise, well-differentiated responses. These differences provide significant performance enhancements in sequence read efficiency and accuracy of Xpandomers relative to native DNA. A generalized overview of the SBX process is depicted in FIGS. 1A, 1B, 1C and 1D.

XNTPs are expandable, 5' triphosphate modified nucleotide substrates compatible with template dependent enzymatic polymerization. A highly simplified XNTP is illustrated in FIG. 1A, which emphasizes the unique features of these nucleotide analogs: XNTP 100 has two distinct functional regions; namely, a selectively cleavable phosphoramidate bond 110, linking the 5' a-phosphate 115 to the nucleobase 105, and a tether 120 that is attached within the nucleoside triphosphoramidate at positions that allow for controlled expansion by intra-nucleotide cleavage of the phosphoramidate bond. The tether of the XNTP is comprised of linker arm moieties 125A and 125B separated by the selectively cleavable phosphoramidate bond. Each linker attaches to one end of a reporter 130 via a linking group (LG), as disclosed in U.S. Pat. No. 8,324,360 to Kokoris et al., which is herein incorporated by reference in its entirety. XNTP 100 is illustrated in the "constrained configuration", characteristic of the XNTP substrates and the daughter strand following polymerization. The constrained configuration of polymerized XNTPs is the precursor to the expanded configuration, as found in Xpandomer products. The transition from the constrained configuration to the expanded configuration occurs upon scission of the P—N bond of the phosphoramidate within the primary backbone of the daughter strand.

Figure 1B:
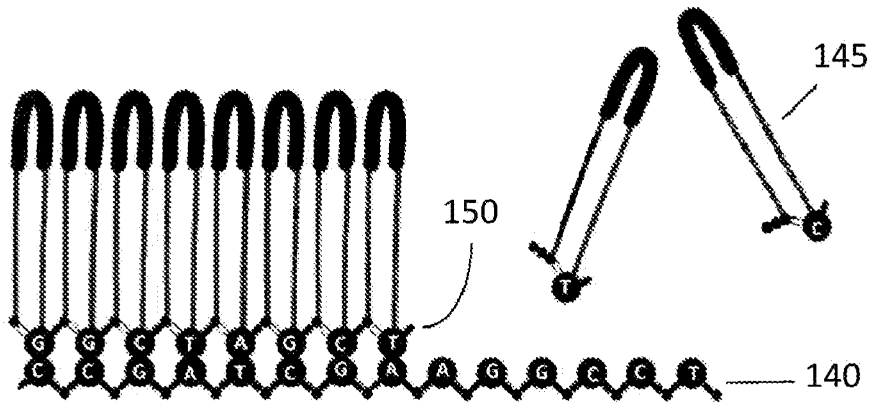
Figure 1C:
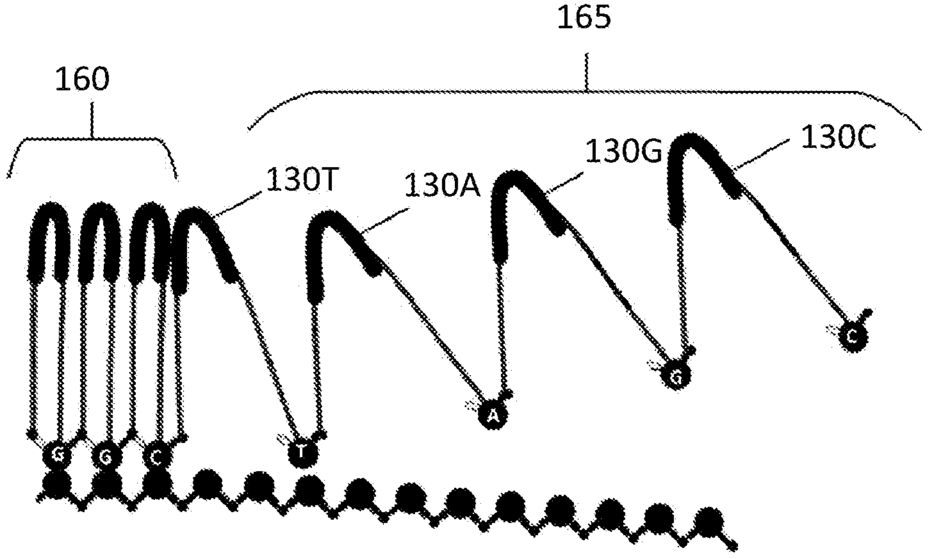

Synthesis of an Xpandomer is summarized in FIGS. 1B and 1C. During assembly, the monomeric XNTP substrates 145 (XATP, XCTP, XGTP and XTTP) are polymerized on the extendable terminus of a nascent daughter strand 150 by a process of template-directed polymerization using single-stranded template 140 as a guide. Generally, this process is initiated from a primer and proceeds in the 5' to 3' direction. Generally, a DNA polymerase or other polymerase is used to form the daughter strand, and conditions are selected so that a complimentary copy of the template strand is obtained. After the daughter strand is synthesized, the coupled tethers comprise the constrained Xpandomer that further comprises the daughter strand. Tethers in the daughter strand have the "constrained configuration" of the XNTP substrates. The constrained configuration of the tether is the precursor to the expanded configuration, as found the Xpandomer product.

As shown in FIG. 1C, the transition from the constrained configuration 160 to the expanded configuration 165 results from cleavage of the selectively cleavable phosphoramidate bonds (illustrated for simplicity by the unshaded ovals) within the primary backbone of the daughter strand. In this embodiment, the tethers comprise one or more reporters or reporter constructs, 130A, 130C, 130G, or 130T, specific for the nucleobase to which they are linked, thereby encoding the sequence information of the template. In this manner, the tethers provide a means to expand the length of the Xpandomer and lower the linear density of the sequence information of the parent strand.

Figure 1D:
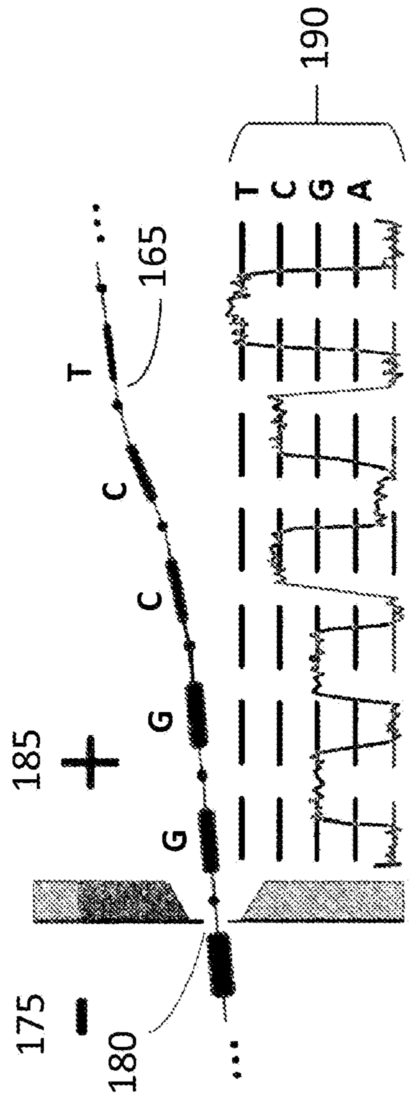

FIG. 1D illustrates an Xpandomer 165 translocating through a nanopore 180, from the cis reservoir 175 to the trans reservoir 185. Upon passage through the nanopore, each of the reporters of the linearized Xpandomer (in this illustration, labeled "G", "C" and "T") generates a distinct and reproducible electronic signal (illustrated by superimposed trace 190), specific for the nucleobase to which it is linked.

Figure 2:
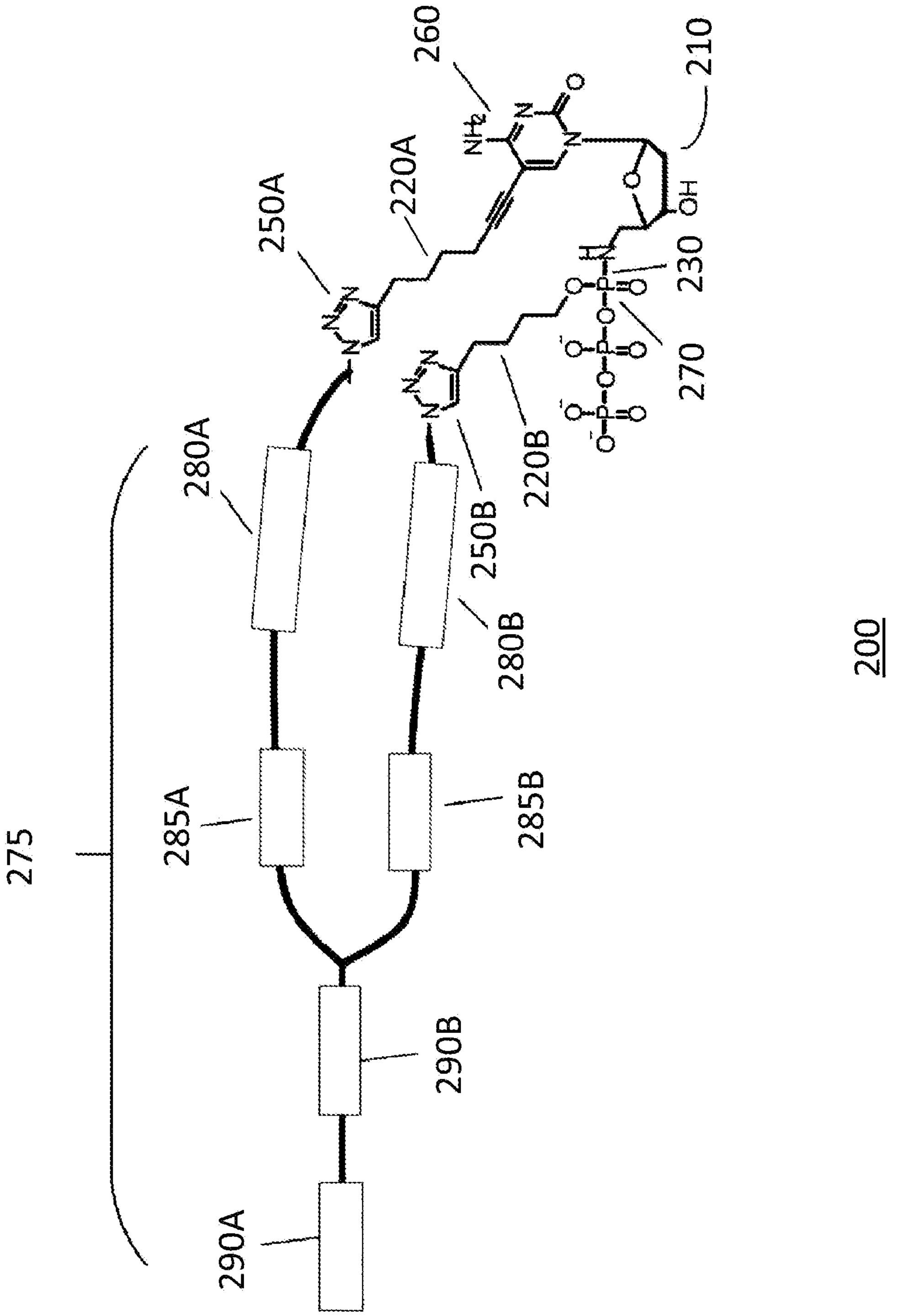
FIG. 2 is a schematic illustrating more details of one embodiment of an XNTP.

FIG. 2 depicts the generalized structure of an XNTP in more detail. XNTP 200 is comprised of nucleobase triphosphoramidate 210 with linker arm moieties 220A and 220B separated by selectively cleavable phosphoramidate bond 230. Tethers are joined to the nucleoside triphosphoramidate at linking groups 250A and 250B, wherein a first tether end is joined to the heterocycle 260 (represented here by cytosine, though the heterocycle may be any one of the four standard nucleobases, A, C, G, or T) and the second tether end is joined to the alpha phosphate 270 of the nucleobase backbone. The skilled artisan will appreciate that many suitable coupling chemistries known in the art may be used to form the final XNTP substrate product, for example, tether conjugation may be accomplished through a triazole linkage.

In this embodiment, tether 275 is comprised of several functional elements, including enhancers 280A and 280B, reporter codes 285A and 285B, and translation control elements (TCEs) 290A and 290B. Each of these features performs a unique function during translocation of the Xpandomer through a nanopore and generation of a unique and reproducible electronic signal. Tether 275 is designed for translocation control by hybridization (TCH). As depicted, the TCEs provide a region of hybridization which can be duplexed to a complementary oligomer (CO) and are positioned adjacent to the reporter codes. Different reporter codes are sized to block ion flow through a nanopore at different measureable levels. Specific reporter codes can be efficiently synthesized using phosphoramidite chemistry typically used for oligonucleotide synthesis. Reporters can be designed by selecting a sequence of specific phosphoramidites from commercially available libraries. Such libraries include but are not limited to polyethylene glycol with lengths of 1 to 12 or more ethylene glycol units, aliphatic with lengths of 1 to 12 or more carbon units, deoxyadenosine (A), deoxycytosine (C), deoxyguanodine (G), deoxythymine (T), abasic (Q). The duplexed TCEs associated with the reporter codes also contribute to the ion current blockage, thus the combination of the reporter code and the TCE can be referred to as a "reporter". Following the reporter codes are the enhancers, which in one embodiment comprise spermine polymers.

Figure 3:
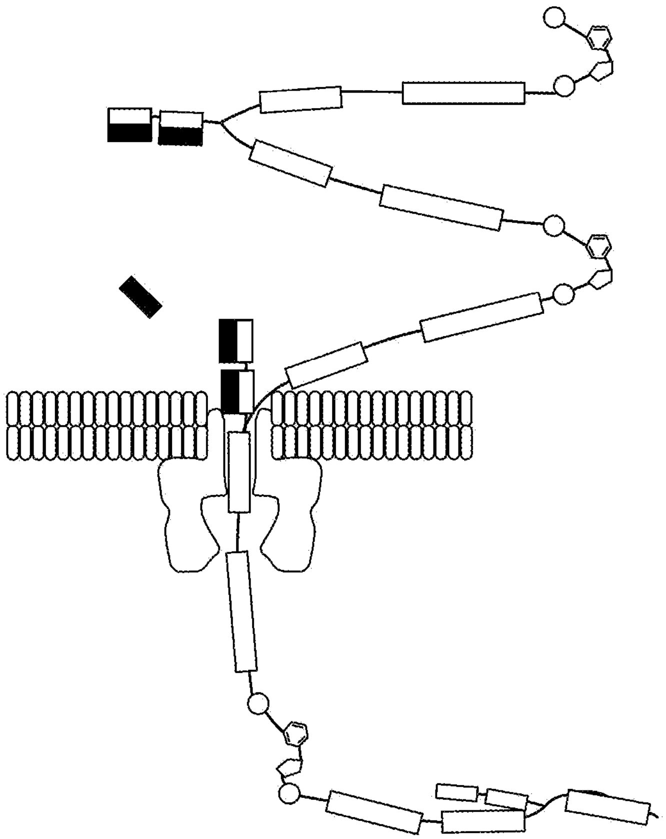
FIG. 3 is a schematic illustrating one embodiment of an Xpandomer passing through a biological nanopore.

FIG. 3 shows one embodiment of a cleaved Xpandomer in the process of translocating an a-hemolysin nanopore. This biological nanopore is embedded into a lipid bilayer membrane which separates and electrically isolates two reservoirs of electrolytes. A typical electrolyte has 1 molar KCl buffered to a pH of 7.0. When a small voltage, typically 100 mV, is applied across the bilayer, the nanopore constricts the flow of ion current and is the primary resistance in the circuit. Xpandomer reporters are designed to give specific ion current blockage levels and sequence information can be read by measuring the sequence of ion current levels as the sequence of reporters translocate the nanopore.

The α-hemolysin nanopore is typically oriented so translocation occurs by entering the vestibule side and exiting the stem side. As shown in FIG. 3, the nanopore is oriented to capture the Xpandomer from the stem side first. This orientation is advantageous using the TCH method because it causes fewer blockage artifacts that occur when entering vestibule first. Unless indicated otherwise, stem side first will be the assumed translocation direction. As the Xpandomer translocates, a reporter enters the stem until its duplexed TCE stops at the stem entrance. The duplex is ~2.4 nm in diameter whereas the stem entrance is ~2.2 nm so the reporter is held in the stem until the complimentary strand 395 of the duplex disassociates (releases) whereupon translocation proceeds to the next reporter. The free complementary strand is highly disfavored from entering the nanopore because the Xpandomer is still translocating and diffuses away from the pore.

In one embodiment, each member of a reporter code (following the duplex) is formed by an ordered choice of phosphoramidites that can be selected from many commercial libraries. Each constituent phosphoramidite contributes to the net ion resistance according to its position in the nanopore (located after the duplex stop), its displacement, its charge, its interaction with the nanopore, its chemical and thermal environment and other factors. The charge on each phosphoramidite is due, in part, to the phosphate ion which has a nominal charge of −1 but is effectively reduced by counterion shielding. The force pulling on the duplex is due to these effective charges along the reporter which are acted upon by the local electric fields. Since each reporter can have a different charge distribution, it can exert a different force on the duplex for a given applied voltage. The force transmitted along the reporter backbone also serves to stretch the reporter out to give a repeatable blocking response.

The Sequencing by Expansion (SBX) methodology developed by the inventors provides significant performance enhancements in sequence read efficiency and accuracy of Xpandomers relative to native DNA. However, initial transcription of the sequence of the natural DNA template onto the measurable Xpandomer relies on the ability of DNA polymerase to utilize XNTPs as substrates (the generalized structure of an XNTP is discussed herein with reference to FIG. 1A and FIG. 2). The inventors have found that most DNA polymerases do not efficiently polymerize XNTPs. However, the inclusion of a suitable additive, such as a PEM of the present disclosure improves the efficiency and accuracy of XNTP polymerization into Xpandomers. Thus, PEMs as disclosed herein may be used in the context of SBX methodology to enhance DNA polymerase primer extension reactions using XNTPs as substrates.

A representative primer extension reaction may include the following reagents: 2 pmol primer, 2.2 pmol 45mer oligonucleotide template, 50 pmol of each XNTP (XATP, XCTP, XGTP, and XTTP), 50 mM Tris HCl, pH 6.79, 200 mM NaCl, 20% PEG, 5% NMS, 0.5 nmol polyphosphate 60.19, 0.3 mM $MnCl_2$, and 0.6 μg of purified recombinant DNA polymerase protein. PEMs are added to this mixture at a concentration typically in the micro to millimolar range. Reactions may also include additional additives, such as single-strand binding protein (SSB), urea, and NMS. Reactions are run for 1 hr at 23° C. Reaction products (i.e., constrained Xpandomers) are treated to cleave the phosphoramidate bonds, thereby to generating linearized Xpandomers. Reaction products are analyzed using gel electrophoresis on 4-12% acrylamide gels to resolve and visualize Xpandomer products of different lengths.

Thus, in one embodiment, the present disclose provides an aqueous (water containing) composition comprising a PEM and a buffer, particularly a buffer suitable for conducting a DNA polymerization reaction, where Tris HCl is an exemplary buffer of this type. In one embodiment, the present disclosure provides a composition comprising a PEM and a DNA polymerase protein. In one embodiment, the present disclosure provides a composition comprising a PEM and a polynucleotide, e.g., a 20-90 mer, 20-60 mer, 30-90 mer, or a 30-60 mer, oligonucleotide. In one embodiment, the present disclosure provides a composition that comprises each of these components, i.e., an aqueous composition comprising a PEM, a buffer, a DNA polymerase protein and a polynucleotide.

To investigate the accuracy of enhancement of XNTP polymerization, primer extension products may be sequenced using the SBX protocol. Briefly, the constrained Xpandomer products of XNTP polymerization are cleaved to generate linearized Xpandomers. This is accomplished by first quenching the extension reaction with a solution containing 100 mM EDTA, 2 mM THPTA, and 2% Tween-20. Then the sample is subjected to amine modification with a solution of 1 M $NaHCO_3$ and 1 M succinic anhydride in DMF. Cleavage of the phosphoramidate bonds is carried out with 37% HCl and linearized Xpandomers are purified with QIAquick columns (QIAGEN, Inc.).

For sequencing, protein nanopores are prepared by inserting a-hemolysin into a DPhPE/hexadecane bilayer member in buffer B1, containing 2 M $NH_4Cl$ and 100 mM HEPES, pH 7.4. The cis well is perfused with buffer B2, containing 0.4 M $NH_4Cl$, 0.6 M GuCl, and 100 mM HEPES, pH 7.4. The Xpandomer sample is heated to 70° C. for 2 minutes, cooled completely, then a 2 μL sample is added to the cis well. A voltage pulse of 90 mV/390 mV/10 μs is then applied and data is acquired via Labview acquisition software.

Sequence data is analyzed by histogram display of the population of sequence reads from a single SBX reaction. The analysis software aligns each sequence read to the sequence of the template and trims the extent of the sequence at the end of the reads that does not align with the correct template sequence.

In one embodiment the present disclosure provides a method of increasing the accuracy of enhancement of XNTP polymerization, where the method comprises adding a PEM as disclosed herein to the DNA polymerization reaction as described above.

In one embodiment, the present disclosure provides a kit, where the kit may be used in a method as described herein. The kit will include at least one compound of the present disclosure, and one or more of a) a molecular crowding agent, b) an aqueous buffer, c) a protein such as a polymerase, d) a polynucleotide which may function, for example, as a primer, and/or a polynucleotide which may function, for example, as a template.

For example, in one embodiment the present disclosure provides a kit for sequencing a nucleic acid template. The kit includes at least one compound of the present disclosure and a mixture of nucleotide analogs. The compound of the present disclosure may be used to increases the number and accuracy of nucleotide analogs incorporated into a daughter strand during a template-dependent polymerization reaction relative to an identical polymerization reaction absent the at least one compound of the present disclosure. Optionally, the mixture of nucleotide analogs comprises nucleoside triphosphoramidates, wherein each of the nucleoside triphosphoramidates comprises a nucleobase selected from the group consisting of adenine, guanine, thymine, and cytosine and a polymeric tether moiety, wherein a first end of the polymeric tether moiety is attached to the nucleobase and a second end of the polymeric ether moiety is attached to the alpha phosphate of the nucleoside triphosphoramidate to provide for expansion of the nucleotide analogs by cleavage of the phosphoramidate bond. Optionally, the mixture of nucleotide analogs comprises nucleotide analogs comprising a detectable label, where the detectable label is an optically detectable label selected from the group consisting of luminescent, chemiluminescent, fluorescent, fluorogenic, chromophoric or chromogenic labels. Optionally, the kit includes an aqueous buffer comprising Tris OAc, $NH_4OAc$, PEG, a water-miscible organic solvent such as dimethylformamide (DMF), N-methyl-2-pyrrolidone (NMP), acetone, etc., polyphosphate 60, NMS, and $MnCl_2$. Optionally, the kit includes a single-strand binding protein. Optionally, the kit includes urea. Optionally, the kit includes two or more of these components, e.g., 3, or 4, or all of the named components.

Compounds may be prepared by methods known to one of ordinary skill in the art, where such methods may be identified through various reference books and databases. Suitable reference books and treatise that detail the synthesis of reactants useful in the preparation of compounds of the present disclosure, or provide references to articles that describe the preparation, include for example, "Synthetic Organic Chemistry," John Wiley & Sons, Inc., New York; S. R. Sandler et al., "Organic Functional Group Preparations," 2nd Ed., Academic Press, New York, 1983; H. O. House, "Modem Synthetic Reactions", 2nd Ed., W. A. Benjamin, Inc. Menlo Park, Calif 1972; T. L. Gilchrist, "Heterocyclic Chemistry", 2nd Ed., John Wiley & Sons, New York, 1992; J. March, "Advanced Organic Chemistry: Reactions, Mechanisms and Structure," 4th Ed., Wiley-Interscience, New York, 1992. Additional suitable reference books and treatise that detail the synthesis of reactants useful in the preparation of compounds of the present disclosure, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

EXAMPLES

Compounds as shown in Table 1 were prepared according to the general Examples disclosed herein.

Materials and Methods. 4-Azido salicylic acid and 2,6-dibromo-4-pyridine carboxylic acid were from Toronto Research Chemicals, Inc. (Toronto, ON, Canada). 4-azido-2-(trifluoromethyl)benzoic acid, 3-Amino-5-hydroxybenzoic acid and 4-aminoisopithalic acid were from Matrix Scientific (Columbia, SC, USA). 3-amino-6-(trifluoromethyl)benzoic acid hydrochloride, 1-(4-aminophenyl)-2,2,2-trifluoroethan-1-one, methyl glycylglycinate hydrochloride, 3,3,3-trifluoropropan-1-amine and diethyl 3-aminopropan-1-ylphosphonate were from Enamine LLC (Monmouth Junction, NJ, USA). Tris[(1-benzyl-1H-1,2,3-triazol-4-yl) methyl]amine (TBTA), 0-(7-Azabenzotriazol-1-yl)-N,N,N',N'-tetramethyluronium hexafluoro-phosphate (HATU), 1,3-diethynylbenzene, 2,6-diethynylpyridine, 3,5-diethynylpyridine, 3,6-diethynylcarbazole, 4-azidobenzoic acid, cyclopropyl amine, 6-amino-2-naphthoic acid, 4-aminophthalic acid, 4-amino-3-hydroxybenzoic acid, 4-amino-2-methylbenzoic acid, 4-amino-2,3,5,6-tetrafluorobenzoic acid, 4-amino-2-nitrobenzoic acid, n-(2-aminoethyl)acetamide, 4-(aminophenyl)phosphonic acid, 2,6-dichloro-9H-purine, Dimethyl aspartate hydrochloride, 4-amino-2-(trifluoromethyl)benzonitrile, 3,5-diaminobenzoic acid and 2,5-dibromofuran were from TCI America (Portland, OR, USA). 4-methoxy-2,6-dibromopyridine,4-nitro-2,6-dibromopyridine and 2,6-dibromo-4-pyridine carboxylic acid, Methyl glycinate hydrochloride were from Chem-Impex International, Inc. (Wood Dale, IL). Tetrakis(triphenylphosphine) palladium (0), ethynyltrimethylsilane, DMSO, DMF, MeOH, EtOAc, sodium ascorbate, copper sulfate, diisorpropylamine, EDTA, morpholine, diethylamine, ammonium hydroxide, ethylamine, ethanol, azetidine, n-ethyl-n-ethylamine, methyl 2,6-dichloropyridine-4-carboxylate, ethyl 2,6-dibromopyridine-4-carboxylate, 4-methyl-2,6-dichloropyridine,2-chloro-4-cyanopyridine, 4-amino-2-(trifluoromethyl)benzoic acid, 2-bromo-4-cyanopyridine, methylazido acetate, 4-azidoaniline hydrochloride, 4-methoxyphenyl azid4-amino-2-fluorobenzoic acid, n-butylamine, 3-amino-5-(trifluoromethyl)benzoic acid, 3-(4-aminophenyl)propionic acid, 4-(4-aminophenyl)-butyric acid, 4-amino-2-methoxybenzoic acid, 2-amino-3-(trifluoromethyl)benzoic acid, aminoethanol, 1,4-diaminobutane and 2,5-dibromothiophene were from Sigma-Aldrich Corp. (St. Louis, MO, USA). TLC and flash chromatography solvents were from Sigma-Aldrich or Thermo Fisher Scientific Inc. (Waltham, MA, USA).

Flash chromatography was performed on a Reveleris Prep Purification System from Buchi Corp. (New Castle, DE). The system was fitted with a hand packed column (2.3 cm diameter×8 cm height) filled with C18 Spherical Silica Gel (Cat. No. 76646-01) from Sorbent Technologies, Inc (Norcross, GA) and sealed with polypropylene frits. Samples of 1 to 1.5 mL were loaded directly on the head of the column. Mobile phases were water (A) and acetonitrile (B). A gradient of 0 to 2% B in 2 minutes followed by 2 to 100% B in 20 minutes at a flow of 28 ml/min. UV was monitored at 220 nm, 260 nm and 280 nm. Fractions were collected at UV threshold of 0.1 AU. Thin layer chromatography was performed with aluminum backed TLC Silica Gel 60 F254 (Cat. No. 1.05534.0001) from EMD Millipore Corp. (Billireca, MA, USA). ESI Mass Spec was performed by Numega Resonance Lab (San Diego, CA, USA) using a Perkin Elmer PE-SCIEX API-150 mass spectrometer in positive and negative mode.

TABLE 1
| Compound | Chemical Name | Structure |
| --- | --- | --- |
| 1 | 4,4'-(pyridine-2,6-diylbis(1H-1,2,3-triazole-4,1-diyl))bis(2-hydroxybenzoic acid) | 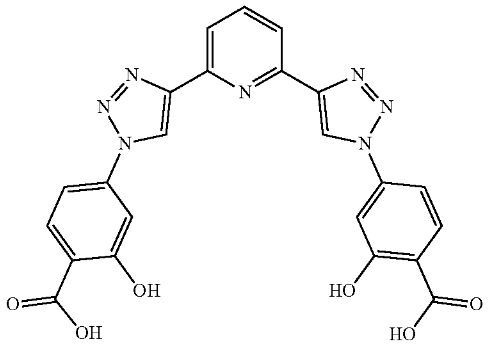 |
| 2 | 4,4'-(pyridine-3,5-diylbis(1H-1,2,3-triazole-4,1-diyl))bis(2-hydroxybenzoic acid) | 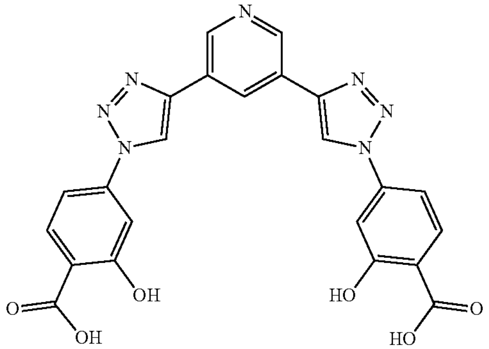 |
| 3 | 4,4'-(1,3-phenylenebis(1H-1,2,3-triazole-4,1-diyl))bis(2-hydroxybenzoic acid) | 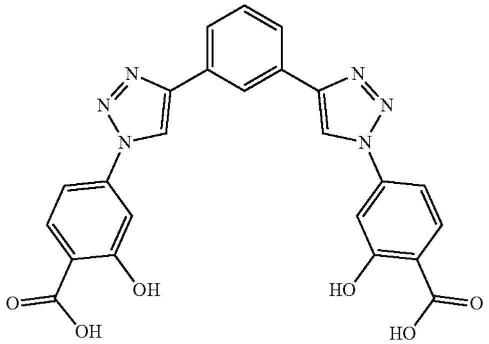 |
| 4 | 4,4'-((9H-carbazole-3,6-diyl)bis(1H-1,2,3-triazole-4,1-diyl))bis(2-hydroxybenzoic acid) | 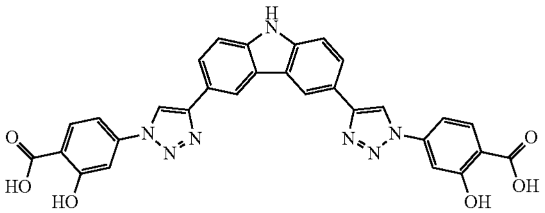 [SMILES: O=C(O)c1ccc(-n2cc(-c3ccc4[nH]c5ccc(-c6cn(-c7ccc(C(=O)O)c(O)c7)nn6)cc5c4c3)nn2)cc1O] |
| 5 | 4,4'-((9H-carbazole-3,6-diyl)bis(1H-1,2,3-triazole-4,1-diyl))dianiline | 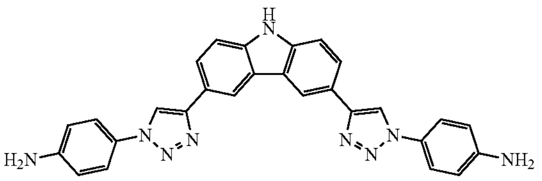 [SMILES: Nc1ccc(-n2cc(-c3ccc4[nH]c5ccc(-c6cn(-c7ccc(N)cc7)nn6)cc5c4c3)nn2)cc1] |

TABLE 1-continued
| Compound | Chemical Name | Structure |
|---|---|---|
| 6 | 4,4'-((9H-carbazole-3,6-diyl)bis(1H-1,2,3-triazole-4,1-diyl))dibenzoic acid | 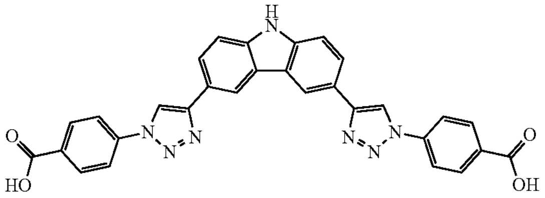 [SMILES: O=C(O)c1ccc(-n2cc(-c3ccc4[nH]c5ccc(-c6cn(-c7ccc(C(=O)O)cc7)nn6)cc5c4c3)nn2)cc1] |
| 7 | 3,6-bis(1-(4-methoxyphenyl)-1H-1,2,3-triazol-4-yl)-9H-carbazole | 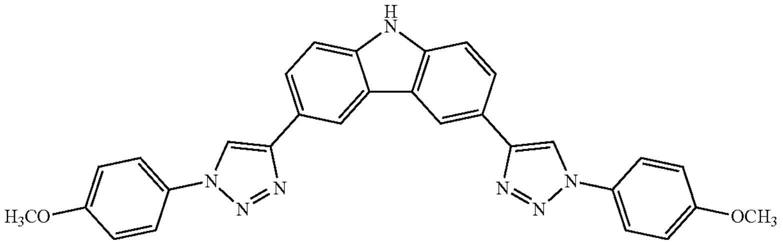 [SMILES: COc1ccc(-n2cc(-c3ccc4[nH]c5ccc(-c6cn(-c7ccc(OC)cc7)nn6)cc5c4c3)nn2)cc1] |
| 8 | dimethyl 2,2'-((9H-carbazole-3,6-diyl)bis(1H-1,2,3-triazole-4,1-diyl))diacetate | 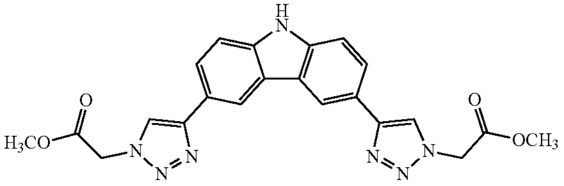 [SMILES: COC(=O)Cn1cc(-c2ccc3[nH]c4ccc(-c5cn(CC(=O)OC)nn5)cc4c3c2)nn1] |
| 9 | 4,4'-((4-methoxypyridine-2,6-diyl)bis(1H-1,2,3-triazole-4,1-diyl))bis(2-hydroxybenzoic acid) | 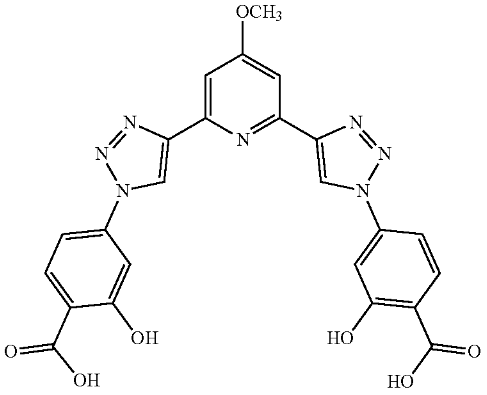 |
| 10 | 4,4'-((4-carboxypyridine-2,6-diyl)bis(1H-1,2,3-triazole-4,1-diyl))bis(2-hydroxybenzoic acid) | 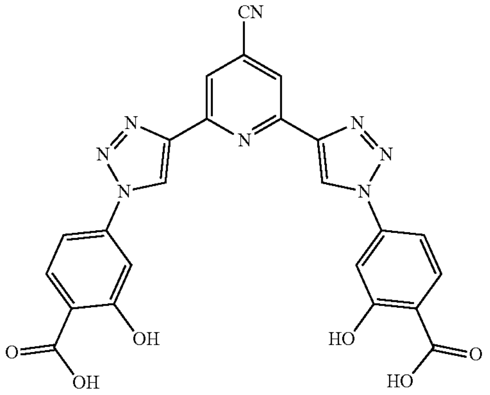 [SMILES: N#Cc1cc(-c2cn(-c3ccc(C(=O)O)c(O)c3)nn2)nc(-c2cn(-c3ccc(C(=O)O)c(O)c3)nn2)c1] |

TABLE 1-continued
| Compound | Chemical Name | Structure |
|---|---|---|
| 11 | 4,4'-((4-nitropyridine-2,6-diyl)bis(1H-1,2,3-triazole-4,1-diyl))bis(2-hydroxybenzoic acid) | 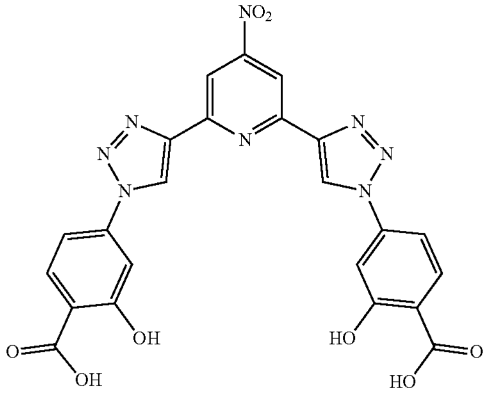 [SMILES: O=C(O)c1ccc(-n2cc(-c3cc([N+](=O)[O-])cc(-c4cn(-c5ccc(C(=O)O)c(O)c5)nn4)n3)nn2)cc1O] |
| 12 | 5,5'-((4-cyanopyridine-2,6-diyl)bis(1H-1,2,3-triazole-4,1-diyl))bis(2-hydroxybenzoic acid) | 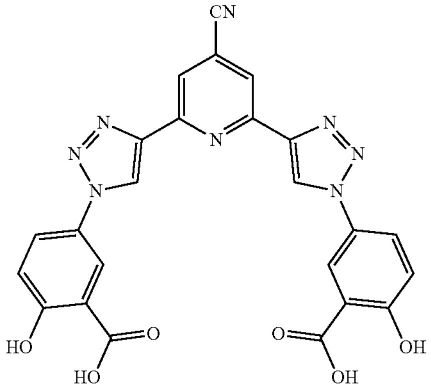 |
| 13 | 4,4'-((4-methylpyridine-2,6-diyl)bis(1H-1,2,3-triazole-4,1-diyl))bis(2-hydroxybenzoic acid) | 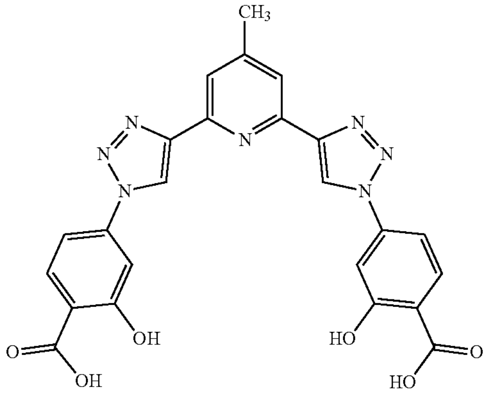 |
| 14 | 4,4'-((4-(ethoxycarbonyl)pyridine-2,6-diyl)bis(1H-1,2,3-triazole-4,1-diyl))bis(2-hydroxybenzoic acid) | 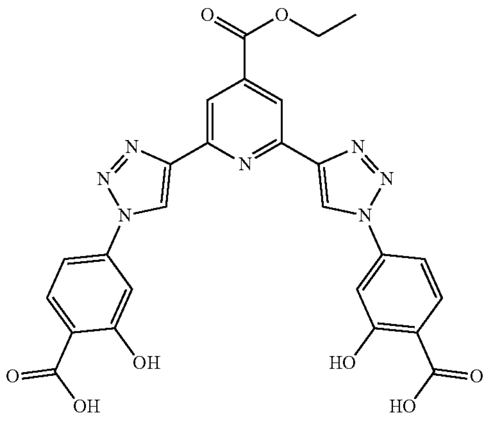 |

TABLE 1-continued
| Compound | Chemical Name | Structure |
| --- | --- | --- |
| 15 | 5,5'-((4-(ethoxycarbonyl)pyridine-2,6-diyl)bis(1H-1,2,3-triazole-4,1-diyl))bis(2-hydroxybenzoic acid) | 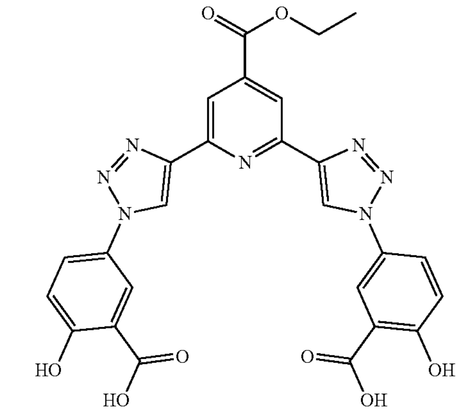 |
| 16 | 4,4'-((4-(methoxycarbonyl) pyridine-2,6-diyl)bis(1H-1,2,3-triazole-4,1-diyl))bis(2-hydroxybenzoic acid) | 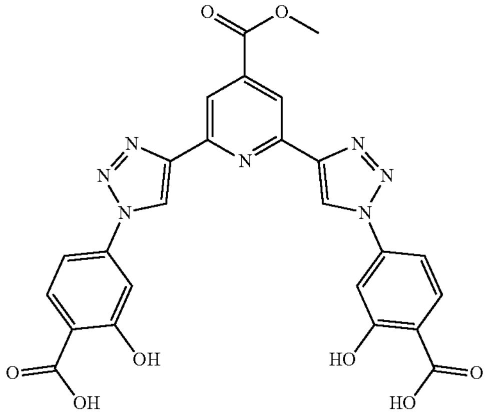 |
| 17 | 4,4'-((4-(ethylcarbamoyl)pyridine-2,6-diyl)bis(1H-1,2,3-triazole-4,1-diyl))bis(2-hydroxybenzoic acid) | 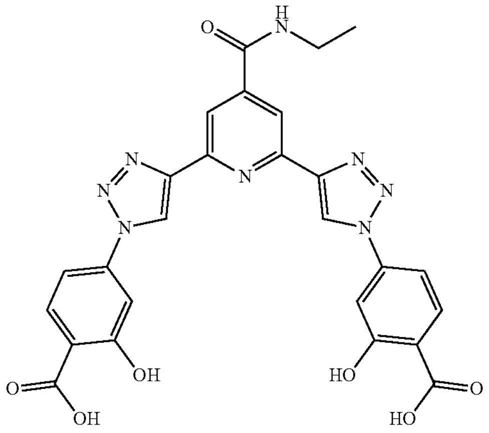 |

TABLE 1-continued
| Compound | Chemical Name | Structure |
| --- | --- | --- |
| 18 | 4,4'-((4-(methylcarbamoyl)pyridine-2,6-diyl)bis(1H-1,2,3-triazole-4,1-diyl))bis(2-hydroxybenzoic acid) | 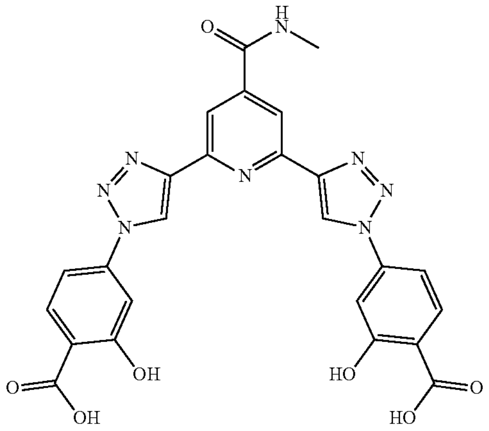 |
| 19 | 4,4'-((4-carbamoylpyridine-2,6-diyl)bis(1H-1,2,3-triazole-4,1-diyl))bis(2-hydroxybenzoic acid) | 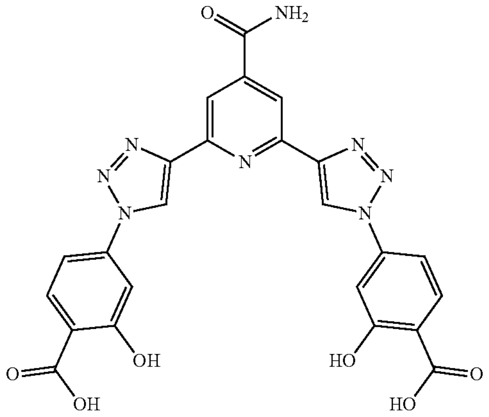 |
| 20 | 4,4'-(pyrazine-2,6-diylbis(1H-1,2,3-triazole-4,1-diyl))bis(2-hydroxybenzoic acid) | 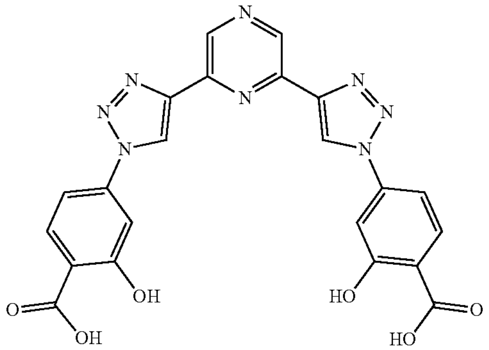 |
| 21 | 4,4'-(1,4-phenylenebis(1H-1,2,3-triazole-4,1-diyl))bis(2-hydroxybenzoic acid) | 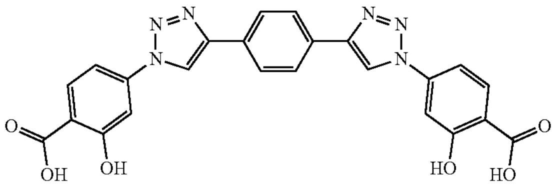 [SMILES: O=C(O)c1ccc(-n2cc(-c3ccc(-c4cn(-c5ccc(C(=O)O)c(O)c5)nn4)cc3)nn2)cc1O] |

TABLE 1-continued
| Compound | Chemical Name | Structure |
| --- | --- | --- |
| 22 | 4,4'-(1,3-phenylenebis(1H-1,2,3-triazole-4,1-diyl))dianiline | 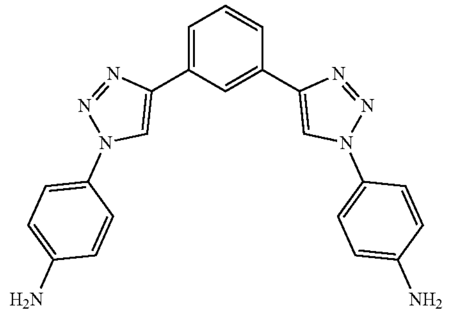 [SMILES: Nc1ccc(-n2cc(-c3cccc(-c4cn(-c5ccc(N)cc5)nn4)c3)nn2)cc1] |
| 23 | 4,4'-(1,3-phenylenebis(1H-1,2,3-triazole-4,1-diyl))dibenzoic acid | 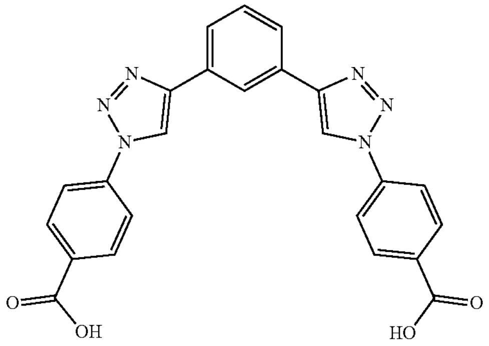 |
| 24 | 1,3-bis(1-(4-methoxyphenyl)-1H-1,2,3-triazol-4-yl)benzene | 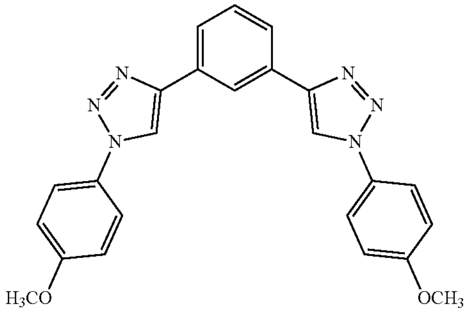 [SMILES: COc1ccc(-n2cc(-c3cccc(-c4cn(-c5ccc(OC)cc5)nn4)c3)nn2)cc1] |
| 25 | 4,4'-(pyridine-2,6-diylbis(1H-1,2,3-triazole-4,1-diyl))dianiline | 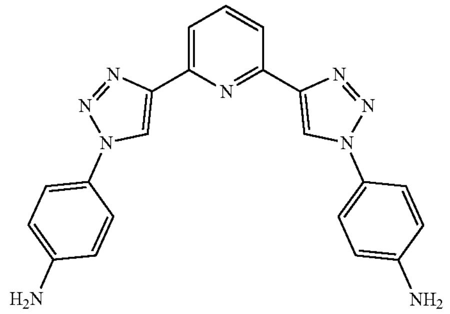 |

TABLE 1-continued
| Compound | Chemical Name | Structure |
| --- | --- | --- |
| 26 | 4,4'-(pyridine-2,6-diylbis(1H-1,2,3-triazole-4,1-diyl))dibenzoic acid | 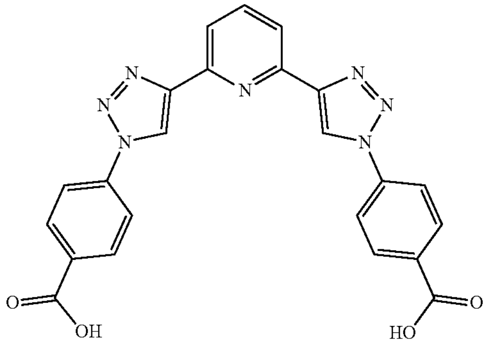 |
| 27 | 2,6-bis(1-(4-methoxyphenyl)-1H-1,2,3-triazol-4-yl)pyridine | 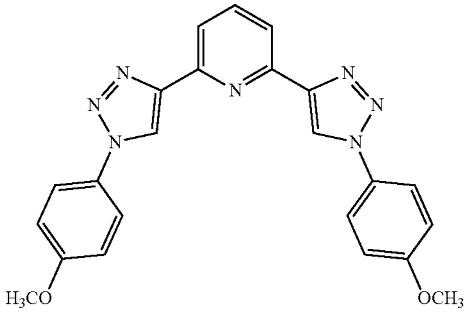 [SMILES: COc1ccc(-n2cc(-c3cccc(-c4cn(-c5ccc(OC)cc5)nn4)n3)nn2)cc1] |
| 28 | 4-(4-(3-(1-(4-carboxyphenyl)-1H-1,2,3-triazol-4-yl)phenyl)-1H-1,2,3-triazol-1-yl)-2-hydroxybenzoic acid | 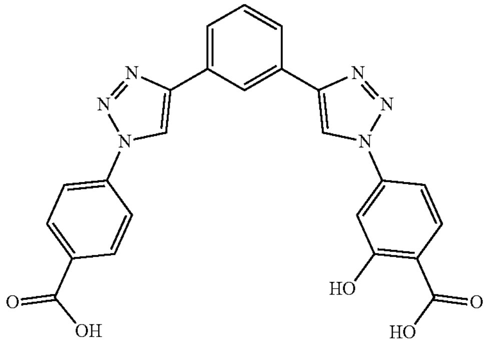 [SMILES: O=C(O)c1ccc(-n2cc(-c3cccc(-c4cn(-c5ccc(C(=O)O)c(O)c5)nn4)c3)nn2)cc1] |
| 29 | 4-(4-(3-(1-(4-methoxyphenyl)-1H-1,2,3-triazol-4-yl)phenyl)-1H-1,2,3-triazol-1-yl)benzoic acid | 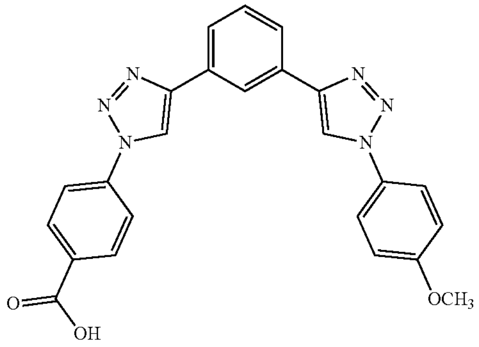 |

TABLE 1-continued
| Compound | Chemical Name | Structure |
| --- | --- | --- |
| 30 | 4,4'-((3,5-dimethylpyridine-2,6-diyl)bis(1H-1,2,3-triazole-4,1-diyl))bis(2-hydroxybenzoic acid) | 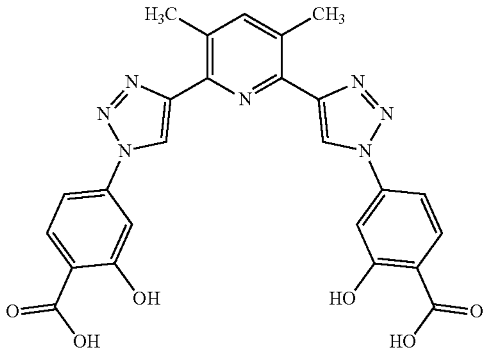 |
| 31 | 4,4'-((pyridine-2,6-diyl)bis(5-iodo-1H-1,2,3-triazole-4,1-diyl))bis(2-hydroxybenzoic acid) | 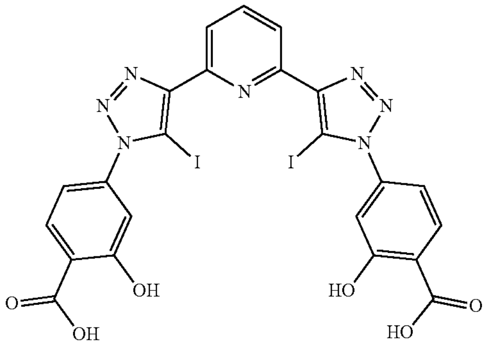 [SMILES: O=C(O)c1ccc(-n2nnc(-c3cccc(-c4nnn(-c5ccc(C(=O)O)c(O)c5)c4I)n3)c2I)cc1O] |
| 32 | 4,4'-((4-acetamidopyridine-2,6-diyl)bis(1H-1,2,3-triazole-4,1-diyl))bis(2-hydroxybenzoic acid) | 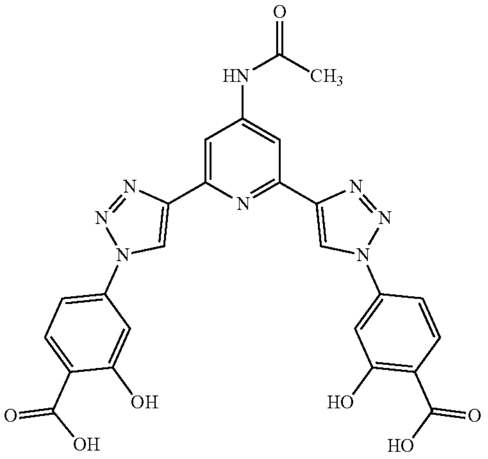 |

TABLE 1-continued
| Compound | Chemical Name | Structure |
| --- | --- | --- |
| 33 | 4,4'-((9-acetyl-9H-carbazole-3,6-diyl)bis(1H-1,2,3-triazole-4,1-diyl))bis(2-hydroxybenzoic acid) | 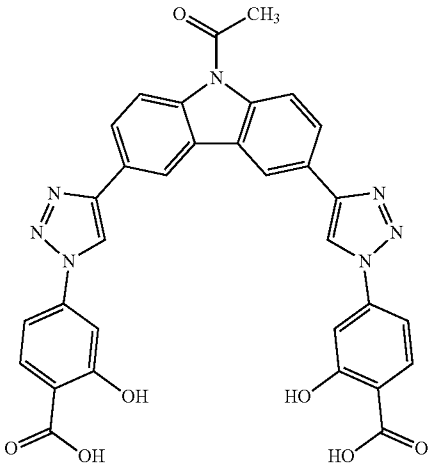 [SMILES: CC(=O)n1c2ccc(-c3cn(-c4ccc(C(=O)O)c(O)c4)nn3)cc2c2cc(-c3cn(-c4ccc(C(=O)O)c(O)c4)nn3)ccc21] |
| 34 | 4,4'-(pyridine-2,6-diylbis(1H-1,2,3-triazole-4,1-diyl))bis(N,2-dihydroxybenzamide) | 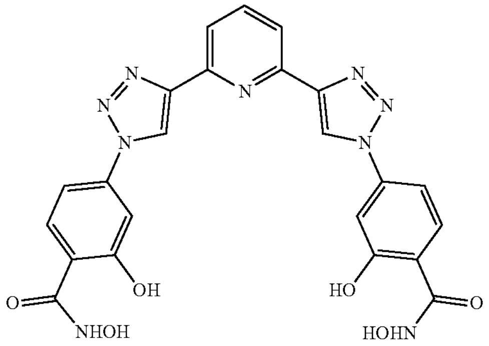 |
| 35 | 4,4'-(pyridine-2,6-diylbis(1H-1,2,3-triazole-4,1-diyl))bis(2-hydroxybenzamide) | 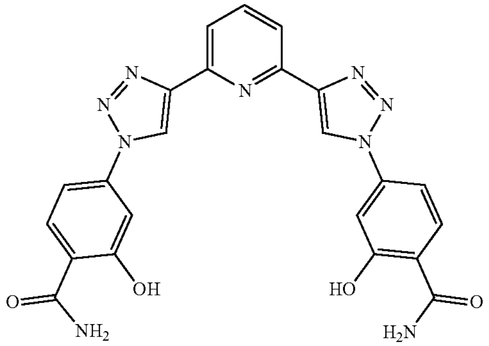 |
| 36 | 4,4'-((4-carboxypyridine-2,6-diyl)bis(1H-1,2,3-triazole-4,1-diyl))bis(2-hydroxybenzoic acid) | 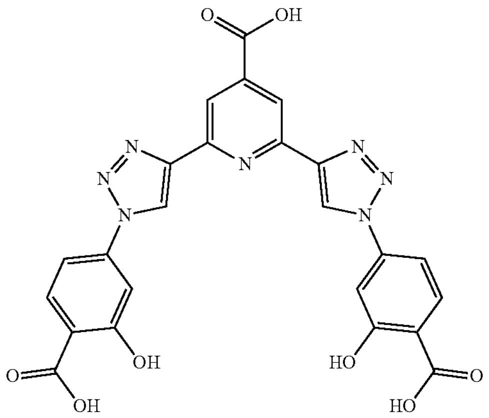 |

TABLE 1-continued
| Compound | Chemical Name | Structure |
| --- | --- | --- |
| 37 | 4,4'-((1,10-phenanthroline-2,9-diyl)bis(1H-1,2,3-triazole-4,1-diyl))bis(2-hydroxybenzoic acid) | 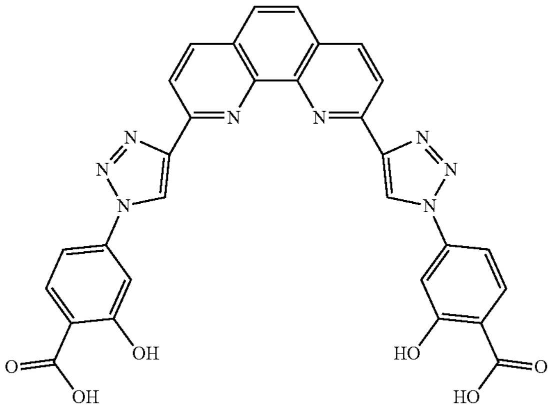 |
| 38 | 4,4'-((4-(trifluoromethyl)pyridine-2,6-diyl)bis(1H-1,2,3-triazole-4,1-diyl))bis(2-hydroxybenzoic acid) | 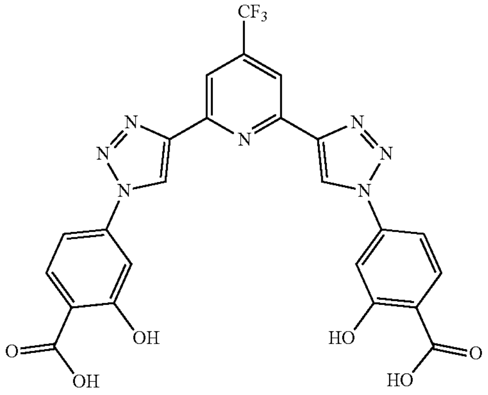 |
| 39 | 4,4'-((3-cyanopyridine-2,6-diyl)bis(1H-1,2,3-triazole-4,1-diyl))bis(2-hydroxybenzoic acid) | 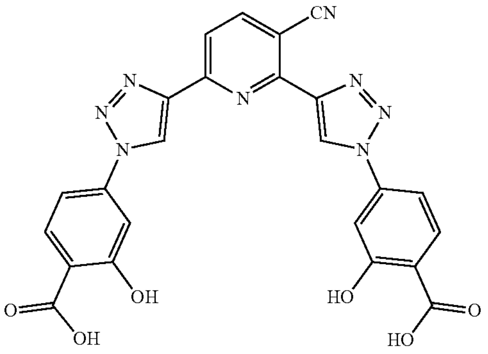 |
| 40 | 4,4'-((3-nitropyridine-2,6-diyl)bis(1H-1,2,3-triazole-4,1-diyl))bis(2-hydroxybenzoic acid) | 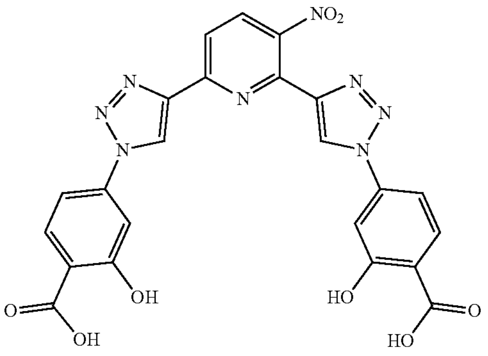 |

TABLE 1-continued

| Compound | Chemical Name | Structure |
|---|---|---|
| 41 | 3,3'-((4-cyanopyridine-2,6-diyl)bis(1H-1,2,3-triazole-4,1-diyl))bis(2-hydroxybenzoic acid) | 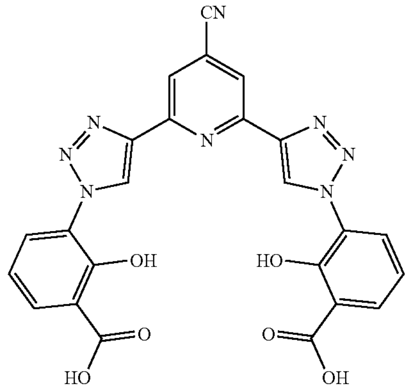 |
| 42 | 4,4'-((4-(tert-butoxycarbonyl)pyridine-2,6-diyl)bis(1H-1,2,3-triazole-4,1-diyl))bis(2-hydroxybenzoic acid) | 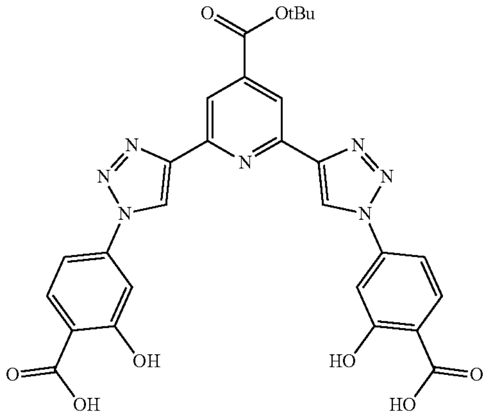 |
| 43 | 4-(4-(4-cyanopyridin-2-yl)-1H-1,2,3-triazol-1-yl)-2-hydroxybenzoic acid | 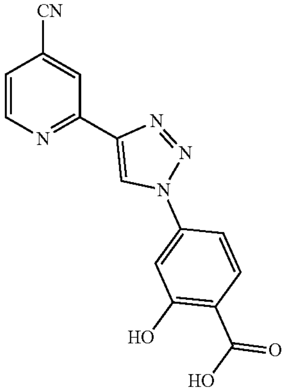 [SMILES: N#Cc1ccnc(-c2cn(-c3ccc(C(=O)O)c(O)c3)nn2)c1] |
| 44 | 5-(4-(6-(4-(3-carboxy-4-hydroxy-5-methylphenyl)-1H-1,2,3-triazol-1-yl)-4-(methoxycarbonyl)pyridin-2-yl)-1H-1,2,3-triazol-1-yl)-2-hydroxy-3-methylbenzoic acid | 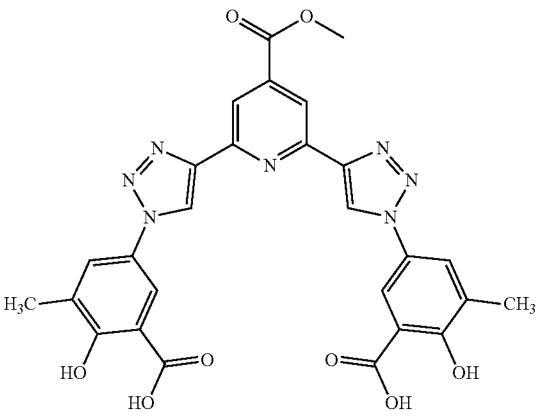 |

TABLE 1-continued
| Compound | Chemical Name | Structure |
|---|---|---|
| 45 | 4,4'-((4-(dimethylcarbamoyl) pyridine-2,6-diyl) bis(1H-1,2,3-triazole-4,1-diyl))bis(2-hydroxybenzoic acid) | 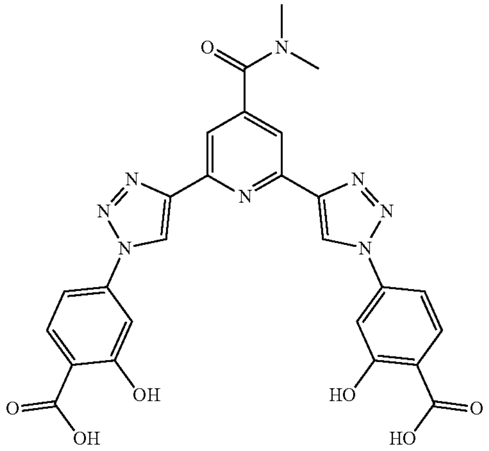 |
| 46 | 4,4'-((4-(cyclopropylcarbamoyl) pyridine-2,6-diyl)bis(1H-1,2,3-triazole-4,1-diyl))bis(2-hydroxybenzoic acid) | 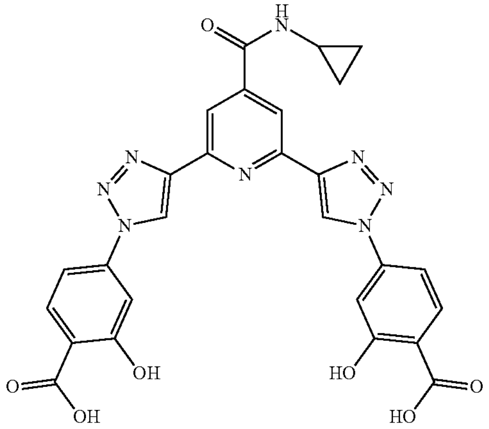 [SMILES: O=C(NC1CC1)c1cc(-c2cn(-c3ccc(C(=O)O)c(O)c3)nn2)nc(-c2cn(-c3ccc(C(=O)O)c(O)c3)nn2)c1] |
| 47 | 4,4'-((4-(but-3-yn-1-ylcarbamoyl)pyridine-2,6-diyl)bis(1H-1,2,3-triazole-4,1-diyl))bis(2-hydroxybenzoic acid) | 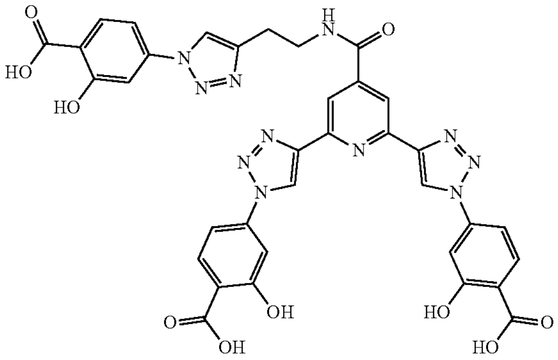 [SMILES: O=C(NCCc1cn(-c2ccc(C(=O)O)c(O)c2)nn1)c1cc(-c2cn(-c3ccc(C(=O)O)c(O)c3)nn2)nc(-c2cn(-c3ccc(C(=O)O)c(O)c3)nn2)c1] |

TABLE 1-continued
| Compound | Chemical Name | Structure |
|---|---|---|
| 48 | 4,4'-((4-(butylcarbamoyl)pyridine-2,6-diyl)bis(1H-1,2,3-triazole-4,1-diyl))bis(2-hydroxybenzoic acid) | 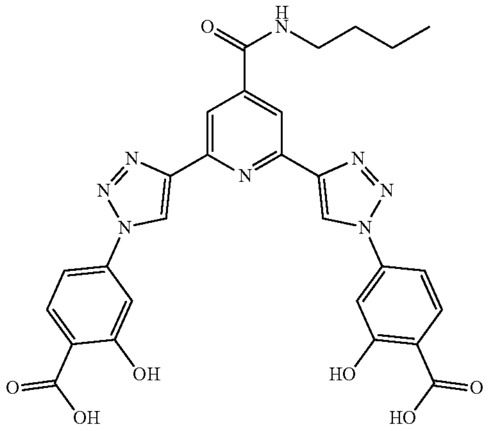 |
| 49 | 4,4'-((4-(diethylcarbamoyl) pyridine-2,6-diyl) bis(1H-1,2,3-triazole-4,1-diyl))bis(2-hydroxybenzoic acid) | 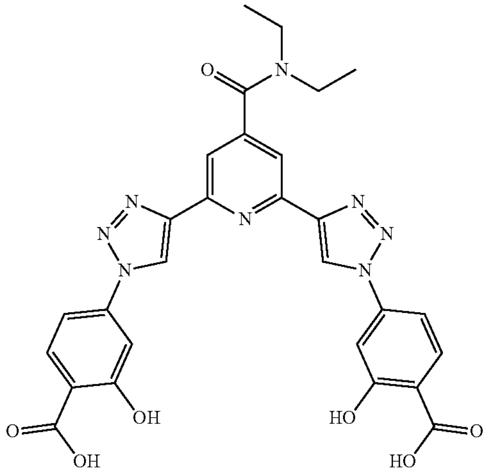 |
| 50 | 4,4'-((4-(tert-butylcarbamoyl)pyridine-2,6-diyl)bis(1H-1,2,3-triazole-4,1-diyl))bis(2-hydroxybenzoic acid) | 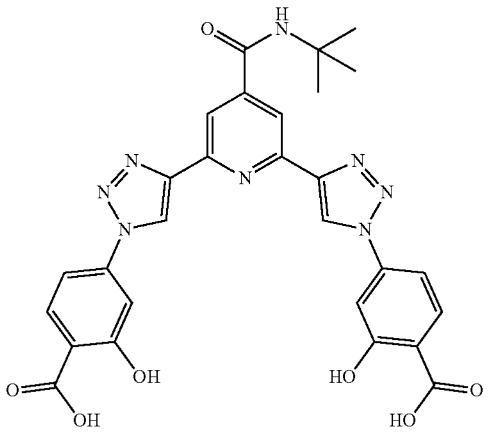 |

TABLE 1-continued
| Compound | Chemical Name | Structure |
|---|---|---|
| 51 | 4,4'-((4-(morpholine-4-carbonyl)pyridine-2,6-diyl)bis(1H-1,2,3-triazole-4,1-diyl))bis(2-hydroxybenzoic acid) | 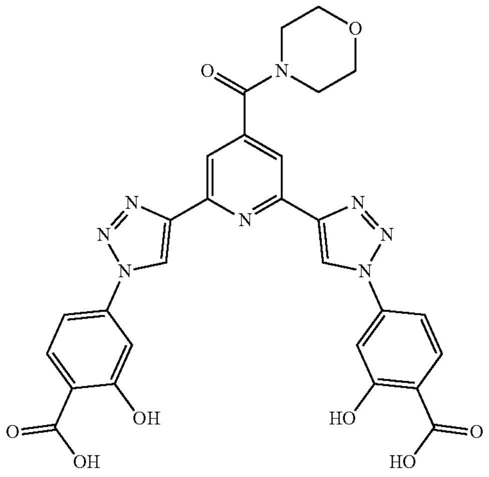 |
| 52 | 4,4'-((4-(propylcarbamoyl) pyridine-2,6-diyl) bis(1H-1,2,3-triazole-4,1-diyl))bis(2-hydroxybenzoic acid) | 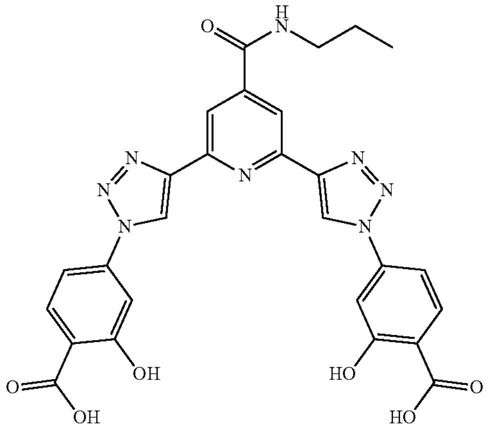 [SMILES: CCCNC(=O)c1cc(-c2cn(-c3ccc(C(=O)O)c(O)c3)nn2)nc(-c2cn(-c3ccc(C(=O)O)c(O)c3)nn2)c1] |
| 53 | 4,4'-((4-(phenylcarbamoyl) pyridine-2,6-diyl) bis(1H-1,2,3-triazole-4,1-diyl))bis(2-hydroxybenzoic acid) | 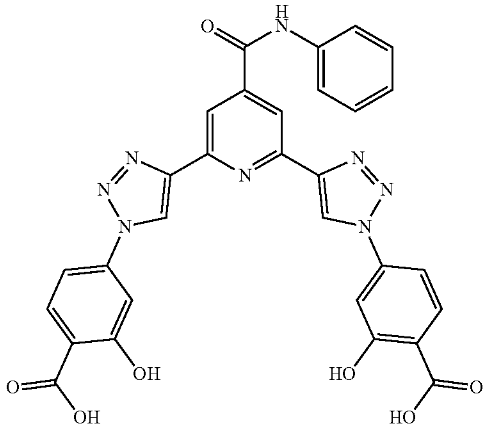 |

TABLE 1-continued
| Compound | Chemical Name | Structure |
|---|---|---|
| 54 | 4,4'-((4-((2-acetamidoethyl) carbamoyl)pyridine-2,6-diyl)bis(1H-1,2,3-triazole-4,1-diyl))bis(2-hydroxybenzoic acid) | 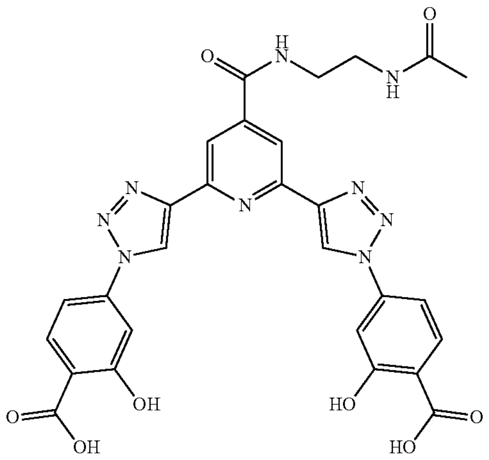 |
| 55 | 4,4'-((4-(4-cyclopropylpiperazine-1-carbonyl)pyridine-2,6-diyl)bis(1H-1,2,3-triazole-4,1-diyl))bis(2-hydroxybenzoic acid) | 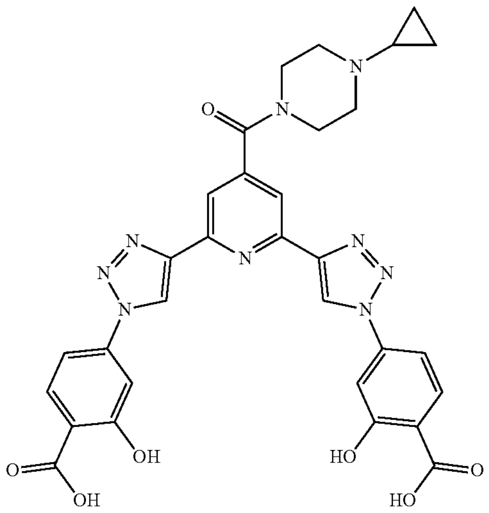 [SMILES: O=C(O)c1ccc(-n2cc(-c3cc(C(=O)N4CCN(C5CC5)CC4)cc(-c4cn(-c5ccc(C(=O)O)c(O)c5)nn4)n3)nn2)cc1O] |
| 56 | 4,4'-((4-(carbamimidoylcarbamoyl) pyridine-2,6-diyl)bis(1H-1,2,3-triazole-4,1-diyl))bis(2-hydroxybenzoic acid) | 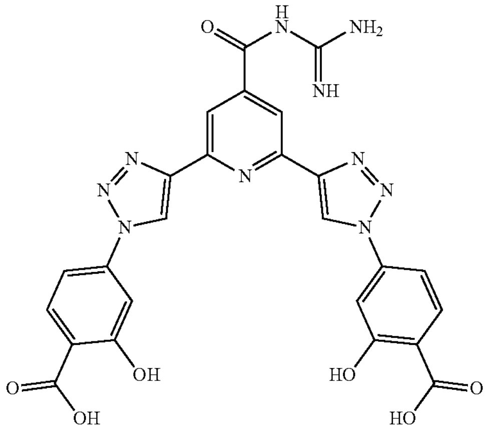 |

TABLE 1-continued

| Compound | Chemical Name | Structure |
| --- | --- | --- |
| 57 | 4,4'-((4-(piperidine-1-carbonyl)pyridine-2,6-diyl)bis(1H-1,2,3-triazole-4,1-diyl))bis(2-hydroxybenzoic acid) | 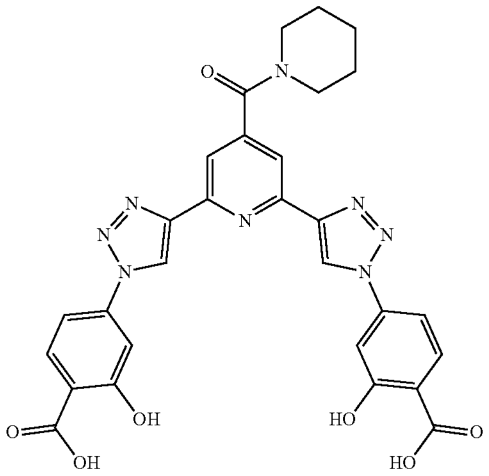 |
| 58 | 4,4'-((4-(cyclobutylcarbamoyl) pyridine-2,6-diyl)bis(1H-1,2,3-triazole-4,1-diyl))bis(2-hydroxybenzoic acid) | 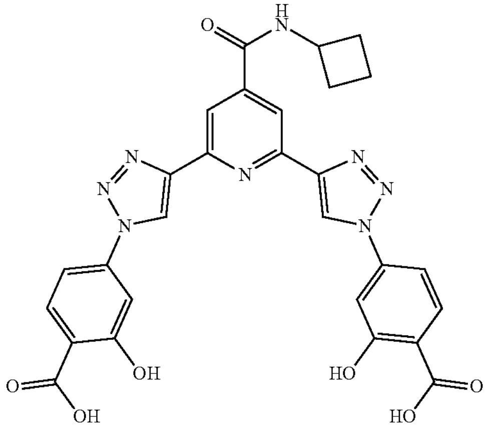 |
| 59 | 4,4'-((1,10-phenanthroline-3,8-diyl)bis(1H-1,2,3-triazole-4,1-diyl))bis(2-hydroxybenzoic acid) | 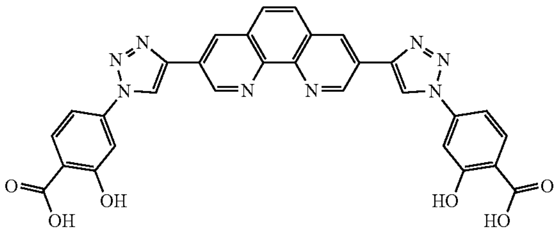 [SMILES: O=C(O)c1ccc(-n2cc(-c3cnc4c(ccc5cc(-c6cn(-c7ccc(C(=O)O)c(O)c7)nn6)cnc54)c3)nn2)cc1O] |
| 60 | 4,4'-((4-(cyclopentylcarbamoyl) pyridine-2,6-diyl)bis (1H-1,2,3-triazole-4,1-diyl))bis(2-hydroxybenzoic acid) | 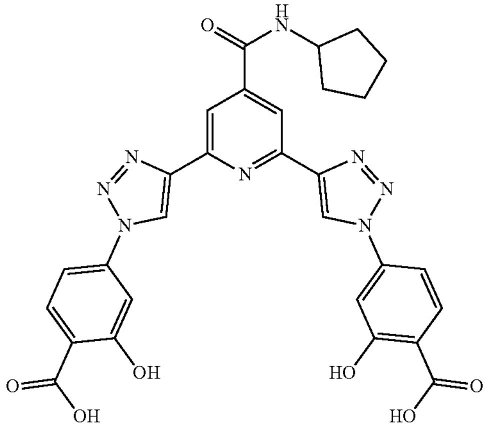 |

TABLE 1-continued
| Compound | Chemical Name | Structure |
|---|---|---|
| 61 | 4,4'-((4-(dipropylcarbamoyl)pyridine-2,6-diyl)bis(1H-1,2,3-triazole-4,1-diyl))bis(2-hydroxybenzoic acid) | 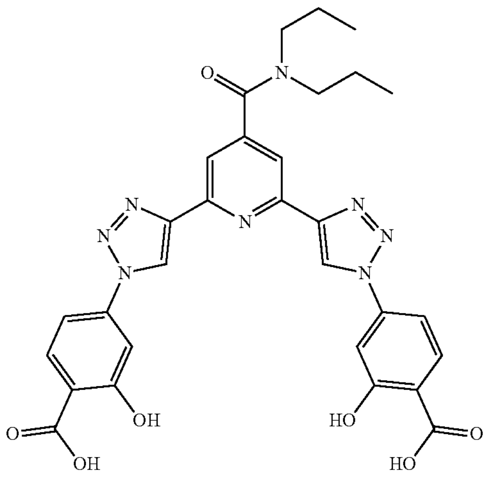 |
| 62 | 4,4'-((4-(di-sec-butylcarbamoyl)pyridine-2,6-diyl)bis(1H-1,2,3-triazole-4,1-diyl))bis(2-hydroxybenzoic acid) | 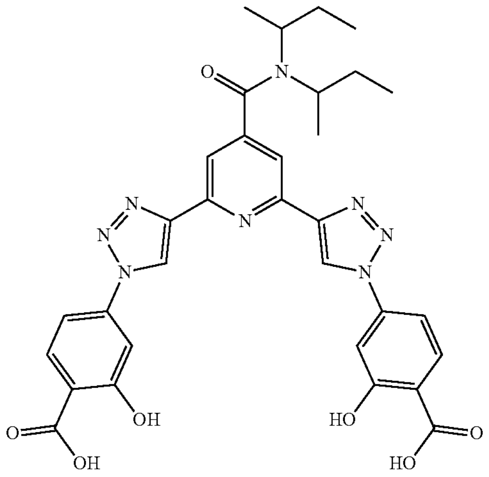 |
| 63 | 4,4'-(naphthalene-2,7-diylbis(1H-1,2,3-triazole-4,1-diyl))bis(2-hydroxybenzoic acid) | 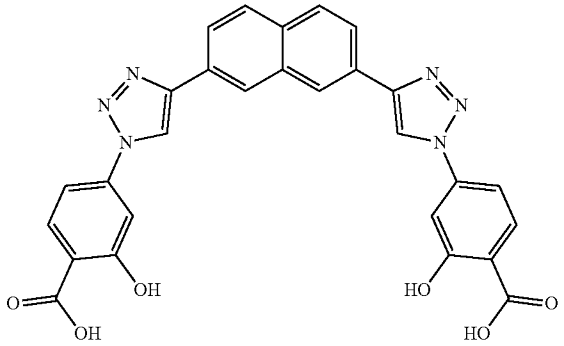 |

TABLE 1-continued
| Compound | Chemical Name | Structure |
|---|---|---|
| 64 | 4,4'-(naphthalene-2,3-diylbis(1H-1,2,3-triazole-4,1-diyl))bis(2-hydroxybenzoic acid) | 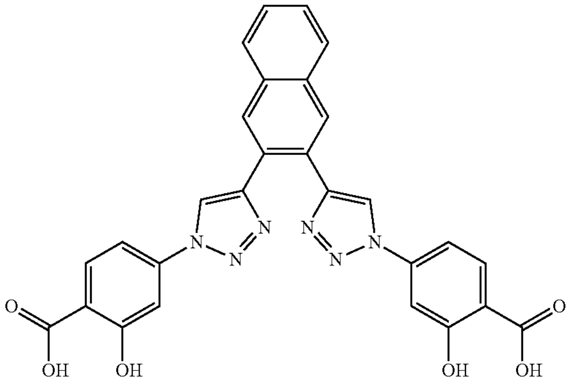 [SMILES: O=C(O)c1ccc(-n2cc(-c3cc4ccccc4cc3-c3cn(-c4ccc(C(=O)O)c(O)c4)nn3)nn2)cc1O] |
| 65 | 4,4'-((4-(dibutylcarbamoyl) pyridine-2,6-diyl) bis(1H-1,2,3-triazole-4,1-diyl))bis(2-hydroxybenzoic acid) | 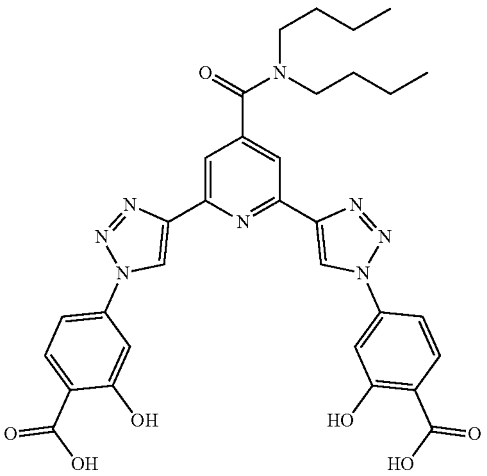 |
| 66 | 4,4'-((4-((2-hydroxyethyl)carbamoyl) pyridine-2,6-diyl)bis(1H-1,2,3-triazole-4,1-diyl))bis(2-hydroxybenzoic acid) | 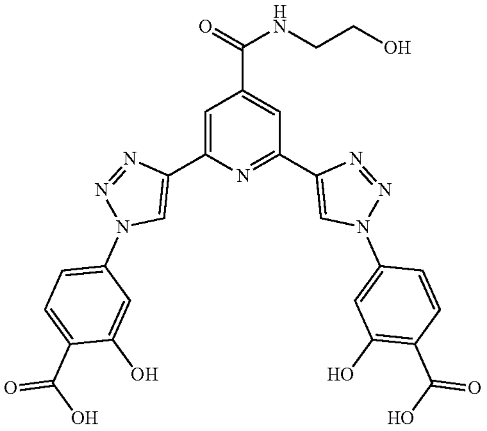 |

TABLE 1-continued
| Compound | Chemical Name | Structure |
| --- | --- | --- |
| 67 | 4,4'-((4-(cyclohexylcarbamoyl) pyridine-2,6-diyl)bis(1H-1,2,3-triazole-4,1-diyl))bis(2-hydroxybenzoic acid) | 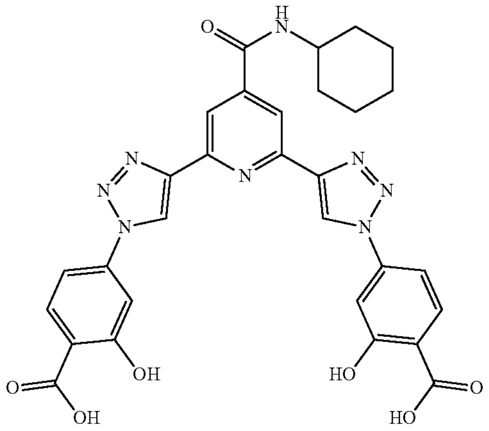 |
| 68 | 4,4'-((4-(benzylcarbamoyl) pyridine-2,6-diyl) bis(1H-1,2,3-triazole-4,1-diyl))bis(2-hydroxybenzoic acid) | 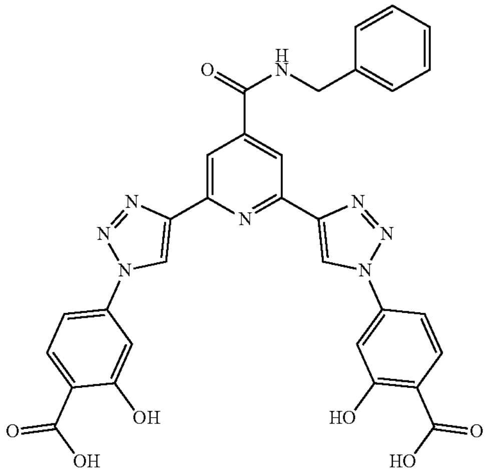 |
| 69 | 4,4'-((4-(4-methylpiperazine-1-carbonyl)pyridine-2,6-diyl)bis(1H-1,2,3-triazole-4,1-diyl))bis(2-hydroxybenzoic acid) | 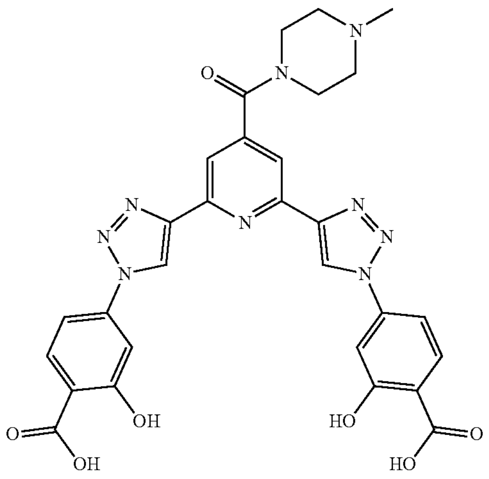 |

TABLE 1-continued
| Compound | Chemical Name | Structure |
| --- | --- | --- |
| 70 | 4-(4-(3-(1-(4-methoxyphenyl)-1H-1,2,3-triazol-4-yl)phenyl)-1H-1,2,3-txiazol-1-yl)benzoic acid | 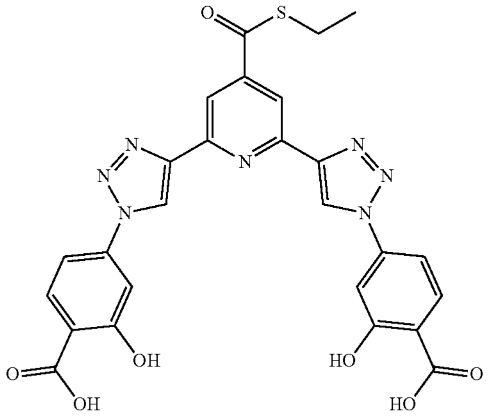 |
| 71 | 4,4',4'',4'''-((((butane-1,4-diylbis(azanediyl))bis(carbonyl))bis(pyridine-4,2,6-triyl))tetrakis(1H-1,2,3-triazole-4,1-diyl))tetrakis(2-hydroxybenzoic acid) | 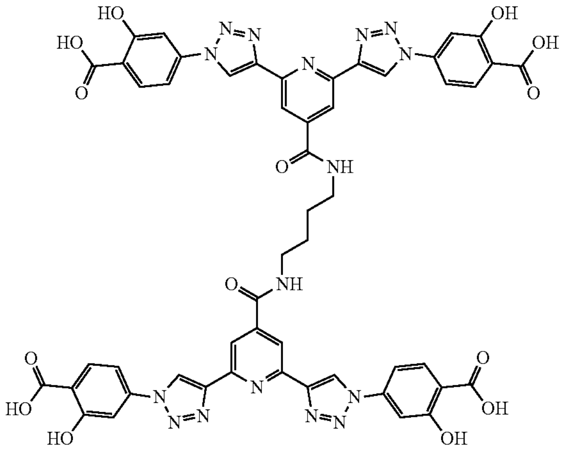 [SMILES: O=C(NCCCCNC(=O)c1cc(-c2cn(-c3ccc(C(=O)O)c(O)c3)nn2)nc(-c2cn(-c3ccc(C(=O)O)c(O)c3)nn2)c1)c1cc(-c2cn(-c3ccc(C(=O)O)c(O)c3)nn2)nc(-c2cn(-c3ccc(C(=O)O)c(O)c3)nn2)c1] |
| 72 | 4,4'-((4-(ethylcarbamoyl)pyridine-2,6-diyl)bis(1H-1,2,3-triazole-4,1-diyl))bis(3,5,6-trichloropicolinic acid) | 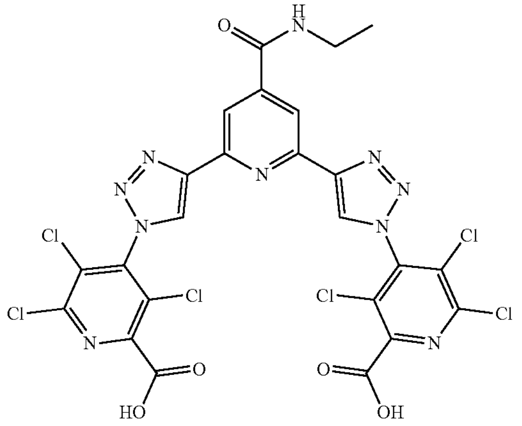 [SMILES: CCNC(=O)c1cc(-c2cn(-c3c(Cl)c(Cl)nc(C(=O)O)c3Cl)nn2)nc(-c2cn(-c3c(Cl)c(Cl)nc(C(=O)O)c3Cl)nn2)c1] |

TABLE 1-continued
| Compound | Chemical Name | Structure |
|---|---|---|
| 73 | 4,4'-((4-(ethylcarbamoyl)pyridine-2,6-diyl)bis(1H-1,2,3-triazole-4,1-diyl))bis(2-(trifluoromethyl)benzoic acid) | 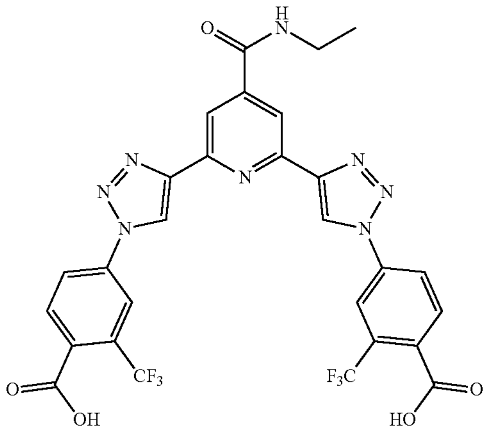 [SMILES: CCNC(=O)c1cc(-c2cn(-c3ccc(C(=O)O)c(C(F)(F)F)c3)nn2)nc(-c2cn(-c3ccc(C(=O)O)c(C(F)(F)F)c3)nn2)c1] |
| 74 | 7,7'-((4-(ethylcarbamoyl)pyridine-2,6-diyl)bis(1H-1,2,3-triazole-4,1-diyl))bis(2-hydroxy-1,8-naphthyridine-4-carboxylic acid) | 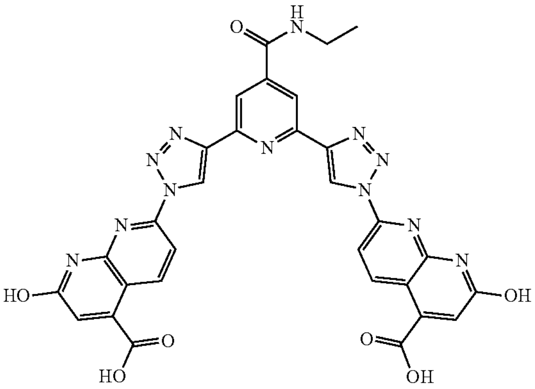 [SMILES: CCNC(=O)c1cc(-c2cn(-c3ccc4c(C(=O)O)cc(O)nc4n3)nn2)nc(-c2cn(-c3ccc4c(C(=O)O)cc(O)nc4n3)nn2)c1] |
| 75 | 5,5'-((4-(ethylcarbamoyl)pyridine-2,6-diyl)bis(1H-1,2,3-triazole-4,1-diyl))bis(2-(trifluoromethyl)benzoic acid) | 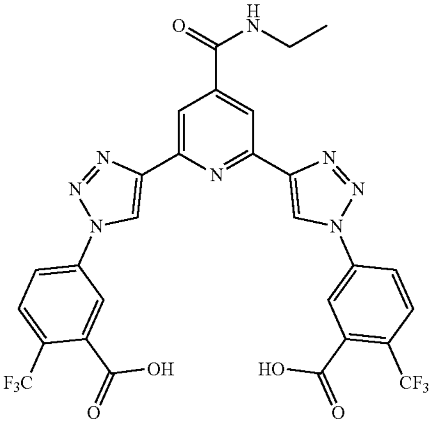 [SMILES: CCNC(=O)c1cc(-c2cn(-c3ccc(C(F)(F)F)c(C(=O)O)c3)nn2)nc(-c2cn(-c3ccc(C(F)(F)F)c(C(=O)O)c3)nn2)c1] |

TABLE 1-continued
| Compound | Chemical Name | Structure |
|---|---|---|
| 76 | 4,4'-((4-(ethylcarbamoyl)pyridine-2,6-diyl)bis(1H-1,2,3-triazole-4,1-diyl))bis(2-fluorobenzoic acid) | 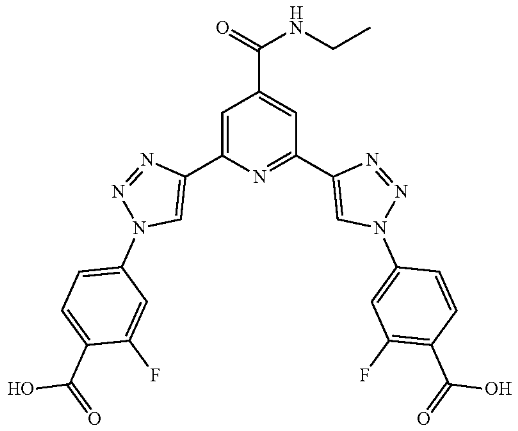 [SMILES: CCNC(=O)c1cc(-c2cn(-c3ccc(C(=O)O)c(F)c3)nn2)nc(-c2cn(-c3ccc(C(=O)O)c(F)c3)nn2)c1] |
| 77 | 5,5'-((4-(ethylcarbamoyl)pyridine-2,6-diyl)bis(1H-1,2,3-triazole-4,1-diyl))bis(3-fluorobenzoic acid) | 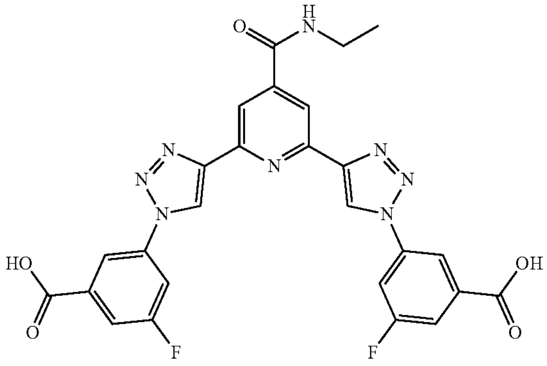 |
| 78 | 2-(1-(1H-benzo[d]imidazol-4-yl)-1H-1,2,3-triazol-4-yl)-6-(1-(1H-benzo[d]imidazol-7-yl)-1H-1,2,3-triazol-4-yl)-N-ethylisonicotinamide | 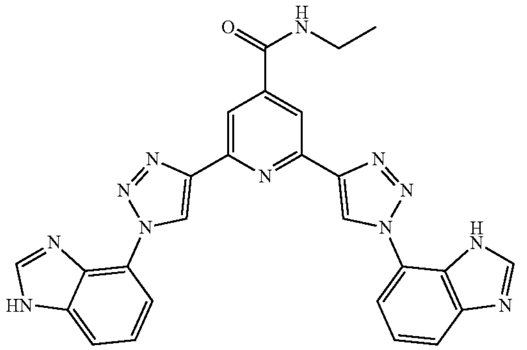 |

TABLE 1-continued
| Compound | Chemical Name | Structure |
| --- | --- | --- |
| Third Generation PEM Compounds | | |
| 79 | 4,4'-((4-(methylcarbamoyl)pyridine-2,6-diyl)bis(1H-1,2,3-triazole-4,1-diyl))bis(2-(trifluoromethyl)benzoic acid) | 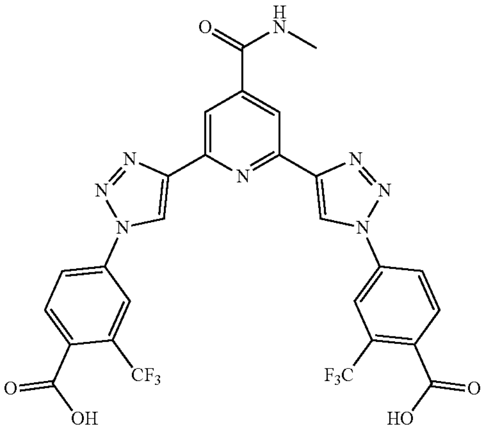 |
| 80 | 4,4'-((4-(morpholine-4-carbonyl)pyridine-2,6-diyl)bis(1H-1,2,3-triazole-4,1-diyl))bis(2-(trifluoromethyl)benzoic acid) | 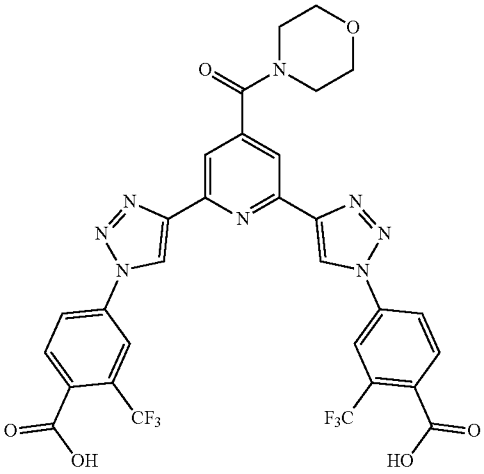 [SMILES: O=C(O)c1ccc(-n2cc(-c3cc(C(=O)N4CCOCC4)cc(-c4cn(-c5ccc(C(=O)O)c(C(F)(F)F)c5)nn4)n3)nn2)cc1C(F)(F)F] |
| 81 | 4,4'-((4-(diethylcarbamoyl)pyridine-2,6-diyl)bis(1H-1,2,3-triazole-4,1-diyl))bis(2-(trifluoromethyl)benzoic acid) | 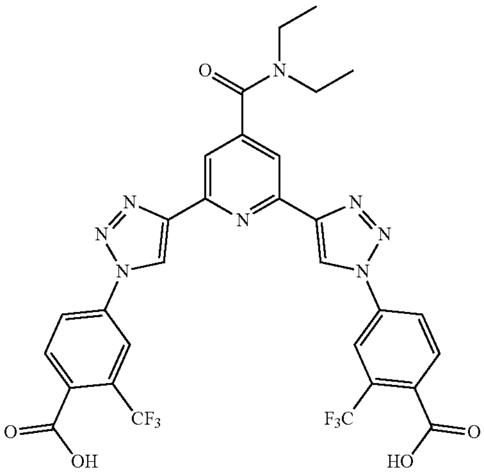 [SMILES: CCN(CC)C(=O)c1cc(-c2cn(-c3ccc(C(=O)O)c(C(F)(F)F)c3)nn2)nc(-c2cn(-c3ccc(C(=O)O)c(C(F)(F)F)c3)nn2)c1] |

TABLE 1-continued
| Compound | Chemical Name | Structure |
|---|---|---|
| 82 | 4,4'-((4-carbamoylpyridine-2,6-diyl)bis(1H-1,2,3-triazole-4,1-diyl))bis(2-(trifluoromethyl)benzoic acid) | 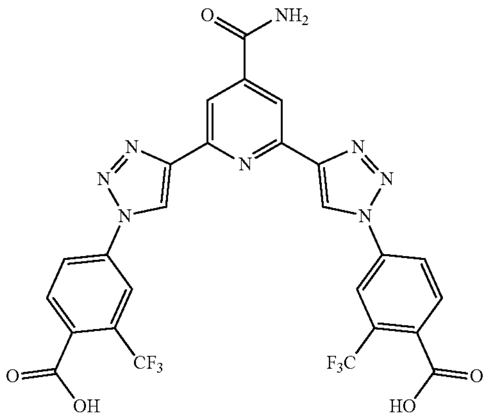 |
| 83 | 4,4'-((4-(ethoxycarbonyl)pyridine-2,6-diyl)bis(1H-1,2,3-triazole-4,1-diyl))bis(2-(trifluoromethyl)benzoic acid) | 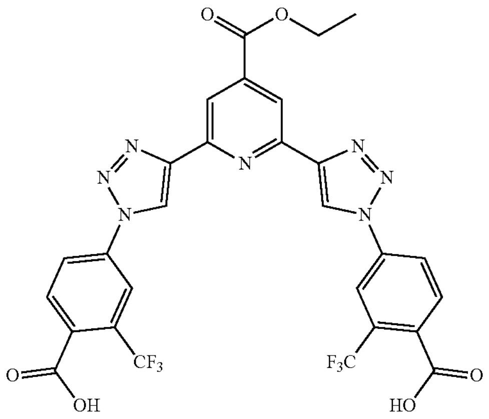 [SMILES: CCOC(=O)c1cc(-c2cn(-c3ccc(C(=O)O)c(C(F)(F)F)c3)nn2)nc(-c2cn(-c3ccc(C(=O)O)c(C(F)(F)F)c3)nn2)c1] |
| 84 | 4,4'-((4-(azetidine-1-carbonyl)pyridine-2,6-diyl)bis(1H-1,2,3-triazole-4,1-diyl))bis(2-hydroxybenzoic acid) | 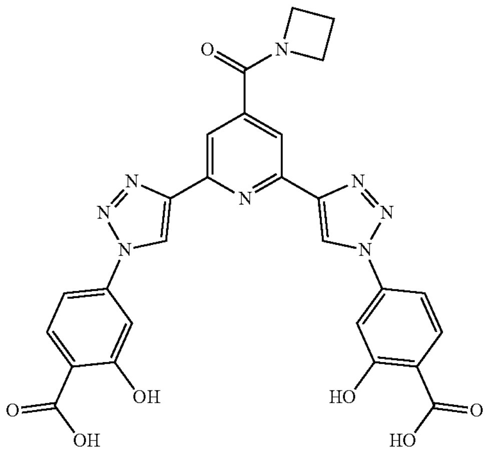 |

TABLE 1-continued
| Compound | Chemical Name | Structure |
| --- | --- | --- |
| 85 | 4,4'-((4-(ethyl(methyl)carbamoyl) pyridine-2,6-diyl)bis(1H-1,2,3-triazole-4,1-diyl))bis(2-hydroxybenzoic acid) | 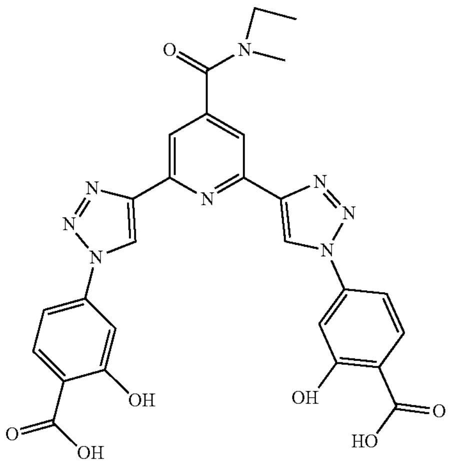 |
| 86 | N-ethyl-2,6-bis(1-(4-(2,2,2-trifluoroacetyl)phenyl)-1H-1,2,3-triazol-4-yl)isonicotinamide | 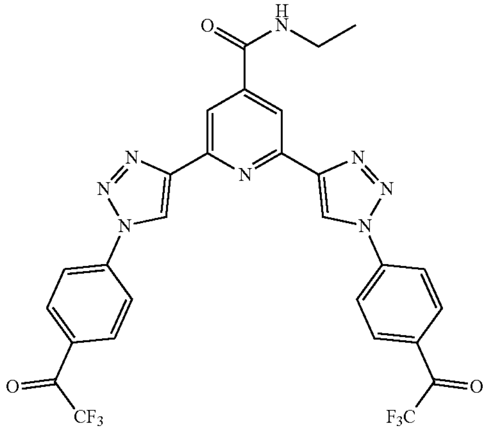 [SMILES: CCNC(=O)c1cc(-c2cn(-c3ccc(C(=O)C(F)(F)F)cc3)nn2)nc(-c2cn(-c3ccc(C(=O)C(F)(F)F)cc3)nn2)c1] |
| 87 | 4,4'-(pyridine-2,6-diylbis(1H-1,2,3-triazole-4,1-diyl))bis(2-(trifluoromethyl)benzoic acid) | 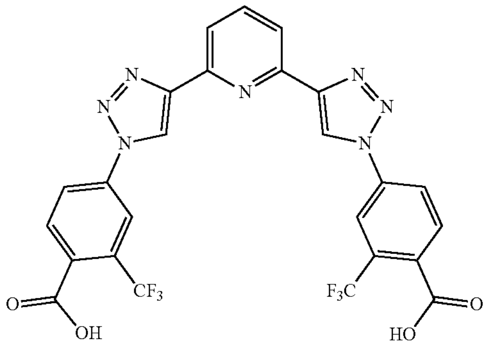 |

TABLE 1-continued
| Compound | Chemical Name | Structure |
| --- | --- | --- |
| 88 | 4,4'-((4-(cyclopropylcarbamoyl) pyridine-2,6-diyl)bis(1H-1,2,3-triazole-4,1-diyl))bis(2-(trifluoromethyl)benzoic acid) | 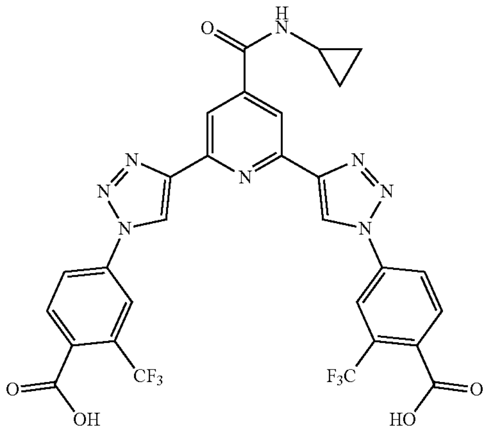 |
| 89 | 4,4'-((4-(butylcarbamoyl)pyridine-2,6-diyl)bis(1H-1,2,3-triazole-4,1-diyl))bis(2-(trifluoromethyl)benzoic acid) | 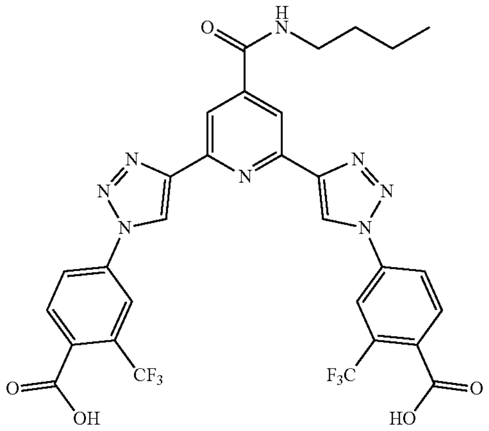 |
| 90 | 5,5'-((4-(diethylcarbamoyl) pyridine-2,6-diyl)bis (1H-1,2,3-triazole-4,1-diyl))bis(2-(trifluoromethyl)benzoic acid) | 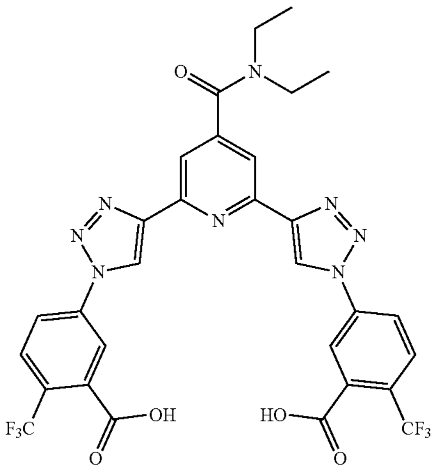 |

TABLE 1-continued

| Compound | Chemical Name | Structure |
|---|---|---|
| 91 | 5,5'-((4-(morpholine-4-carbonyl)pyridine-2,6-diyl)bis(1H-1,2,3-triazole-4,1-diyl))bis(2-(trifluoromethyl)benzoic acid) | 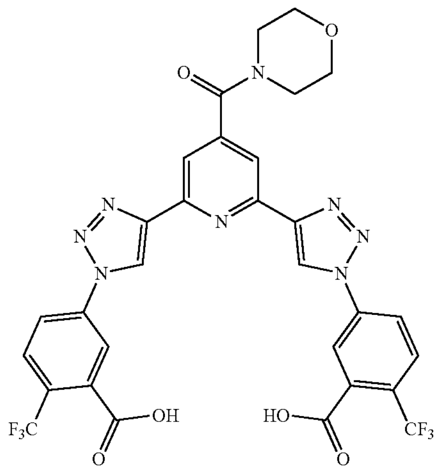 |
| 92 | 4,4'-(pyridazine-3,6-diylbis(1H-1,2,3-triazole-4,1-diyl))bis(2-hydroxybenzoic acid) | 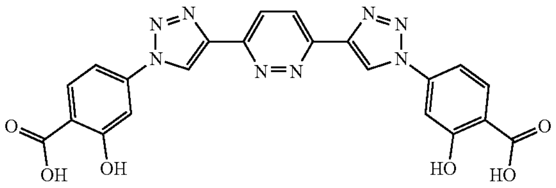 [SMILES: O=C(O)c1ccc(-n2cc(-c3ccc(-c4cn(-c5ccc(C(=O)O)c(O)c5)nn4)nn3)nn2)cc1O] |
| 93 | 5,5'-((4-(ethylcarbamoyl)pyridine-2,6-diyl)bis(1H-1,2,3-triazole-4,1-diyl))bis(3-(trifluoromethyl)benzoic acid) | 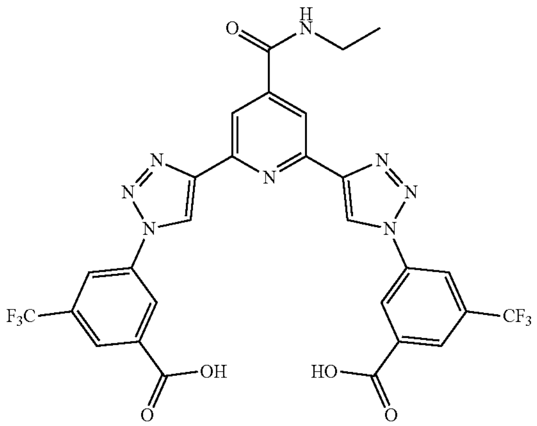 [SMILES: CCNC(=O)c1cc(-c2cn(-c3cc(C(=O)O)cc(C(F)(F)F)c3)nn2)nc(-c2cn(-c3cc(C(=O)O)cc(C(F)(F)F)c3)nn2)c1] |
| 94 | 4,4'-((4-carboxypyridine-2,6-diyl)bis(1H-1,2,3-triazole-4,1-diyl))bis(2-(trifluoromethyl)benzoic acid) | 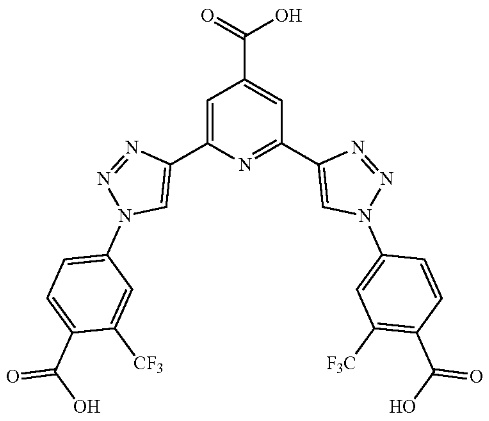 [SMILES: O=C(O)c1cc(-c2cn(-c3ccc(C(=O)O)c(C(F)(F)F)c3)nn2)nc(-c2cn(-c3ccc(C(=O)O)c(C(F)(F)F)c3)nn2)c1] |

TABLE 1-continued
| Compound | Chemical Name | Structure |
| --- | --- | --- |
| 95 | 3,3'-(((4-(ethylcarbamoyl)pyridine-2,6-diyl)bis(1H-1,2,3-triazole-4,1-diyl))bis(4,1-phenylene))dipropionic acid | 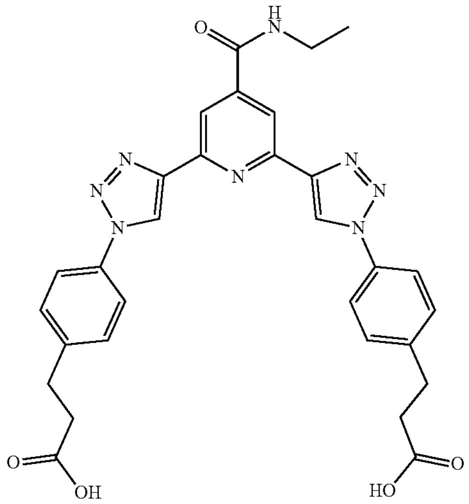 [SMILES: CCNC(=O)c1cc(-c2cn(-c3ccc(CCC(=O)O)cc3)nn2)nc(-c2cn(-c3ccc(CCC(=O)O)cc3)nn2)c1] |
| 96 | 4,4'-(((4-(ethylcarbamoyl)pyridine-2,6-diyl)bis(1H-1,2,3-triazole-4,1-diyl))bis(4,1-phenylene))dibutyric acid | 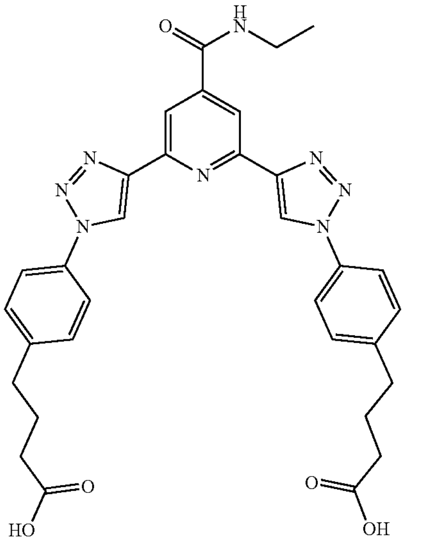 [SMILES: CCNC(=O)c1cc(-c2cn(-c3ccc(CCCC(=O)O)cc3)nn2)nc(-c2cn(-c3ccc(CCCC(=O)O)cc3)nn2)c1] |
| 97 | 4,4'-((4-(ethylcarbamoyl)pyridine-2,6-diyl)bis(1H-1,2,3-triazole-4,1-diyl))diphthalic acid | 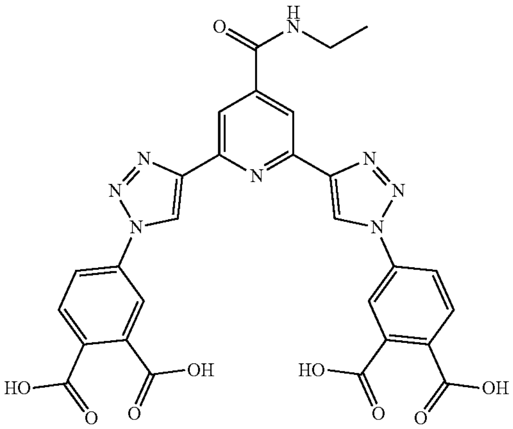 |

TABLE 1-continued
| Compound | Chemical Name | Structure |
| --- | --- | --- |
| 98 | 4,4'-((4-(ethylcarbamoyl)pyridine-2,6-diyl)bis(1H-1,2,3-triazole-4,1-diyl))bis(2-methoxybenzoic acid) | 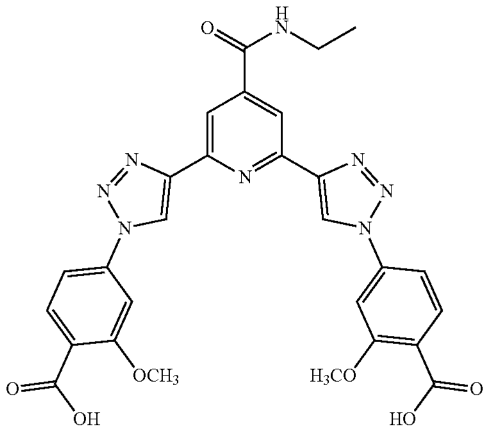 |
| 99 | 5,5'-((4-(ethylcarbamoyl)pyridine-2,6-diyl)bis(1H-1,2,3-triazole-4,1-diyl))diisophthalic acid | 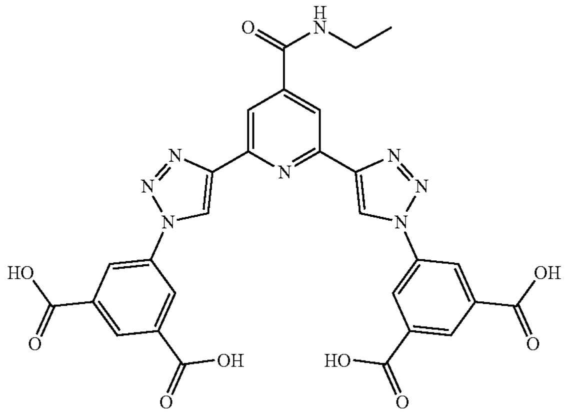 |
| 100 | 4,4'-((4-(ethylcarbamoyl)pyridine-2,6-diyl)bis(1H-1,2,3-triazole-4,1-diyl))bis(3-hydroxybenzoic acid) | 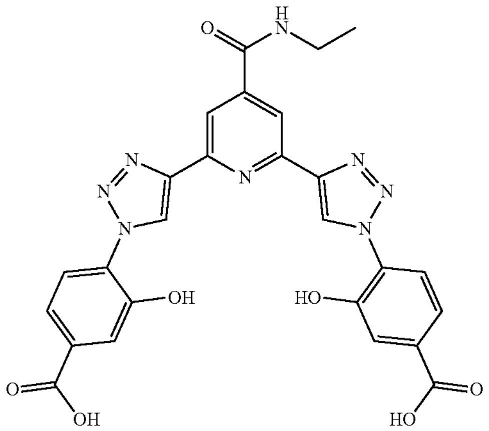 |

TABLE 1-continued

| Compound | Chemical Name | Structure |
| --- | --- | --- |
| 101 | diethyl (3-(4-(6-(1-(3-(diethoxyphosphoryl) propyl)-1H-1,2,3-triazol-4-yl)-4-(ethylcarbamoyl) 118yridine-2-yl)-1H-1,2,3-triazol-1-yl)propyl) phosphonate | 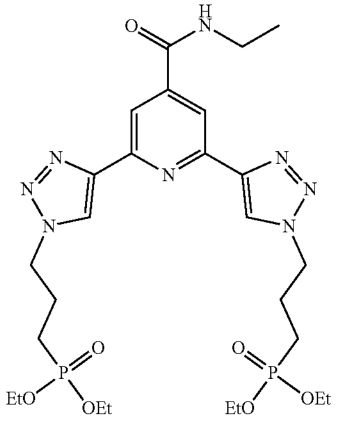 |
| 102 | 4,4'-((4-(ethylcarbamoyl)pyridine-2,6-diyl)bis(1H-1,2,3-triazole-4,1-diyl))bis(2-methylbenzoic acid) | 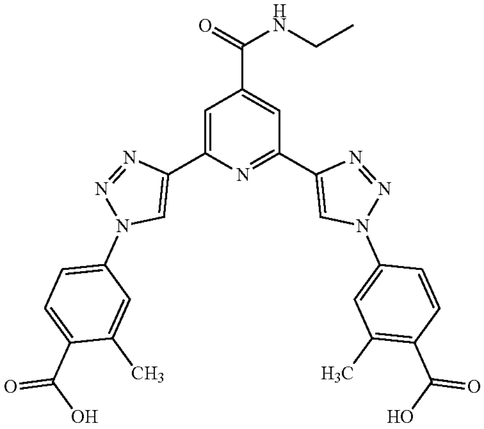 |
| 103 | 4,4'-((5-carboxy-1,3-phenylene)bis(1H-1,2,3-triazole-4,1-diyl))bis(2-(trifluoromethyl)benzoic acid) | 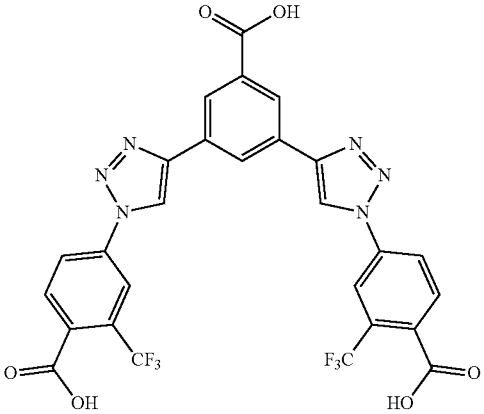 |
| 104 | 2,2'-((4-(ethylcarbamoyl)pyridine-2,6-diyl)bis(1H-1,2,3-triazole-4,1-diyl))bis(3-(trifluoromethyl)benzoic acid) | 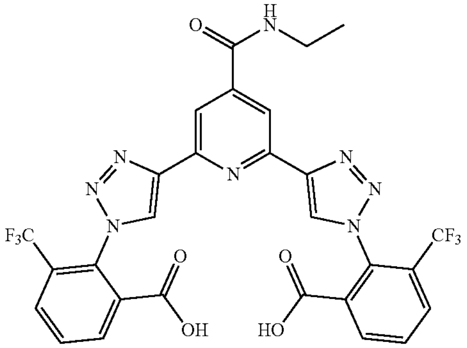 |

TABLE 1-continued
| Compound | Chemical Name | Structure |
| --- | --- | --- |
| 105 | 4,4'-((4-((2-hydroxyethyl)carbamoyl)pyridine-2,6-diyl)bis(1H-1,2,3-triazole-4,1-diyl))bis(2-(trifluoromethyl)benzoic acid) | 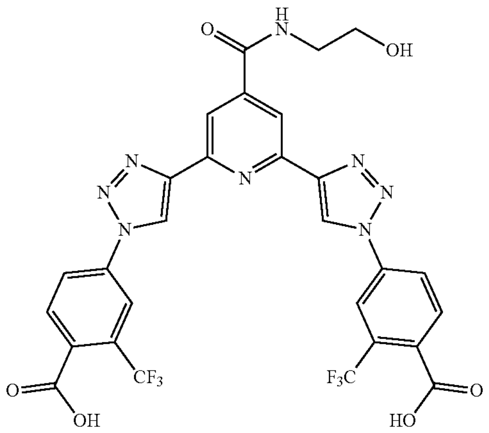 [SMILES: O=C(NCCO)c1cc(-c2cn(-c3ccc(C(=O)O)c(C(F)(F)F)c3)nn2)nc(-c2cn(-c3ccc(C(=O)O)c(C(F)(F)F)c3)nn2)c1] |
| 106 | 4,4'-((4-(ethylcarbamoyl)pyridine-2,6-diyl)bis(1H-1,2,3-triazole-4,1-diyl))bis(2-nitrobenzoic acid) | 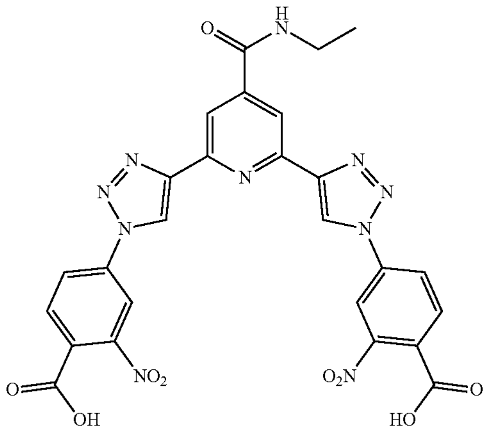 |
| 107 | 4,4'-((4-((3,3,3-trifluoropropyl)carbamoyl)pyridine-2,6-diyl)bis(1H-1,2,3-triazole-4,1-diyl))bis(2-(trifluoromethyl)benzoic acid) | 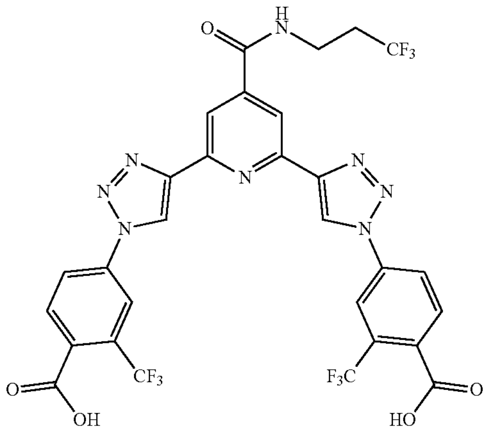 [SMILES: O=C(NCCC(F)(F)F)c1cc(-c2cn(-c3ccc(C(=O)O)c(C(F)(F)F)c3)nn2)nc(-c2cn(-c3ccc(C(=O)O)c(C(F)(F)F)c3)nn2)c1] |

TABLE 1-continued

| Compound | Chemical Name | Structure |
|---|---|---|
| 108 | 4,4',4",4'"-((((butane-1,4-diylbis(azanediyl))bis(carbonyl))bis(pyridine-4,2,6-triyl))tetrakis(1H-1,2,3-triazole-4,1-diyl))tetrakis(2-(trifluoromethyl)benzoic acid) | 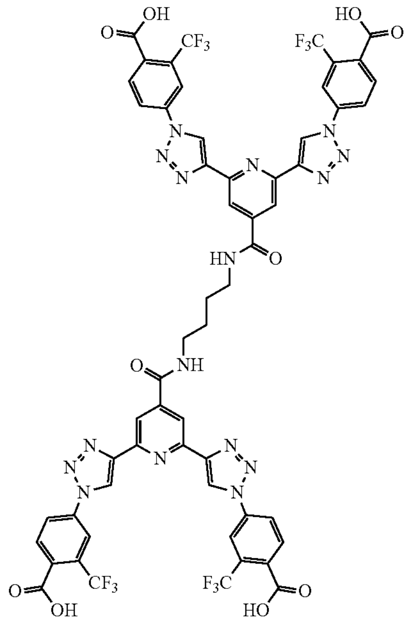 |
| 109 | (4-(4-(4-(ethylcarbamoyl)-6-(1-(4-phosphonophenyl)-1H-1,2,3-triazol-4-yl)121yridine-2-yl)-1H-1,2,3-triazol-1-yl)phenyl)phosphonic acid | 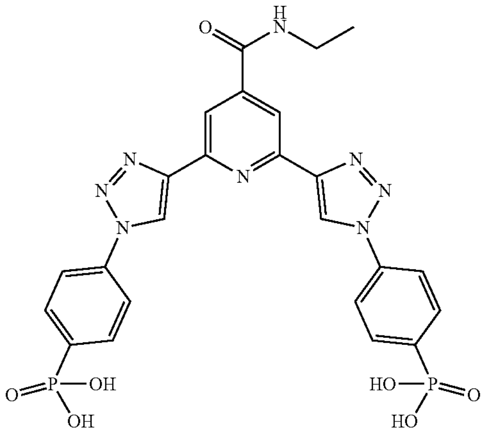 |
| 110 | 2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))diacetic acid | 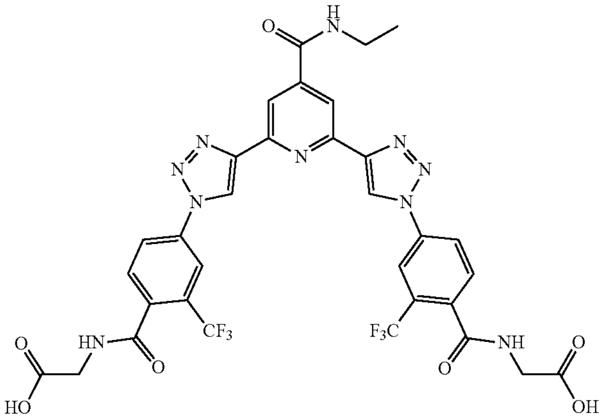 [SMILES: CCNC(=O)c1cc(-c2cn(-c3ccc(C(=O)NCC(=O)O)c(C(F)(F)F)c3)nn2)nc(-c2cn(-c3ccc(C(=O)NCC(=O)O)c(C(F)(F)F)c3)nn2)c1] |

TABLE 1-continued

| Compound | Chemical Name | Structure |
| --- | --- | --- |
| 111 | dimethyl 2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))diacetate | 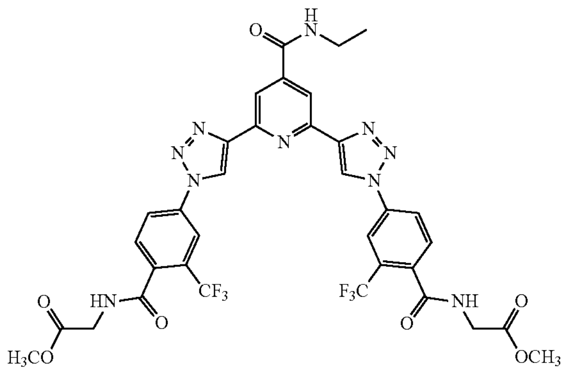 [SMILES: CCNC(=O)c1cc(-c2cn(-c3ccc(C(=O)NCC(=O)OC)c(C(F)(F)F)c3)nn2)nc(-c2cn(-c3ccc(C(=O)NCC(=O)OC)c(C(F)(F)F)c3)nn2)c1] |
| 112 | (2S,2'S)-2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))disuccinic acid | 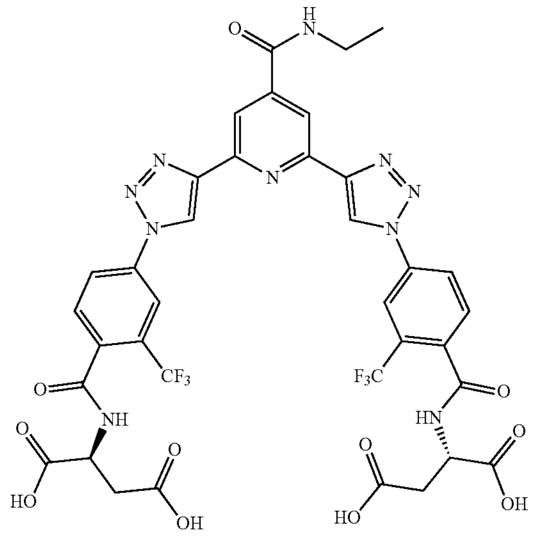 |
| 113 | 2,2'-((2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))bis(acetyl))bis(azanediyl))diacetic acid | 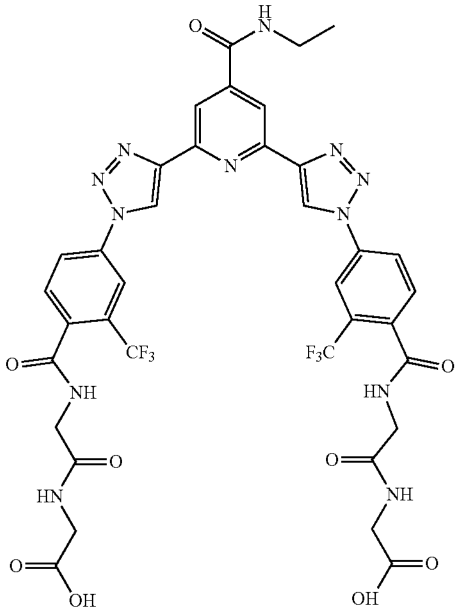 |

TABLE 1-continued
| Compound | Chemical Name | Structure |
| --- | --- | --- |
| 114 | 2,6-bis(1-(4-cyano-3-(trifluoromethyl)phenyl)-1H-1,2,3-triazol-4-yl)-N-ethylisonicotinamide | 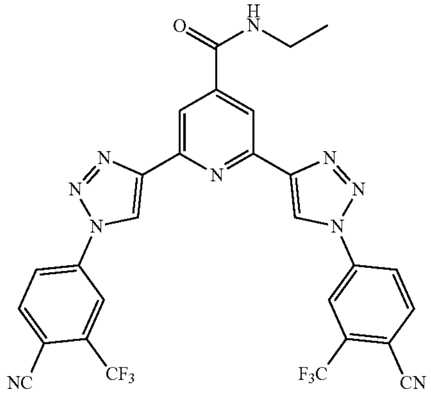 [SMILES: CCNC(=O)c1cc(-c2cn(-c3ccc(C#N)c(C(F)(F)F)c3)nn2)nc(-c2cn(-c3ccc(C#N)c(C(F)(F)F)c3)nn2)c1] |
| 115 | 4,4'-((5-carboxy-1,3-phenylene)bis(1H-1,2,3-triazole-1,4-diyl))bis(2-(trifluoromethyl)benzoic acid) | 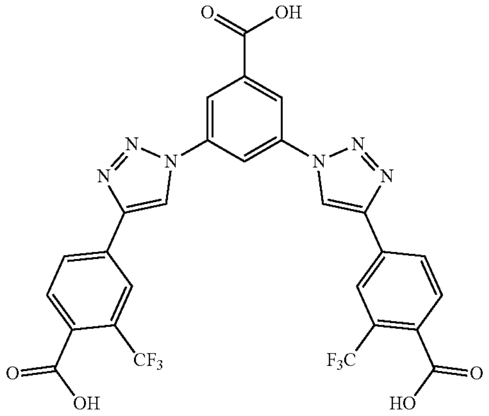 [SMILES: O=C(O)c1cc(-n2cc(-c3ccc(C(=O)O)c(C(F)(F)F)c3)nn2)cc(-n2cc(-c3ccc(C(=O)O)c(C(F)(F)F)c3)nn2)c1] |
| 116 | 4,4'-((5-(ethylcarbamoyl)-1,3-phenylene)bis(1H-1,2,3-triazole-1,4-diyl))bis(2-(trifluoromethyl)benzoic acid) | 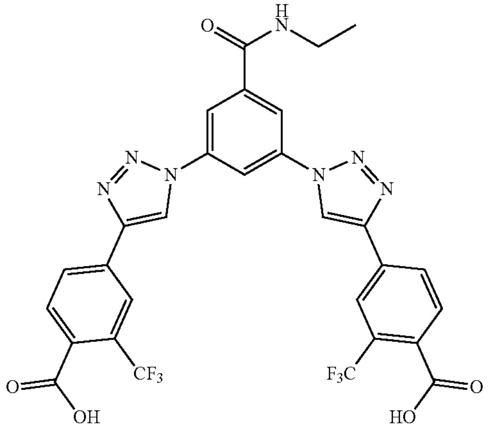 [SMILES: CCNC(=O)c1cc(-n2cc(-c3ccc(C(=O)O)c(C(F)(F)F)c3)nn2)cc(-n2cc(-c3ccc(C(=O)O)c(C(F)(F)F)c3)nn2)c1] |
| 117 | 4,4'-(thiophene-2,5-diylbis(1H-1,2,3-triazole-4,1-diyl))bis(2-(trifluoromethyl)benzoic acid) | 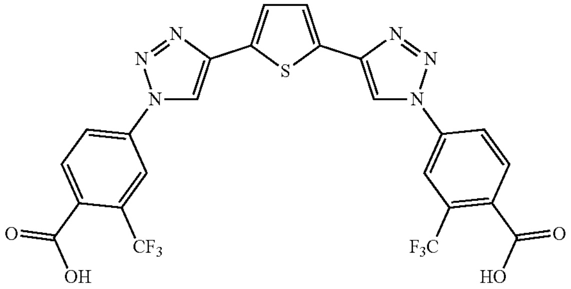 [SMILES: O=C(O)c1ccc(-n2cc(-c3ccc(-c4cn(-c5ccc(C(=O)O)c(C(F)(F)F)c5)nn4)s3)nn2)cc1C(F)(F)F] |

TABLE 1-continued

| Compound | Chemical Name | Structure |
|---|---|---|
| 118 | 4,4'-(furan-2,5-diylbis(1H-1,2,3-triazole-4,1-diyl))bis(2-(trifluoromethyl)benzoic acid) | 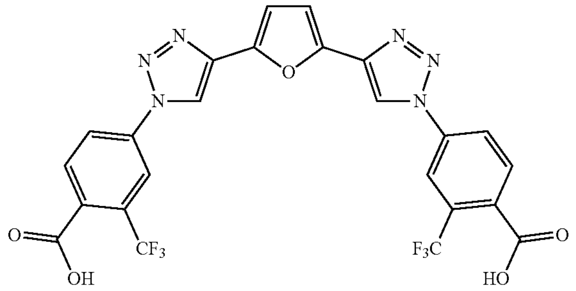 [SMILES: O=C(O)c1ccc(-n2cc(-c3ccc(-c4cn(-c5ccc(C(=O)O)c(C(F)(F)F)c5)nn4)o3)nn2)cc1C(F)(F)F] |
| 119 | 3'-(4-(4-(ethylcarbamoyl)-6-(1-(3'-(trifluoromethyl)-[1,1'-biphenyl]-3-yl)-1H-1,2,3-triazol-4-yl)pyridin-2-yl)-1H-1,2,3-triazol-1-yl)-3-(trifluoromethyl)-[1,1'-biphenyl]-4-carboxylic acid | 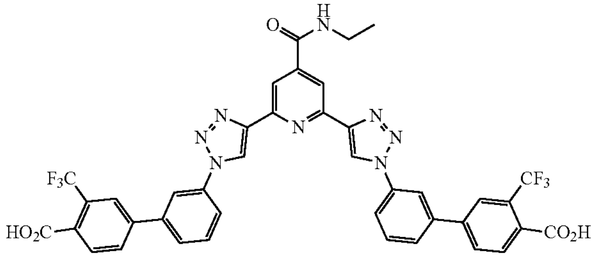 [SMILES: CCNC(=O)c1cc(-c2cn(-c3cccc(-c4ccc(C(=O)O)c(C(F)(F)F)c4)c3)nn2)nc(-c2cn(-c3cccc(-c4ccc(C(=O)O)c(C(F)(F)F)c4)c3)nn2)c1] |
| 120 | 4,4'-((4-(ethylcarbamoyl)pyridine-2,6-diyl)bis(1H-1,2,3-triazole-4,1-diyl))bis(2-cyanobenzoic acid) | 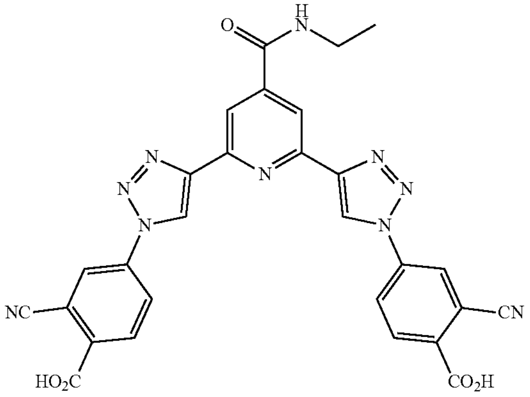 [SMILES: CCNC(=O)c1cc(-c2cn(-c3ccc(C(=O)O)c(C#N)c3)nn2)nc(-c2cn(-c3ccc(C(=O)O)c(C#N)c3)nn2)c1] |
| 121 | 4,4'-((4-(ethylcarbamoyl)pyridine-2,6-diyl)bis(1H-1,2,3-triazole-4,1-diyl))bis(2-chlorobenzoic acid) | 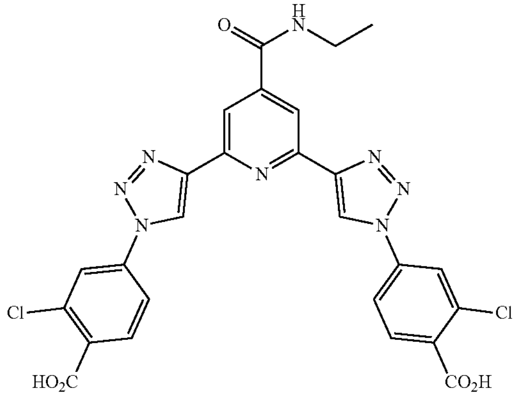 [SMILES: CCNC(=O)c1cc(-c2cn(-c3ccc(C(=O)O)c(Cl)c3)nn2)nc(-c2cn(-c3ccc(C(=O)O)c(Cl)c3)nn2)c1] |

Example 1

Synthesis of 4,4'-(pyridine-2,6-diylbis(1H-1,2,3-triazole-4,1-diyl))bis(2-hydroxybenzoic acid)

(1)

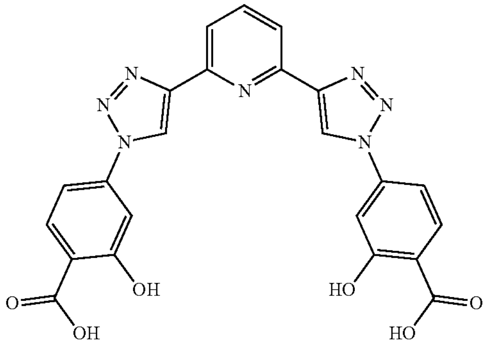

(A)

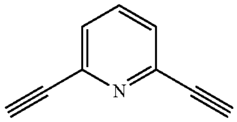

(B)

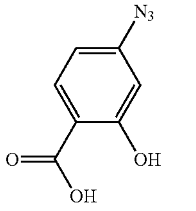

Compound 1 was prepared by mixing 4-azidosalicylic acid B (1.79 mg, 10 μmol) and 2,6-diethynylpyridine A (0.67 mg, 5 μmol) in DMSO (150 μL). This solution was mixed with a solution of TBTA (5.1 mg, 0.96 μmol) and sodium ascorbate (6.4 mg, 32 μmol) in DMSO (95 μL). The click reaction was initiated by the addition of 20 Mm copper sulfate (5 μL) with agitation. The extent of reaction was analyzed by TLC (94:5:1 ethyl acetate:methanol:acetic acid) and the reaction was complete in 5 minutes based on the consumption of azide and alkyne. The reaction mixture volume was brought to 1 Ml with DMSO and 0.5 M EDTA (100 μL). Solids were isolated and dissolved in additional DMSO. The DMSO solutions were combined and purified by flash chromatography as described above in Materials and Methods. The product formed a glassy solid upon rotary evaporation in a 50 to 75% yield. $^1$H NMR (300 MHz, DMSO-d6) δ ppm 3.29 (2H, br. S., (O(18)H and O(33)H)), 7.17-7.29 (4H,m, (C(7)H, C(11)H, C(28)H, C(32)H)) 7.85 (2H, d, J=8.11 (C(10)H and C(31)H)), 8.06 (3H, s, (C(15)H, C(16)H, C(17)H)) 9.36 (2H, s, (C(5)H and C(25)H)).

Example 2

Synthesis of 4,4'-(pyridine-3,5-diylbis(1H-1,2,3-triazole-4,1-diyl))bis(2-hydroxybenzoic acid)

(2)

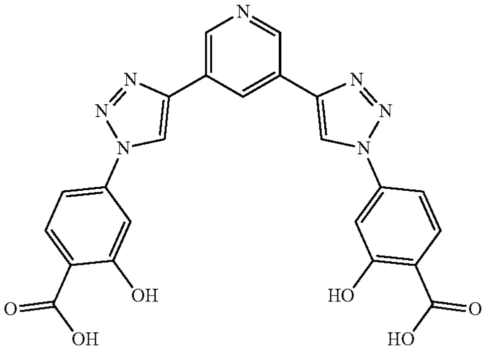

(C)

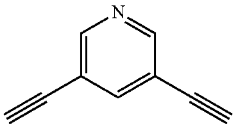

Compound 2 was prepared using 4-azidosalicylic acid B and 3,5-diethynylpyridine C according to the method of Example 1. $^1$H NMR (300 MHz, DMSO-d6) δ ppm 3.29 (2H, br. S., (O(18)H and O(33)H)) 7.17-7.29 (4H, m, (C(7)H, C(11)H, C(28)H, C(31)H)) 7.85 (2H, d, J=8.11 Hz, (C(10)H and C(31)H)) 8.06 (3H, s, (C(13)H, C(15)H, C(17)H)) 9.36 (2H,s, (C(5)H and C(25)H)).

Example 3

Synthesis of 4,4'-(1,3-phenylenebis(1H-1,2,3-triazole-4,1-diyl))bis(2-hydroxybenzoic acid)

(3)

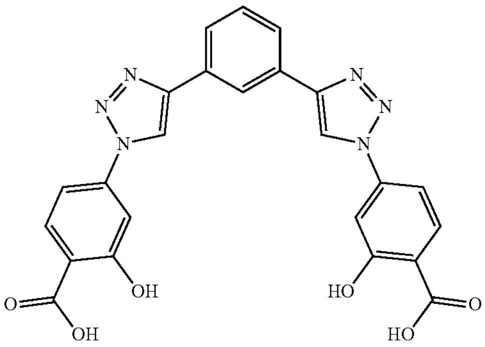

(D)

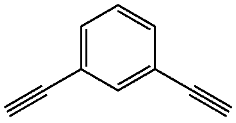

Compound 3 was prepared using 4-azidosalicylic acid B and 1,3-diethynylbenzene D according to the method of Example 1. $^1$H NMR (300 MHz, DMSO-d6) δ ppm 3.29 (2H, br. S., (O(18)H and O(33)H)) 7.16-7.27 (4H, m, (C(7)H, C(11)H, C(28)H, C(32)H)) 7.57-7.67 (1H,m, (C(16)H)) 7.80-7.88 (2H,m, (C(10)H and C(31)H)) 7.94 (2H,d, J=7.63 Hz, (C(15)H and C(17)H) 8.57 (1H,s, (C(13)H)) 9.35 (2H,s, (C(5)H and C(25)H).

Example 4

Synthesis of 4,4'-((9H-carbazole-3,6-diyl)bis(1H-1,2,3-triazole-4,1-diyl))bis(2-hydroxybenzoic acid)

(4)

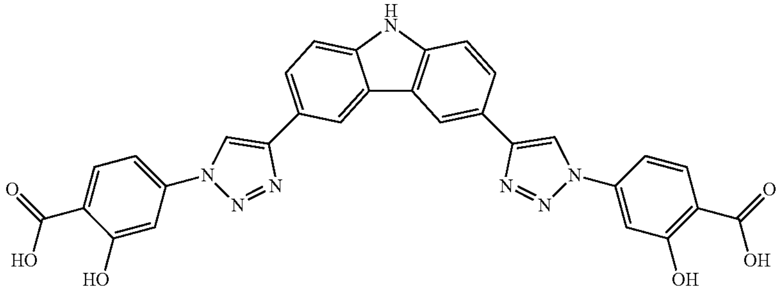

(E)

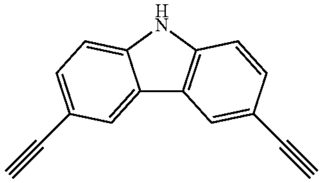

Compound 4 was prepared using 4-azidosalicylic acid B and 3,6-diethynylcarbazole E according to the method of Example 1. $^{1}$H NMR (300 MHz, DMSO-d6) δ ppm 3.29 (2H, br. S., (O(25)H and O(40)H)) 7.16-7.27 (4H, m, (C(7)H, C(11)H, C(35)H, C(39)H)) 7.61 (2H,d, J=8.34 Hz, (C(10)H and C(38)H)) 7.84 (2H,d, J=7.87 Hz, (C(22)H and C(24)H)) 8.02 (2H,d, J=8.34 Hz, (C(21)H and C(23)H)) 8.79 (2H,s, (C(13)H and C(19)H)) 9.28 (2H,s, (C(5)H and C(32)H)) 11.53 (1H,s, (N(16)H).

Example 5

Synthesis of 4,4'-((9H-carbazole-3,6-diyl)bis(1H-1,2,3-triazole-4,1-diyl))dianiline (5)

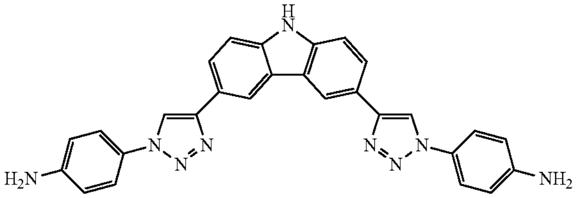

(F)

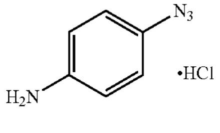

Compound 5 was prepared using 4-azidoaniline hydrochloride F and 3,6-diethynylcarbazole E according to the method of Example 1.

Example 6
Synthesis of 4,4'-((9H-carbazole-3,6-diyl)bis(1H-1,2,3-triazole-4,1-diyl))dibenzoic acid
(6)
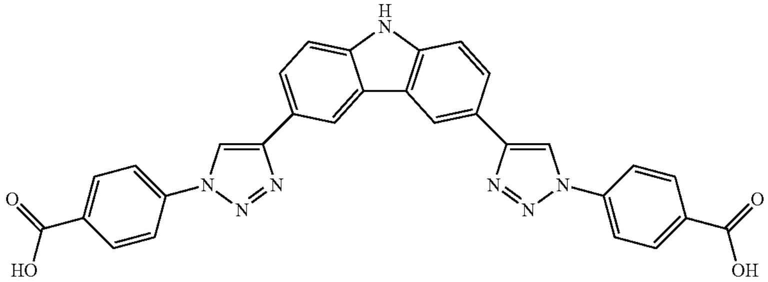
(G)
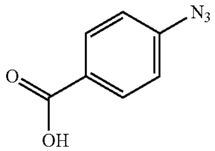
Compound 6 was prepared using 4-azidobenzoic acid G and 3,6-diethynylcarbazole E according to the method of Example 1.
Example 7
Synthesis of 3,6-bis(1-(4-methoxyphenyl)-1H-1,2,3-triazol-4-yl)-9H-carbazole
(7)
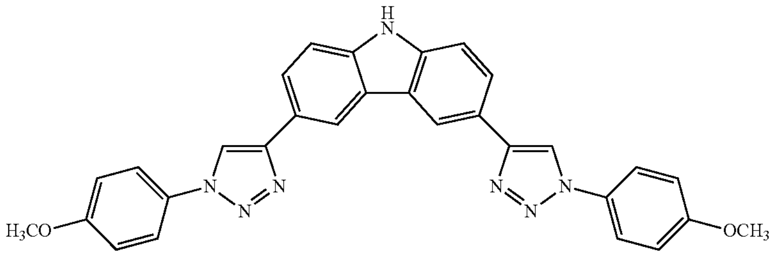
(H)
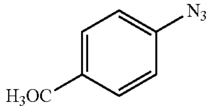

Compound 7 was prepared using 4-azidoanisole H and 3,6-diethynylcarbazole E according to the method of Example 1.

Example 8

Synthesis of dimethyl 2,2'-((9H-carbazole-3,6-diyl) bis(1H-1,2,3-triazole-4,1-diyl))diacetate (8)

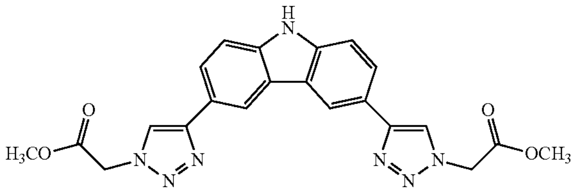

(I)

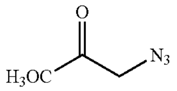

Compound 8 was prepared using methyl azidoacetate I and 3,6-diethynylcarbazole E according to the method of Example 1.

Example 9

Synthesis of 4,4'-((4-methoxypyridine-2,6-diyl)bis (1H-1,2,3-triazole-4,1-diyl))bis(2-hydroxybenzoic acid)

(9)

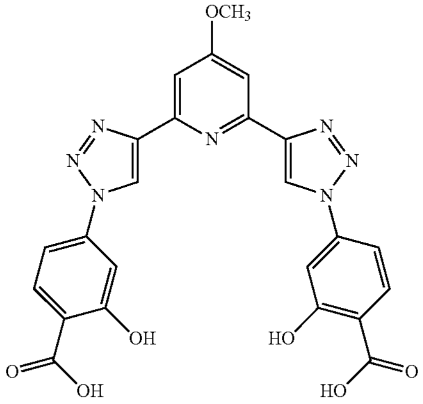

(J)

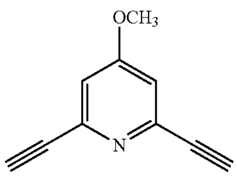

Preparation of compound 9 started with the synthesis of 4-methoxy-2,6-diethynylpyridine J from 4-methoxy-2,6-dibromopyridine and ethynyltrimethylsilane using conditions described by Sonogashira (Organomet. Chem., 653: 46-49 (2002). doi:10.1016/s0022-328x(02)$_{01158}$-0). Synthesis of compound 9 was completed by clicking 4-azidosalicylic acid B and compound J according to the method of Example 1.

Example 10

Synthesis of 4,4'-((4-carboxypyridine-2,6-diyl)bis (1H-1,2,3-triazole-4,1-diyl))bis(2-hydroxybenzoic acid)

(10)

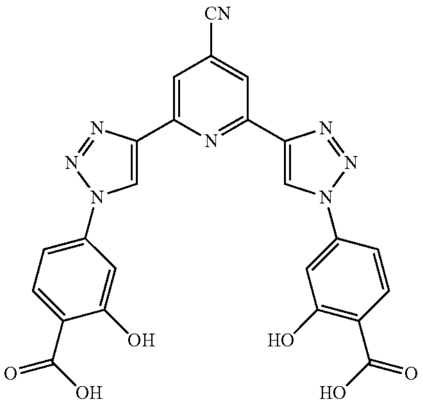

(K)

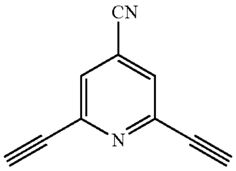

Preparation of compound 10 started with the synthesis of 4-cyano-2,6-diethynylpyridine K from 4-cyano-2,6-dibromopyridine and ethynyltrimethylsilane using conditions described by Sonogashira (Organomet. Chem., 653: 46-49 (2002). doi:10.1016/s0022-328x(02)$_{01158}$-0). Synthesis of compound 10 was completed by clicking 4-azidosalicylic acid B and compound K according to the method of Example 1.

Example 11

Synthesis of 4,4'-((4-nitropyridine-2,6-diyl)bis(1H-1,2,3-triazole-4,1-diyl))bis(2-hydroxybenzoic acid)

(11)

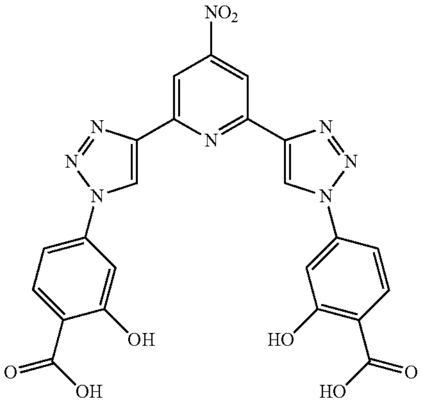

-continued (L)

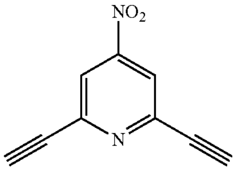

Preparation of compound 11 started with synthesis of 4-nitro-2,6-diethynylpyridine L from 4-nitro-2,6-dibromopyridine and ethynyltrimethylsilane using conditions described by Sonogashira (Organomet. Chem., 653: 46-49 (2002). doi:10.1016/s0022-328x(02)$_{01158}$-0). Synthesis of compound 11 was completed by clicking 4-azidosalicylic acid B and compound L according to the method of Example 1.

Example 12

Synthesis of 5,5'-((4-cyanopyridine-2,6-diyl)bis(1H-1,2,3-triazole-4,1-diyl))bis(2-hydroxybenzoic acid)

(12)

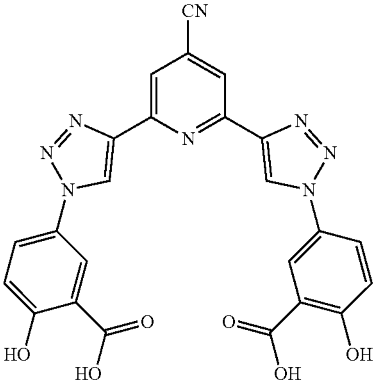

(M)

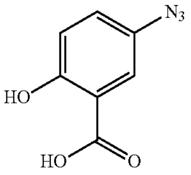

Compound 12 was prepared using 5-azidosalicylic acid M and 4-cyano-2,6-diethynylpyridine K according to the method of Example 10.

Example 13

Synthesis of 4,4'-((4-methylpyridine-2,6-diyl)bis(1H-1,2,3-triazole-4,1-diyl))bis(2-hydroxybenzoic acid)

(13)

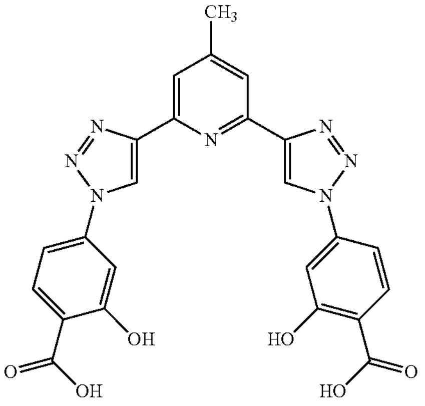

(N)

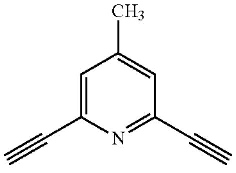

Compound 13 started with synthesis of 4-methyl-2,6-diethynylpyridine N from 4-methyl-2,6-dichloropyridine and ethynyltrimethylsilane using conditions described by Sonogashira (Organomet. Chem., 653: 46-49 (2002). doi: 10.1016/s0022-328x(02)$_{01158}$-0). Synthesis of compound 11 was completed by clicking 4-azidosalicylic acid B and 4-methyl-2,6-diethynylpyridine N according to the method of Example 1.

Example 14

Synthesis of 4,4'-((4-(ethoxycarbonyl)pyridine-2,6-diyl)bis(1H-1,2,3-triazole-4,1-diyl))bis(2-hydroxybenzoic acid)

(14)

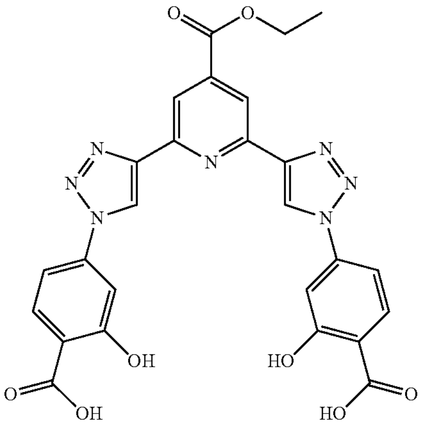

-continued (O)

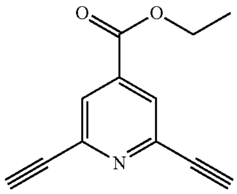

Compound 14 started with synthesis of ethyl 2,6-diethynylpyridine-4-carboxylate O from ethyl 2,6-dibromopyridine-4-carboxylate and ethynyltrimethylsilane using conditions described by Sonogashira (Organomet. Chem., 653: 46-49 (2002). doi:10.1016/s0022-328x$(02)_{01158}$-0). Synthesis of compound 14 was completed by clicking 4-azidosalicylic acid B and ethyl 2,6-diethynylpyridine-4-carboxylate O according to the method of Example 1.

Example 15

Synthesis of 5,5'-((4-(ethoxycarbonyl)pyridine-2,6-diyl)bis(1H-1,2,3-triazole-4,1-diyl))bis(2-hydroxybenzoic acid)

(15)

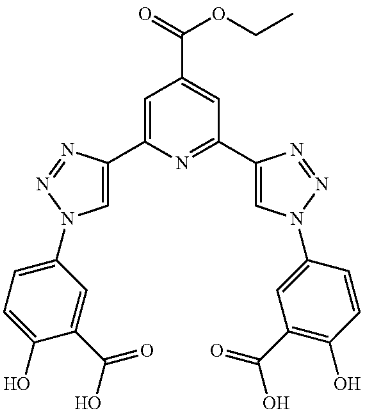

Compound 15 was prepared using 5-azidosalicylic acid M and ethyl 2,6-diethynylepyridine-4-carboxylate O clicked according to the method of Example 14.

Example 16

Synthesis of 4,4'-((4-(methoxycarbonyl)pyridine-2,6-diyl)bis(1H-1,2,3-triazole-4,1-diyl))bis(2-hydroxybenzoic acid)

(16)

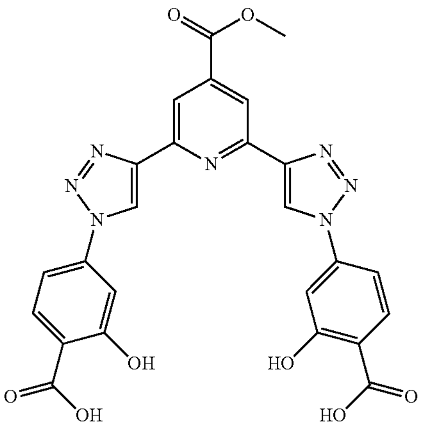

(P)

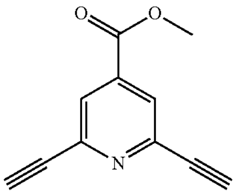

Compound 16 started with synthesis of methyl 2,6-diethynylpyridine-4-carboxylate P from methyl 2,6-dichloropyridine-4-carboxylate and ethynyltrimethylsilane using conditions described by Sonogashira (Organomet. Chem., 653: 46-49(2002). doi:10.1016/s0022-328x$(02)_{01158}$-0). Synthesis of compound 16 was completed by clicking 4-azidosalicylic acid B and methyl 2,6-diethynylpyridine-4-carboxylate P according to the method of Example 1.

Example 17

Synthesis of 4,4'-((4-(ethylcarbamoyl)pyridine-2,6-diyl)bis(1H-1,2,3-triazole-4,1-diyl))bis(2-hydroxybenzoic acid)

(17)

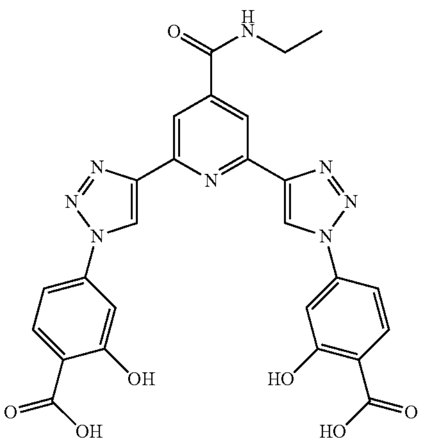

-continued (Q)

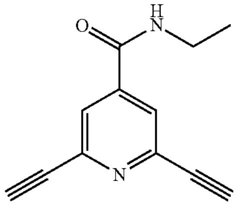

Synthesis of compound 17 commenced with mixing 2,6-dibromo-4-pyridine carboxylic acid (0.2 g, 0.71 mmol), DIPEA (0.18 g, 1.42 mmol) and HATU (0.27 g, 0.71 mmol) in DMF (900 ul). Ethyl amine (0.154 ml, 1.78 mmol) was added immediately and mixed for 1 hour. The reaction was completed by TLC and purified by flash chromatography on silica gel using a gradient of ethyl acetate/hexane. N-ethyl-2,6-dibromo-4-carboxamide was isolated as a yellow solid in 69% yield. N-ethyl-2,6-diethynl-4-carboxamide Q was made with ethyltrimethylsilane using the Sonogashira method described in Example 16. Synthesis of compound 17 was completed by clicking 4-azidosalicylic acid B and N-ethyl-2,6-diethynl-4-carboxamide Q according to the method of Example 1.

Example 18

Synthesis of 4,4'-((4-(methylcarbamoyl)pyridine-2,6-diyl)bis(1H-1,2,3-triazole-4,1-diyl))bis(2-hydroxybenzoic acid)

(18)

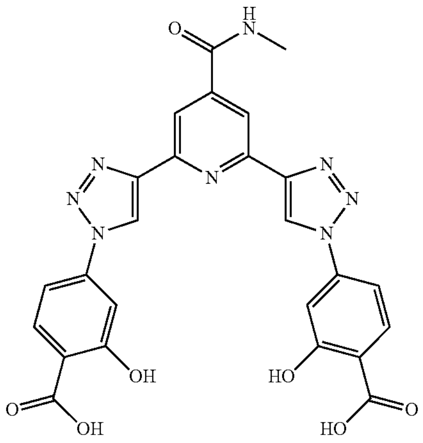

Compound 18 was prepared with methyl amine to form the amide according to the method of Example 17.

Example 19

Synthesis of 4,4'-((4-carbamoylpyridine-2,6-diyl)bis(1H-1,2,3-triazole-4,1-diyl))bis(2-hydroxybenzoic acid)

(19)

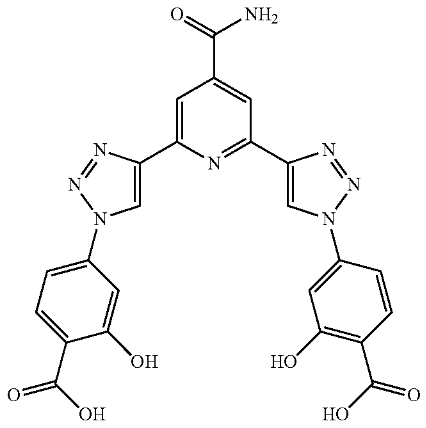

Compound 19 was prepared with ammonia to form the amide according to the method of Example 17.

Example 20

Synthesis of 4,4'-(pyrazine-2,6-diylbis(1H-1,2,3-triazole-4,1-diyl))bis(2-hydroxybenzoic acid)

(20)

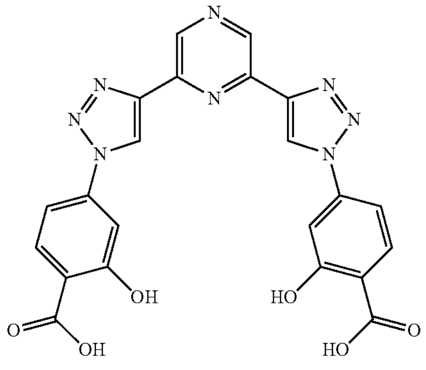

(T)

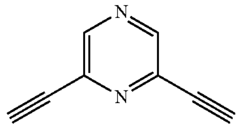

Compound 20 was started with synthesis of 2,6-diethynylpyrazine T from 2,6-dichloropyrazine and ethynyltrimethylsilane using Sonogashira method described by Bhowmick, S. et al. (App. Organomet. Chem. 31(12):e3824 (2017)). Synthesis of compound 20 was completed by clicking 4-azidosalicylic acid B and 2,6-diethynylpyrazine T according to the method of Example 1.

Example 21

Synthesis of 4,4'-((4-(ethylcarbamoyl)pyridine-2,6-diyl)bis(1H-1,2,3-triazole-4,1-diyl))bis(2-(trifluoromethyl)benzoic acid)

(73)

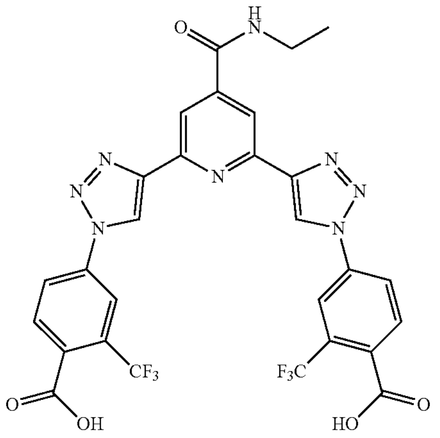

(U)

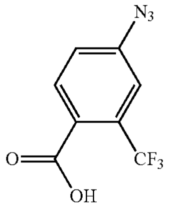

Synthesis of compound 73 started with diazotization of 4-amino-2-(trifluoromethyl)benzoic acid with sodium nitrite and sulfuric acid followed by nucleophilic displacement with azide (Org. Synth. 1942, 22, 96) to form 4-azido-2-(trifluoromethyl)benzoic acid (U) which was purified via flash chromatography. Synthesis of compound 73 was completed by clicking 4-azido-2-(trifluoromethyl)benzoic acid U and N-ethyl-2,6-diethynl-4-carboxamide Q according to Example 1.

Example 22

Synthesis of 7,7'-((4-(ethylcarbamoyl)pyridine-2,6-diyl)bis(1H-1,2,3-triazole-4,1-diyl))bis(2-hydroxy-1,8-naphthyridine-4-carboxylic acid)

(74)

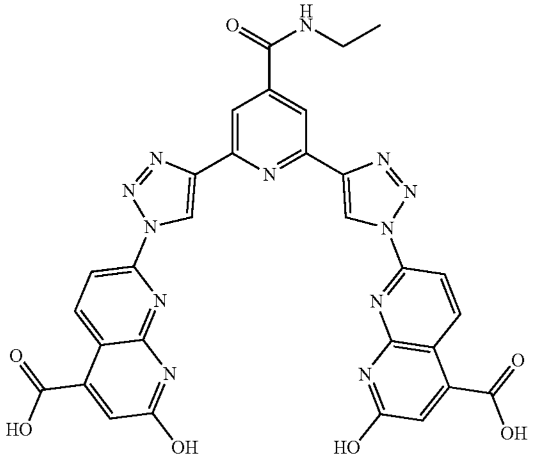

-continued (V)

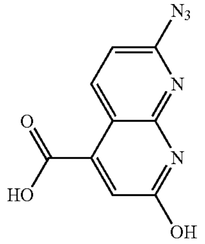

Synthesis of compound 74 started with diazotization of 7-amino-2-hydroxy-1,8-naphthyridine-4-carboxylic acid with sodium nitrite and sulfuric acid followed by nucleophilic displacement with azide (Org. Synth. 1942, 22, 96) to form 7-azido-2-hydroxy-1,8-naphthyridine-4-carboxylic acid (V) which was purified via flash chromatography. Synthesis of compound 74 was completed by clicking 7-azido-2-hydroxy-1,8-naphthyridine-4-carboxylic acid V and N-ethyl-2,6-diethynl-4-carboxamide Q according to Example 1.

Example 23

Synthesis of 4-(4-(3-(1-(4-carboxyphenyl)-1H-1,2,3-triazol-4-yl)phenyl)-1H-1,2,3-triazol-1-yl)-2-hydroxybenzoic acid (28)

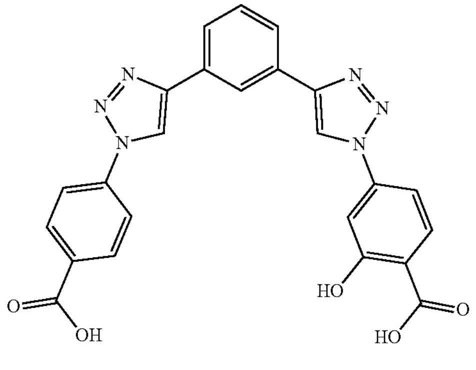

Synthesis of compound 28 was completed in two steps. First, 2,6-diethynylbenzene D was clicked with half the 138yridine138etric amount of 4-azidosalicylic acid B according to the method of Example 3 to make 4-(4-(3-ethynylphenyl)-1H-1,2,3-triazol-1-yl)-2-hydroxybenzoic acid. The second step was clicking 4-azidobenzoic acid G according to the method of Example 1 to give 4-(4-(3-(1-(4-carboxyphenyl)-1H-1,2,3-triazol-4-yl)phenyl)-1H-1,2,3-triazol-1-yl)-2-hydroxybenzoic acid 28.

Example 24

Synthesis of 4-(4-(4-cyanopyridin-2-yl)-1H-1,2,3-triazol-1-yl)-2-hydroxybenzoic acid (43)

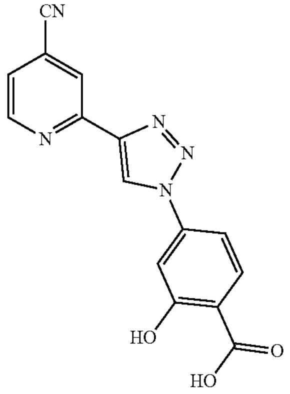

(W)

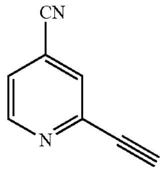

Preparation of compound 43 started with synthesis of 4-cyano-2-ethynylpyridine W from 4-cyano-2-chloropyridine and ethynyltrimethylsilane using conditions described by Sonogashira (Organomet. Chem., 653: 46-49 (2002). doi:10.1016/s0022-328x(02)01158-0). Synthesis of compound 43 was completed by clicking 4-azidosalicylic acid B and compound W according to the method of Example 1.

Example 25

Synthesis of 4,4'-((pyridine-2,6-diyl)bis(5-iodo-1H-1,2,3-triazole-4,1-diyl))bis(2-hydroxybenzoic acid)

(31)

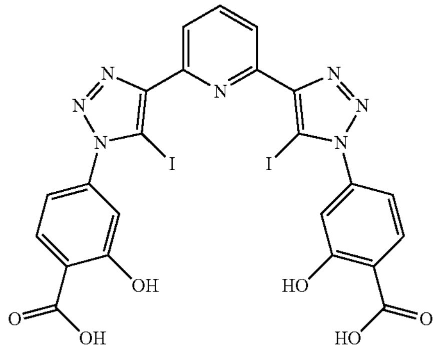

-continued (X)

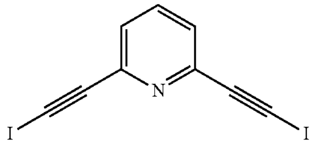

Preparation of compound 31 started with the synthesis of 2,6-bis(iodoethynyl)pyridine X from 2,6-diethynylpyridine A following the method of Tepper et. al, (Org. Lett., 2015, 17 (23), pp 5740-574) which involved treatment with n-iodosuccinimide and silver nitrate and isolation by flash chromatography. Synthesis of compound 31 was completed by clicking 4-azidosalicylic acid B and compound X according to the method of Example 1.

Example 26

Synthesis of 4,4'-((3,5-dimethylpyridine-2,6-diyl)bis(1H-1,2,3-triazole-4,1-diyl))bis(2-hydroxybenzoic acid)

(30)

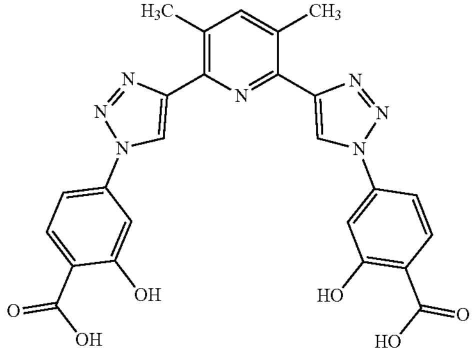

(Y)

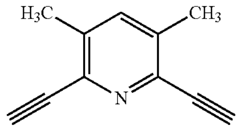

Compound 30 was started with synthesis of 2,6-diethynyl-3,5-dimethylpyridine Y from 2,6-dibromo-3,5-dimethylpyridine and ethynyltrimethylsilane using Sonogashira method described by Bhowmick, S. et al. (App. Organomet. Chem. 31(12):e3824 (2017)). Synthesis of compound 30 was completed by clicking 4-azidosalicylic acid B and 2,6-diethynyl-3,5-dimethylpyridine Y according to the method of Example 1.

Example 27

Synthesis of 4,4'-((9-acetyl-9H-carbazole-3,6-diyl) bis(1H-1,2,3-triazole-4,1-diyl))bis(2-hydroxybenzoic acid)

(33)

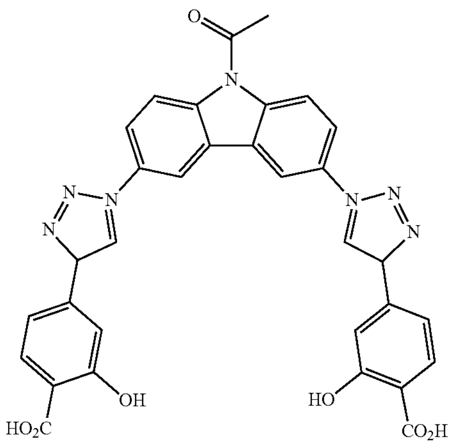

(Z)

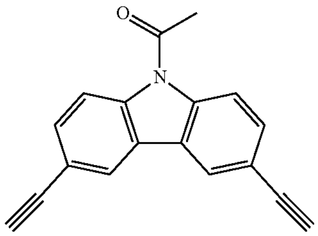

Compound 33 was started with synthesis of 9-acetyl-3,6-diethynylcarbazole Z from 9-acetyl-3,6-diiodocarbazole and ethynyltrimethylsilane using Sonogashira method described by Bhowmick, S. et al. (App. Organomet. Chem. 31(12):e3824 (2017)). Synthesis of compound 33 was completed by clicking 4-azidosalicylic acid B and 9-acetyl-3,6-diethynylcarbazole Z according to the method of Example 1.

Example 28

Synthesis of 4,4'-(pyridine-2,6-diylbis(1H-1,2,3-triazole-4,1-diyl))bis(N,2-dihydroxybenzamide)

(34)

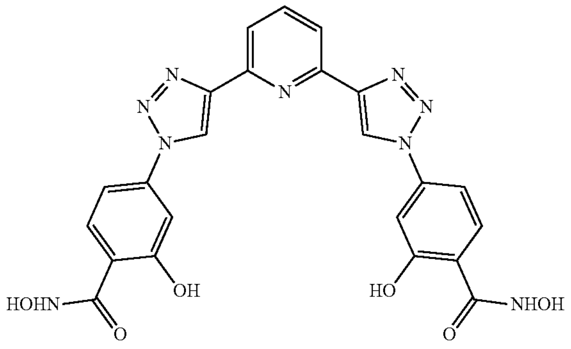

-continued (AA)

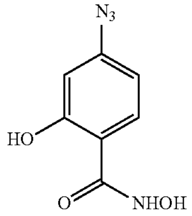

Synthesis of compound 34 commenced with mixing N hydroxysuccinimide 4-azidosalicylate (40 mg, 0.145 mmol) in DMF (72 ul) to this was added hydroxyl amine hydrochloride (30 mg, 0.43 mmol) in water (72 ul) and mixed overnight. Product was detected by TLC and the reaction was purified by flash chromatography on silica gel using a gradient of methylene chloride and methylene 141yridine-MeOH. 4-Azido-N,2-dihydroxybenzamide AA was isolated in 57% yield. Synthesis of compound 34 was completed by clicking 4-azido-N,2-dihydroxybenzamide AA and 2,6-diethynylpyridine A according to the method of Example 1.

Example 29

Synthesis of 5-(4-(6-(4-(3-carboxy-4-hydroxy-5-methylphenyl)-1H-1,2,3-triazol-1-yl)-4-(methoxycarbonyl)pyridin-2-yl)-1H-1,2,3-triazol-1-yl)-2-hydroxy-3-methylbenzoic acid (44)

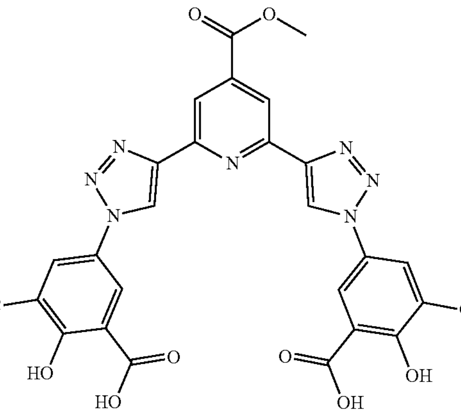

(BB)

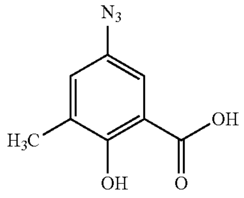

Synthesis of compound 44 started with diazotization of 5-amino-2-hydroxy-3-methylbenzoic acid with sodium nitrite and sulfuric acid followed by nucleophilic displacement with azide (Org. Synth. 1942, 22, 96) to form 5-azido-2-hydroxy-3-methylbenzoic acid (BB) which was purified via flash chromatography. Synthesis of compound 44 was completed by clicking 5-azido-2-hydroxy-3-methylbenzoic acid BB with 2,6-diethynylpyridine-4-carboxylate P according to Example 1.

Example 30

Synthesis of 4,4'-((4-(but-3-yn-1-ylcarbamoyl)pyridine-2,6-diyl)bis(1H-1,2,3-triazole-4,1-diyl))bis(2-hydroxybenzoic acid)

(47)

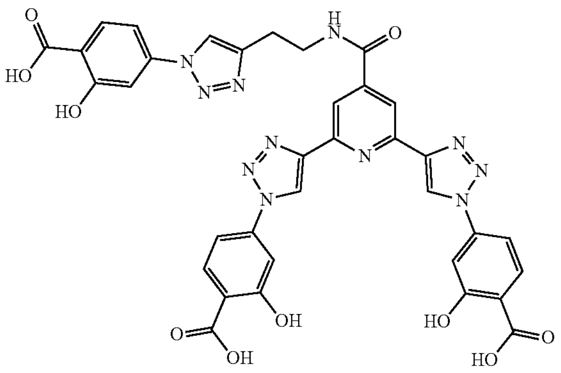

(CC)

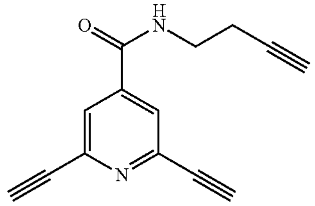

Synthesis of compound 47 commenced with mixing 2,6-dibromo-4-pyridine carboxylic acid (0.2 g, 0.71 mmol), DIPEA (0.18 g, 1.42 mmol) and HATU (0.27 g, 0.71 mmol) in DMF (900 ul). Butynyl amine (0.154 ml, 1.78 mmol) was added immediately and mixed for 1 hour. The reaction was completed by TLC and purified by flash chromatography on silica gel using a gradient of ethyl acetate/hexane. N-(but-3-yn-1-yl)-2,6-dibromoisonicotinamide was isolated as a solid. N-(but-3-yn-1-yl)-2,6-diethynylisonicotinamide CC was made with ethyltrimethylsilane using the Sonogashira method described in Example 16. Synthesis of compound 47 was completed by clicking 4-azidosalicylic acid B and N-(but-3-yn-1-yl)-2,6-diethynylisonicotinamide CC according to the method of Example 1.

Example 31

Synthesis of 4,4'-(naphthalene-2,7-diylbis(1H-1,2,3-triazole-4,1-diyl))bis(2-hydroxybenzoic acid)

(63)

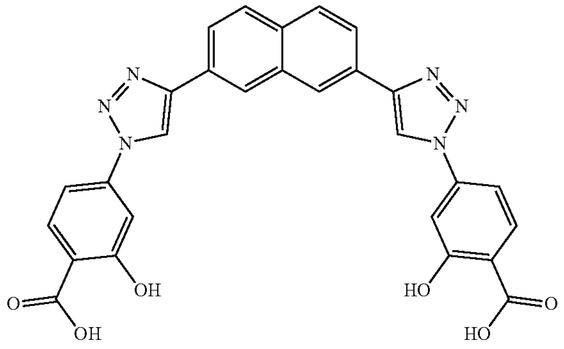

(DD)

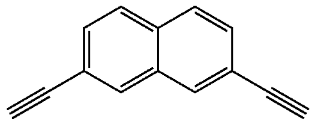

Compound 63 was started with synthesis of 2,7-diethynylnaphthalene DD from 2,7-dibromonaphthalene and ethynyltrimethylsilane using the Sonogashira method described by Bhowmick, S. et al. (App. Organomet. Chem. 31(12): e3824 (2017)). Synthesis of compound 63 was completed by clicking 4-azidosalicylic acid B and 2,7-diethynylnaphthalene DD according to the method of Example 1.

Example 32

Synthesis of 4,4'-(naphthalene-2,3-diylbis(1H-1,2,3-triazole-4,1-diyl))bis(2-hydroxybenzoic acid)

(64)

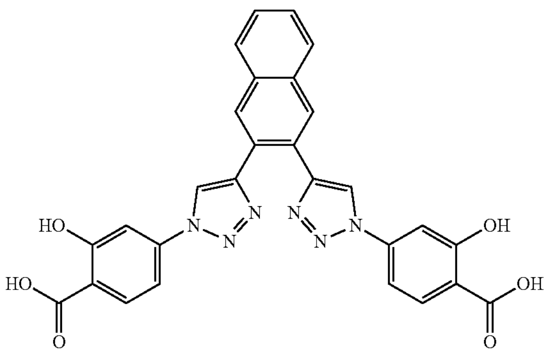

-continued

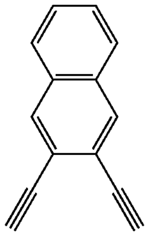

(EE)

Compound 64 was started with synthesis of 2,3-diethynylnaphthalene EE from 2,3-dibromonaphthalene and ethynyltrimethylsilane using the Sonogashira method described by Bhowmick, S. et al. (App. Organomet. Chem. 31(12): e3824 (2017). Synthesis of compound 64 was completed by clicking 4-azidosalicylic acid B and 2,3-diethynylnaphthalene EE according to the method of Example 1.

Example 33

Synthesis of 4,4',4",4'"-((((butane-1,4-diylbis (azanediyl))bis(carbonyl))bis(pyridine-4,2,6-triyl)) tetrakis(1H-1,2,3-triazole-4,1-diyl))tetrakis(2-hydroxybenzoic acid)

(71)

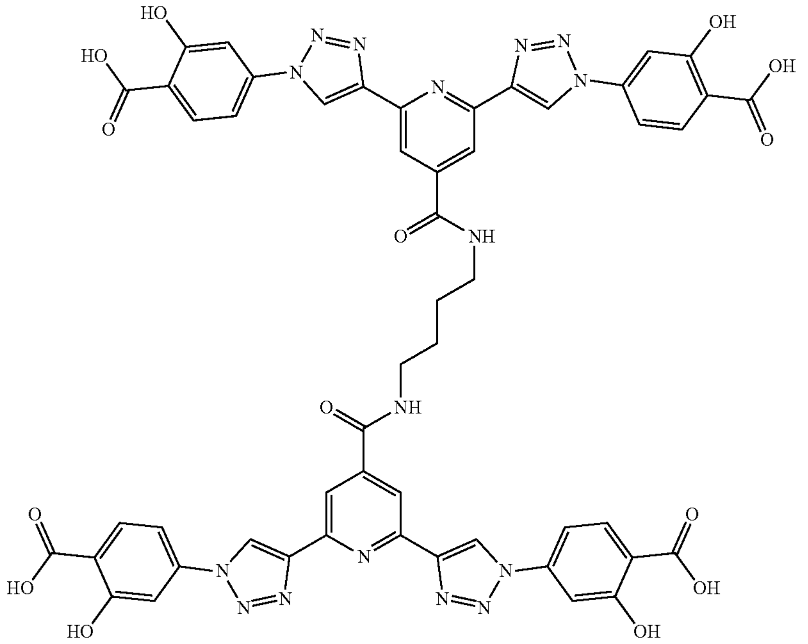

(FF)

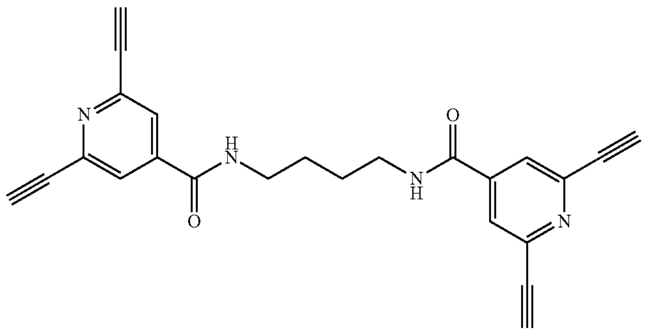

Compound 71 was started with synthesis of 2,6-diethynyl-4-pyridine carboxylic acid from 2,6-dibromo-4-pyridine carboxylic acid and ethynyltrimethylsilane using the Sonogashira method described by Bhowmick, S. et al. (App. Organomet. Chem. 31(12):e3824 (2017)). 2,6-Diethynyl-4-pyridine carboxylic acid was treated with HATU, DIPEA and 1,4-diaminobutane to give N,N'-(butane-1,4-diyl)bis(2,6-diethynylisonicotinamide) (FF) after isolation by flash chromatography. Synthesis of compound 71 was completed by clicking 4-azidosalicylic acid B and N,N'-(butane-1,4-diyl)bis(2,6-diethynylisonicotinamide) (FF) according to the method of Example 1.

Example 34

Synthesis of 4,4'-((4-(ethylcarbamoyl)pyridine-2,6-diyl)bis(1H-1,2,3-triazole-4,1-diyl))bis(3,5,6-trichloropicolinic acid)

(72)

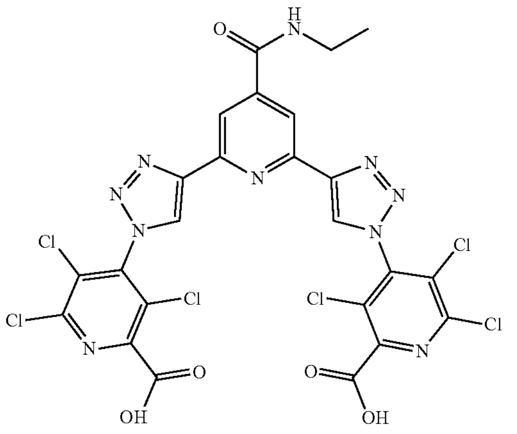

(GG)

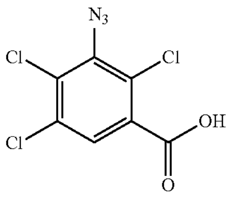

Synthesis of compound 72 started with diazotization of 4-Amino-3,5,6-trichloropyridine 2-carboxylic acid with sodium nitrite and sulfuric acid followed by nucleophilic displacement with azide (Org. Synth. 1942, 22, 96) to form 4-Azido-3,5,6-trichloropyridine-2-carboxylic acid (GG) which was purified via flash chromatography. Synthesis of compound 72 was completed by clicking 4-Azido-3,5,6-trichloropyridine-2-carboxylic acid GG with N-ethyl-2,6-diethynl-4-carboxamide Q according to Example 1.

Example 35

Synthesis of 4,4'-((4-(methylcarbamoyl)pyridine-2,6-diyl)bis(1H-1,2,3-triazole-4,1-diyl))bis(2-(trifluoromethyl)benzoic acid)

(79)

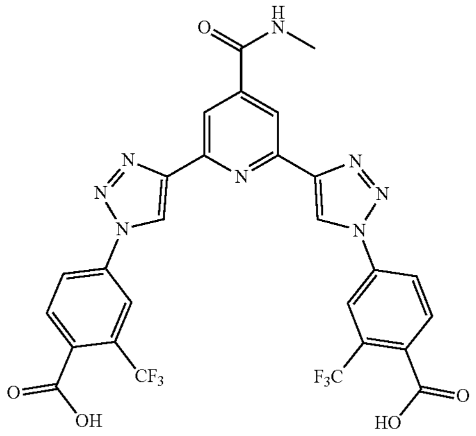

(HH)

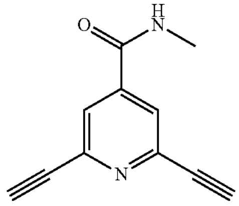

N-Methyl-2,6-diethynylpyridine-4-carboxamide HH was prepared according to Example 17 using HATU coupling of 2,6-diethynylpyridine-4-carboxylic acid with methylamine. Compound 79 was made using the copper click method in Example 1 using diethynyl HH and azide U. Compound 79 Mass Spec (ESI Negative Mode): Calcd for $C_{27}H_{16}F_6N_8O_5$ 646.47; Found: 645 [M-H$^+$]

Example 36

Synthesis of 4,4'-((4-(morpholine-4-carbonyl)pyridine-2,6-diyl)bis(1H-1,2,3-triazole-4,1-diyl))bis(2-(trifluoromethyl)benzoic acid)

(80)

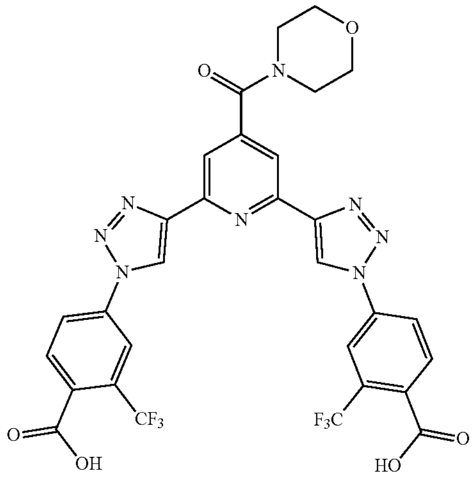

-continued (II)

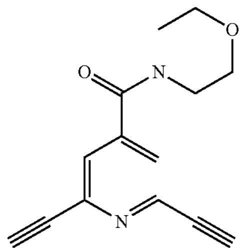

N-Morpholino-2,6-diethynylpyridine-4-carboxamide II was prepared according to Example 17 using HATU coupling of 2,6-diethynylpyridine-4-carboxylic acid with morpholine. Compound 80 was made using the copper click method in Example 1 using diethynyl II and azide U. Compound 80 Mass Spec (ESI Negative Mode): Calcd for C30H20F6N8O6 702.53; Found: 701.1 [M-$H^+$]

Example 37

Synthesis of 4,4'-((4-(diethylcarbamoyl)pyridine-2,6-diyl)bis(1H-1,2,3-triazole-4,1-diyl))bis(2-(trifluoromethyl)benzoic acid)

(81)

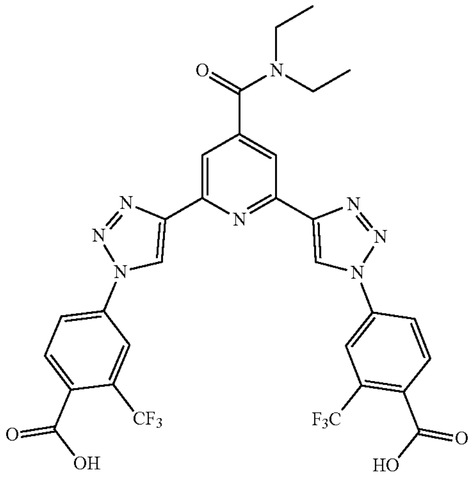

(JJ)

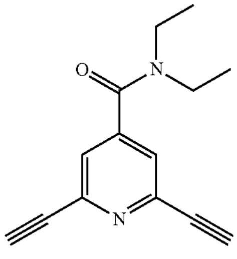

N,N-diethylamino-2,6-diethynylpyridine-4-carboxamide JJ was prepared according to Example 17 using the HATU coupling of 2,6-diethynylpyridine-4-carboxylic acid with N,N-diethylamine. Compound 81 was made using the copper click method in Example 1 using diethynyl JJ and azide U. Compound 81 Mass Spec (ESI Negative Mode): Calcd for $C_{30}H_{22}F_6N_8O_5$ 688.55; Found: 687 [M-$H^+$]

Example 38

Synthesis of 4,4'-((4-carbamoylpyridine-2,6-diyl)bis(1H-1,2,3-triazole-4,1-diyl))bis(2-(trifluoromethyl)benzoic acid)

(82)

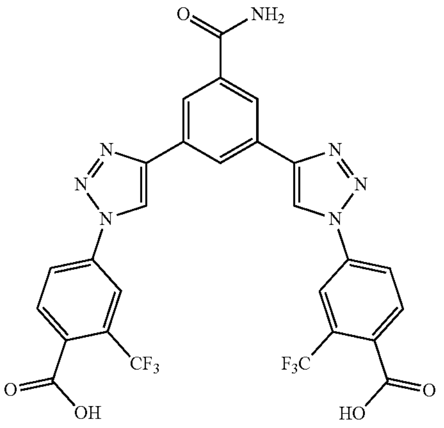

(KK)

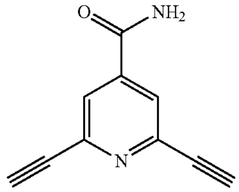

2,6-Diethynylpyridine-4-carboxamide KK was prepared according to Example 17 using the HATU coupling of 2,6-diethynylpyridine-4-carboxylic acid with ammonia. Compound 82 was made using the copper click method in Example 1 using diethynyl KK and azide U. Compound 82 Mass Spec (ESI Negative Mode): Calcd for $C_{26}H_{14}F_6N_8O_5$ 632.44; Found: 631.1 [M-$H^+$]

Example 39

Synthesis of 4,4'-((4-(ethoxycarbonyl)pyridine-2,6-diyl)bis(1H-1,2,3-triazole-4,1-diyl))bis(2-(trifluoromethyl)benzoic acid)

(83)

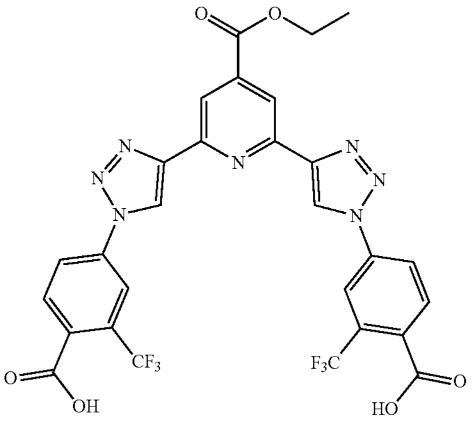

Compound 83 was made using the copper click method in Example 1 using ethyl-2,6-diethynylpyridine-4-carboxylate O and azide U. Compound 83 Mass Spec (ESI Negative Mode): Calcd for $C_{28}H_{17}F_6N_7O_6$ 661.48; Found: 659.9 [M-H$^+$].

Example 40

Synthesis of 4,4'-((4-(azetidine-1-carbonyl)pyridine-2,6-diyl)bis(1H-1,2,3-triazole-4,1-diyl))bis(2-hydroxybenzoic acid)

(84)

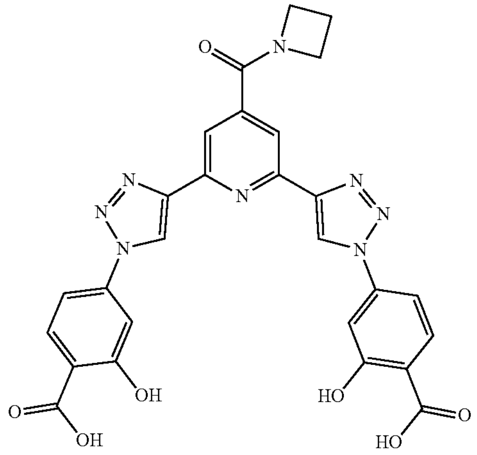

(LL)

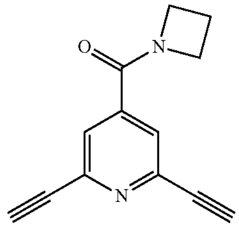

N-Azetidinyl-2,6-diethynylpyridine-4-carboxamide LL was prepared according to Example 17 using the HATU coupling of 2,6-diethynylpyridine-4-carboxylic acid with azetidine. Compound 84 was made using the copper click method in Example 1 using diethynyl LL and azide B. Compound 84 Mass Spec (ESI Negative Mode): Calcd for $C_{27}H_{20}N_8O_7$ 568.51; Found: 567 [M-H$^+$].

Example 41

Synthesis of 4,4'-((4-(ethyl(methyl)carbamoyl)pyridine-2,6-diyl)bis(1H-1,2,3-triazole-4,1-diyl))bis(2-hydroxybenzoic acid)

(85)

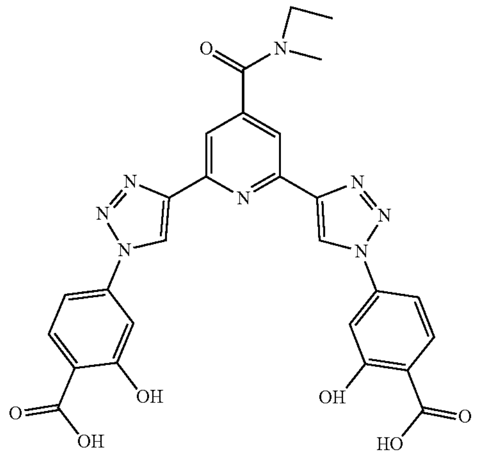

(MM)

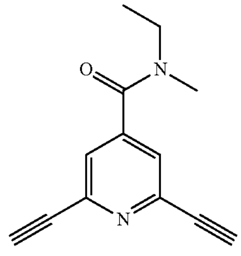

N-Methyl-N-ethyl-2,6-diethynylpyridine-4-carboxamide MM was prepared according to Example 17 using the HATU coupling of 2,6-diethynylpyridine-4-carboxylic acid with N-methyl-N-ethylamine. Compound 85 was made using the copper click method in Example 1 using diethynyl MM and azide B. Compound 85 Mass Spec (ESI Negative Mode): Calcd for $C_{27}H_{22}N_8O_7$ 570.52; Found: 569.1 [M-H$^+$].

Example 42

Synthesis of n-ethyl-2,6-bis(1-(4-(2,2,2-trifluoroacetyl)phenyl)-1H-1,2,3-triazol-4-yl)isonicotinamide (86)

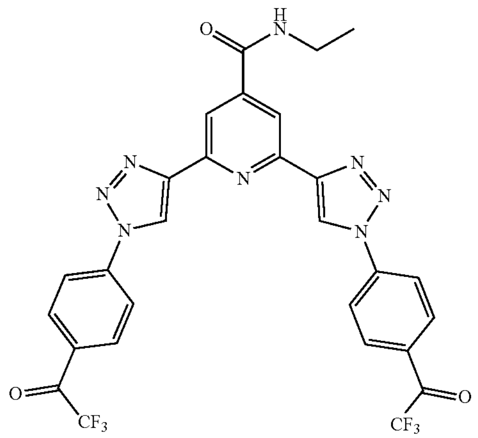

-continued (NN)

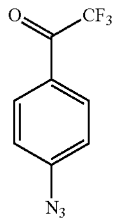

Diazotization of 1-(4-Aminophenyl)-2,2,2-trifluoroethan-1-one with sodium nitrite and sulfuric acid followed by displacement with azide (Org. Synth. 1942, 22, 96 DOI: 10.15227/orgsyn.022.0096) to form 1-(4-azidophenyl)-2,2,2-trifluoroethan-1-one NN which was purified via flash chromatography. Compound 86 was made using the copper click method in Example 1 using azide NN and diethynyl Q. Compound 86 Mass Spec (ESI Negative Mode): Calcd for $C_{28}H_{18}F_6N_8O_3$ 628.5; Found: 627 [M-H$^+$].

Example 43

Synthesis of 4,4'-(pyridine-2,6-diylbis(1H-1,2,3-triazole-4,1-diyl))bis(2-(trifluoromethyl)benzoic acid)

(87)

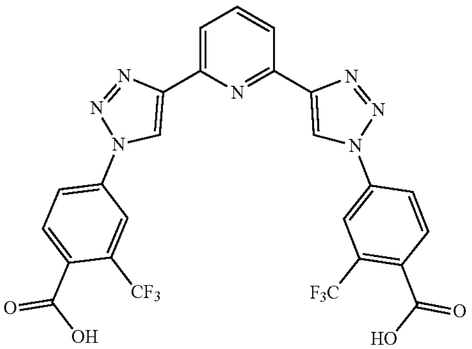

Compound 87 was made using the copper click method in Example 1 using azide U and 2,6-diethynylpyridine A. Compound 87 Mass Spec (ESI Negative Mode): Calcd for $C_{25}H_{13}F_6N_7O_4$ 589.41; Found: 588.1 [M-H$^+$].

Example 44

Synthesis of 4,4'-((4-(cyclopropylcarbamoyl)pyridine-2,6-diyl)bis(1H-1,2,3-triazole-4,1-diyl))bis(2-(trifluoromethyl)benzoic acid)

(88)

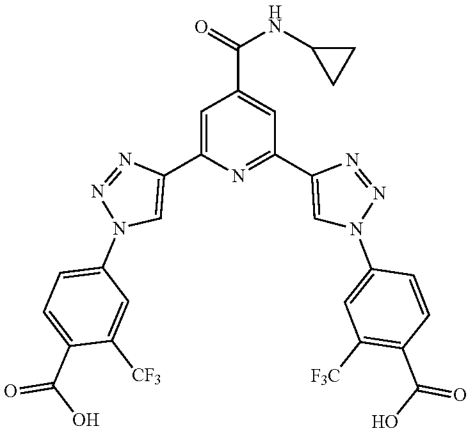

(OO)

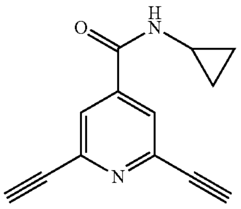

N-Cyclopropylamido-2,6-diethynylpyridine-4-carboxamide 00 was prepared according to Example 17 using the HATU coupling of 2,6-diethynylpyridine-4-carboxylic acid with cyclopropylamine. Compound 88 was made using the copper click method in Example 1 using diethynyl 00 and azide U. Compound 88 Mass Spec (ESI Negative Mode): Calcd for $C_{29}H_{18}F_6N_8O_5$ 672.50; Found: 671.1 [M-H$^+$].

Example 45

Synthesis of 4,4'-((4-(butylcarbamoyl)pyridine-2,6-diyl)bis(1H-1,2,3-triazole-4,1-diyl))bis(2-(trifluoromethyl)benzoic acid)

(89)

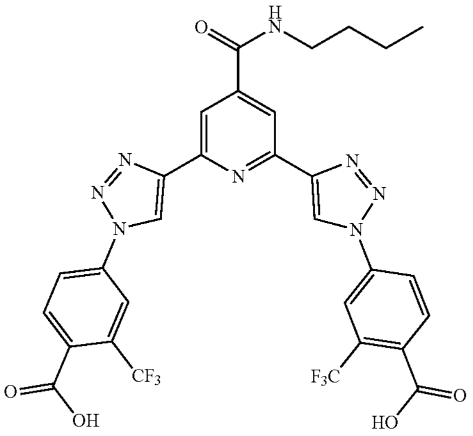

-continued (PP)

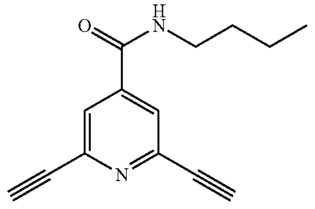

N-Butylamido-2,6-diethynylpyridine-4-carboxamide PP was prepared according to Example 17 using the HATU coupling of 2,6-diethynylpyridine-4-carboxylic acid with 1-aminobutane. Compound 89 was made using the copper click method in Example 1 using diethynyl PP and azide U. Compound 89 Mass Spec (ESI Negative Mode): Calcd for $C_{30}H_{22}F_6N_8O_5$ 688.55; Found: 687.1 [M-H$^+$].

Example 46

Synthesis of 5,5'-((4-(diethylcarbamoyl)pyridine-2,6-diyl)bis(1H-1,2,3-triazole-4,1-diyl))bis(2-(trifluoromethyl)benzoic acid)

(90)

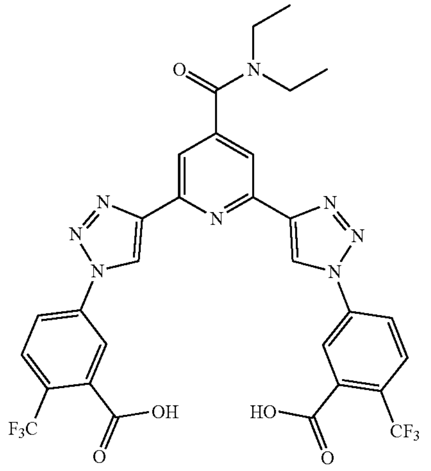

(QQ)

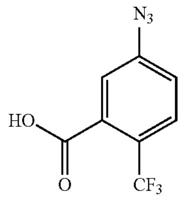

Diazotization of 5-amino-2-(trifluoromethyl)benzoic acid was done according to Example 22 to make 5-azido-2-(trifluoromethyl)benzoic acid QQ. Compound 90 was made using the copper click method in Example 1 using azide QQ and diethynyl JJ. Compound 90 Mass Spec (ESI Negative Mode): Calcd for $C_{30}H_{22}F_6N_8O_5$ 688.55; Found: 687.1 [M-H$^+$].

Example 47

Synthesis of 5,5'-((4-(morpholine-4-carbonyl)pyridine-2,6-diyl)bis(1H-1,2,3-triazole-4,1-diyl))bis(2-(trifluoromethyl)benzoic acid)

(91)

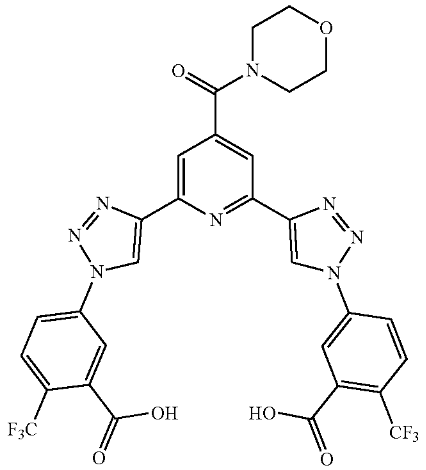

Compound 91 was made using the copper click method in Example 1 using azide QQ and diethynyl II. Compound 91 Mass Spec (ESI Negative Mode): Calcd for $C_{30}H_{20}F_6N_8O_6$ 702.53; Found: 701 [M-H$^+$].

Example 48

Synthesis of 4,4'-(pyridazine-3,6-diylbis(1H-1,2,3-triazole-4,1-diyl))bis(2-hydroxybenzoic acid)

(92)

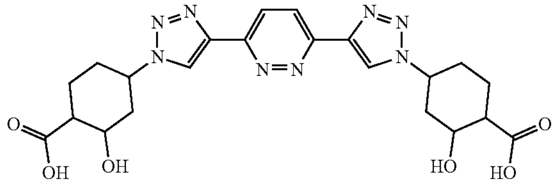

3,6-diethynylpyridazine was prepared according to the Sonogashira method described in Example 9 using 3,6-dibromopyridazine. Compound 92 was made using the copper click method in Example 1 using azide B and 3,6-diethynylpyridazine. Compound 92 Mass Spec (ESI Negative Mode): Calcd for $C_{22}H_{14}N_8O_6$ 486.1; Found: 485 [M-H$^+$].

Example 49

Synthesis of 5,5'-((4-(ethylcarbamoyl)pyridine-2,6-diyl)bis(1H-1,2,3-triazole-4,1-diyl))bis(3-(trifluoromethyl)benzoic acid)

(93)

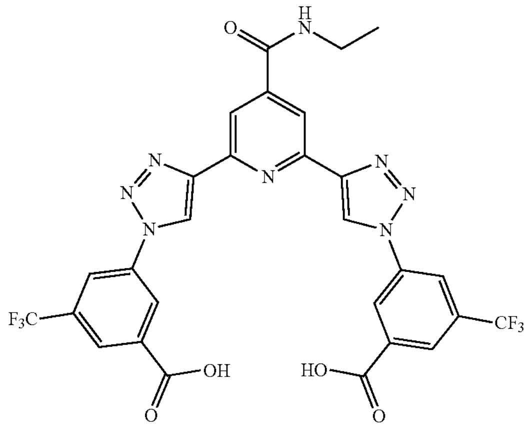

(RR)

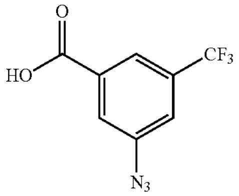

Diazotization of 3-amino-5-(trifluoromethyl)benzoic acid was done according to Example 22 to make 3-azido-5-(trifluoromethyl)benzoic acid RR. Compound 93 was made using the copper click method in Example 1 using azide RR and diethynyl Q. Compound 93 Mass Spec (ESI Negative Mode): Calcd for $C_{28}H_{18}F_6N_8O_5$ 660.49; Found: 659 $[M-H^+]$.

Example 50

Synthesis of 4,4'-((4-carboxypyridine-2,6-diyl)bis(1H-1,2,3-triazole-4,1-diyl))bis(2-(trifluoromethyl)benzoic acid)

(94)

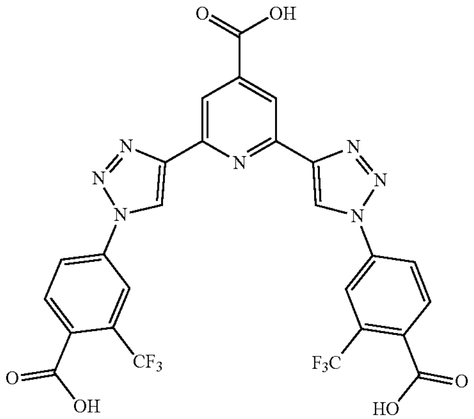

Compound 94 was made using the copper click method in Example 1 using azide U and 2,6-diethynylpyridine-4-carboxylic acid. Compound 94 Mass Spec (ESI Negative Mode): Calcd for $C_{26}H_{13}F_6N_7O_6$ 633.42; Found: 632 [M-H].

Example 51

Synthesis of 3,3'-(((4-(ethylcarbamoyl)pyridine-2,6-diyl)bis(1H-1,2,3-triazole-4,1-diyl))bis(4,1-phenylene))dipropionic acid (95)

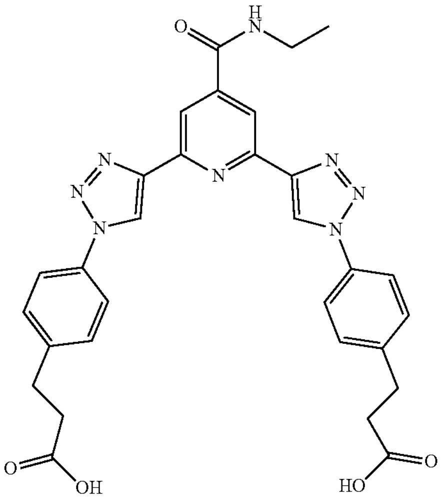

(SS)

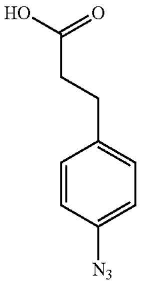

Diazotization of 3-(4-aminophenyl)propanoic acid was done according to Example 22 to make 3-(4-azidophenyl)propanoic acid SS. Compound 95 was made using the copper click method in Example 1 using azide SS and diethynyl Q. Compound 95 Mass Spec (ESI Negative Mode): Calcd for $C_{30}H_{28}N_8O_5$ 580.61; Found: 579 $[M-H^+]$.

Example 52

Synthesis of 4,4'-(((4-(ethylcarbamoyl)pyridine-2,6-diyl)bis(1H-1,2,3-triazole-4,1-diyl))bis(4,1-phenylene))dibutyric acid (96)

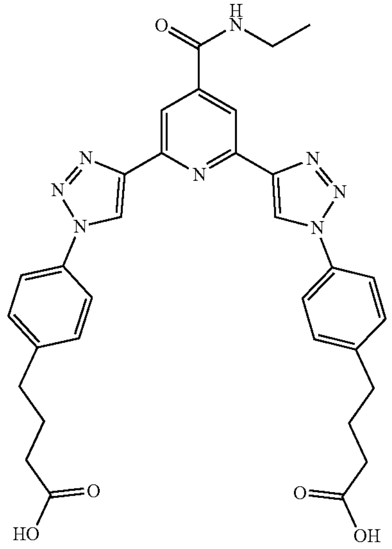

(TT)

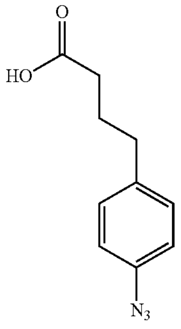

Diazotization of 4-(4-aminophenyl)butanoic acid was done according to Example 22 to make 4-(4-azidophenyl) butanoic acid TT. Compound 96 was made using the copper click method in Example 1 using azide TT and diethynyl Q. Compound 96 Mass Spec (ESI Negative Mode): Calcd for $C_{32}H_{32}N_8O_5$ 608.66; Found: 607 [M-H$^+$].

Example 53

Synthesis of 4,4'-((4-(ethylcarbamoyl)pyridine-2,6-diyl)bis(1H-1,2,3-triazole-4,1-diyl))diphthalic acid (97)

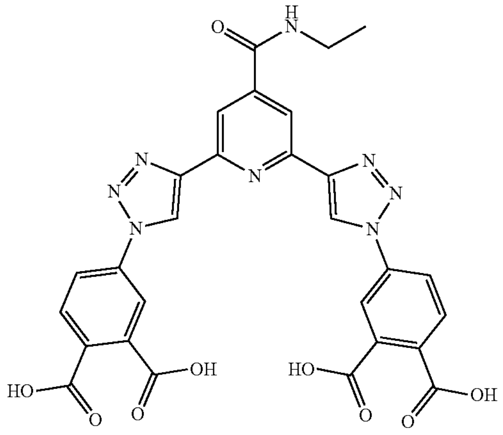

(UU)

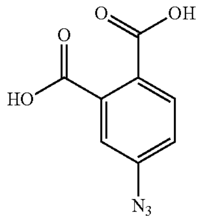

Diazotization of 4-aminophthalic acid was done according to Example 22 to make 4-azidophthalic acid UU. Compound 97 was made using the copper click method in Example 1 using azide UU and diethynyl Q. Compound 97 Mass Spec (ESI Negative Mode): Calcd for $C_{28}H_{20}N_8O_9$ 612.52; Found: 611.1 [M-H$^+$].

Example 54

Synthesis of 4,4'-((4-(ethylcarbamoyl)pyridine-2,6-diyl)bis(1H-1,2,3-triazole-4,1-diyl))bis(2-methoxybenzoic acid)

(98)

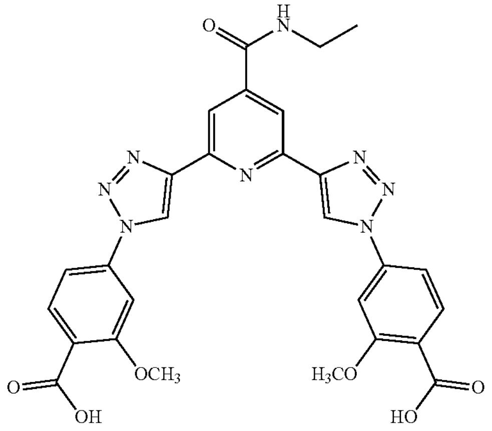

-continued (VV)

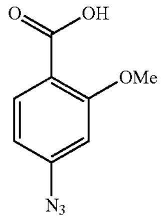

Diazotization of 4-amino-2-methoxybenzoic acid was done according to Example 22 to make 4-azido-2-methoxybenzoic acid VV. Compound 98 was made using the copper click method in Example 1 using azide VV and diethynyl Q. Compound 98 Mass Spec (ESI Negative Mode): Calcd for $C_{28}H_{24}N_8O_7$ 584.55; Found: 583 [M-$H^+$].

Example 55

Synthesis of 5,5'-((4-(ethylcarbamoyl)pyridine-2,6-diyl)bis(1H-1,2,3-triazole-4,1-diyl))diisophthalic acid (99)

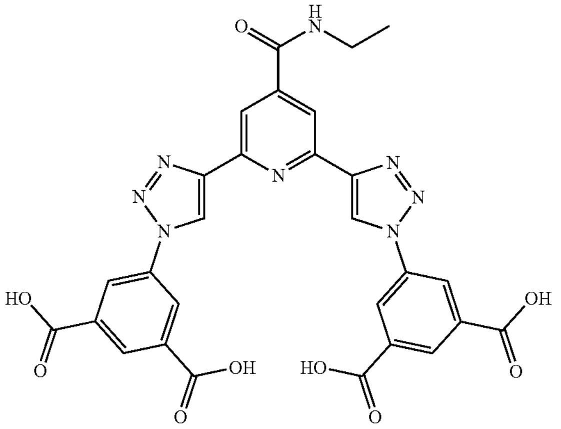

(WW)

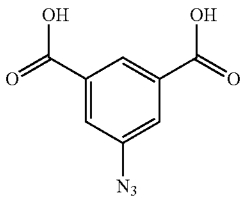

Diazotization of 4-aminoisophthalic acid was done according to Example 22 to make 4-azidoisophthalic acid WW. Compound 99 was made using the copper click method in Example 1 using azide WW and diethynyl Q. Compound 99 Mass Spec (ESI Negative Mode): Calcd for $C_{28}H_{20}N_8O_9$ 612.52; Found: 611 [M-$H^+$].

Example 56

Synthesis of 4,4'-((4-(ethylcarbamoyl)pyridine-2,6-diyl)bis(1H-1,2,3-triazole-4,1-diyl))bis(3-hydroxybenzoic acid)

(100)

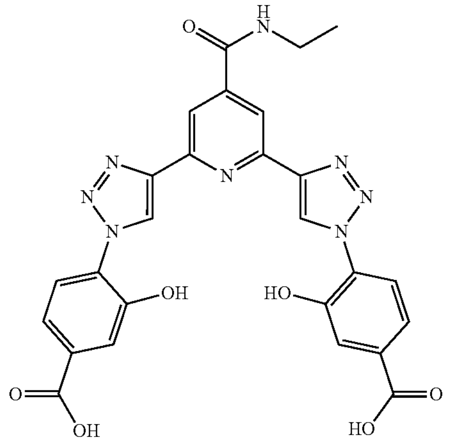

(XX)

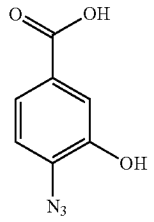

Diazotization of 4-amino-3-hydroxybenzoic acid was done according to Example 22 to make 4-azido-3-hydroxybenzoic acid XX. Compound 100 was made using the copper click method in Example 1 using azide XX and diethynyl Q. Compound 100 Mass Spec (ESI Negative Mode): Calcd for $C_{26}H_{20}N_8O_7$ 556.50; Found: 555.1 [M-$H^+$].

Example 57

Synthesis of diethyl (3-(4-(6-(1-(3-(diethoxyphosphoryl)propyl)-1H-1,2,3-triazol-4-yl)-4-(ethylcarbamoyl) 161yridine-2-yl)-1H-1,2,3-triazol-1-yl)propyl) phosphonate (101)

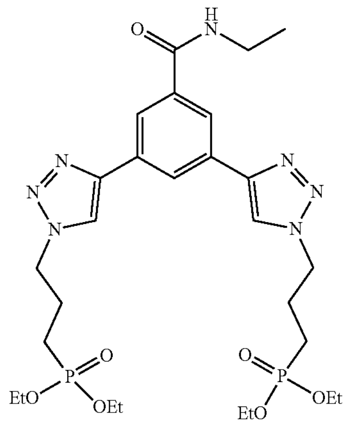

-continued (YY)

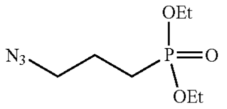

Diazotization of 0,0-diethyl (3-aminopropyl)phophonate was done according to Example 22 to make 0,0-diethyl (3-azidopropyl)phophonate YY. Compound 101 was made using the copper click method in Example 1 using azide YY and diethynyl Q. Compound 101 Mass Spec (ESI Negative Mode): Calcd for $C_{26}H_{42}N_8O_7P_2$ 640.62; Found: 639.3 [M-H$^+$].

Example 58

Synthesis of 4,4'-((4-(ethylcarbamoyl)pyridine-2,6-diyl)bis(1H-1,2,3-triazole-4,1-diyl))bis(2-methylbenzoic acid)

(102)

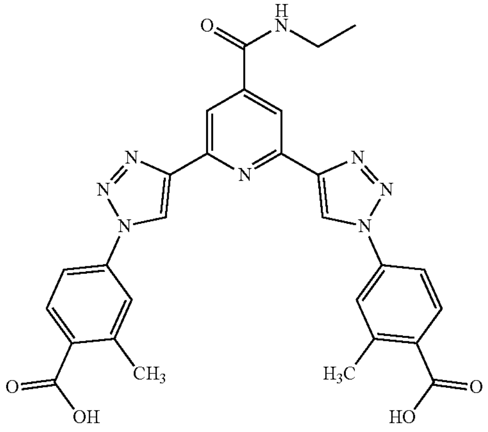

(ZZ)

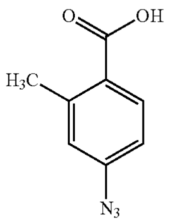

Diazotization of 4-amino-2-methylbenzoic acid was done according to Example 22 to make 4-amino-2-methylbenzoic acid ZZ. Compound 102 was made using the copper click method in Example 1 using azide ZZ and diethynyl Q. Compound 102 Mass Spec (ESI Negative Mode): Calcd for $C_{28}H_{24}N_8O_5$ 552.55; Found: 551.1 [M-H$^+$].

Example 59

Synthesis of 4,4'-((5-carboxy-1,3-phenylene)bis(1H-1,2,3-triazole-4,1-diyl))bis(2-(trifluoromethyl)benzoic acid)

(103)

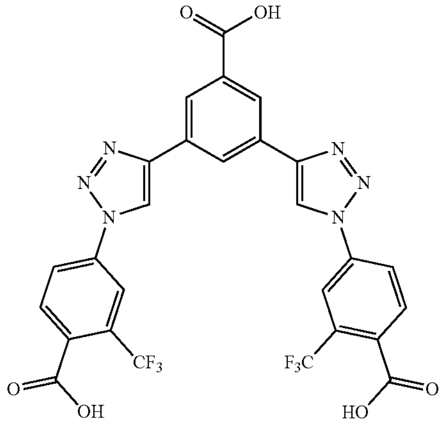

Compound 103 was made using the copper click method in Example 1 using azide Q and 3,5-diethynylbenzoic acid. Compound 103 Mass Spec (ESI Negative Mode): Calcd for $C_{27}H_{14}F_6N_6O_6$ 632.44; Found: 631 [M-H$^+$].

Example 60

Synthesis of 2,2'-((4-(ethylcarbamoyl)pyridine-2,6-diyl)bis(1H-1,2,3-triazole-4,1-diyl))bis(3-(trifluoromethyl)benzoic acid)

(104)

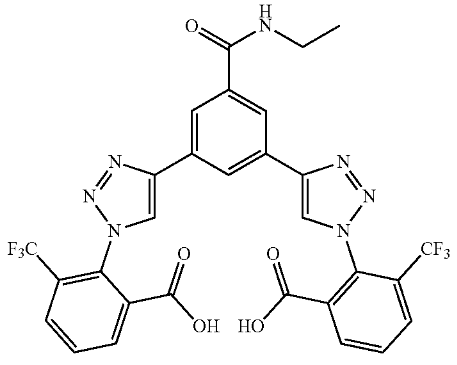

(AAA)

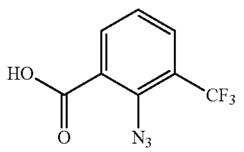

Diazotization of 2-amino-3-(trifluoromethyl)benzoic acid was done according to Example 22 to make 2-azido-3-(trifluoromethyl)benzoic acid AAA. Compound 104 was made using the copper click method in Example 1 using azide AAA and diethynyl Q. Compound 104 Mass Spec (ESI Negative Mode): Calcd for $C_{28}H_{18}F_6N_8O_5$ 660.49; Found: 659 [M-H$^+$].

Example 61

Synthesis of 4,4'-((4-((2-hydroxyethyl)carbamoyl)pyridine-2,6-diyl)bis(1H-1,2,3-triazole-4,1-diyl))bis(2-(trifluoromethyl)benzoic acid)

(105)

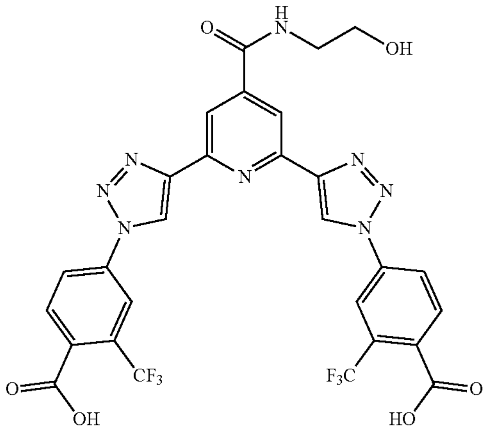

(BBB)

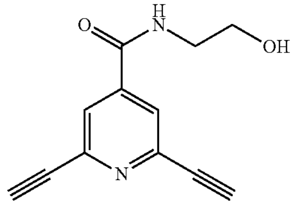

N-(2-Hydroxyethyl)amino-2,6-diethynylpyridine-4-carboxamide BBB was prepared according to Example 17 using the HATU coupling of 2,6-diethynylpyridine-4-carboxylic acid with aminoethanol. Compound 105 was made using the copper click method in Example 1 using diethynyl BBB and azide U. Compound 105 Mass Spec (ESI Negative Mode): Calcd for $C_{28}H_{18}F_6N_8O_6$ 676.49; Found: 675 [M-H$^+$].

Example 62

Synthesis of 4,4'-((4-(ethylcarbamoyl)pyridine-2,6-diyl)bis(1H-1,2,3-triazole-4,1-diyl))bis(2-nitrobenzoic acid)

(106)

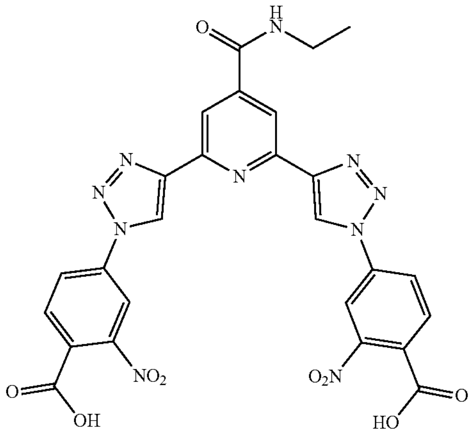

-continued (CCC)

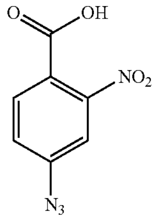

Diazotization of 4-amino-2-nitrobenzoic acid was done according to Example 22 to make 4-azido-2-nitrobenzoic acid CCC. Compound 106 was made using the copper click method in Example 1 using azide CCC and diethynyl Q. Compound 106 Mass Spec (ESI Negative Mode): Calcd for $C_{26}H_{18}N_{10}O_9$ 614.49; Found: 613 [M-H$^+$].

Example 63

Synthesis of 4,4'-((4-((3,3,3-trifluoropropyl)carbamoyl)pyridine-2,6-diyl)bis(1H-1,2,3-triazole-4,1-diyl))bis(2-(trifluoromethyl)benzoic acid)

(107)

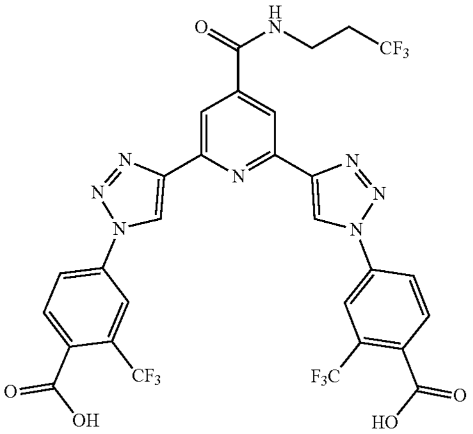

(DDD)

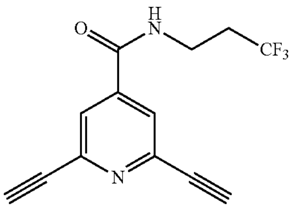

N-(3,3,3-trifluoropropyl)-2,6-diethynylpyridine-4-carboxamide DDD was prepared according to Example 17 using the HATU coupling of 2,6-diethynylpyridine-4-carboxylic acid with 3,3,3-trifluoropropan-1-amine. Compound 107 was made using the copper click method in Example 1 using diethynyl DDD and azide U. Compound 107 Mass Spec (ESI Negative Mode): Calcd for $C_{29}H_{17}F_9N_8O_5$ 728.49; Found: 727 [M-H$^+$].

Example 64

Synthesis of 4,4',4'',4'''-((((butane-1,4-diylbis(azanediyl))bis(carbonyl))bis(pyridine-4,2,6-triyl))tetrakis(1H-1,2,3-triazole-4,1-diyl))tetrakis(2-(trifluoromethyl)benzoic acid)

(108)

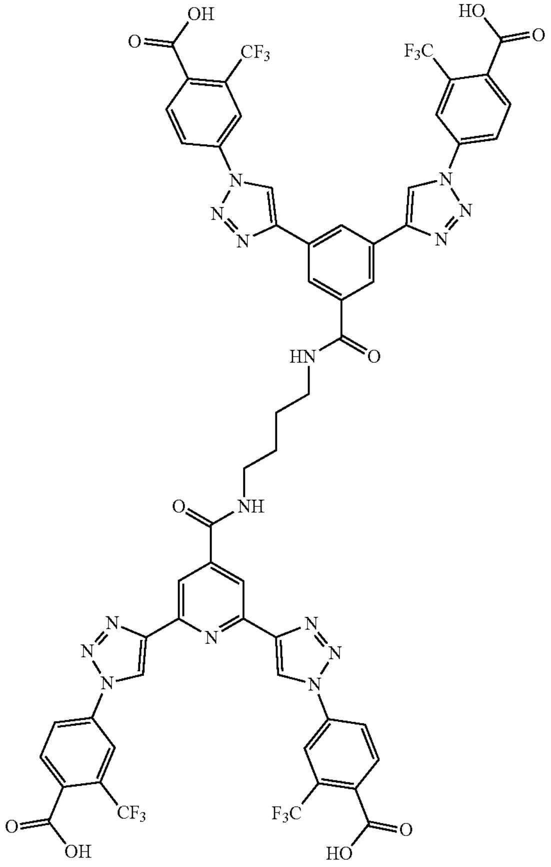

Compound 108 was made using the copper click method in Example 1 using diethynyl FF and azide U. Compound 108 Mass Spec (ESI Negative Mode): Calcd for $C_{56}H_{34}F_{12}N_{16}O_{10}$ 1318.97; Found: 1316.9 [M-H$^+$].

Example 65

Synthesis of (4-(4-(4-(ethylcarbamoyl)-6-(1-(4-phosphonophenyl)-1H-1,2,3-triazol-4-yl)167yridine-2-yl)-1H-1,2,3-triazol-1-yl)phenyl)phosphonic acid (109)

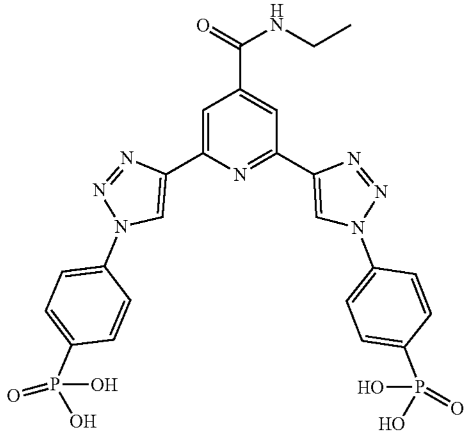

(EEE)

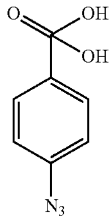

Diazotization of (4-aminophenyl)phosphonic acid was done according to Example 22 to make (4-azidophenyl) phosphonic acid EEE. Compound 109 was made using the copper click method in Example 1 using azide EEE and diethynyl Q. Compound 109 Mass Spec (ESI Negative Mode): Calcd for $C_{24}H_{22}N8O_7P_2$ 596.44; Found: 595 [M-H$^+$].

Example 66

Synthesis of 2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))diacetic acid (110)

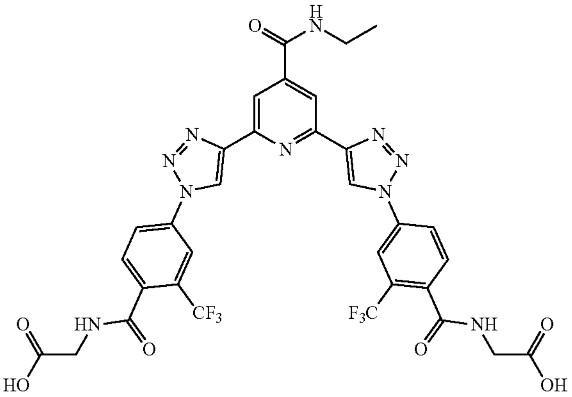

-continued (FFF)

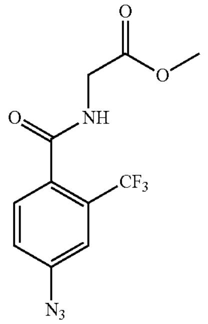

(GGG)

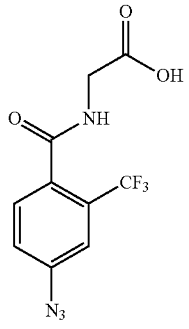

Methyl (4-Azido-2-(trifluoromethyl)benzoyl)glycine FFF was prepared according to the HATU condensation method described in Example 17 coupling of azide U with methyl glycinate. The methyl ester FFF was saponified with 1N NaOH followed by neutralization to give (4-Azido-2-(trifluoromethyl)benzoyl)glycine GGG. Compound 110 was made using the copper click method in Example 1 using diethynyl Q and azide GGG. Compound 110 Mass Spec (ESI Negative Mode): Calcd for $C_{32}H_{24}F_6N_{10}O_7$ 774.60; Found: 773 [M-H$^+$].

Example 67

Synthesis of dimethyl 2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))diacetate (111)

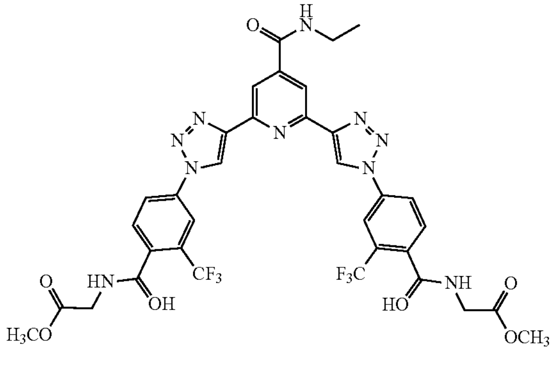

Compound 111 was made using the copper click method in Example 1 using azide FFF and diethynyl Q. Compound 111 Mass Spec (ESI Negative Mode): Calcd for $C_{34}H_{28}F_6N_{10}O_7$ 802.65; Found: 801.1 [M-H$^+$].

Example 68

Synthesis of (2S,2'S)-2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))disuccinic acid (112)

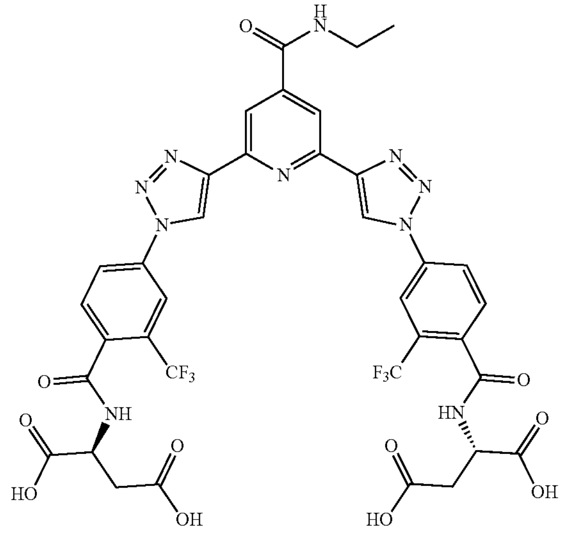

(HHH)

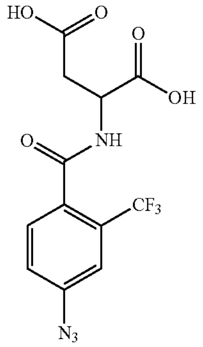

(4-azido-2-(trifluoromethyl)benzoyl)aspartate HHH was prepared according to the HATU condensation method described in Example 17 coupling of azide U with dimethyl aspartate to give dimethyl (4-azido-2-(trifluoromethyl)benzoyl)aspartate. The dimethyl ester of was saponified with 1N NaOH followed by neutralization to give HHH. Compound 112 was made using the copper click method in Example 1 using diethynyl Q and azide HHH. Compound 112 Mass Spec (ESI Negative Mode): Calcd for $C_{36}H_{28}F_6N_{10}O_{11}$ 890.67; Found: 889 [M-H$^+$].

Example 69

Synthesis of 2,2'-((2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))bis(acetyl))bis(azanediyl))diacetic acid (113)

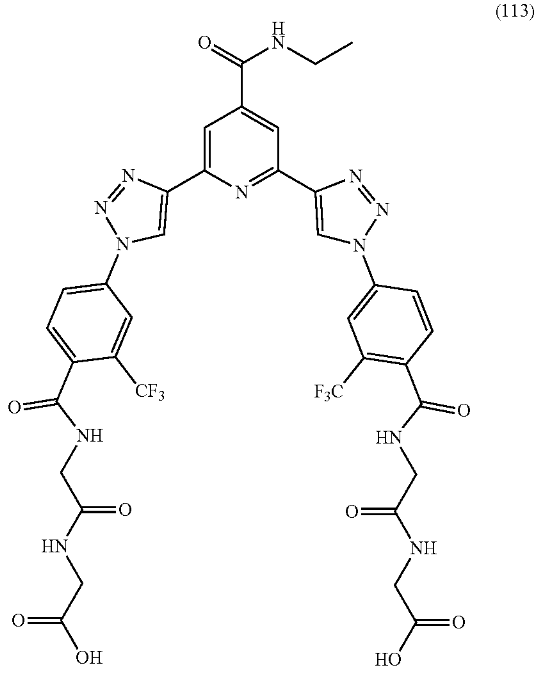

(III)

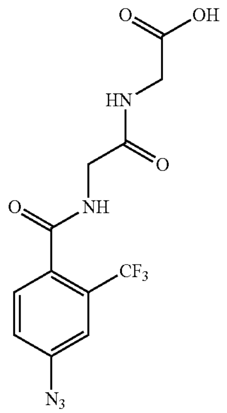

(4-azido-2-(trifluoromethyl)benzoyl)glycylglycine III was prepared according to the HATU condensation method described in Example 17 coupling azide U with methyl-glycylglycinate. The methyl ester was saponified with 1N NaOH followed by neutralization to give (4-azido-2-(trifluoromethyl)benzoyl)-glycylglycine III. Compound 113 was made using the copper click method in Example 1 using diethynyl Q and azide III. Compound 113 Mass Spec (ESI Negative Mode): Calcd for $C_{36}H_{30}F_6N_{12}O_9$ 888.70; Found: 887 [M-H$^+$].

Example 70

Synthesis of 2,6-bis(1-(4-cyano-3-(trifluoromethyl)phenyl)-1H-1,2,3-triazol-4-yl)-N-ethylisonicotinamide (114)

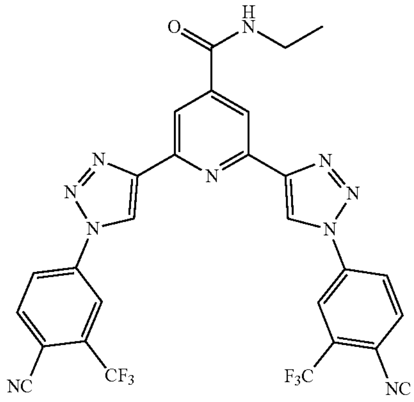

(JJJ)

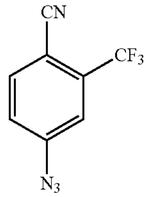

Diazotization of 4-amino-2-(trifluoromethyl)benzonitrile was done according to Example 22 to make 4-azido-2-(trifluoromethyl)benzonitrile JJJ. Compound 114 was made using the copper click method in Example 1 using azide JJJ and diethynyl Q. Compound 114 Mass Spec (ESI Negative Mode): Calcd for $C_{28}H_{16}F_6N_{10}O$ 622.50; Found: 621 [M-H$^+$].

Example 71

Synthesis of 4,4'-((5-carboxy-1,3-phenylene)bis(1H-1,2,3-triazole-1,4-diyl))bis(2-(trifluoromethyl)benzoic acid)

(115)

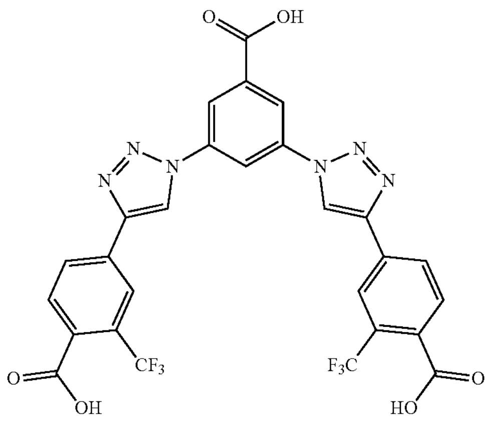

-continued (KKK)

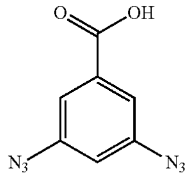

(LLL)

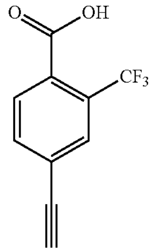

Diazotization of 3,5-diaminobenzoic acid was done according to Example 22 to make 3,5-diazidobenzoic acid KKK. 4-Ethynyl-2-(trifluoromethyl)benzoic acid LLL was prepared according to the Sonogashira method described in Example 9 using 4-bromo-2-(trifluoromethyl)benzoic acid. Compound 115 was made using the copper click method in Example 1 using bis-azide KKK and mono-ethynyl LLL. Compound 115 Mass Spec (ESI Negative Mode): Calcd for $C_{27}H_{14}F_6N_6O_6$ 632.44; Found: 631 [M-H].

Example 72

Synthesis of 4,4'-((5-(ethylcarbamoyl)-1,3-phenylene)bis(1H-1,2,3-triazole-1,4-diyl))bis(2-(trifluoromethyl)benzoic acid)

(116)

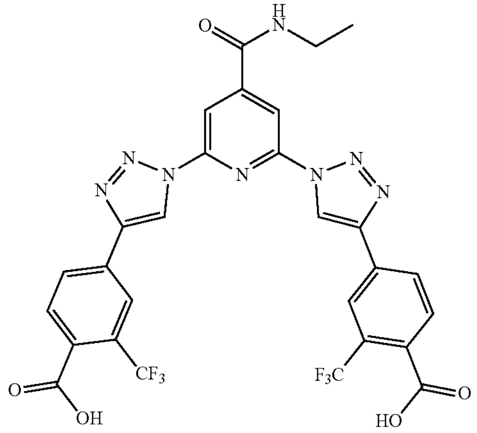

(MMM)

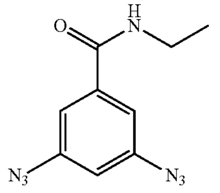

3,5-Diazido-N-ethylbenzamide MMM was prepared according to the HATU condensation method described in Example 17 coupling Bis-azide acid KKK with ethylamine. Compound 116 was made using the copper click method in Example 1 using mono-ethynyl LLL and bis-azide MMM. Compound 116 Mass Spec (ESI Negative Mode): Calcd for $C_{29}H_{19}F_6N_7O_5$ 659.51; Found: 658.1 [M-H$^+$].

Example 73

Synthesis of 4,4'-(thiophene-2,5-diylbis(1H-1,2,3-triazole-4,1-diyl))bis(2-(trifluoromethyl)benzoic acid)

(117)

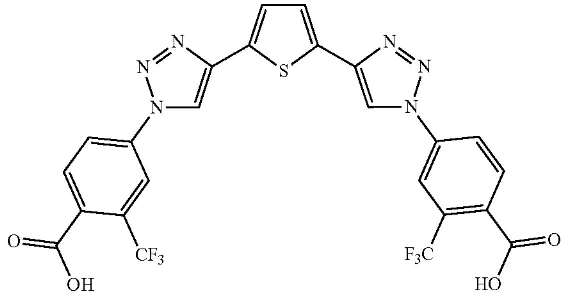

(NNN)

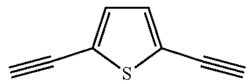

2,5-Diethynylthiophene NNN was prepared according to the Sonogashira method described in Example 9 using 2,5-dibromothiophene. Compound 117 was made using the copper click method in Example 1 using azide U and diethynyl NNN. Compound 117 Mass Spec (ESI Negative Mode): Calcd for $C_{24}H_{12}F_6N_6O_4$ 594.45; Found: 593 [M-H$^+$].

Example 74

Synthesis of 4,4'-(furan-2,5-diylbis(1H-1,2,3-triazole-4,1-diyl))bis(2-(trifluoromethyl)benzoic acid)

(118)

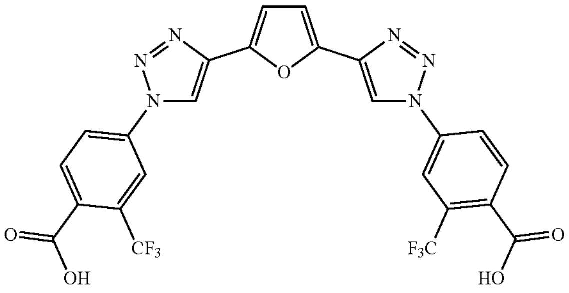

(OOO)

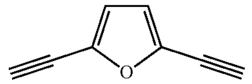

2,5-Diethynylfuran 000 was prepared according to the Sonogashira method described in Example 9 using 2,5-dibromofuran. Compound 118 was made using the copper click method in Example 1 using azide U and diethynyl 000. Compound 118 Mass Spec (ESI Negative Mode): Calcd for $C_{24}H_{12}F_6N_6O_5$ 578.39; Found: 577 [M-H$^+$].

Example 75

Synthesis of 3'-(4-(4-(ethylcarbamoyl)-6-(1-(3'-(trifluoromethyl)-[1,1'-biphenyl]-3-yl)-1H-1,2,3-triazol-4-yl)pyridin-2-yl)-1H-1,2,3-triazol-1-yl)-3-(trifluoromethyl)-[1,1'-biphenyl]-4-carboxylic acid-carbon dioxide (1/1)

(119)

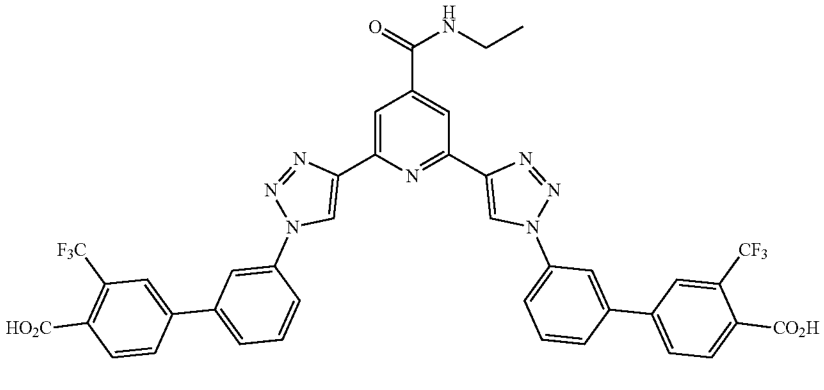

(PPP)

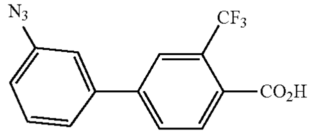

Synthesis of 3'-amino-3-(trifluoromethyl)-[1,1'-biphenyl]-4-carboxylic acid commenced with mixing methyl 4-bromo-2-(trifluoromethyl)benzoate (142 mg, 0.5 mmol), 3-aminophenyl boronic acid (137 mg, 1 mmol), $Pd(PPh_3)_2C_{12}$ (35 mg, 0.1 mmol) and $K_2CO_3$ (138 mg, 2 mmol) was added methanol (2 ml). The solution was heated at 45 C for 1.5 hr. The methanol was removed by evaporation. The residual solid was dissolved in dimethylformamide (1 ml) and purified by silica chromatography using a Reveleris Prep eluting with a EtOAc/hexane mobile phase. Appropriate fractions were collected based on UV and evaporated to give methyl 3'-amino-3-(trifluoromethyl)-[1,1'-biphenyl]-4-carboxylate (101 mg, 68% yield).

Diazotization of methyl 3'-amino-3-(trifluoromethyl)-[1,1'-biphenyl]-4-carboxylate was done according to Example 22 to make methyl 3'-azido-3-(trifluoromethyl)-[1,1'-biphenyl]-4-carboxylate. The methyl ester was saponified KOH, neutralized with 0.25 HCl and recovered with EtOAc to give 3'-azido-3-(trifluoromethyl)-[1,1'-biphenyl]-4-carboxylic acid PPP. Compound 119 was made using the copper click method in Example 1 using azide PPP and diethynyl Q. Compound 119 Mass Spec (ESI Negative Mode): Calcd for $C_{40}H_{26}N_8O_5$ 812.69.

Example 76

Synthesis of 4,4'-((4-(ethylcarbamoyl)pyridine-2,6-diyl)bis(1H-1,2,3-triazole-4,1-diyl))bis(2-cyanobenzoic acid)

(120)

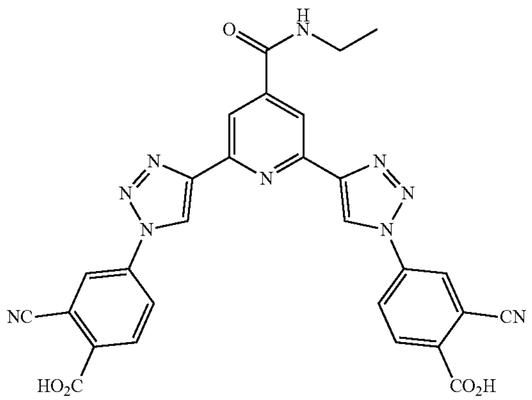

-continued (QQQ)

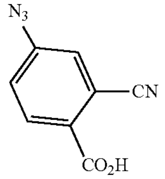

Diazotization of 4-amino-2-cyanobenzoic acid was done according to Example 22 to make 4-azido-2-cyanobenzoic acid QQQ. Compound 120 was made using the copper click method in Example 1 using azide QQQ and diethynyl Q. Compound 120 Mass Spec (ESI Negative Mode): Calcd for $C_{28}H_{18}N_{10}O_5$ 574.50.

Example 77

Synthesis of 4,4'-((4-(ethylcarbamoyl)pyridine-2,6-diyl)bis(1H-1,2,3-triazole-4,1-diyl))bis(2-chlorobenzoic acid)

(121)

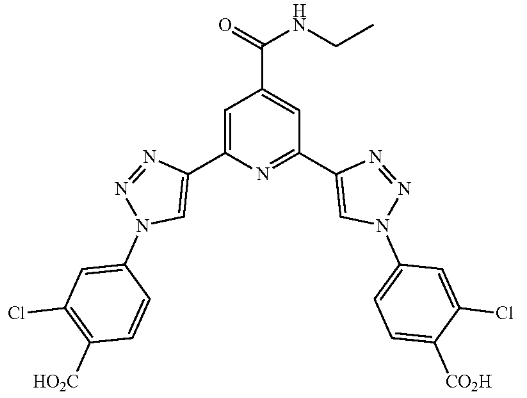

(RRR)

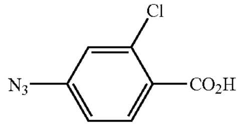

Diazotization of 4-amino-2-chlorobenzoic acid was done according to Example 22 to make 4-azido-2-chlorobenzoic acid RRR. Compound 121 was made using the copper click method in Example 1 using azide RRR and diethynyl Q. Compound 121 Mass Spec (ESI Negative Mode): Calcd for $C_{26}H_{18}C_{12}N_8O_5$ 593.38.

Example 78

Screen of PEMs for Enhancement of XNTP Polymerization

The Sequencing by Expansion (SBX) methodology developed by the inventors provides significant performance enhancements in sequence read efficiency and accuracy of Xpandomers relative to native DNA. However, initial transcription of the sequence of the natural DNA template onto the measurable Xpandomer relies on the ability of DNA polymerase to utilize XNTPs as substrates (the generalized structure of an XNTP is discussed herein with reference to FIG. 1A and FIG. 2). The inventors have found that most DNA polymerases do not efficiently polymerize XNTPs. In an effort to improve the efficiency and accuracy of XNTP polymerization into Xpandomers, several PEMs were screened for the ability to enhance DNA polymerase primer extension reactions using XNTPs as substrates.

A representative primer extension reaction may include the following reagents: 2 pmol primer, 2.2 pmol 45mer oligonucleotide template, 50 pmol of each XNTP (XATP, XCTP, XGTP, and XTTP), 50 Mm Tris HCl, Ph 6.79, 200 Mm NaCl, 20% PEG, 5% NMS, 0.5 nmol polyphosphate 60.19, 0.3 Mm MnC12, and 0.6 μg of purified recombinant DNA polymerase protein. Reactions may be run for 1 hr at 23° C. Reaction products (i.e., constrained Xpandomers) are treated to cleave the phosphoramidate bonds, thereby generating linearized Xpandomers. Reaction products may be analyzed using gel electrophoresis on 4-12% acrylamide gels to resolve and visualize Xpandomer products of different lengths. For the PEM screen described above, PEMs were typically tested in the micro to millimolar range.

Figure 4:
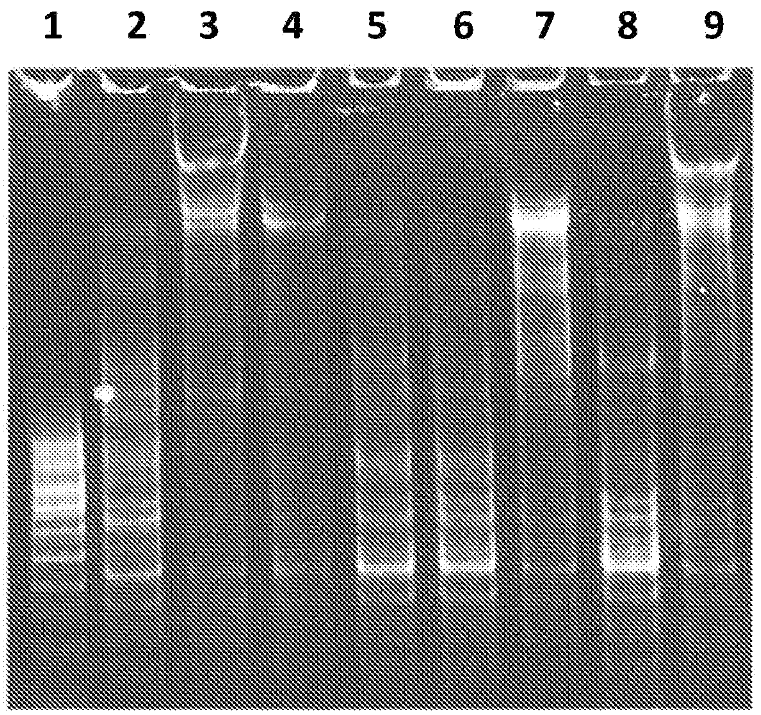
FIG. 4 is a gel showing primer extension products.

Surprisingly, several PEMs were observed to significantly and reproducibly enhance DNA polymerase-mediated primer extension with XNTPs. Representative gels demonstrating this enhancement are presented in FIGS. 4 and 5. With reference to FIG. 4, as can be seen in lane 1 (no PEM additive), DNA polymerase extends the template bound primer with up to only around 14 XNTPs under these conditions. However, addition certain PEMs to the primer extension reaction enables the polymerase to synthesize considerably longer extension products as can be seen, e.g., in lanes 3 (compound 4) 7 (compound 3) and 9 (compound 1). In contrast, several different aromatic compounds had little or no effect on XNTP polymerization (see, e.g, lanes 2, 4-6, and 8), indicating that PEM activity is specific for compounds 1, 3, and 4.

Figure 5:
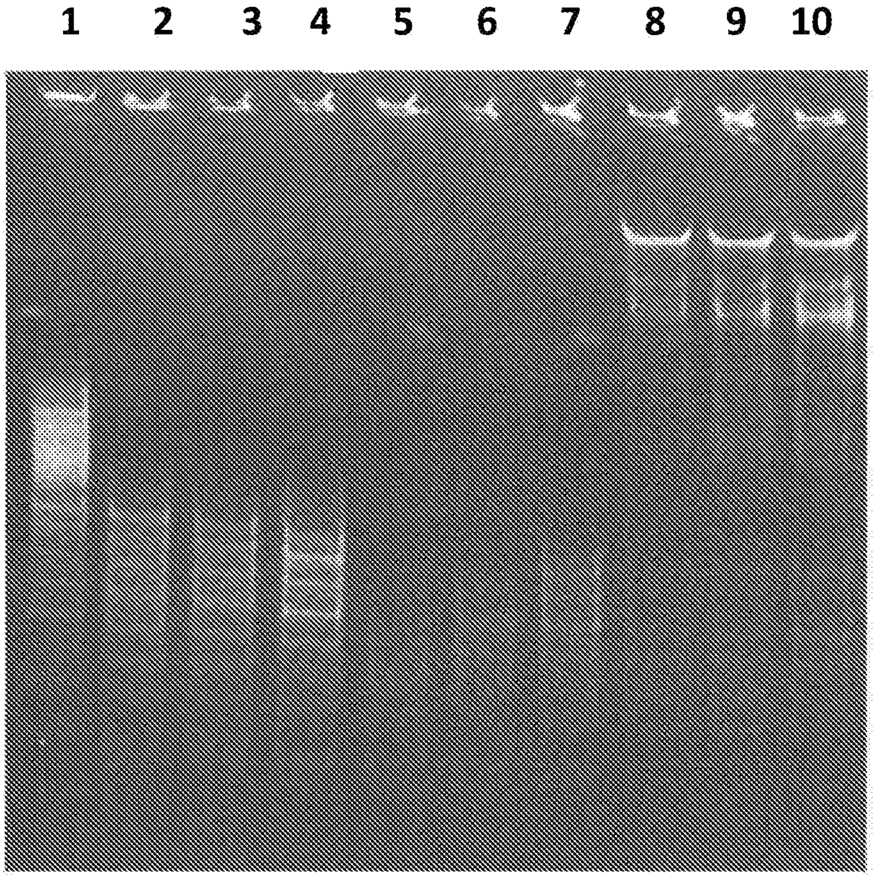
FIG. 5 is a gel showing primer extension products.

Similarly, with reference to FIG. 5, in the absence of PEM additive, DNA polymerase shows modest primer extension activity with XNTPs (lane 1, no PEM additive), while addition of compound 2 at various concentrations (lanes 8-10) significantly enhances primer extension activity. Again, this PEM activity is specific for compound 2, as other unrelated aromatic compounds had no effect (lanes 2-7).

Example 79

PEMs Enhance Sequencing by Expansion (SBX)

To investigate the accuracy of PEM-dependent enhancement of XNTP polymerization, primer extension products were sequenced using the SBX protocol. Briefly, the constrained Xpandomer products of XNTP polymerization are cleaved to generate linearized Xpandomers. This is accomplished by first quenching the extension reaction with a solution containing 100 Mm EDTA, 2 Mm THPTA, and 2% Tween-20. Then the sample is subjected to amine modification with a solution of 1 M $NaHCO_3$ and 1 M succinic anhydride in DMF. Cleavage of the phosphoramidate bonds is carried out with 37% HCl and linearized Xpandomers are purified with QIAquick columns (QIAGEN, Inc.).

For sequencing, protein nanopores are prepared by inserting a-hemolysin into a DphPE/hexadecane bilayer member in buffer B1, containing 2 M $NH_4Cl$ and 100 Mm HEPES, Ph 7.4. The cis well is perfused with buffer B2, containing 0.4 M $NH_4Cl$, 0.6 M GuCl, and 100 Mm HEPES, Ph 7.4. The Xpandomer sample is heated to 70° C. for 2 minutes, cooled completely, then a 2 μL sample is added to the cis well. A voltage pulse of 90 Mv/390 Mv/10 μs is then applied and data is acquired via Labview acquisition software.

Figure 6A:
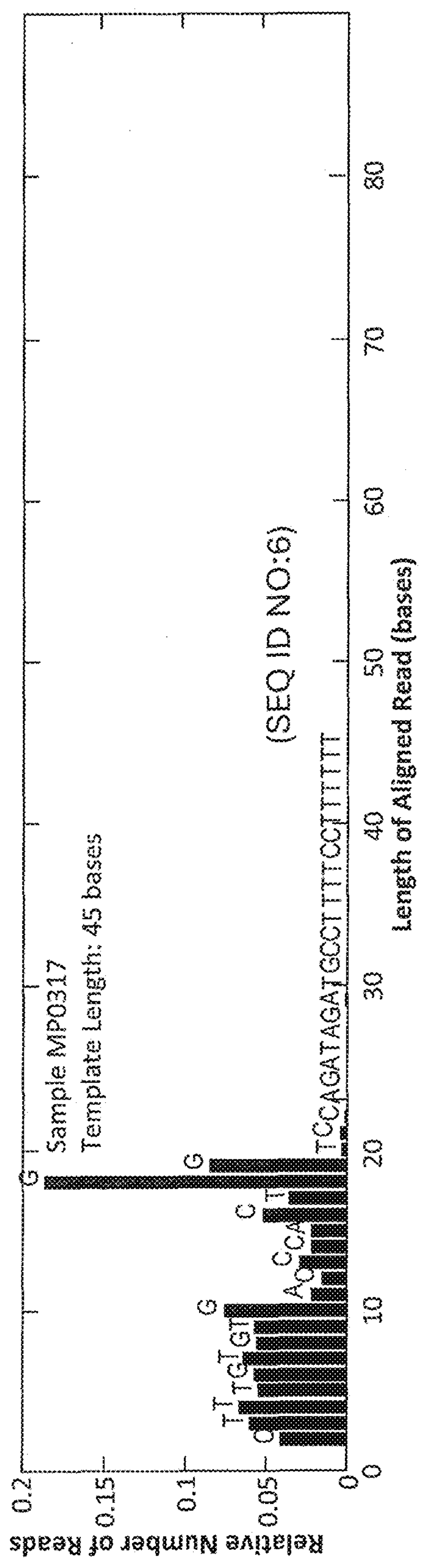
FIGS. 6A and 6B are histogram displays of populations of aligned reads of nanopore-derived sequences.
Figure 6B:
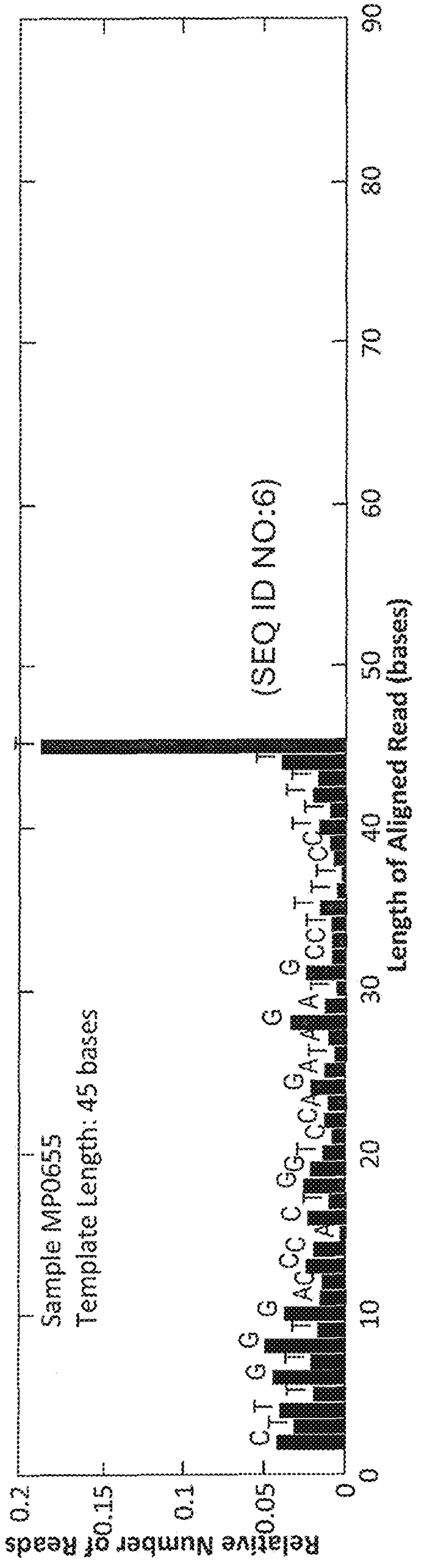

Sequence data is analyzed by histogram display of the population of sequence reads from a single SBX reaction. The analysis software aligns each sequence read to the sequence of the template and trims the extent of the sequence at the end of the reads that does not align with the correct template sequence. Representative histograms of SBX sequencing of a 45mer template are presented in FIG. 6A (no additive control) and FIG. 6B (SBX in the presence of PEM compound 1). As can be seen, in the absence of compound 1, sequence reads are not accurate past around base 18 of the template. Notably, addition of compound 1 to the SBX reaction increased the accuracy of the sequence reads across the entire length of the 45mer template.

Figure 7A:
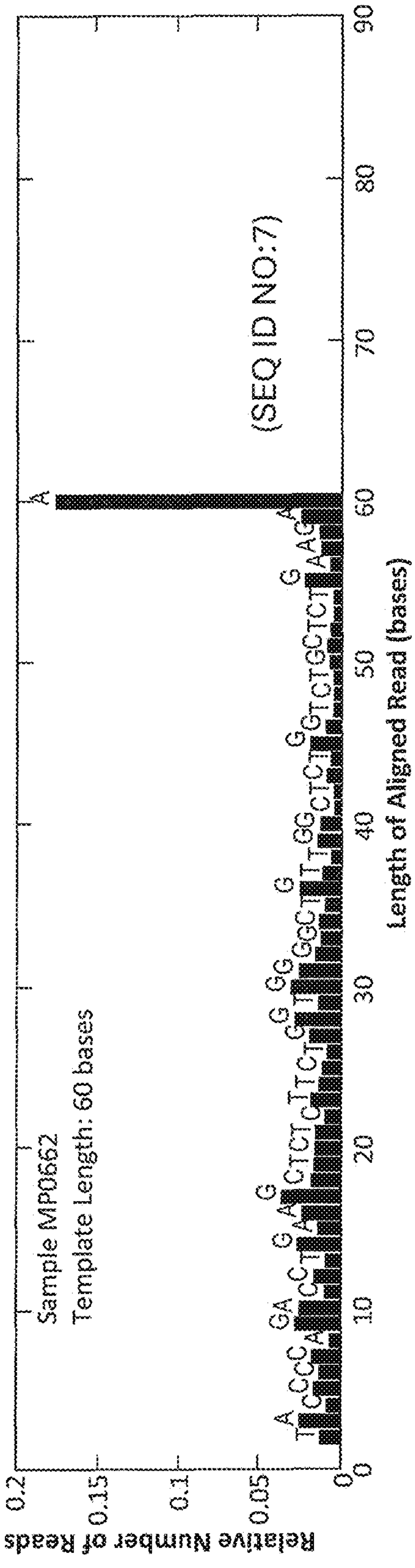
FIGS. 7A and 7B are histogram displays of populations of aligned reads of nanopore-derived sequences.
Figure 7B:
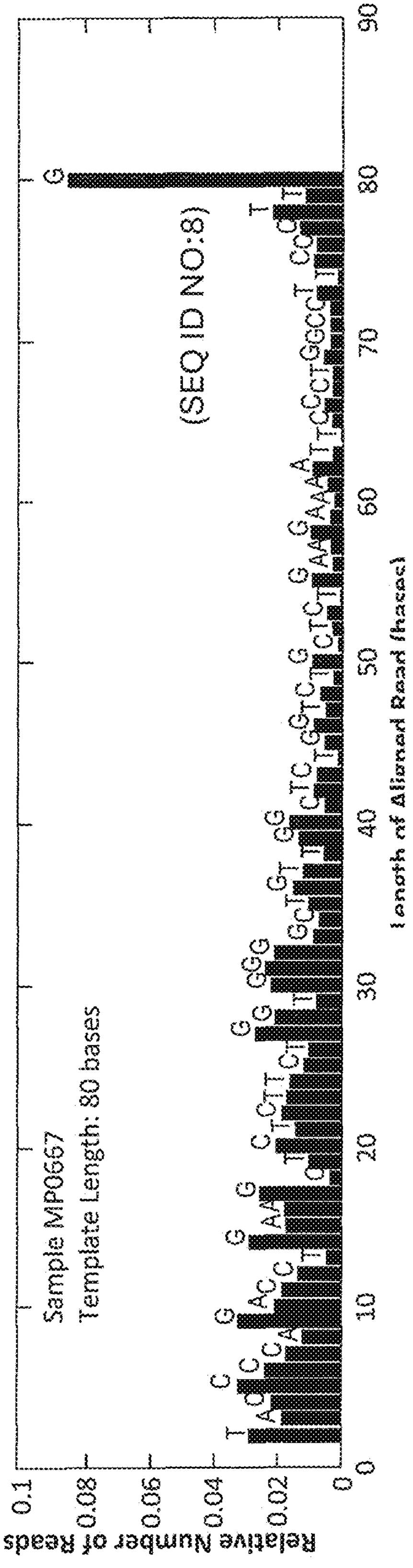

These results inspired additional experiments to test the ability of PEM compound 1 to enhance SBX of even longer templates. FIGS. 7A and 7B show histograms of SBX sequencing of 60mer and 80mer templates, respectively. Surprisingly, compound 1 enabled accurate sequence reads completely to the end of each of these longer templates. These results demonstrate robust and accurate enhancement of XNTP polymerization activity by a novel PEM that powerfully increases the capability of SBX to provide nanopore-based nucleic acid sequence information.

Example 80

PEMs Enable Synthesis of Long Xpandomer Products

Figure 8:
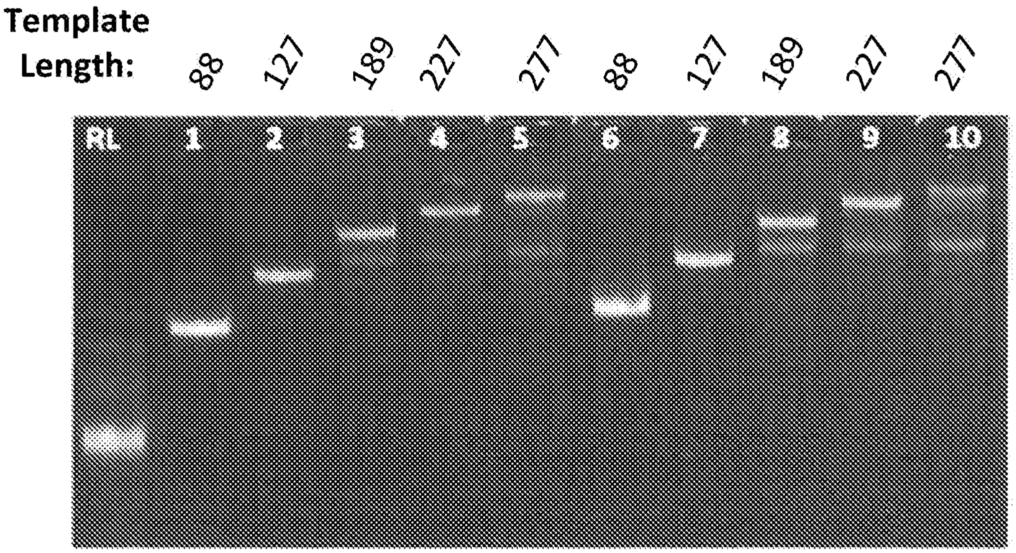
FIG. 8 is a gel showing primer extension products.

Following the success of accurately replicating templates of up to 80 nucleotides in length into Xpandomers, XNTP polymerization reactions were conducted using four longer templates, consisting of 88, 127, 227, and 277 nucleotides in length. A variant of DPO4 DNA polymerase, referred to as C4552 (SEQ ID NO:1), was used in these polymerization reactions and reaction conditions were optimized for C4552 activity in the presence of PEM compound 1. Other suitable DPO4 polymerase variants include, but are not limited to, those of SEQ ID NO:s 2-5. In addition to 1 Mm compound 1, reaction additives included 1 Mm urea and 2.75 µg single-strand binding protein (Eco SSB). Extension reactions were carried out with 0.85 pmol template, 0.5 pmol oligonucleotide primer, and 1 nmol each XNTP in a final volume of 10 µL. Reactions were run in buffer composed of 50 Mm TrisCl, Ph 8.84, 200 Mm $NH_4Oac$, and 20% PEG8K supplemented with 5% NMS, polyphosphate PP-60.20 in amounts of 3 or 4 nmol, and 2 Mm $MnCl_2$. 1.2 µg purified recombinant DNA polymerase protein was used in each extension reaction and reactions were run for 1-2 hr at 23° C. Results of representative extension reactions using the longer templates are shown in FIG. 8. Notably, in the presence of compound 1, the polymerase was able polymerize XNTPs to generate complete Xpandomer copies of each longer template, ranging from 88 (lanes 1 and 6) to 277 (lanes 5 and 10) nucleotides in length. Lanes 1-5 and 6-10 represent identical extension reactions with the exception of the amount of PP-60.20 additive, which was 3 nmol in lanes 1-5 and 4 nmol in lanes 6-10. These results underscore the surprising advantages conferred by compound 1 in reactions requiring polymerization of non-natural, highly substituted nucleotide analogs by DNA polymerase and suggest that this compound, as well as other PEMs, could greatly expand the potential of the SBX sequencing protocol.

Example 81

Next Generation PEMs Enhance Polymerization of XNTPs to Generate Long Xpandomer Products Based on the advantageous properties observed with PEM compound 1, a next generation of PEM compounds was designed with the objective of improving certain properties, including, but not limited to, water solubility of the molecules. Representative next generation PEM structures are described in Examples 9-34 and Table 7.

Figure 9:
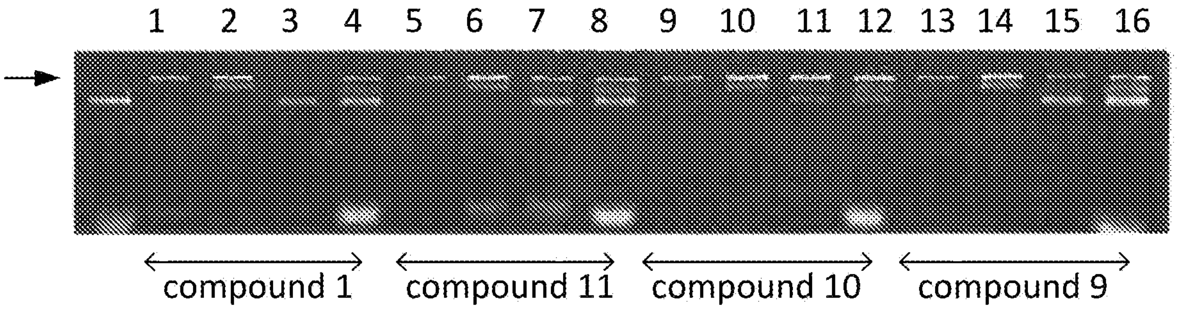
FIG. 9 is a gel showing primer extension products.

PEM activity of compounds 9-11 was tested in primer extension assays using three 100mer templates, derived from the HIV1, 2, and 3 genomes. Primer extension reactions included the following reagents: 75 Mm TrisCl, Ph 8.44, 175 Mm $NH_4Oac$, 20% PEG8K, 5% NMS, 0.8 nmol PP-60.20, 0.6 Mm $MnCl_2$, 2.3 µg Tth single-strand binding protein (SSB), 0.5 M or 1 M urea, 200 pmol each XNTP, 1.1 pmol template, 1 pmol oligonucleotide primer, 1.2 µg purified recombinant C4552 DNA polymerase, and 0.5 Mm PEM. 10 µL primer extension reactions were run for 30 minutes at 23° C. and reaction products were analyzed by gel electrophoresis. A representative gel showing primer extension products is presented in FIG. 9. As shown in lanes 1 (HIV1 template), 2 (HIV2 template), and 4 (HIV3 template, no SSB and 1 M urea), compound 1 enables polymerization of XNTPs into full length Xpandomer copies of the three different 100mer templates (gel migration position of the 100mer indicated by the arrow). Likewise, each of compounds 9 (lanes 13-16), 10 (lanes 9-12), and 11 (lanes 5-8) enable XNTP polymerization at least as efficiently as compound 1 on each of the three different 100mer templates. These results suggest that PEM activity may be optimized by increasing various physicochemical properties of the compounds, such as water solubility.

Figure 10:
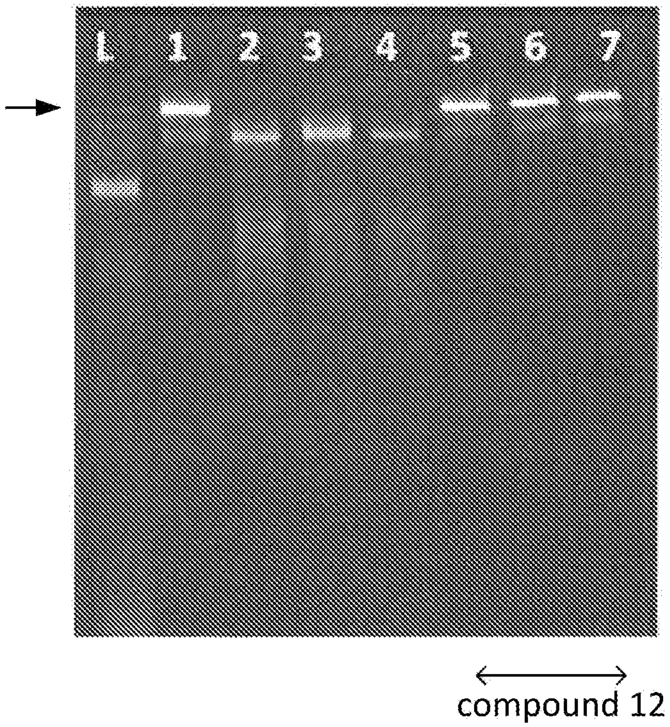
FIG. 10 is a gel showing primer extension products.

PEM activity of compound 12 was tested in primer extension assays using the HIV2 100mer template. Primer extension reactions included the following reagents: 50 Mm TrisCl, 200 Mm $NH_4Oac$, 20% PEG8K, 5% NMS, 0.6 nmol PP-60.20, 0.6 Mm $MnCl_2$, 2.75 µg/µl Eco single-strand binding protein (SSB), 1 M urea, 50 pmol each XNTP, 1.1 pmol template, 1 pmol oligonucleotide primer, 1.2 µg/µl purified recombinant C4760 DNA polymerase (SEQ ID NO:2), and 0.5, 1, or 1.5 Mm PEM. 10 µL primer extension reactions were run for 30 minutes at 23° C. and reaction products were analyzed by gel electrophoresis. A representative gel showing primer extension products is presented in FIG. 10. As shown in lanes 5 (0.5 Mm PEM), 6 (1 Mm PEM), and 7 (1.5 Mm PEM), compound 12 enables polymerization of XNTPs into full length Xpandomer copies of the 100mer template (gel migration position of the 100mer indicated by the arrow) in a manner comparable to that of compound 10 (lane 1). Lanes 2-4 show primer extension products from reactions with a structurally related additive lacking robust PEM activity. These results suggest that PEM activity may be determined by very specific chemical structures.

Figure 11:
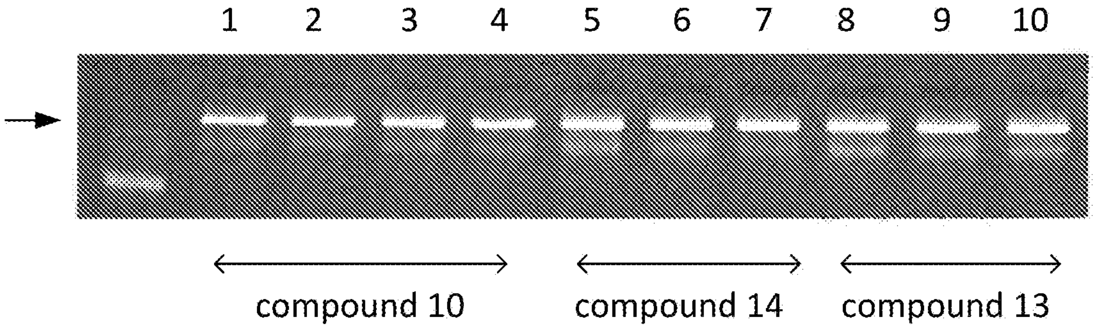
FIG. 11 is a gel showing primer extension products.

PEM activity of compounds 13 and 14 was tested in primer extension assays using the HIV2 100mer template. Primer extension reactions included the following reagents: 50 Mm TrisCl, 200 Mm $NH_4Oac$, 20% PEG8K, 5% NMS, 0.6 nmol PP-60.20, 0.6 Mm $MnCl_2$, 2.75 µg/µl Eco single-strand binding protein (SSB), 1 M urea, 50 pmol each XNTP, 1.1 pmol template, 1 pmol oligonucleotide primer, 1.2 µg/µl purified recombinant C4760 DNA polymerase (a variant of DPO4, see SEQ ID NO:2), and 0.5, 1, 1.52, or 2.5 Mm PEM. 10 µL primer extension reactions were run for 30 minutes at 23° C. and reaction products were analyzed by gel electrophoresis. A representative gel showing primer extension products is presented in FIG. 11 (the position of the full length HIV2 100mer is indicated by the arrow). As shown in lanes 5-7 (compound 14 at various concentrations) and 8-10 (compound 13 at various concentrations), each of these next generation PEMs enables polymerization of XNTPs into full length Xpandomer copies of the 100mer template in a manner comparable to that of compound 10 (lanes 1-4).

Figure 12:
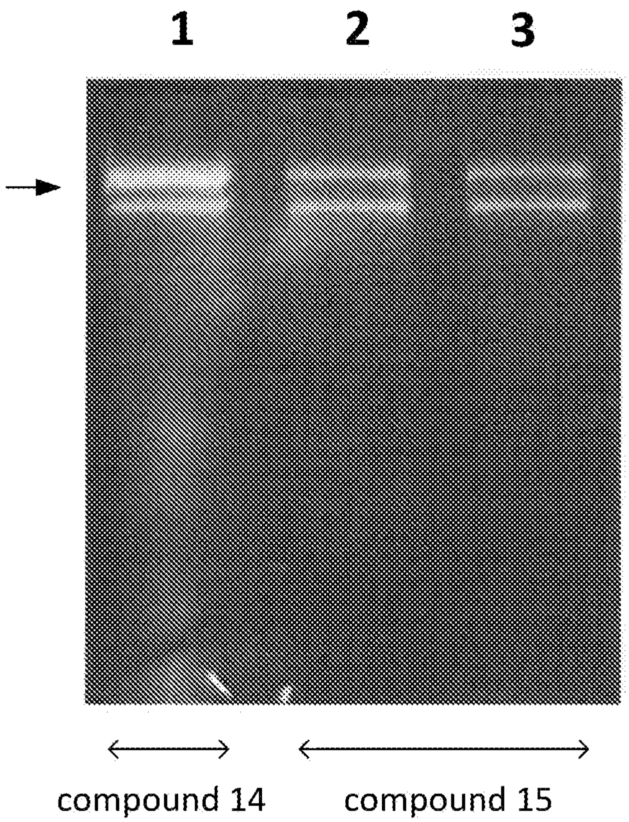
FIG. 12 is a gel showing primer extension products.

PEM activity of compound 15 was tested in primer extension assays using a 411mer amplicon template. Primer extension reactions included the following reagents: 50 Mm TrisCl, 200 Mm $NH_4Oac$, 20% PEG8K, 5% NMS, 3 nmol PP-60.20, 2 Mm $MnCl_2$, 2 μg Kod single-strand binding protein (SSB), 1 M urea, 250 pmol each XNTP, 1 pmol template, 1 pmol oligonucleotide primer, 1.2 μg purified recombinant C4760 DNA polymerase (a variant of DPO4, see SEQ ID NO:2), and 2 (lane 2) or 3 (lane 3) Mm PEM. 10 μL primer extension reactions were run for 20 minutes at 37° C. and reaction products were analyzed by gel electrophoresis. A representative gel showing primer extension products is presented in FIG. 12 (the position of a 277mer is indicated by the arrow). As shown in lanes 2 and 3 (compound 15 at two different concentrations) this next generation PEM enables polymerization of XNTPs into lengthy Xpandomer copies of the 411mer template in a manner comparable to that of compound 14 (lane 1). Remarkably, the polymerase is completely dependent upon the addition of PEM to the reaction in order to be capable of synthesizing these lengthy Xpandomer products. Even longer extension products may be obtained by optimizing various reaction parameters, e.g., extension time and/or concentrations of various additives.

Figure 13:
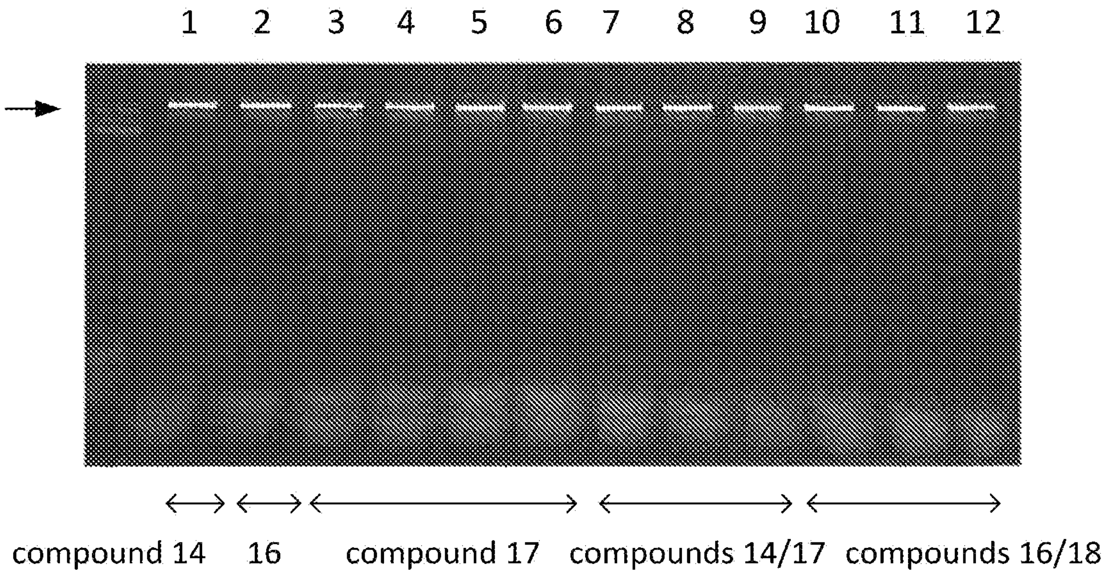
FIG. 13 is a gel showing primer extension products.

PEM activity of compounds 16, 17, and 18 and combinations thereof were tested in primer extension assays using the HIV2-derived 100mer template. Primer extension reactions included the following reagents: 50 Mm TrisCl, 200 Mm $NH_4Oac$, 20% or 25% PEG8K, 5% NMS, 0.6 nmol PP-60.20, 0.6 Mm $MnCl_2$, 2 μg Kod single-strand binding protein (SSB), 1 M urea, 50 pmol each XNTP, 1 pmol template, 1 pmol oligonucleotide primer, 1.2 μg purified recombinant C4760 DNA polymerase (a variant of DPO4, see SEQ ID NO:2), and 0.5-2 Mm PEM. 10 μL primer extension reactions were run for 30 minutes at 37° C. and reaction products were analyzed by gel electrophoresis. A representative gel showing primer extension products is presented in FIG. 13 (the position of a 100mer product is indicated by the arrow). As shown in lanes 2 (2 Mm compound 16) and 3-6 (0.5, 1, 2, and 3 Mm compound 17) these next generation PEMs enable polymerization of XNTPs into lengthy Xpandomer copies of the 100mer template in a manner comparable to that of compound 14 (lane 1). In addition, combinations of 2 Mm compound 14 and 0.1 Mm (lane 7), or 0.3 Mm (lanes 8 and 9) compound 17 also enabled polymerization of XNTPs into lengthy Xpandomer copies of the 100mer template, indicating that combinations of PEMs may permit use of lower doses of each individual PEM. Similarly, combinations of 2 Mm compound 16 and 0.1 Mm (lane 10), or 0.3 Mm (lanes 11 and 12) compound 18 also appeared to permit use of lower doses of each individual PEM to enable polymerization of XNTPS into full length copies of the 100mer template.

Figure 14:
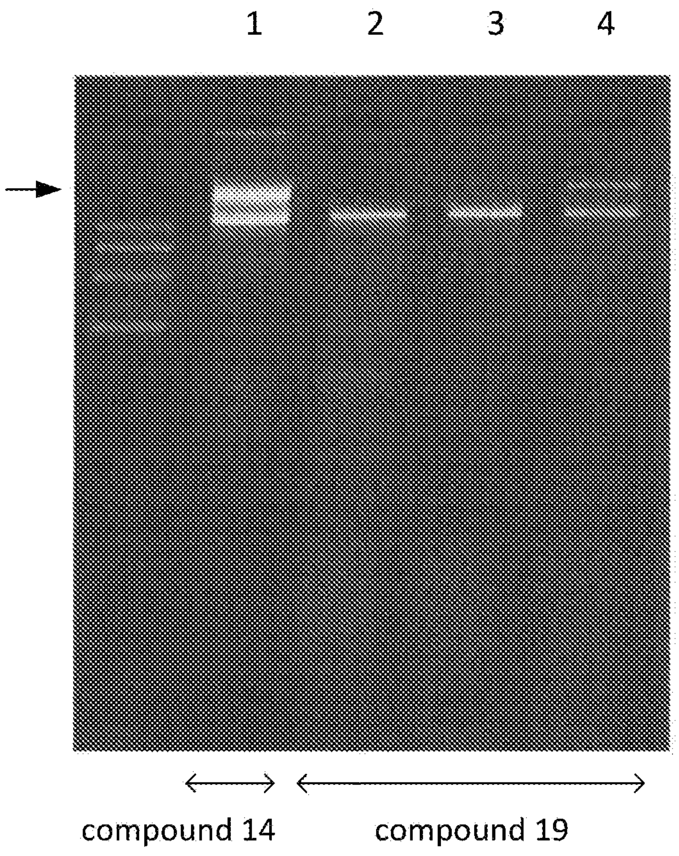
FIG. 14 is a gel showing primer extension products.

PEM activity of compound 19, was tested in primer extension assays using the 411mer amplicon template. Primer extension reactions included the following reagents: 50 Mm TrisCl, 200 Mm $NH_4Oac$, 20% PEG8K, 5% NMS, 3 nmol PP-60.20, 2 Mm $MnCl_2$, 2 μg Kod single-strand binding protein (SSB), 1 M urea, 250 pmol each XNTP, 0.5 pmol template, 0.5 pmol oligonucleotide primer, 1.2 μg purified recombinant C4760 DNA polymerase (a variant of DPO4, see SEQ ID NO:2), and 0.5 (lane 2), 1 (lane 3), or 1.5 Mm (lane 4) PEM. 10 μL primer extension reactions were run for 30 minutes at 37° C. and reaction products were analyzed by gel electrophoresis. A representative gel showing primer extension products is presented in FIG. 14 (the position of a 277mer product is indicated by the arrow). As shown in lanes 2-4 this next generation PEM enables polymerization of XNTPs into lengthy Xpandomer copies of the 411mer template, albeit in a manner less efficient than that of compound 14 (lane 1). These results suggest that PEM activity may be specific to the structure of the PEM and/or the length of the template.

Example 82

Third Generation PEM Compounds

To further explore the relationship between PEM structure and polymerase-enhancing activities, as well as to optimize various physicochemical properties, a "third generation" of PEM compounds was synthesized, as described herein, e.g., in Table 1 (compounds 79-118) and Examples 35-74. These PEMs were tested in primer extension reactions using DNA templates of the following lengths: A) 45mer; B) 100mer; C) 150mer; and D) 222mer. Primer extension reactions were run under conditions comparable to those described in Examples 77 and 78 and extension products were similarly analyzed by gel electrophoresis. The preliminary functional characterization of third generation compounds displaying PEM activity is summarized in Table 2 below.

TABLE 2

PEM Activity Summary

| Functional Catagory | PEM compounds |
|---|---|
| Slight PEM effect | 98, 99, 100, 101, 102, 103, 104, 109, 119 |
| A (replication of 45 mer template) | 95, 96, 97, 108, 110, 111, 114, 116 |
| B (replication of 100 mer template) | 81, 82, 83, 84, 85, 86, 87, 88, 89, 90, 91, 92, 93, 94, 106, 107, 112, 113, 115, 117, 118 |
| C (replication of 150 mer template) | 80 |
| D (replication of 222 mer template) | 79, 105, 120, 121 |

Example 83

PEMs Enable Synthesis of Xpandomer Copies of an RNA Template

To begin to investigate the potential of PEMs to enhance diverse polymerase reactions, the ability of PEMS to enable DNA polymerase to utilize RNA as a template was tested. An initial screen of several compounds set forth in Table I was conducted using a 45mer RNA template derived from the HIV2 genome sequence. Primer extension reactions included the following reagents: 50 Mm TrisCl, 200 Mm $NH_4Oac$, 20% PEG8K, 5% NMS, 0.6 nmol PP-60.20, 0.6 Mm $MnCl_2$, 2 μg Kod single-strand binding protein (SSB), 1 M urea, 50 pmol each XNTP, 0.5 pmol template, 0.5 pmol oligonucleotide primer, 1.2 μg purified recombinant C4760 DNA polymerase (a variant of DPO4, see SEQ ID NO:2), and 2 Mm PEM. 10 μL primer extension reactions were run for 30 minutes at 37° C. and reaction products were analyzed by gel electrophoresis. Surprisingly, several compounds were found to display PEM activity on an RNA template; these RNA PEMs include the following compounds: compound 51, 73, 49, 17, 75, 76, 93, 105, 106, 110, 116, and 118. These results suggest that certain PEMs may find utility in enabling Sequencing by Expansion of RNA templates.

All of the U.S. patents, U.S. patent application publications, U.S. patent applications, foreign patents, foreign patent applications and non-patent publications referred to in this specification and/or listed in the Application Data Sheet, including but not limited to, U.S. Provisional Patent Application No. 62/867,049 filed on Jun. 26, 2019, are incorporated herein by reference, in their entirety. Such documents may be incorporated by reference for the purpose of describing and disclosing, for example, materials and methodologies described in the publications, which might be used in connection with the presently described invention. The publications discussed above and throughout the text are provided solely for their disclosure prior to the filing date of the present application. Nothing herein is to be construed as an admission that the inventors are not entitled to antedate any referenced publication by virtue of prior invention.

SPECIFICALLY INCLUDED EMBODIMENTS

The following embodiments are specifically contemplated as part of the disclosure. This is not intended to be an exhaustive listing of potentially claimed embodiments included within the scope of the disclosure.

Embodiment 1. A method of enhancing a nucleic acid polymerase reaction, the method comprising:

a. forming a nucleic acid polymerase reaction composition comprising:
i. a template nucleic acid,
ii. a nucleic acid polymerase,
iii. a mixture of nucleotides or nucleotide analogs, and
iv. at least one compound of Formula (I); and
b. incubating the nucleic acid polymerase reaction composition under conditions allowing a nucleic acid polymerization reaction, wherein the at least one compound of Formula (I) increases the processivity, rate, or fidelity of the nucleic acid polymerase reaction;

wherein the compound of Formula (I) is represented by:

(I)

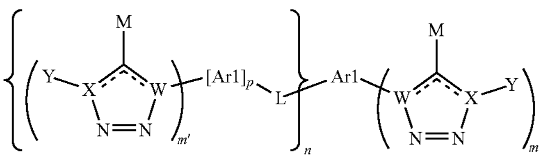

or a solvate, hydrate, tautomer, chelate or salt thereof, wherein:

m is 1, 2 or 3;

m' is 1, 2 or 3;

n is 0, 1 or 2;

p is 0, 1 or 2;

W is N when X is C or W is C when X is N;

--- is a single or double bond, wherein the double bond begins at whichever of W or X is carbon;

L is a linking group;

M is, at each occurrence, independently selected from hydrogen, halogen and $C_1$-$C_4$alkyl;

Ar1 is, at each occurrence, independently selected from optionally substituted pyridine, pyrazine, pyridazine, furan, thiophene, naphthalene, fluorene, phenanthrene, cinnoline, phthalazine, quinazoline, quinoxaline, naphthyridine, phenanthroline, purine, and carbazole, wherein:

substituents for Ar1 are, at each occurrence, independently selected from halogen, —OH, —CN, —$NO_2$, $C_1$-$C_6$alkyl, $C_1$-$C_6$haloalkyl, $C_1$-$C_6$heteroalkyl, $C_1$-$C_6$cycloloalkyl, —$OR^0$, —$CONH_2$, —C(O)$NR^1R^{1'}$, —$NR^1R^{1'}$, —$NR^1C(O)R^3$, —$C(O)SR^3$, —$COR^3$, —$OC(O)R^3$, —$C(O)OR^3$, mercaptan, —$R^4$—H, —$SOR^1$, —$S(O)_2R^1$, —$S(O)_2NR^1R^{1'}$, and —$NS(O)_2R^3$; and wherein $R^0$ is, at each occurrence, independently selected from $C_1$-$C_6$alkyl, $C_1$-$C_6$haloalkyl, $C_2$-$C_6$alkenyl, $C_2$-$C_6$alkynyl, substituted or unsubstituted cycloalkyl, substituted or unsubstituted heterocyclyl, substituted or unsubstituted aryl, and substituted or unsubstituted heteroaryl;

$R^1$ and $R^{1'}$ are, at each occurrence, independently selected from H, hydroxyl, $C_1$-$C_6$alkyl, $C_1$-$C_6$haloalkyl, $C_1$-$C_6$heteroalkyl, $C_2$-$C_6$alkenyl, $C_2$-$C_6$alkynyl, substituted or unsubstituted cycloalkyl, substituted or unsubstituted heterocyclyl, substituted or unsubstituted aryl, substituted or unsubstituted arylalkyl, and substituted or unsubstituted heteroaryl, —C(=NH)$NH_2$, —$CH_2CO_2R^0$, —$CH_2C(O)NHCH_2CO_2H$, —$CH_2CH_2OH$, —$CH_2CH_2NHC(O)R^3$, —$CH_2C(O)NHCH_2CO_2H$,

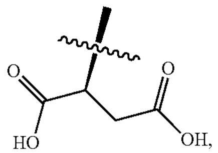

and

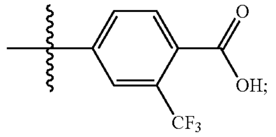

wherein $R^1$ and $R^{1'}$ can come together to form a heterocyclic ring, including, but not limited to, azetidine, pyrrolidine, piperidine, piperazine, morpholine,

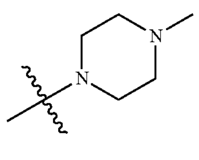

, or

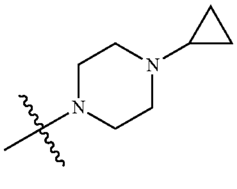

;

$R^2$ is, at each occurrence, independently selected from $C_2$-$C_6$alkyl, $C_1$-$C_6$haloalkyl, $C_1$-$C_6$heteroalkyl, or substituted or unsubstituted cycloalkyl, substituted or unsubstituted heterocyclyl, substituted or unsubstituted aryl, substituted or unsubstituted heteroaryl, and substituted or unsubstituted haloalkoxy;

$R^3$ is, at each occurrence, independently selected from H, $C_1$-$C_6$alkyl, $C_1$-$C_6$haloalkyl, $C_1$-$C_6$heteroalkyl, or substituted or unsubstituted cycloalkyl, substituted or unsubstituted heterocyclyl, substituted or unsubstituted aryl, and substituted or unsubstituted heteroaryl, substituted or unsubstituted haloalkoxy, and guanidine;

$R^4$ is, at each occurrence, independently selected from one or more heteroatom interrupted alkylene wherein the heteroatom is O, S, NH or a combination thereof, Y is, at each occurrence, independently selected from Ar2, —$(CH_2)_3PO(OEt)_2$, or —CH2$CO_2$Me;

Ar2 is, at each occurrence, independently selected from substituted 5- and 6-membered monocyclic aromatic rings and 9- and 10-membered fused bicyclic rings comprising two monocyclic rings together, where at least one of the two monocyclic rings is an aromatic ring, wherein:

Ar2 is substituted with $G^1$, $G^2$, $G^3$, $G^4$ and $G^5$, wherein:

when Ar2 is monosubstituted, $G^1$ is, at each occurrence, independently selected from oxo, —$NH_2$, —$COR^3$, -E-$CO_2$H, —C(O)$NR^1R^{1'}$, -E-PO$(OR^1)_2$, and aryl substituted with $G^2$, $G^3$, $G^4$ and $G^5$;

$G^2$, $G^3$, $G^4$ and $G^5$ are, at each occurrence, independently selected from absent or selected from the groups comprising, halogen, —CN, $C_1$-$C_6$alkyl, $C_1$-$C_6$haloalkyl, -E-$CO_2$H, -E-CHO, -E-C(O)$R^3$, -E-C(O)NH(OH), -E-C(O)$NHR^1$, -E-$CONR^1R^{1'}$, -E-$NR^1R^{1'}$, and -E-$OR^2$, wherein:

E is, at each occurrence, independently selected from a direct bond and $C_1$-$C_6$alkylene.

Embodiment 2. The method of embodiment 1, wherein Ar1 is monocyclic carbocyclic aryl.

Embodiment 3. The method of embodiment 1, wherein Ar1 is monocyclic heterocyclic aryl.

Embodiment 4. The method of embodiment 1, wherein Ar1 is bicyclic aryl.

Embodiment 5. The method of embodiment 1, wherein Ar1 is tricyclic aryl.

Embodiment 6. The method of embodiment 1, wherein Ar1 is unsubstituted aryl.

Embodiment 7. The method of embodiment 1, wherein Ar1 is substituted aryl.

Embodiment 8. The method of embodiment 1, wherein Ar2 is a 5-membered monocyclic aromatic ring selected from the group consisting of thiophene, 1,2-thiazole, 1,3-thiazole, furan, 1,2-oxazole, 1,3-oxazole, 1H-pyrrole, 1H-pyrazole, oxadiazole, thiadiazole, 1,2,4-triazole, 1,2,3-triazole and 1H-imidazole.

Embodiment 9. The method of embodiment 1, wherein Ar2 is a 6-membered monocyclic aromatic ring selected from the group consisting of benzene, pyridine, pyridazine, pyrimidine and pyrazine.

Embodiment 10. The method of embodiment 1, wherein Ar2 is a 9-membered fused bicyclic aromatic ring system selected from the group consisting of benzofuran, 1,3-benzoxazole, furo[3,2-b]pyridine, furo[3,2-c]pyridine, furo[2,3-c]pyridine, furo[2,3-b]pyridine, indole, 1H-benzimidazole, 1H-pyrrolo[3,2-b]pyridine, 1H-pyrrolo[3,2-c]pyridine, 1H-pyrrolo[2,3-c]pyridine, 1H-pyrrolo[2,3-b]pyridine, benzothiophene, 1,3-benzothiazole, thienol[3,2-b]pyridine, thieno[3,2-c]pyridine, thieno[2,3-c]pyridine, benzoxadiazole, benzothiadiazole, benzisoxazole, benzotriazole and thieno[2,3-b]pyridine.

Embodiment 11. The method of embodiment 1, wherein Ar2 is a 10-membered fused bicyclic aromatic ring system selected from the group consisting of naphthylene, quinoline, quinazoline, quinoxaline, 1,5-naphthyridine, 1,6-naphthyridine, 1,7-naphthyridine, 1,8-naphthyridine, isoquinoline, phthalazine, 2,6-naphthyridine and 2,7-naphthyridine.

Embodiment 12. The method of embodiment 1, wherein the substitution on Ar2 includes carboxylic acid.

Embodiment 13. The method of embodiment 1, wherein the substitution on Ar2 includes carboxamide.

Embodiment 14. The method of embodiment 1, wherein substitution on Ar2 includes trifluormethyl.

Embodiment 15. The method of embodiment 1, wherein substitution on Ar2 includes hydroxyl.

Embodiment 16. The method of embodiment 1, wherein n is 0 and m is 2, and at least one compound of Formula (I) is described by a formula selected from (III) or (IV):

(III)

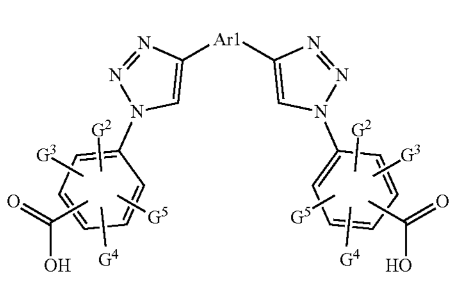

or (IV)

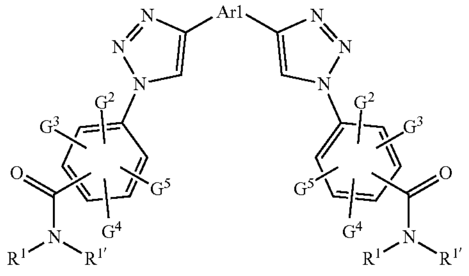

Embodiment 17. The method of embodiment 1, wherein substitution on Ar2 includes at least two of hydroxyl, carboxylic acid and trifluoromethyl.

Embodiment 18. The method of embodiment 15, wherein the at least one compound of Formula (I) is described by a formula selected from (V), (VI), (VII), (VIII) or (IX):

(V)

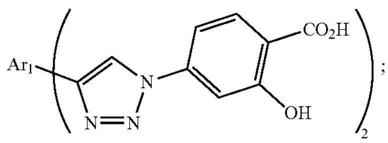

;

(VI)

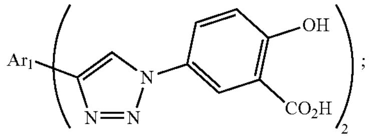

;

(VII)

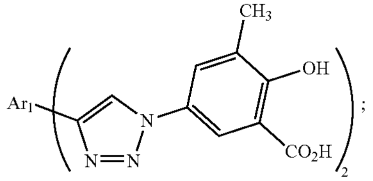

;

-continued (VIII)

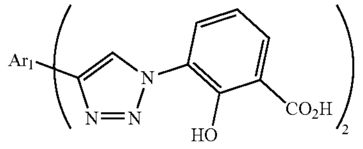

or (IX)

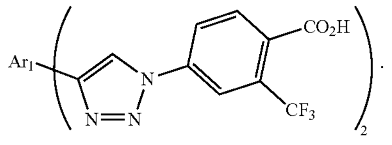

.

Embodiment 19. The method of embodiment 1, wherein the compound of Formula (I) is in a form of a chelate.

Embodiment 20. The method of embodiment 19, wherein the chelate is a copper chelate.

Embodiment 21. The method of embodiment 1, wherein the compound of Formula (I) has a log P of at least 4.9.

Embodiment 22. The method of embodiment 1, wherein the compound of Formula (I) is selected from:

4,4'-(pyridine-2,6-diylbis(1H-1,2,3-triazole-4,1-diyl))bis(2-hydroxybenzoic acid);

4,4'-(pyridine-3,5-diylbis(1H-1,2,3-triazole-4,1-diyl))bis(2-hydroxybenzoic acid);

4,4'-((9H-carbazole-3,6-diyl)bis(1H-1,2,3-triazole-4,1-diyl))bis(2-hydroxybenzoic acid);

4,4'-((9H-carbazole-3,6-diyl)bis(1H-1,2,3-triazole-4,1-diyl))dibenzoic acid;

4,4'-((4-methoxypyridine-2,6-diyl)bis(1H-1,2,3-triazole-4,1-diyl))bis(2-hydroxybenzoic acid);

4,4'-((4-carboxypyridine-2,6-diyl)bis(1H-1,2,3-triazole-4,1-diyl))bis(2-hydroxybenzoic acid);

4,4'-((4-nitropyridine-2,6-diyl)bis(1H-1,2,3-triazole-4,1-diyl))bis(2-hydroxybenzoic acid);

5,5'-((4-cyanopyridine-2,6-diyl)bis(1H-1,2,3-triazole-4,1-diyl))bis(2-hydroxybenzoic acid);

4,4'-((4-methylpyridine-2,6-diyl)bis(1H-1,2,3-triazole-4,1-diyl))bis(2-hydroxybenzoic acid);

4,4'-((4-(ethoxycarbonyl)pyridine-2,6-diyl)bis(1H-1,2,3-triazole-4,1-diyl))bis(2-hydroxybenzoic acid);

5,5'-((4-(ethoxycarbonyl)pyridine-2,6-diyl)bis(1H-1,2,3-triazole-4,1-diyl))bis(2-hydroxybenzoic acid);

4,4'-((4-(methoxycarbonyl)pyridine-2,6-diyl)bis(1H-1,2,3-triazole-4,1-diyl))bis(2-hydroxybenzoic acid);

4,4'-((4-(ethylcarbamoyl)pyridine-2,6-diyl)bis(1H-1,2,3-triazole-4,1-diyl))bis(2-hydroxybenzoic acid);

4,4'-((4-(methylcarbamoyl)pyridine-2,6-diyl)bis(1H-1,2,3-triazole-4,1-diyl))bis(2-hydroxybenzoic acid);

4,4'-((4-carbamoylpyridine-2,6-diyl)bis(1H-1,2,3-triazole-4,1-diyl))bis(2-hydroxybenzoic acid);

4,4'-(pyrazine-2,6-diylbis(1H-1,2,3-triazole-4,1-diyl))bis(2-hydroxybenzoic acid);

4,4'-(1,3-phenylenebis(1H-1,2,3-triazole-4,1-diyl))dianiline;

4,4'-(1,3-phenylenebis(1H-1,2,3-triazole-4,1-diyl))dibenzoic acid;

4-(4-(3-(1-(4-methoxyphenyl)-1H-1,2,3-triazol-4-yl)phenyl)-1H-1,2,3-triazol-1-yl)benzoic acid;

4,4'-(pyridine-2,6-diylbis(1H-1,2,3-triazole-4,1-diyl))dibenzoic acid;

4-(4-(3-(1-(4-methoxyphenyl)-1H-1,2,3-triazol-4-yl)phenyl)-1H-1,2,3-triazol-1-yl)benzoic acid;

4,4'-((3,5-dimethylpyridine-2,6-diyl)bis(1H-1,2,3-triazole-4,1-diyl))bis(2-hydroxybenzoic acid);

4,4'-((413-pyridine-2,6-diyl)bis(5-iodo-1H-1,2,3-triazole-4,1-diyl))bis(2-hydroxybenzoic acid);

4,4'-((4-acetamidopyridine-2,6-diyl)bis(1H-1,2,3-triazole-4,1-diyl))bis(2-hydroxybenzoic acid);

4,4'-((9-acetyl-9H-carbazole-3,6-diyl)bis(1H-1,2,3-triazole-4,1-diyl))bis(2-hydroxybenzoic acid);

4,4'-(pyridine-2,6-diylbis(1H-1,2,3-triazole-4,1-diyl))bis(N,2-dihydroxybenzamide);

4,4'-(pyridine-2,6-diylbis(1H-1,2,3-triazole-4,1-diyl))bis(2-hydroxybenzamide);

4,4'-((4-carboxypyridine-2,6-diyl)bis(1H-1,2,3-triazole-4,1-diyl))bis(2-hydroxybenzoic acid);

4,4'-((1,10-phenanthroline-2,9-diyl)bis(1H-1,2,3-triazole-4,1-diyl))bis(2-hydroxybenzoic acid);

4,4'-((4-(trifluoromethyl)pyridine-2,6-diyl)bis(1H-1,2,3-triazole-4,1-diyl))bis(2-hydroxybenzoic acid);

4,4'-((3-cyanopyridine-2,6-diyl)bis(1H-1,2,3-triazole-4,1-diyl))bis(2-hydroxybenzoic acid);

4,4'-((3-nitropyridine-2,6-diyl)bis(1H-1,2,3-triazole-4,1-diyl))bis(2-hydroxybenzoic acid);

3,3'-((4-cyanopyridine-2,6-diyl)bis(1H-1,2,3-triazole-4,1-diyl))bis(2-hydroxybenzoic acid);

4,4'-((4-(tert-butoxycarbonyl)pyridine-2,6-diyl)bis(1H-1,2,3-triazole-4,1-diyl))bis(2-hydroxybenzoic acid);

4-(4-(4-cyanopyridin-2-yl)-1H-1,2,3-triazol-1-yl)-2-hydroxybenzoic acid;

5-(4-(6-(4-(3-carboxy-4-hydroxy-5-methylphenyl)-1H-1,2,3-triazol-1-yl)-4-(methoxycarbonyl)pyridin-2-yl)-1H-1,2,3-triazol-1-yl)-2-hydroxy-3-methylbenzoic acid;

4,4'-((4-(dimethylcarbamoyl)pyridine-2,6-diyl)bis(1H-1,2,3-triazole-4,1-diyl))bis(2-hydroxybenzoic acid);

4,4'-((4-(cyclopropylcarbamoyl)pyridine-2,6-diyl)bis(1H-1,2,3-triazole-4,1-diyl))bis(2-hydroxybenzoic acid);

4,4'-((4-(but-3-yn-1-ylcarbamoyl)pyridine-2,6-diyl)bis(1H-1,2,3-triazole-4,1-diyl))bis(2-hydroxybenzoic acid);

4,4'-((4-(butylcarbamoyl)pyridine-2,6-diyl)bis(1H-1,2,3-triazole-4,1-diyl))bis(2-hydroxybenzoic acid);

4,4'-((4-(diethylcarbamoyl)pyridine-2,6-diyl)bis(1H-1,2,3-triazole-4,1-diyl))bis(2-hydroxybenzoic acid);

4,4'-((4-(tert-butylcarbamoyl)pyridine-2,6-diyl)bis(1H-1,2,3-triazole-4,1-diyl))bis(2-hydroxybenzoic acid);

4,4'-((4-(morpholine-4-carbonyl)pyridine-2,6-diyl)bis(1H-1,2,3-triazole-4,1-diyl))bis(2-hydroxybenzoic acid);

4,4'-((4-(propylcarbamoyl)pyridine-2,6-diyl)bis(1H-1,2,3-triazole-4,1-diyl))bis(2-hydroxybenzoic acid);

4,4'-((4-(phenylcarbamoyl)pyridine-2,6-diyl)bis(1H-1,2,3-triazole-4,1-diyl))bis(2-hydroxybenzoic acid);

4,4'-((4-((2-acetamidoethyl)carbamoyl)pyridine-2,6-diyl)bis(1H-1,2,3-triazole-4,1-diyl))bis(2-hydroxybenzoic acid);

4,4'-((4-(4-cyclopropylpiperazine-1-carbonyl)pyridine-2,6-diyl)bis(1H-1,2,3-triazole-4,1-diyl))bis(2-hydroxybenzoic acid);

4,4'-((4-(carbamimidoylcarbamoyl)pyridine-2,6-diyl)bis(1H-1,2,3-triazole-4,1-diyl))bis(2-hydroxybenzoic acid);

4,4'-((4-(piperidine-1-carbonyl)pyridine-2,6-diyl)bis(1H-1,2,3-triazole-4,1-diyl))bis(2-hydroxybenzoic acid);

4,4'-((4-(cyclobutylcarbamoyl)pyridine-2,6-diyl)bis(1H-1,2,3-triazole-4,1-diyl))bis(2-hydroxybenzoic acid);

4,4'-((1,10-phenanthroline-3,8-diyl)bis(1H-1,2,3-triazole-4,1-diyl))bis(2-hydroxybenzoic acid);

4,4'-((4-(cyclopentylcarbamoyl)pyridine-2,6-diyl)bis(1H-1,2,3-triazole-4,1-diyl))bis(2-hydroxybenzoic acid);

4,4'-((4-(dipropylcarbamoyl)pyridine-2,6-diyl)bis(1H-1,2,3-triazole-4,1-diyl))bis(2-hydroxybenzoic acid);

4,4'-((4-(di-sec-butylcarbamoyl)pyridine-2,6-diyl)bis(1H-1,2,3-triazole-4,1-diyl))bis(2-hydroxybenzoic acid);

4,4'-(naphthalene-2,7-diylbis(1H-1,2,3-triazole-4,1-diyl))bis(2-hydroxybenzoic acid);
4,4'-(naphthalene-2,3-diylbis(1H-1,2,3-triazole-4,1-diyl))bis(2-hydroxybenzoic acid);
4,4'-((4-(dibutylcarbamoyl)pyridine-2,6-diyl)bis(1H-1,2,3-triazole-4,1-diyl))bis(2-hydroxybenzoic acid);
4,4'-((4-((2-hydroxyethyl)carbamoyl)pyridine-2,6-diyl)bis(1H-1,2,3-triazole-4,1-diyl))bis(2-hydroxybenzoic acid);
4,4'-((4-(cyclohexylcarbamoyl)pyridine-2,6-diyl)bis(1H-1,2,3-triazole-4,1-diyl))bis(2-hydroxybenzoic acid);
4,4'-((4-(benzylcarbamoyl)pyridine-2,6-diyl)bis(1H-1,2,3-triazole-4,1-diyl))bis(2-hydroxybenzoic acid);
4,4'-((4-(4-methylpiperazine-1-carbonyl)pyridine-2,6-diyl)bis(1H-1,2,3-triazole-4,1-diyl))bis(2-hydroxybenzoic acid);
4-(4-(3-(1-(4-methoxyphenyl)-1H-1,2,3-triazol-4-yl)phenyl)-1H-1,2,3-triazol-1-yl)benzoic acid;
4,4',4'',4'''-((((butane-1,4-diylbis(azanediyl))bis(carbonyl))bis(pyridine-4,2,6-triyl))tetrakis(1H-1,2,3-triazole-4,1-diyl))tetrakis(2-hydroxybenzoic acid);
4,4'-((4-(ethylcarbamoyl)pyridine-2,6-diyl)bis(1H-1,2,3-triazole-4,1-diyl))bis(3,5,6-trichloropicolinic acid);
4,4'-((4-(ethylcarbamoyl)pyridine-2,6-diyl)bis(1H-1,2,3-triazole-4,1-diyl))bis(2-(trifluoromethyl)benzoic acid);
7,7'-((4-(ethylcarbamoyl)pyridine-2,6-diyl)bis(1H-1,2,3-triazole-4,1-diyl))bis(2-hydroxy-1,8-naphthyridine-4-carboxylic acid);
5,5'-((4-(ethylcarbamoyl)pyridine-2,6-diyl)bis(1H-1,2,3-triazole-4,1-diyl))bis(2-(trifluoromethyl)benzoic acid);
4,4'-((4-(ethylcarbamoyl)pyridine-2,6-diyl)bis(1H-1,2,3-triazole-4,1-diyl))bis(2-fluorobenzoic acid);
5,5'-((4-(ethylcarbamoyl)pyridine-2,6-diyl)bis(1H-1,2,3-triazole-4,1-diyl))bis(3-fluorobenzoic acid);
4,4'-((4-(methylcarbamoyl)pyridine-2,6-diyl)bis(1H-1,2,3-triazole-4,1-diyl))bis(2-(trifluoromethyl)benzoic acid);
4,4'-((4-(morpholine-4-carbonyl)pyridine-2,6-diyl)bis(1H-1,2,3-triazole-4,1-diyl))bis(2-(trifluoromethyl)benzoic acid);
4,4'-((4-(diethylcarbamoyl)pyridine-2,6-diyl)bis(1H-1,2,3-triazole-4,1-diyl))bis(2-(trifluoromethyl)benzoic acid);
4,4'-((4-carbamoylpyridine-2,6-diyl)bis(1H-1,2,3-triazole-4,1-diyl))bis(2-(trifluoromethyl)benzoic acid);
4,4'-((4-(ethoxycarbonyl)pyridine-2,6-diyl)bis(1H-1,2,3-triazole-4,1-diyl))bis(2-(trifluoromethyl)benzoic acid);
4,4'-((4-(azetidine-1-carbonyl)pyridine-2,6-diyl)bis(1H-1,2,3-triazole-4,1-diyl))bis(2-hydroxybenzoic acid);
4,4'-((4-(ethyl(methyl)carbamoyl)pyridine-2,6-diyl)bis(1H-1,2,3-triazole-4,1-diyl))bis(2-hydroxybenzoic acid);
N-ethyl-2,6-bis(1-(4-(2,2,2-trifluoroacetyl)phenyl)-1H-1,2,3-triazol-4-yl)isonicotinamide;
4,4'-(pyridine-2,6-diylbis(1H-1,2,3-triazole-4,1-diyl))bis(2-(trifluoromethyl)benzoic acid);
4,4'-((4-(cyclopropylcarbamoyl)pyridine-2,6-diyl)bis(1H-1,2,3-triazole-4,1-diyl))bis(2-(trifluoromethyl)benzoic acid);
4,4'-((4-(butylcarbamoyl)pyridine-2,6-diyl)bis(1H-1,2,3-triazole-4,1-diyl))bis(2-(trifluoromethyl)benzoic acid);
5,5'-((4-(diethylcarbamoyl)pyridine-2,6-diyl)bis(1H-1,2,3-triazole-4,1-diyl))bis(2-(trifluoromethyl)benzoic acid);
5,5'-((4-(morpholine-4-carbonyl)pyridine-2,6-diyl)bis(1H-1,2,3-triazole-4,1-diyl))bis(2-(trifluoromethyl)benzoic acid);
4,4'-(pyridazine-3,6-diylbis(1H-1,2,3-triazole-4,1-diyl))bis(2-hydroxybenzoic acid);
5,5'-((4-(ethylcarbamoyl)pyridine-2,6-diyl)bis(1H-1,2,3-triazole-4,1-diyl))bis(3-(trifluoromethyl)benzoic acid);
3,3'-(((4-(ethylcarbamoyl)pyridine-2,6-diyl)bis(1H-1,2,3-triazole-4,1-diyl))bis(4,1-phenylene))dipropionic acid;
4,4'-(((4-(ethylcarbamoyl)pyridine-2,6-diyl)bis(1H-1,2,3-triazole-4,1-diyl))bis(4,1-phenylene))dibutyric acid;
4,4'-((4-(ethylcarbamoyl)pyridine-2,6-diyl)bis(1H-1,2,3-triazole-4,1-diyl))diphthalic acid;
4,4'-((4-(ethylcarbamoyl)pyridine-2,6-diyl)bis(1H-1,2,3-triazole-4,1-diyl))bis(2-methoxybenzoic acid);
5,5'-((4-(ethylcarbamoyl)pyridine-2,6-diyl)bis(1H-1,2,3-triazole-4,1-diyl))diisophthalic acid;
4,4'-((4-(ethylcarbamoyl)pyridine-2,6-diyl)bis(1H-1,2,3-triazole-4,1-diyl))bis(3-hydroxybenzoic acid);
diethyl (3-(4-(6-(1-(3-(diethoxyphosphoryl)propyl)-1H-1,2,3-triazol-4-yl)-4-(ethylcarbamoyl) pyridin-2-yl)-1H-1,2,3-triazol-1-yl)propyl) phosphonate;
4,4'-((4-(ethylcarbamoyl)pyridine-2,6-diyl)bis(1H-1,2,3-triazole-4,1-diyl))bis(2-methylbenzoic acid);
2,2'-((4-(ethylcarbamoyl)pyridine-2,6-diyl)bis(1H-1,2,3-triazole-4,1-diyl))bis(3-(trifluoromethyl)benzoic acid);
4,4'-((4-((2-hydroxyethyl)carbamoyl)pyridine-2,6-diyl)bis(1H-1,2,3-triazole-4,1-diyl))bis(2-(trifluoromethyl)benzoic acid);
4,4'-((4-(ethylcarbamoyl)pyridine-2,6-diyl)bis(1H-1,2,3-triazole-4,1-diyl))bis(2-nitrobenzoic acid);
4,4'-((4-((3,3,3-trifluoropropyl)carbamoyl)pyridine-2,6-diyl)bis(1H-1,2,3-triazole-4,1-diyl))bis(2-(trifluoromethyl)benzoic acid);
(4-(4-(4-(ethylcarbamoyl)-6-(1-(4-phosphonophenyl)-1H-1,2,3-triazol-4-yl)pyridin-2-yl)-1H-1,2,3-triazol-1-yl)phenyl)phosphonic acid;
4,4',4'',4'''-((((butane-1,4-diylbis(azanediyl))bis(carbonyl))bis(pyridine-4,2,6-triyl))tetrakis(1H-1,2,3-triazole-4,1-diyl))tetrakis(2-(trifluoromethyl)benzoic acid);
2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))diacetic acid;
dimethyl 2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))diacetate;
(2S,2'S)-2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))disuccinic acid;
2,2'-((2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))bis(acetyl))bis(azanediyl))diacetic acid;
2,6-bis(1-(4-cyano-3-(trifluoromethyl)phenyl)-1H-1,2,3-triazol-4-yl)-N-ethylisonicotinamide;
4,4'-(thiophene-2,5-diylbis(1H-1,2,3-triazole-4,1-diyl))bis(2-(trifluoromethyl)benzoic acid); and
4,4'-(furan-2,5-diylbis(1H-1,2,3-triazole-4,1-diyl))bis(2-(trifluoromethyl)benzoic acid);
3'-(4-(4-(ethylcarbamoyl)-6-(1-(3'-(trifluoromethyl)-[1,1'-biphenyl]-3-yl)-1H-1,2,3-triazol-4-yl)pyridin-2-yl)-1H-1,2,3-triazol-1-yl)-3-(trifluoromethyl)-[1,1'-biphenyl]-4-carboxylic acid;
4,4'-((4-(ethylcarbamoyl)pyridine-2,6-diyl)bis(1H-1,2,3-triazole-4,1-diyl))bis(2-cyanobenzoic acid); and
4,4'-((4-(ethylcarbamoyl)pyridine-2,6-diyl)bis(1H-1,2,3-triazole-4,1-diyl))bis(2-chlorobenzoic acid).

Embodiment 23. The method of any one of embodiments 1-22, wherein the compound of Formula (I) increases the length of a resulting nucleic acid product compared to a nucleic acid polymerase reaction lacking the compound of Formula (I).

Embodiment 24. The method of any one of embodiments 1-22, wherein the at least one compound of Formula (I) comprises a plurality of compounds of Formula (I).

Embodiment 25. The method of any one of embodiments 1-22, wherein the nucleic acid polymerase is a DNA polymerase.

Embodiment 26. The method of embodiment 25, wherein the DNA polymerase is DPO4 or a variant thereof.

Embodiment 27. The method of any one of embodiments 1-22, wherein the mixture of nucleotides or nucleotide analogs is a mixture of nucleotide analogs comprising nucleoside triphosphoramidates, wherein each of the nucleoside triphosphoramidates comprises a nucleobase selected from the group consisting of adenine, guanine, thymine, and cytosine and a polymeric tether moiety, wherein a first end of the polymeric tether moiety is attached to the nucleobase and a second end of the polymeric tether moiety is attached to the alpha phosphate of the nucleoside triphosphoramidate to provide for expansion of the nucleotide analogs by cleavage of the phosphoramidate bond.

Embodiment 28. The method of any one of embodiments 1-22, wherein the nucleic acid polymerization reaction produces an expandable polymer of nucleotide analogs, wherein the expandable polymer encodes the nucleobase sequence information of the template nucleic acid.

Embodiment 29. The method of any one of embodiments 1-22, wherein the conditions for allowing a nucleic acid polymerization reaction comprise a suitable polymerization buffer and an oligonucleotide primer.

Embodiment 30. The method of any one of embodiments 1-22, wherein the suitable buffer comprises at least one of Tris OAc, $NH_4OAc$, PEG, a water-miscible organic solvent, polyphosphate 60, NMS, and $MnCl_2$.

Embodiment 31. The method of any one of embodiments 1-22, wherein the reaction mixture further comprises a single-strand binding protein.

Embodiment 32. The method of any one of embodiments 1-22, wherein the reaction mixture further comprises urea.

Embodiment 33. The method of any one of embodiments 1-22, wherein the mixture of nucleotides or nucleotide analogs comprises nucleotide analogs comprising a detectable label.

Embodiment 34. The method of embodiment 31, wherein the detectable label is an optically detectable label selected from the group consisting of luminescent, chemiluminescent, fluorescent, fluorogenic, chromophoric or chromogenic labels.

Embodiment 35. A method of sequencing a DNA or RNA template, the method comprising the steps of:

a. forming a DNA polymerase reaction composition comprising:

i. a DNA or RNA template, ii. a replication primer that complexes with the template, iii. a DNA polymerase, iv. a mixture of nucleotides or nucleotide analogs, v. at least one compound of Formula (I), b. incubating the DNA polymerase reaction composition under conditions allowing a DNA polymerization reaction, wherein the at least one compound of Formula (I) increases the rate, fidelity or processivity of the DNA polymerase reaction; and c. determining the sequence of the nucleotides or nucleotide analogs in the resulting polymer of nucleotides or nucleotide analogs;

wherein the compound of Formula (I) is:

(I)

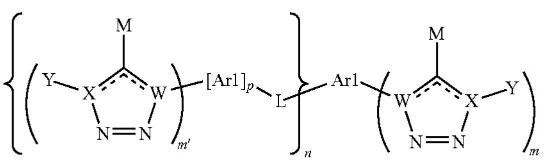

or a solvate, hydrate, tautomer, chelate or salt thereof, wherein:

m is 1, 2 or 3;

m' is 1, 2 or 3;

n is 0, 1 or 2;

p is 0, 1 or 2;

W is N when X is C or W is C when X is N;

----- is a single or double bond, wherein the double bond begins at whichever of W or X is carbon;

L is a linking group;

M is, at each occurrence, independently selected from hydrogen, halogen and $C_1$-$C_4$alkyl;

Ar1 is, at each occurrence, independently selected from optionally substituted pyridine, pyrazine, pyridazine, furan, thiophene, naphthalene, fluorene, phenanthrene, cinnoline, phthalazine, quinazoline, quinoxaline, naphthyridine, phenanthroline, purine, and carbazole, wherein:

substituents for Ar1 are, at each occurrence, independently selected from halogen, —OH, —CN, $—NO_2$, $C_1$-$C_6$alkyl, $C_1$-$C_6$haloalkyl, $C_1$-$C_6$heteroalkyl, $C_1$-$C_6$cycloloalkyl, $—OR^0$, $—CONH_2$, $—C(O)NR^1R^{1'}$, $—NR^1R^{1'}$, $—NR^1C(O)R^3$, $—C(O)SR^3$, $—COR^3$, $—OC(O)R^3$, $—C(O)OR^3$, mercaptan, $—R^4—H$, $—SOR^1$, $—S(O)_2R^1$, $—S(O)_2NR^1R^{1'}$, and $—NS(O)_2R^3$; and wherein $R^0$ is, at each occurrence, independently selected from $C_1$-$C_6$alkyl, $C_1$-$C_6$haloalkyl, $C_2$-$C_6$alkenyl, $C_2$-$C_6$alkynyl, substituted or unsubstituted cycloalkyl, substituted or unsubstituted heterocyclyl, substituted or unsubstituted aryl, and substituted or unsubstituted heteroaryl;

$R^1$ and $R^{1'}$ are, at each occurrence, independently selected from H, hydroxyl, $C_1$-$C_6$alkyl, $C_1$-$C_6$haloalkyl, $C_1$-$C_6$heteroalkyl, $C_2$-$C_6$alkenyl, $C_2$-$C_6$alkynyl, substituted or unsubstituted cycloalkyl, substituted or unsubstituted heterocyclyl, substituted or unsubstituted aryl, substituted or unsubstituted arylalkyl, and substituted or unsubstituted heteroaryl, $—C(=NH)NH_2$, $—CH_2CO_2R^0$, $—CH_2C(O)NHCH_2CO_2H$, $—CH_2CH_2OH$, $—CH_2CH_2NHC(O)R^3$, $—CH_2C(O)NHCH_2CO_2H$,

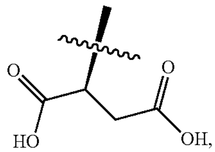

and

-continued

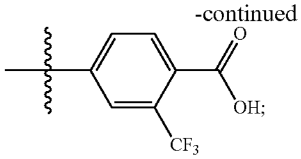

wherein $R^1$ and $R^{1'}$ can come together to form a heterocyclic ring, including, but not limited to, azetidine, pyrrolidine, piperidine, piperazine, morpholine,

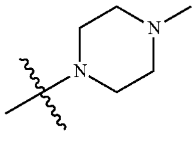 , or 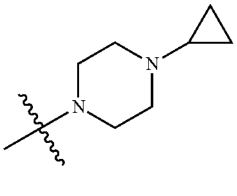 ;

$R^2$ is, at each occurrence, independently selected from $C_2$-$C_6$alkyl, $C_1$-$C_6$haloalkyl, $C_1$-$C_6$heteroalkyl, or substituted or unsubstituted cycloalkyl, substituted or unsubstituted heterocyclyl, substituted or unsubstituted aryl, substituted or unsubstituted heteroaryl, and substituted or unsubstituted haloalkoxy;

$R^3$ is, at each occurrence, independently selected from H, $C_1$-$C_6$alkyl, $C_1$-$C_6$haloalkyl, $C_1$-$C_6$heteroalkyl, or substituted or unsubstituted cycloalkyl, substituted or unsubstituted heterocyclyl, substituted or unsubstituted aryl, and substituted or unsubstituted heteroaryl, substituted or unsubstituted haloalkoxy, and guanidine;

$R^4$ is, at each occurrence, independently selected from one or more heteroatom interrupted alkylene wherein the heteroatom is O, S, NH or a combination thereof, Y is, at each occurrence, independently selected from Ar2, —$(CH_2)_3PO(OEt)_2$, or —CH2$CO_2$Me;

Ar2 is, at each occurrence, independently selected from substituted 5- and 6-membered monocyclic aromatic rings and 9- and 10-membered fused bicyclic rings comprising two monocyclic rings together, where at least one of the two monocyclic rings is an aromatic ring, wherein:

Ar2 is substituted with $G^1$, $G^2$, $G^3$, $G^4$ and $G^5$, wherein:

when Ar2 is monosubstituted, $G^1$ is, at each occurrence, independently selected from oxo, —$NH_2$, —$COR^3$, -E-$CO_2$H, —C(O)$NR^1R^{1'}$, -E-PO$(OR^1)_2$, and aryl substituted with $G^2$, $G^3$, $G^4$ and $G^5$;

$G^2$, $G^3$, $G^4$ and $G^5$ are, at each occurrence, independently selected from absent or selected from the groups comprising, halogen, —CN, $C_1$-$C_6$alkyl, $C_1$-$C_6$haloalkyl, -E-$CO_2$H, -E-CHO, -E-C(O)$R^3$, -E-C(O)NH(OH), -E-C(O)$NHR^1$, -E-CON$R^1R^{1'}$, -E-N$R^1R^{1'}$, and -E-$OR^2$, wherein:

E is, at each occurrence, independently selected from a direct bond and $C_1$-$C_6$alkylene.

Embodiment 36. The method of embodiment 35, wherein the mixture of nucleotide analogs comprises nucleoside triphosphoramidates, wherein each of the nucleoside triphosphoramidates comprises a nucleobase selected from the group consisting of adenine, guanine, thymine, and cytosine and a polymeric tether moiety, wherein a first end of the polymeric tether moiety is attached to the nucleobase and a second end of the polymeric ether moiety is attached to the alpha phosphate of the nucleoside triphosphoramidate to provide for expansion of the nucleotide analogs by cleavage of the phosphoramidate bond.

Embodiment 37. The method of embodiment 36, wherein the DNA polymerase is DPO4 or a variant thereof.

Embodiment 38. The method of embodiment 37, wherein the resulting polymer of nucleotide analogs is an expandable polymer.

Embodiment 39. The method of embodiment 38, further including the step of contacting the expandable polymer with a phosphoramidate cleavage agent to produce an expanded polymer of nucleotide analogs.

Embodiment 40. The method of embodiment 36, wherein the polymeric tether moiety of each of the nucleotide analogs comprises a reporter moiety unique to the nucleobase of the analog.

Embodiment 41. The method of embodiment 36, wherein the reporter moieties produce a characteristic electronic signal.

Embodiment 42. The method of embodiment 36, wherein the step of determining the sequence of the nucleotide analogs comprises the step of translocating the expanded polymer of nucleotide analogs through a nanopore.

Embodiment 43. A compound of formula (I)

(I)

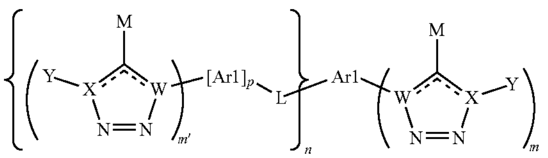

or a solvate, hydrate, tautomer, chelate or salt thereof, wherein:

m is 1, 2 or 3;

m' is 1, 2 or 3;

n is 0, 1 or 2;

p is 0, 1 or 2;

W is N when X is C or W is C when X is N;

----- is a single or double bond, wherein the double bond begins at whichever of W or X is carbon;

L is a linking group;

M is, at each occurrence, independently selected from hydrogen, halogen and $C_1$-$C_4$alkyl;

Ar1 is, at each occurrence, independently selected from optionally substituted pyridine, pyrazine, pyridazine, furan, thiophene, naphthalene, fluorene, phenanthrene, cinnoline, phthalazine, quinazoline, quinoxaline, naphthyridine, phenanthroline, purine, and carbazole, wherein:

substituents for Ar1 are, at each occurrence, independently selected from halogen, —OH, —CN, —$NO_2$, $C_1$-$C_6$alkyl, $C_1$-$C_6$haloalkyl, $C_1$-$C_6$heteroalkyl, $C_1$-$C_6$cycloloalkyl, —$OR^0$, —$CONH_2$, —C(O)$NR^1R^{1'}$, —$NR^1R^{1'}$, —$NR^1$C(O)$R^3$, —C(O)$SR^3$, —$COR^3$, —OC(O)$R^3$, —C(O)$OR^3$, mercaptan, —$R^4$—H, —$SOR^1$, —S$(O)_2R^1$, —S$(O)_2NR^1R^{1'}$, and —NS$(O)_2R^3$; and wherein $R^0$ is, at each occurrence, independently selected from $C_1$-$C_6$alkyl, $C_1$-$C_6$haloalkyl, $C_2$-$C_6$alkenyl, $C_2$-$C_6$alkynyl, substituted or unsubstituted cycloalkyl, substituted or unsubstituted heterocyclyl, substituted or unsubstituted aryl, and substituted or unsubstituted heteroaryl;

$R^1$ and $R^{1'}$ are, at each occurrence, independently selected from H, hydroxyl, $C_1$-$C_6$alkyl, $C_1$-$C_6$haloalkyl, $C_1$-$C_6$heteroalkyl, $C_2$-$C_6$alkenyl, $C_2$-$C_6$alkynyl, substituted or unsubstituted cycloalkyl, substituted or unsubstituted heterocyclyl, substituted or unsubstituted aryl, substituted or unsubstituted arylalkyl, and substituted or unsubstituted heteroaryl, —C(=NH)$NH_2$, —$CH_2CO_2R^0$, —$CH_2C(O)NHCH_2CO_2H$, —$CH_2CH_2OH$, —$CH_2CH_2NHC(O)R^3$, —$CH_2C(O)NHCH_2CO_2H$,

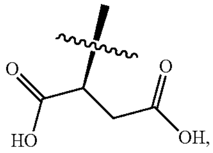

and

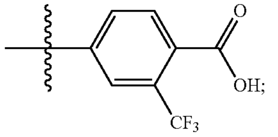

wherein $R^1$ and $R^{1'}$ can come together to form a heterocyclic ring, including, but not limited to, azetidine, pyrrolidine, piperidine, piperazine, morpholine,

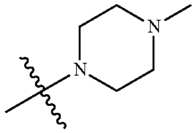

, or

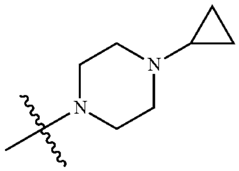

;

$R^2$ is, at each occurrence, independently selected from $C_2$-$C_6$alkyl, $C_1$-$C_6$haloalkyl, $C_1$-$C_6$heteroalkyl, or substituted or unsubstituted cycloalkyl, substituted or unsubstituted heterocyclyl, substituted or unsubstituted aryl, substituted or unsubstituted heteroaryl, and substituted or unsubstituted haloalkoxy;

$R^3$ is, at each occurrence, independently selected from H, $C_1$-$C_6$alkyl, $C_1$-$C_6$haloalkyl, $C_1$-$C_6$heteroalkyl, or substituted or unsubstituted cycloalkyl, substituted or unsubstituted heterocyclyl, substituted or unsubstituted aryl, and substituted or unsubstituted heteroaryl, substituted or unsubstituted haloalkoxy, and guanidine;

$R^4$ is, at each occurrence, independently selected from one or more heteroatom interrupted alkylene wherein the heteroatom is O, S, NH or a combination thereof, Y is, at each occurrence, independently selected from Ar2, —$(CH_2)_3PO(OEt)_2$, or —$CH_2CO_2Me$;

Ar2 is, at each occurrence, independently selected from substituted 5- and 6-membered monocyclic aromatic rings and 9- and 10-membered fused bicyclic rings comprising two monocyclic rings together, where at least one of the two monocyclic rings is an aromatic ring, wherein:

Ar2 is substituted with $G^1$, $G^2$, $G^3$, $G^4$ and $G^5$, wherein:

when Ar2 is monosubstituted, $G^1$ is, at each occurrence, independently selected from oxo, —$NH_2$, —$COR^3$, -E-$CO_2H$, —$C(O)NR^1R^{1'}$, -E-$PO(OR^1)_2$, and aryl substituted with $G^2$, $G^3$, $G^4$ and $G^5$;

$G^2$, $G^3$, $G^4$ and $G^5$ are, at each occurrence, independently selected from absent or selected from the groups comprising, halogen, —CN, $C_1$-$C_6$alkyl, $C_1$-$C_6$haloalkyl, -E-$CO_2H$, -E-CHO, -E-$C(O)R^3$, -E-C(O)NH(OH), -E-$C(O)NHR^1$, -E-$CONR^1R^{1'}$, -E-$NR^1R^{1'}$, and -E-$OR^2$, wherein;

E is, at each occurrence, independently selected from a direct bond and $C_1$-$C_6$alkylene.

Embodiment 44. The compound of embodiment 43, wherein Ar1 is monocyclic heterocyclic aryl.

Embodiment 45. The compound of embodiment 44, wherein Ar1 is selected from:

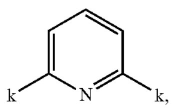

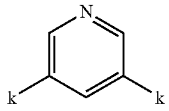

and

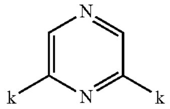

wherein triazole rings are located at positions k on Ar1.

Embodiment 46. The compound of embodiment 43, wherein Ar1 is bicyclic aryl.

Embodiment 47. The compound of embodiment 46, wherein Ar1 is a bicyclic carbocyclic aryl selected from:

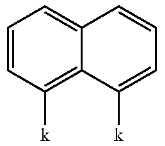

,

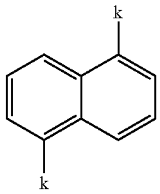

,

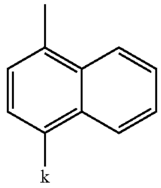

,

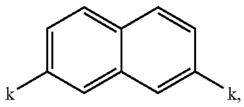

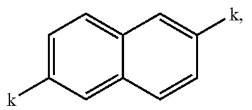

and

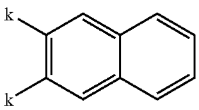

wherein triazole rings are located at positions k on Ar1.

Embodiment 48. The compound of embodiment 46, wherein Ar1 is a bicyclic heterocyclic aryl selected from:

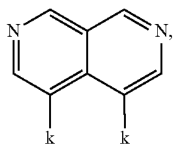

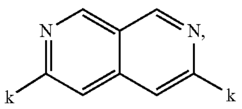

-continued

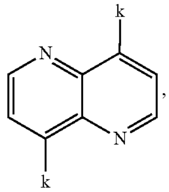, 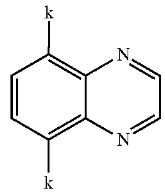,

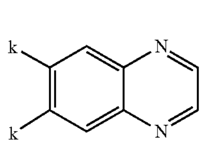 and 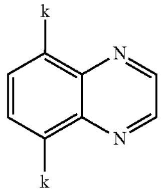

wherein triazole rings are located at positions k on Ar1.

Embodiment 49. The compound of embodiment 43, wherein Ar1 is tricyclic aryl.

Embodiment 50. The compound of embodiment 49, wherein Ar1 is a tricyclic carbocyclic aryl selected from:

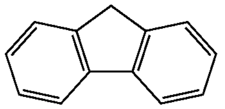 and 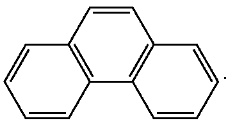.

Embodiment 51. The compound of embodiment 49, wherein Ar1 is tricyclic heteroaryl selected from:

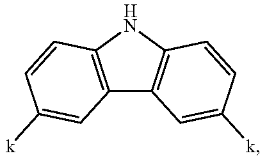,

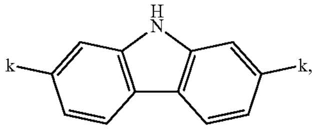, and

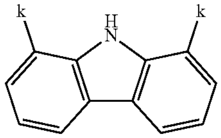

wherein triazole rings are located at positions k on Ar1.

Embodiment 52. The compound of embodiment 49, wherein Ar1 is a tricyclic heteroaryl selected from

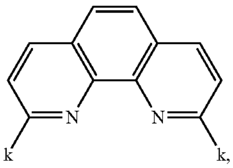,

-continued

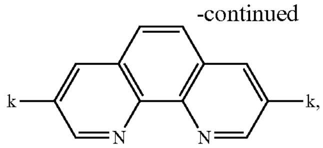,

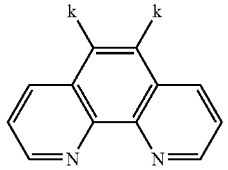, and

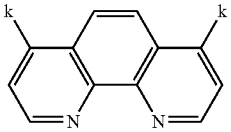

wherein the triazole rings are located at positions k on Ar1.

Embodiment 53. The compound of embodiment 43, wherein Ar2 is a substituted 5-membered monocyclic aromatic ring selected from the group consisting of thiophene, 1,2-thiazole, 1,3-thiazole, furan, 1,2-oxazole, 1,3-oxazole, 1H-pyrrole, 1H-pyrazole, oxadiazole, thiadiazole, 1,2,4-triazole, 1,2,3-triazole and 1H-imidazole.

Embodiment 54. The compound of embodiment 43, wherein Ar2 is a 6-membered monocyclic aromatic ring selected from the group consisting of benzene, pyridine, pyridazine, pyrimidine and pyrazine.

Embodiment 55. The compound of embodiment 43, wherein Ar2 is a 9-membered fused bicyclic aromatic ring system selected from the group consisting of benzofuran, 1,3-benzoxazole, furo[3,2-b]pyridine, furo[3,2-c]pyridine, furo[2,3-c]pyridine, furo[2,3-b]pyridine, indole, 1H-benzimidazole, 1H-pyrrolo[3,2-b]pyridine, 1H-pyrrolo[3,2-c]pyridine, 1H-pyrrolo[2,3-c]pyridine, 1H-pyrrolo[2,3-b]pyridine, benzothiophene, 1,3-benzothiazole, thienol[3,2-b]pyridine, thieno[3,2-c]pyridine, thieno[2,3-c]pyridine, benzoxadiazole, benzothiadiazole, benzisoxazole, benzotriazole and thieno[2,3-b]pyridine.

Embodiment 56. The compound of embodiment 43, wherein Ar2 is a 10-membered fused bicyclic aromatic ring system selected from the group consisting of naphthylene, quinoline, quinazoline, quinoxaline, 1,5-naphthyridine, 1,6-naphthyridine, 1,7-naphthyridine, 1,8-naphthyridine, isoquinoline, phthalazine, 2,6-naphthyridine and 2,7-naphthyridine.

Embodiment 57. The compound of embodiment 43, wherein Ar2 is a pyridinyl ring selected from

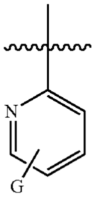, 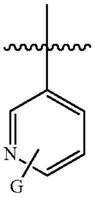 and 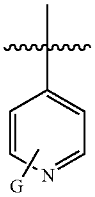;

wherein the substituent G is present 0, 1 or 2 times on the pyridinyl ring.

Embodiment 58. The compound of embodiment 43, wherein Ar2 is a phenyl ring of the formula

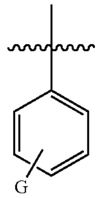

wherein the substituent G is present 0, 1 or 2 times on the phenyl ring.

Embodiment 59. The compound of embodiment 43, wherein Ar2 is a phenyl ring selected from

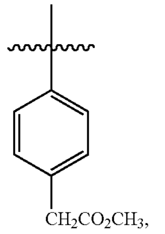

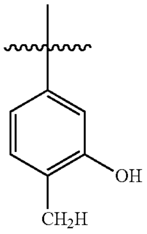

,

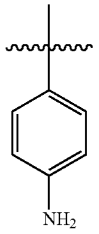

,

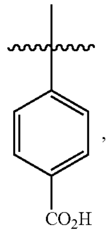

, and

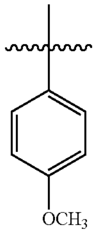

.

Embodiment 60. The compound of embodiment 43, wherein Ar2 is a substituted phenyl group, wherein the substituent of the phenyl group is aryl further substituted with $G^2$, $G^3$, $G^4$ and $G^5$.

Embodiment 61. The compound of embodiment 43, wherein the substitution on Ar2 includes amino.

Embodiment 62. The compound of embodiment 43, wherein the substitution on Ar2 includes methoxy.

Embodiment 63. The compound of embodiment 43, wherein the substitution on Ar2 includes carboxylic acid.

Embodiment 64. The compound of embodiment 43, wherein the substitution on Ar2 includes $-CH_2-CO_2-CH_3$.

Embodiment 65. The compound of embodiment 43, wherein substitution on Ar2 includes trifluormethyl.

Embodiment 66. The compound of embodiment 43, wherein substitution on Ar2 includes hydroxyl.

Embodiment 67. The compound of embodiment 43, wherein substitution on Ar2 is one carboxylic acid and one hydroxyl.

Embodiment 68. The compound of embodiment 43, wherein substitution on Ar2 is one carboxylic acid and one trifluoromethyl.

Embodiment 69. The compound of embodiment 43, in a form of a chelate.

Embodiment 70. The compound of embodiment 68, wherein the chelate is a copper chelate.

Embodiment 71. The compound of embodiment 43, having a log P of at least 4.9.

Embodiment 72. The compound of embodiment 43, wherein n is 0 and m is 2, having one of the following structures (III) or (IV):

(III)

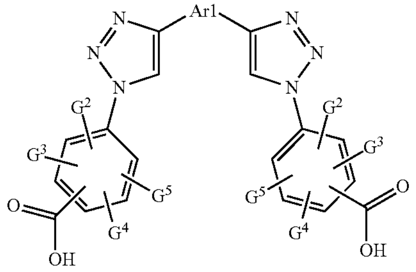

or (IV)

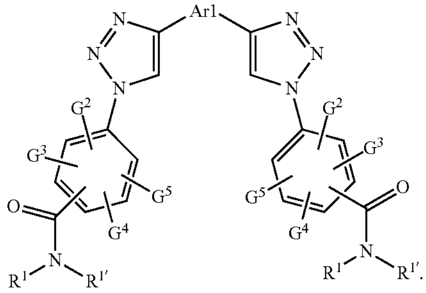

Embodiment 73. The compound of embodiment 43, having substitution on Ar2 including at least two of hydroxyl, carboxylic acid carboxamide and trifluoromethyl.

Embodiment 74. The compound of embodiment 43, wherein the compound has one of the following structures (V), (VI), (VII), (VIII), or (IX):

(V)

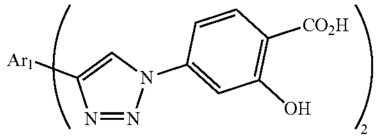

;

(VI)

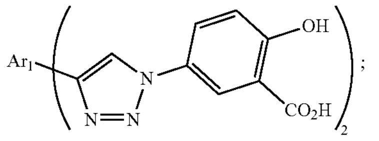

;

(VII)

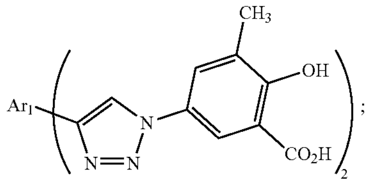

;

(VIII)

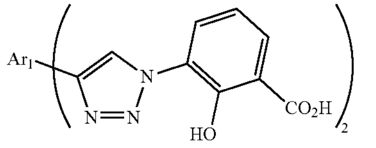

or (IX)

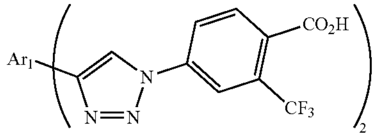

.

Embodiment 75. The compound of embodiment 43, wherein the compound has one of the following structures (X), (XI) or (XII):

(X)

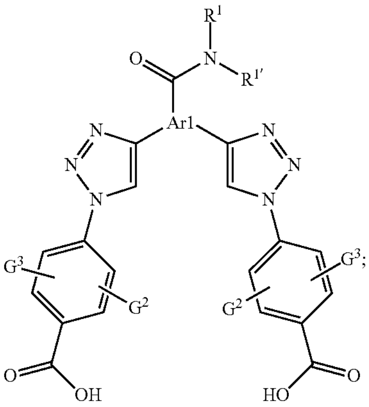

(XI)

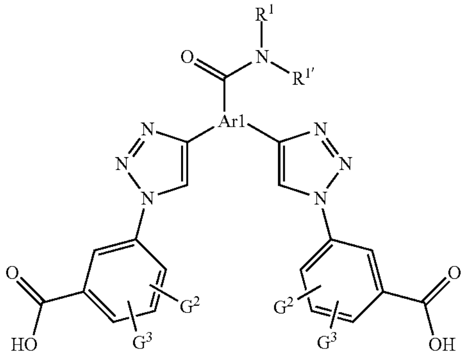

or (XII)

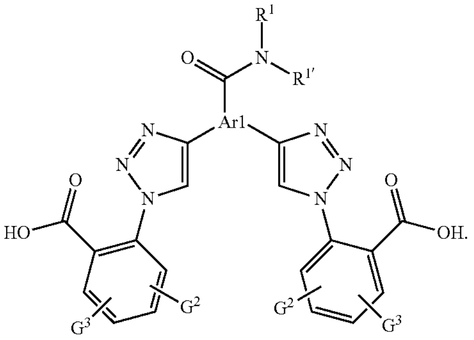

Embodiment 76. The compound of embodiment 43, wherein the compound has one of the following structures (XIII), (XIV) or (XV):

(XIII)

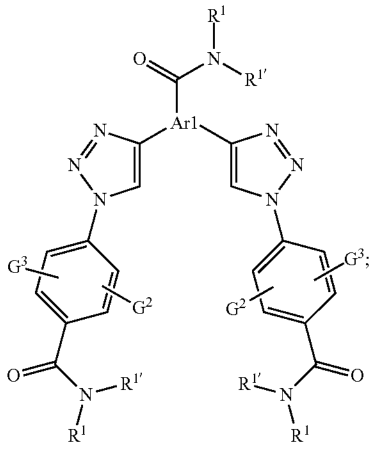

(XIV)

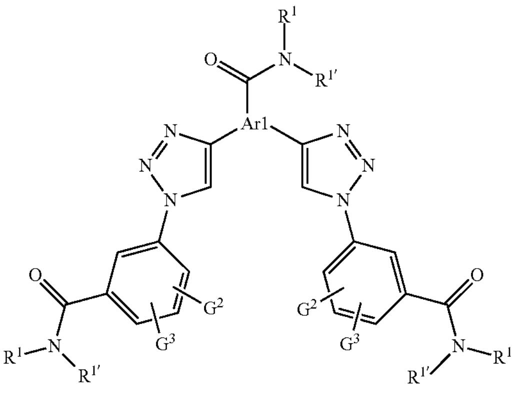

or (XV)

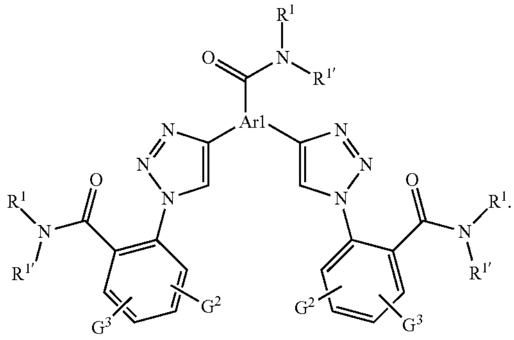

Embodiment 77. The compound of embodiment 43, wherein the compound has one of the following structures (XVI), (XVII), (XVIII), (XIX), (XX), (XXI) or (XXII):

-continued
(XVI)
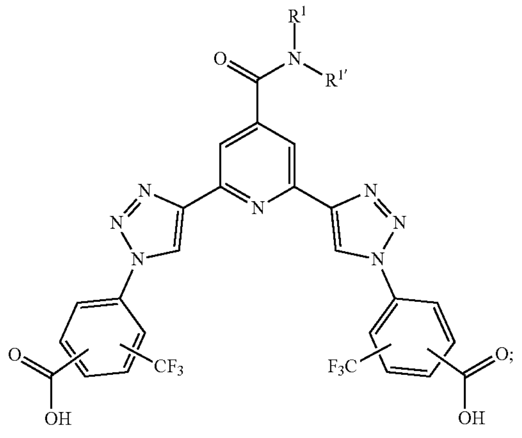
(XVII)
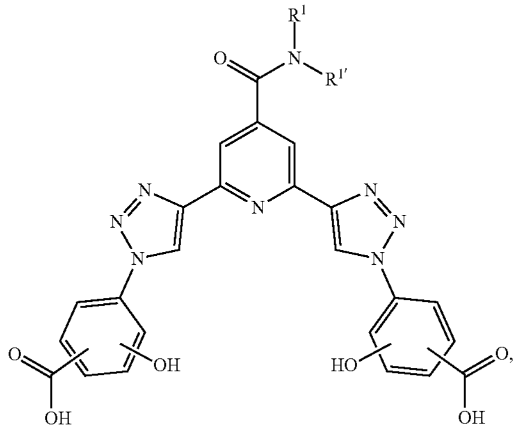
(XVIII)
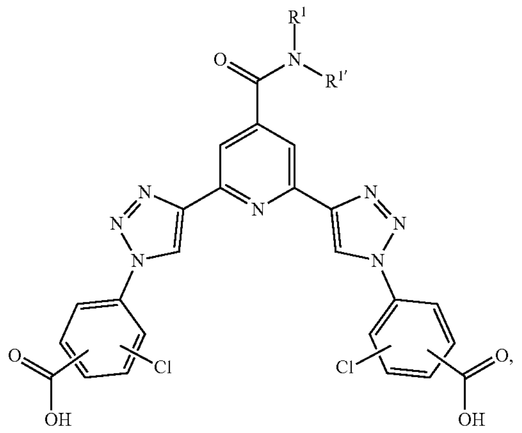
(XIX)
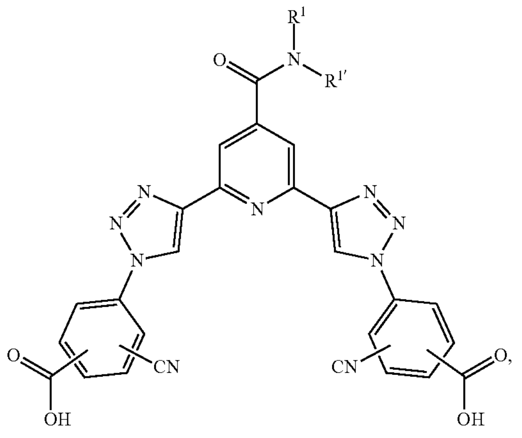
(XX)
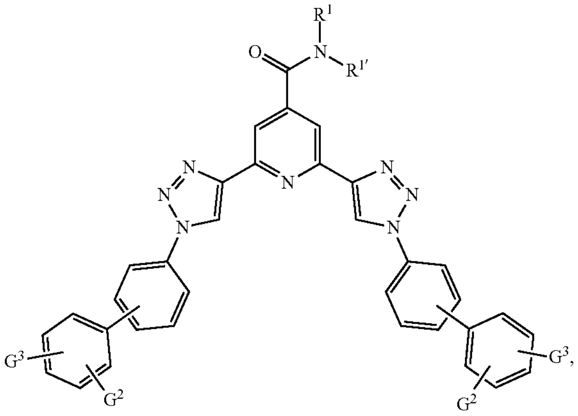
(XXI)
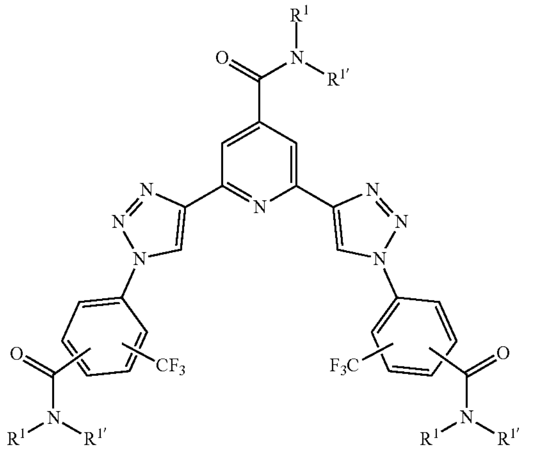
or -continued (XXII)

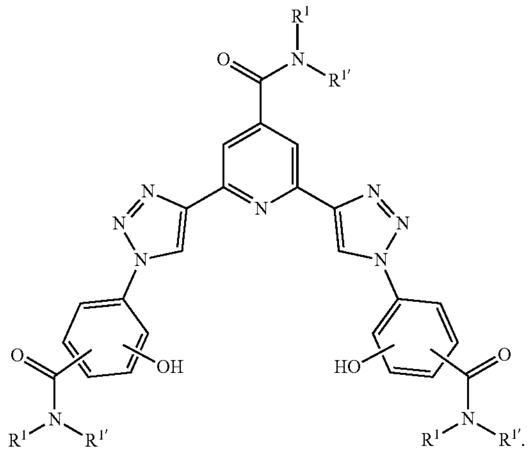

Embodiment 78. The compound of embodiment 43, wherein the compound has one of the following structures (XXIII), (XXIV) or (XXV):

(XXIII)

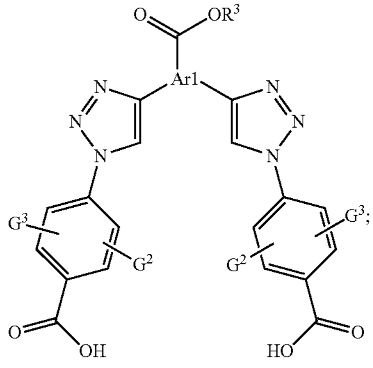

(XXIV)

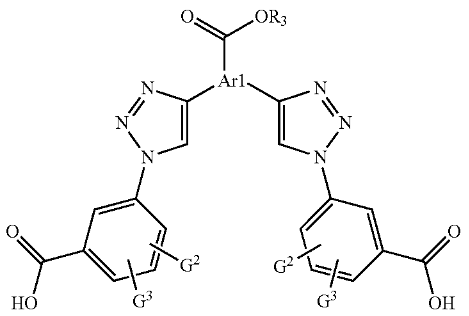

or

-continued (XXV)

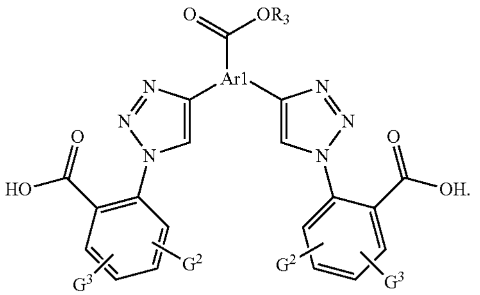

Embodiment 79. The compound of embodiment 43, wherein the compound has one of the following structures (XXVI), (XXVII) or (XXVIII):

(XXVI)

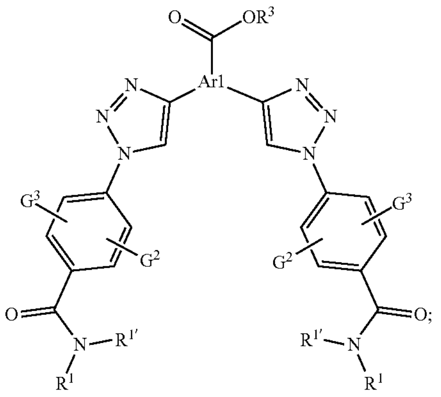

(XXVII)

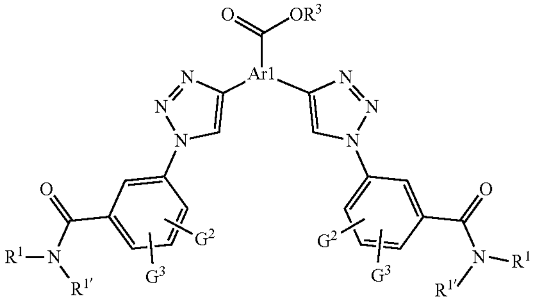

or (XXVIII)

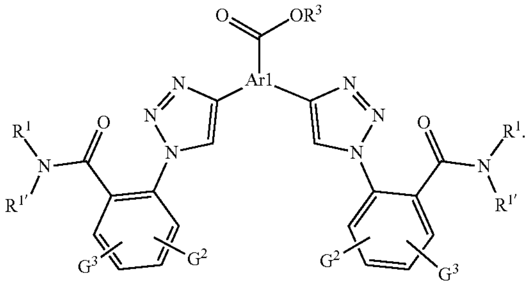

Embodiment 80. The compound of embodiment 43, wherein the compound has one of the following structures (XXIX), (XXX), (XXXI) or (XXXII):

(XXIX)

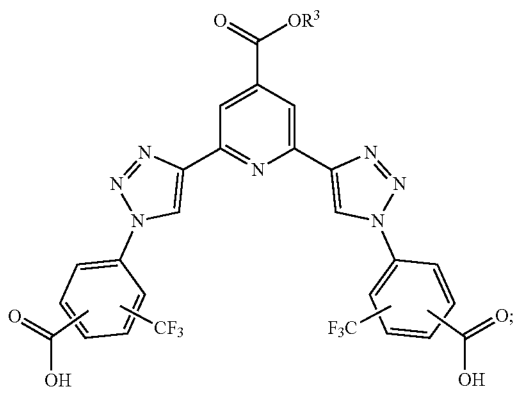

(XXX)

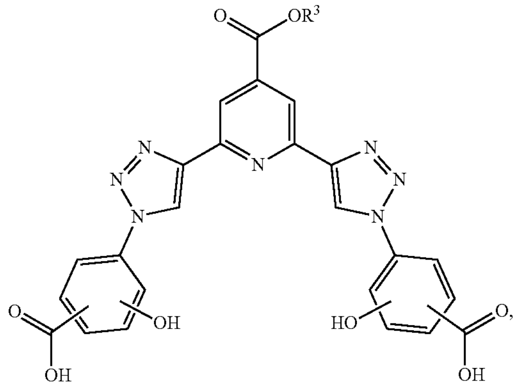

(XXXI)

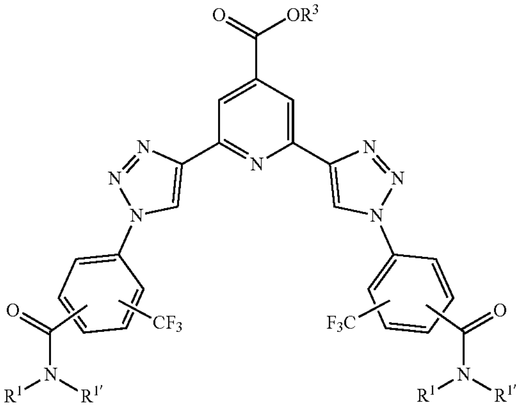

or

-continued (XXXII)

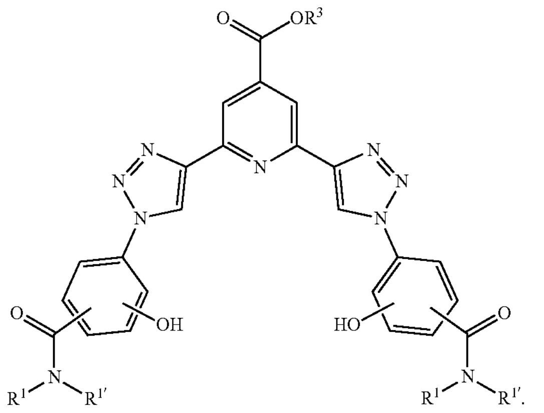

Embodiment 81. The compound of embodiment 43, selected from:

4,4'-(pyridine-2,6-diylbis(1H-1,2,3-triazole-4,1-diyl))bis(2-hydroxybenzoic acid);

4,4'-(pyridine-3,5-diylbis(1H-1,2,3-triazole-4,1-diyl))bis(2-hydroxybenzoic acid);

4,4'-((9H-carbazole-3,6-diyl)bis(1H-1,2,3-triazole-4,1-diyl))bis(2-hydroxybenzoic acid);

4,4'-((9H-carbazole-3,6-diyl)bis(1H-1,2,3-triazole-4,1-diyl))dibenzoic acid;

4,4'-((4-methoxypyridine-2,6-diyl)bis(1H-1,2,3-triazole-4,1-diyl))bis(2-hydroxybenzoic acid);

4,4'-((4-carboxypyridine-2,6-diyl)bis(1H-1,2,3-triazole-4,1-diyl))bis(2-hydroxybenzoic acid);

4,4'-((4-nitropyridine-2,6-diyl)bis(1H-1,2,3-triazole-4,1-diyl))bis(2-hydroxybenzoic acid);

5,5'-((4-cyanopyridine-2,6-diyl)bis(1H-1,2,3-triazole-4,1-diyl))bis(2-hydroxybenzoic acid);

4,4'-((4-methylpyridine-2,6-diyl)bis(1H-1,2,3-triazole-4,1-diyl))bis(2-hydroxybenzoic acid);

4,4'-((4-(ethoxycarbonyl)pyridine-2,6-diyl)bis(1H-1,2,3-triazole-4,1-diyl))bis(2-hydroxybenzoic acid);

5,5'-((4-(ethoxycarbonyl)pyridine-2,6-diyl)bis(1H-1,2,3-triazole-4,1-diyl))bis(2-hydroxybenzoic acid);

4,4'-((4-(methoxycarbonyl)pyridine-2,6-diyl)bis(1H-1,2,3-triazole-4,1-diyl))bis(2-hydroxybenzoic acid);

4,4'-((4-(ethylcarbamoyl)pyridine-2,6-diyl)bis(1H-1,2,3-triazole-4,1-diyl))bis(2-hydroxybenzoic acid);

4,4'-((4-(methylcarbamoyl)pyridine-2,6-diyl)bis(1H-1,2,3-triazole-4,1-diyl))bis(2-hydroxybenzoic acid);

4,4'-((4-carbamoylpyridine-2,6-diyl)bis(1H-1,2,3-triazole-4,1-diyl))bis(2-hydroxybenzoic acid);

4,4'-(pyrazine-2,6-diylbis(1H-1,2,3-triazole-4,1-diyl))bis(2-hydroxybenzoic acid);

4,4'-(1,3-phenylenebis(1H-1,2,3-triazole-4,1-diyl))dianiline;

4,4'-(1,3-phenylenebis(1H-1,2,3-triazole-4,1-diyl))dibenzoic acid;

4-(4-(3-(1-(4-methoxyphenyl)-1H-1,2,3-triazol-4-yl)phenyl)-1H-1,2,3-triazol-1-yl)benzoic acid;

4,4'-(pyridine-2,6-diylbis(1H-1,2,3-triazole-4,1-diyl))dibenzoic acid;

4-(4-(3-(1-(4-methoxyphenyl)-1H-1,2,3-triazol-4-yl)phenyl)-1H-1,2,3-triazol-1-yl)benzoic acid;

4,4'-((3,5-dimethylpyridine-2,6-diyl)bis(1H-1,2,3-triazole-4,1-diyl))bis(2-hydroxybenzoic acid);

4,4'-((413-pyridine-2,6-diyl)bis(5-iodo-1H-1,2,3-triazole-4,1-diyl))bis(2-hydroxybenzoic acid);

4,4'-((4-acetamidopyridine-2,6-diyl)bis(1H-1,2,3-triazole-4,1-diyl))bis(2-hydroxybenzoic acid);

4,4'-((9-acetyl-9H-carbazole-3,6-diyl)bis(1H-1,2,3-triazole-4,1-diyl))bis(2-hydroxybenzoic acid);

4,4'-(pyridine-2,6-diylbis(1H-1,2,3-triazole-4,1-diyl))bis(N,2-dihydroxybenzamide);

4,4'-(pyridine-2,6-diylbis(1H-1,2,3-triazole-4,1-diyl))bis(2-hydroxybenzamide);

4,4'-((4-carboxypyridine-2,6-diyl)bis(1H-1,2,3-triazole-4,1-diyl))bis(2-hydroxybenzoic acid);

4,4'-((1,10-phenanthroline-2,9-diyl)bis(1H-1,2,3-triazole-4,1-diyl))bis(2-hydroxybenzoic acid);

4,4'-((4-(trifluoromethyl)pyridine-2,6-diyl)bis(1H-1,2,3-triazole-4,1-diyl))bis(2-hydroxybenzoic acid);

4,4'-((3-cyanopyridine-2,6-diyl)bis(1H-1,2,3-triazole-4,1-diyl))bis(2-hydroxybenzoic acid);

4,4'-((3-nitropyridine-2,6-diyl)bis(1H-1,2,3-triazole-4,1-diyl))bis(2-hydroxybenzoic acid);

3,3'-((4-cyanopyridine-2,6-diyl)bis(1H-1,2,3-triazole-4,1-diyl))bis(2-hydroxybenzoic acid);

4,4'-((4-(tert-butoxycarbonyl)pyridine-2,6-diyl)bis(1H-1,2,3-triazole-4,1-diyl))bis(2-hydroxybenzoic acid);

4-(4-(4-cyanopyridin-2-yl)-1H-1,2,3-triazol-1-yl)-2-hydroxybenzoic acid;

5-(4-(6-(4-(3-carboxy-4-hydroxy-5-methylphenyl)-1H-1,2,3-triazol-1-yl)-4-(methoxycarbonyl)pyridin-2-yl)-1H-1,2,3-triazol-1-yl)-2-hydroxy-3-methylbenzoic acid;

4,4'-((4-(dimethylcarbamoyl)pyridine-2,6-diyl)bis(1H-1,2,3-triazole-4,1-diyl))bis(2-hydroxybenzoic acid);

4,4'-((4-(cyclopropylcarbamoyl)pyridine-2,6-diyl)bis(1H-1,2,3-triazole-4,1-diyl))bis(2-hydroxybenzoic acid);

4,4'-((4-(but-3-yn-1-ylcarbamoyl)pyridine-2,6-diyl)bis(1H-1,2,3-triazole-4,1-diyl))bis(2-hydroxybenzoic acid);

4,4'-((4-(butylcarbamoyl)pyridine-2,6-diyl)bis(1H-1,2,3-triazole-4,1-diyl))bis(2-hydroxybenzoic acid);

4,4'-((4-(diethylcarbamoyl)pyridine-2,6-diyl)bis(1H-1,2,3-triazole-4,1-diyl))bis(2-hydroxybenzoic acid);

4,4'-((4-(tert-butylcarbamoyl)pyridine-2,6-diyl)bis(1H-1,2,3-triazole-4,1-diyl))bis(2-hydroxybenzoic acid);

4,4'-((4-(morpholine-4-carbonyl)pyridine-2,6-diyl)bis(1H-1,2,3-triazole-4,1-diyl))bis(2-hydroxybenzoic acid);

4,4'-((4-(propylcarbamoyl)pyridine-2,6-diyl)bis(1H-1,2,3-triazole-4,1-diyl))bis(2-hydroxybenzoic acid);

4,4'-((4-(phenylcarbamoyl)pyridine-2,6-diyl)bis(1H-1,2,3-triazole-4,1-diyl))bis(2-hydroxybenzoic acid);

4,4'-((4-((2-acetamidoethyl)carbamoyl)pyridine-2,6-diyl)bis(1H-1,2,3-triazole-4,1-diyl))bis(2-hydroxybenzoic acid);

4,4'-((4-(4-cyclopropylpiperazine-1-carbonyl)pyridine-2,6-diyl)bis(1H-1,2,3-triazole-4,1-diyl))bis(2-hydroxybenzoic acid);

4,4'-((4-(carbamimidoylcarbamoyl)pyridine-2,6-diyl)bis(1H-1,2,3-triazole-4,1-diyl))bis(2-hydroxybenzoic acid);

4,4'-((4-(piperidine-1-carbonyl)pyridine-2,6-diyl)bis(1H-1,2,3-triazole-4,1-diyl))bis(2-hydroxybenzoic acid);

4,4'-((4-(cyclobutylcarbamoyl)pyridine-2,6-diyl)bis(1H-1,2,3-triazole-4,1-diyl))bis(2-hydroxybenzoic acid);

4,4'-((1,10-phenanthroline-3,8-diyl)bis(1H-1,2,3-triazole-4,1-diyl))bis(2-hydroxybenzoic acid);

4,4'-((4-(cyclopentylcarbamoyl)pyridine-2,6-diyl)bis(1H-1,2,3-triazole-4,1-diyl))bis(2-hydroxybenzoic acid);

4,4'-((4-(dipropylcarbamoyl)pyridine-2,6-diyl)bis(1H-1,2,3-triazole-4,1-diyl))bis(2-hydroxybenzoic acid);

4,4'-((4-(di-sec-butylcarbamoyl)pyridine-2,6-diyl)bis(1H-1,2,3-triazole-4,1-diyl))bis(2-hydroxybenzoic acid);

4,4'-(naphthalene-2,7-diylbis(1H-1,2,3-triazole-4,1-diyl))bis(2-hydroxybenzoic acid);

4,4'-(naphthalene-2,3-diylbis(1H-1,2,3-triazole-4,1-diyl))bis(2-hydroxybenzoic acid);

4,4'-((4-(dibutylcarbamoyl)pyridine-2,6-diyl)bis(1H-1,2,3-triazole-4,1-diyl))bis(2-hydroxybenzoic acid);

4,4'-((4-((2-hydroxyethyl)carbamoyl)pyridine-2,6-diyl)bis(1H-1,2,3-triazole-4,1-diyl))bis(2-hydroxybenzoic acid);

4,4'-((4-(cyclohexylcarbamoyl)pyridine-2,6-diyl)bis(1H-1,2,3-triazole-4,1-diyl))bis(2-hydroxybenzoic acid);

4,4'-((4-(benzylcarbamoyl)pyridine-2,6-diyl)bis(1H-1,2,3-triazole-4,1-diyl))bis(2-hydroxybenzoic acid);

4,4'-((4-(4-methylpiperazine-1-carbonyl)pyridine-2,6-diyl)bis(1H-1,2,3-triazole-4,1-diyl))bis(2-hydroxybenzoic acid);

4-(4-(3-(1-(4-methoxyphenyl)-1H-1,2,3-triazol-4-yl)phenyl)-1H-1,2,3-triazol-1-yl)benzoic acid;

4,4',4'',4'''-((((butane-1,4-diylbis(azanediyl))bis(carbonyl))bis(pyridine-4,2,6-triyl))tetrakis(1H-1,2,3-triazole-4,1-diyl))tetrakis(2-hydroxybenzoic acid);

4,4'-((4-(ethylcarbamoyl)pyridine-2,6-diyl)bis(1H-1,2,3-triazole-4,1-diyl))bis(3,5,6-trichloropicolinic acid);

4,4'-((4-(ethylcarbamoyl)pyridine-2,6-diyl)bis(1H-1,2,3-triazole-4,1-diyl))bis(2-(trifluoromethyl)benzoic acid);

7,7'-((4-(ethylcarbamoyl)pyridine-2,6-diyl)bis(1H-1,2,3-triazole-4,1-diyl))bis(2-hydroxy-1,8-naphthyridine-4-carboxylic acid);

5,5'-((4-(ethylcarbamoyl)pyridine-2,6-diyl)bis(1H-1,2,3-triazole-4,1-diyl))bis(2-(trifluoromethyl)benzoic acid);

4,4'-((4-(ethylcarbamoyl)pyridine-2,6-diyl)bis(1H-1,2,3-triazole-4,1-diyl))bis(2-fluorobenzoic acid);

5,5'-((4-(ethylcarbamoyl)pyridine-2,6-diyl)bis(1H-1,2,3-triazole-4,1-diyl))bis(3-fluorobenzoic acid);

4,4'-((4-(methylcarbamoyl)pyridine-2,6-diyl)bis(1H-1,2,3-triazole-4,1-diyl))bis(2-(trifluoromethyl)benzoic acid);

4,4'-((4-(morpholine-4-carbonyl)pyridine-2,6-diyl)bis(1H-1,2,3-triazole-4,1-diyl))bis(2-(trifluoromethyl)benzoic acid);

4,4'-((4-(diethylcarbamoyl)pyridine-2,6-diyl)bis(1H-1,2,3-triazole-4,1-diyl))bis(2-(trifluoromethyl)benzoic acid);

4,4'-((4-carbamoylpyridine-2,6-diyl)bis(1H-1,2,3-triazole-4,1-diyl))bis(2-(trifluoromethyl)benzoic acid);

4,4'-((4-(ethoxycarbonyl)pyridine-2,6-diyl)bis(1H-1,2,3-triazole-4,1-diyl))bis(2-(trifluoromethyl)benzoic acid);

4,4'-((4-(azetidine-1-carbonyl)pyridine-2,6-diyl)bis(1H-1,2,3-triazole-4,1-diyl))bis(2-hydroxybenzoic acid);

4,4'-((4-(ethyl(methyl)carbamoyl)pyridine-2,6-diyl)bis(1H-1,2,3-triazole-4,1-diyl))bis(2-hydroxybenzoic acid);

N-ethyl-2,6-bis(1-(4-(2,2,2-trifluoroacetyl)phenyl)-1H-1,2,3-triazol-4-yl)isonicotinamide;

4,4'-(pyridine-2,6-diylbis(1H-1,2,3-triazole-4,1-diyl))bis(2-(trifluoromethyl)benzoic acid);

4,4'-((4-(cyclopropylcarbamoyl)pyridine-2,6-diyl)bis(1H-1,2,3-triazole-4,1-diyl))bis(2-(trifluoromethyl)benzoic acid);

4,4'-((4-(butylcarbamoyl)pyridine-2,6-diyl)bis(1H-1,2,3-triazole-4,1-diyl))bis(2-(trifluoromethyl)benzoic acid);

5,5'-((4-(diethylcarbamoyl)pyridine-2,6-diyl)bis(1H-1,2,3-triazole-4,1-diyl))bis(2-(trifluoromethyl)benzoic acid);

5,5'-((4-(morpholine-4-carbonyl)pyridine-2,6-diyl)bis(1H-1,2,3-triazole-4,1-diyl))bis(2-(trifluoromethyl)benzoic acid);

4,4'-(pyridazine-3,6-diylbis(1H-1,2,3-triazole-4,1-diyl))bis(2-hydroxybenzoic acid);

5,5'-((4-(ethylcarbamoyl)pyridine-2,6-diyl)bis(1H-1,2,3-triazole-4,1-diyl))bis(3-(trifluoromethyl)benzoic acid);

3,3'-(((4-(ethylcarbamoyl)pyridine-2,6-diyl)bis(1H-1,2,3-triazole-4,1-diyl))bis(4,1-phenylene))dipropionic acid;

4,4'-(((4-(ethylcarbamoyl)pyridine-2,6-diyl)bis(1H-1,2,3-triazole-4,1-diyl))bis(4,1-phenylene))dibutyric acid;

4,4'-((4-(ethylcarbamoyl)pyridine-2,6-diyl)bis(1H-1,2,3-triazole-4,1-diyl))diphthalic acid;

4,4'-((4-(ethylcarbamoyl)pyridine-2,6-diyl)bis(1H-1,2,3-triazole-4,1-diyl))bis(2-methoxybenzoic acid);

5,5'-((4-(ethylcarbamoyl)pyridine-2,6-diyl)bis(1H-1,2,3-triazole-4,1-diyl))diisophthalic acid;

4,4'-((4-(ethylcarbamoyl)pyridine-2,6-diyl)bis(1H-1,2,3-triazole-4,1-diyl))bis(3-hydroxybenzoic acid);

diethyl (3-(4-(6-(1-(3-(diethoxyphosphoryl)propyl)-1H-1,2,3-triazol-4-yl)-4-(ethylcarbamoyl) pyridin-2-yl)-1H-1,2,3-triazol-1-yl)propyl) phosphonate;

4,4'-((4-(ethylcarbamoyl)pyridine-2,6-diyl)bis(1H-1,2,3-triazole-4,1-diyl))bis(2-methylbenzoic acid);

2,2'-((4-(ethylcarbamoyl)pyridine-2,6-diyl)bis(1H-1,2,3-triazole-4,1-diyl))bis(3-(trifluoromethyl)benzoic acid);

4,4'-((4-((2-hydroxyethyl)carbamoyl)pyridine-2,6-diyl)bis(1H-1,2,3-triazole-4,1-diyl))bis(2-(trifluoromethyl)benzoic acid);

4,4'-((4-(ethylcarbamoyl)pyridine-2,6-diyl)bis(1H-1,2,3-triazole-4,1-diyl))bis(2-nitrobenzoic acid);

4,4'-((4-((3,3,3-trifluoropropyl)carbamoyl)pyridine-2,6-diyl)bis(1H-1,2,3-triazole-4,1-diyl))bis(2-(trifluoromethyl)benzoic acid);

(4-(4-(4-(ethylcarbamoyl)-6-(1-(4-phosphonophenyl)-1H-1,2,3-triazol-4-yl)pyridin-2-yl)-1H-1,2,3-triazol-1-yl)phenyl)phosphonic acid;

4,4',4'',4'''-((((butane-1,4-diylbis(azanediyl))bis(carbonyl))bis(pyridine-4,2,6-triyl))tetrakis(1H-1,2,3-triazole-4,1-diyl))tetrakis(2-(trifluoromethyl)benzoic acid);

2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))diacetic acid;

dimethyl 2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))diacetate;

(2S,2'S)-2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))disuccinic acid;

2,2'-((2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))bis(acetyl))bis(azanediyl))diacetic acid;

2,6-bis(1-(4-cyano-3-(trifluoromethyl)phenyl)-1H-1,2,3-triazol-4-yl)-N-ethylisonicotinamide;

4,4'-(thiophene-2,5-diylbis(1H-1,2,3-triazole-4,1-diyl))bis(2-(trifluoromethyl)benzoic acid); and 4,4'-(furan-2,5-diylbis(1H-1,2,3-triazole-4,1-diyl))bis(2-(trifluoromethyl)benzoic acid);

3'-(4-(4-(ethylcarbamoyl)-6-(1-(3'-(trifluoromethyl)-[1,1'-biphenyl]-3-yl)-1H-1,2,3-triazol-4-yl)pyridin-2-yl)-1H-1,2,3-triazol-1-yl)-3-(trifluoromethyl)-[1,1'-biphenyl]-4-carboxylic acid;

4,4'-((4-(ethylcarbamoyl)pyridine-2,6-diyl)bis(1H-1,2,3-triazole-4,1-diyl))bis(2-cyanobenzoic acid); and 4,4'-((4-(ethylcarbamoyl)pyridine-2,6-diyl)bis(1H-1,2,3-triazole-4,1-diyl))bis(2-chlorobenzoic acid).

Embodiment 82. A compound selected from the following:

4,4'-(1,3-phenylenebis(1H-1,2,3-triazole-4,1-diyl))bis(2-hydroxybenzoic acid);

4,4'-((9H-carbazole-3,6-diyl)bis(1H-1,2,3-triazole-4,1-diyl))dianiline;

3,6-bis(1-(4-methoxyphenyl)-1H-1,2,3-triazol-4-yl)-9H-carbazole;

4,4'-(1,4-phenylenebis(1H-1,2,3-triazole-4,1-diyl))bis(2-hydroxybenzoic acid);

4,4'-(1,3-phenylenebis(1H-1,2,3-triazole-4,1-diyl))dianiline;

4,4'-(1,3-phenylenebis(1H-1,2,3-triazole-4,1-diyl))dibenzoic acid;

1,3-bis(1-(4-methoxyphenyl)-1H-1,2,3-triazol-4-yl)benzene;

4,4'-(pyridine-2,6-diylbis(1H-1,2,3-triazole-4,1-diyl))dianiline;

4-(4-(3-(1-(4-carboxyphenyl)-1H-1,2,3-triazol-4-yl)phenyl)-1H-1,2,3-triazol-1-yl)-2-hydroxybenzoic acid;

4-(4-(3-(1-(4-methoxyphenyl)-1H-1,2,3-triazol-4-yl)phenyl)-1H-1,2,3-triazol-1-yl)benzoic acid;

4,4'-((4-carboxypyridine-2,6-diyl)bis(1H-1,2,3-triazole-4,1-diyl))bis(2-hydroxybenzoic acid);

2-(1-(1H-benzo[d]imidazol-4-yl)-1H-1,2,3-triazol-4-yl)-6-(1-(1H-benzo[d]imidazol-7-yl)-1H-1,2,3-triazol-4-yl)-N-ethylisonicotinamide;

4,4'-((4-carboxypyridine-2,6-diyl)bis(1H-1,2,3-triazole-4,1-diyl))bis(2-(trifluoromethyl)benzoic acid);

4,4'-((5-carboxy-1,3-phenylene)bis(1H-1,2,3-triazole-4,1-diyl))bis(2-(trifluoromethyl)benzoic acid);

4,4'-((5-carboxy-1,3-phenylene)bis(1H-1,2,3-triazole-1,4-diyl))bis(2-(trifluoromethyl)benzoic acid); and 4,4'-((5-(ethylcarbamoyl)-1,3-phenylene)bis(1H-1,2,3-triazole-1,4-diyl))bis(2-(trifluoromethyl)benzoic acid).

Embodiment 83. A composition comprising a compound of any one of embodiments 43-82 and a molecular crowding agent.

Embodiment 84. The composition of embodiment 83 wherein the molecular crowding agent is a polyalkylene glycol.

Embodiment 85. A composition comprising a compound of any one of embodiments 43-82, and an aqueous buffer.

Embodiment 86. The composition of embodiment 85, wherein the aqueous buffer is Tris HCl.

Embodiment 87. A composition comprising a compound of any one of embodiments 43-82, and a polynucleotide.

Embodiment 88. The composition of embodiment 87, wherein the polynucleotide is a 20-60 mer oligonucleotide.

Embodiment 89. A composition comprising a compound of any one of embodiments 43-82, and a protein.

Embodiment 90. The composition of embodiment 89, wherein the protein is a DNA polymerase.

Embodiment 91. A composition comprising a compound of any one of embodiments 43-82 and a mixture of nucleotides or nucleotide analogs.

Embodiment 92. A composition for enhancing the processivity, fidelity, or rate of a DNA polymerase reaction comprising at least one compound of any one of embodiments 43-82 and a mixture of nucleotide analogs.

Embodiment 93. A composition comprising at least one compound of any one of embodiments 43-82 and a mixture of nucleotide analogs wherein the at least one compound of any of embodiments 43-82 increases the number and accuracy of nucleotide analogs incorporated into a daughter strand during a template-dependent polymerization reaction relative to an identical polymerization reaction absent the at least one compound of any of embodiments 43-82.

Embodiment 94. The composition of embodiment 92, wherein the mixture of nucleotide analogs comprises nucleoside triphosphoramidates, wherein each of the nucleoside triphosphoramidates comprises a nucleobase selected from the group consisting of adenine, guanine, thymine, and cytosine and a polymeric tether moiety, wherein a first end of the polymeric tether moiety is attached to the nucleobase and a second end of the polymeric ether moiety is attached to the alpha phosphate of the nucleoside triphosphoramidate to provide for expansion of the nucleotide analogs by cleavage of the phosphoramidate bond.

Embodiment 95. The composition of embodiment 92 further comprising a buffer component selected from at least one of Tris OAc, $NH_4OAc$, PEG, a water-miscible organic solvent, polyphosphate 60, NMS, and $MnCl_2$.

Embodiment 96. The composition of embodiment 92, further comprising a single-strand binding protein.

Embodiment 97. The composition of embodiment 92, further comprising urea.

Embodiment 98. The composition of embodiment 92, wherein the mixture of nucleotide analogs comprises nucleotide analogs comprising a detectable label.

Embodiment 99. The composition of embodiment 98, wherein the detectable label is an optically detectable label selected from the group consisting of luminescent, chemiluminescent, fluorescent, fluorogenic, chromophoric or chromogenic labels.

Embodiment 100. A kit for sequencing a nucleic acid template comprising at least one composition of any of embodiments 83-99.

The invention claimed is:

1. A method of enhancing a nucleic acid polymerase reaction, the method comprising:

a. forming a nucleic acid polymerase reaction composition comprising:

i. a template nucleic acid, ii. a nucleic acid polymerase, iii. a mixture of nucleotides or nucleotide analogs, and iv. at least one compound of Formula (I); and b. incubating the nucleic acid polymerase reaction composition under conditions allowing a nucleic acid polymerization reaction, wherein the at least one compound of Formula (I) increases the processivity, rate, or fidelity of the nucleic acid polymerase reaction;

wherein the compound of Formula (I) is represented by:

(I)

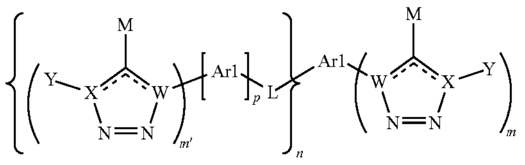

or a solvate, hydrate, tautomer, chelate or salt thereof, wherein:

m is 1, 2 or 3;

m' is 1, 2 or 3;

n is 0, 1 or 2;

p is 0, 1 or 2;

W is N when X is C or W is C when X is N;

--- is a single or double bond, wherein the double bond begins at whichever of W or X is carbon;

L is a linking group;

M is, at each occurrence, independently selected from hydrogen, halogen and $C_1$-$C_4$alkyl;

Ar1 is, at each occurrence, independently selected from optionally substituted benzene, pyridine, pyrazine, pyridazine, furan, thiophene, naphthalene, fluorene, phenanthrene, cinnoline, phthalazine, quinazoline, quinoxaline, naphthyridine, phenanthroline, purine, and carbazole, wherein:

substituents for Ar1 are, at each occurrence, independently selected from halogen, —OH, —CN, —$NO_2$, $C_1$-$C_6$alkyl, $C_1$-$C_6$haloalkyl, $C_1$-$C_6$heteroalkyl, $C_1$-$C_6$cycloloalkyl, —$OR^0$, —$CONH_2$, —C(O)$NR^1R^{1'}$, —$NR^1R^{1'}$, —$NR^1C(O)R^3$, —$C(O)SR^3$, —$COR^3$, —$OC(O)R^3$, —$C(O)OR^3$, mercaptan, —$R^4$—H, —$SOR^1$, —$S(O)_2R^1$, —$S(O)_2NR^1R^{1'}$, and —$NS(O)_2R^3$;

and wherein $R^0$ is, at each occurrence, independently selected from $C_1$-$C_6$alkyl, $C_1$-$C_6$haloalkyl, $C_2$-$C_6$alkenyl, $C_2$-$C_6$alkynyl, substituted or unsubstituted cycloalkyl, substituted or unsubstituted heterocyclyl, substituted or unsubstituted aryl, and substituted or unsubstituted heteroaryl;

$R^1$ and $R^{1'}$ are, at each occurrence, independently selected from H, hydroxyl, $C_1$-$C_6$alkyl, $C_1$-$C_6$haloalkyl, $C_1$-$C_6$heteroalkyl, $C_2$-$C_6$alkenyl, $C_2$-$C_6$alkynyl, substituted or unsubstituted cycloalkyl, substituted or unsubstituted heterocyclyl, substituted or unsubstituted aryl, substituted or unsubstituted arylalkyl, and substituted or unsubstituted heteroaryl, —C(=NH)$NH_2$, —$CH_2CO_2R^0$, —$CH_2C(O)NHCH_2CO_2H$, —$CH_2CH_2OH$, —$CH_2CH_2NHC(O)R^3$, —$CH_2C(O)NHCH_2CO_2H$,

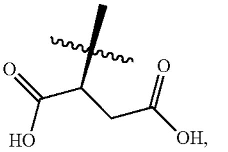

and

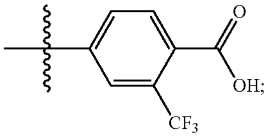

wherein $R^1$ and $R^{1'}$ can come together to form a heterocyclic ring, including, but not limited to, azetidine, pyrrolidine, piperidine, piperazine, morpholine,

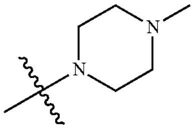

, or

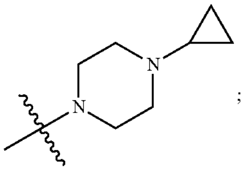

;

$R^2$ is, at each occurrence, independently selected from $C_2$-$C_6$alkyl, $C_1$-$C_6$haloalkyl, $C_1$-$C_6$heteroalkyl, or substituted or unsubstituted cycloalkyl, substituted or unsubstituted heterocyclyl, substituted or unsubstituted aryl, substituted or unsubstituted heteroaryl, and substituted or unsubstituted haloalkoxy;

$R^3$ is, at each occurrence, independently selected from H, $C_1$-$C_6$alkyl, $C_1$-$C_6$haloalkyl, $C_1$-$C_6$heteroalkyl, or substituted or unsubstituted cycloalkyl, substituted or unsubstituted heterocyclyl, substituted or unsubstituted aryl, and substituted or unsubstituted heteroaryl, substituted or unsubstituted haloalkoxy, and guanidine;

$R^4$ is, at each occurrence, independently selected from one or more heteroatom interrupted alkylene wherein the heteroatom is O, S, NH or a combination thereof, Y is, at each occurrence, independently selected from Ar2, —$(CH_2)_3PO(OEt)_2$, or —CH2$CO_2$Me;

Ar2 is, at each occurrence, independently selected from substituted 5- and 6-membered monocyclic aromatic rings and 9- and 10-membered fused bicyclic rings comprising two monocyclic rings together, where at least one of the two monocyclic rings is an aromatic ring, wherein:

Ar2 is substituted with $G^1$, $G^2$, $G^3$, $G^4$ and $G^5$, wherein:

when Ar2 is monosubstituted, $G^1$ is, at each occurrence, independently selected from oxo, —$NH_2$, —$COR^3$, -E-$CO_2$H, —C(O)$NR^1R^{1'}$, -E-PO($OR^1$)$_2$, and aryl substituted with $G^2$, $G^3$, $G^4$ and $G^5$;

$G^2$, $G^3$, $G^4$ and $G^5$ are, at each occurrence, independently selected from absent or selected from the groups comprising, halogen, —CN, $C_1$-$C_6$alkyl, $C_1$-$C_6$haloalkyl, -E-$CO_2$H, -E-CHO, -E-$C(O)R^3$, -E-C(O)NH(OH), -E-C(O)NHR$^1$, -E-CONR$^1$R$^{1'}$, -E-NR$^1$R$^{1'}$, and -E-OR$^2$, wherein:

E is, at each occurrence, independently selected from a direct bond and $C_1$-$C_6$alkylene.

2. The method of claim 1, wherein Ar1 is monocyclic carbocyclic aryl.

3. The method of claim 1, wherein Ar1 is monocyclic heterocyclic aryl.

4. The method of claim 1, wherein Ar1 is bicyclic aryl.

5. The method of claim 1, wherein Ar1 is tricyclic aryl.

6. The method of claim 1, wherein Ar1 is unsubstituted aryl.

7. The method of claim 1, wherein Ar1 is substituted aryl.

8. The method of claim 1, wherein Ar2 is a 5-membered monocyclic aromatic ring selected from the group consisting of thiophene, 1,2-thiazole, 1,3-thiazole, furan, 1,2-oxazole, 1,3-oxazole, 1H-pyrrole, 1H-pyrazole, oxadiazole, thiadiazole, 1,2,4-triazole, 1,2,3-triazole and 1H-imidazole.

9. The method of claim 1, wherein Ar2 is a 6-membered monocyclic aromatic ring selected from the group consisting of benzene, pyridine, pyridazine, pyrimidine and pyrazine.

10. The method of claim 1, wherein Ar2 is a 9-membered fused bicyclic aromatic ring system selected from the group consisting of benzofuran, 1,3-benzoxazole, furo[3,2-b]pyridine, furo[3,2-c]pyridine, furo[2,3-c]pyridine, furo[2,3-b]pyridine, indole, 1H-benzimidazole, 1H-pyrrolo[3,2-b]pyridine, 1H-pyrrolo[3,2-c]pyridine, 1H-pyrrolo[2,3-c]pyridine, 1H-pyrrolo[2,3-b]pyridine, benzothiophene, 1,3-benzothiazole, thienol[3,2-b]pyridine, thieno[3,2-c]pyridine, thieno[2,3-c]pyridine, benzoxadiazole, benzothiadiazole, benzisoxazole, benzotriazole and thieno[2,3-b]pyridine.

11. The method of claim 1, wherein Ar2 is a 10-membered fused bicyclic aromatic ring system selected from the group consisting of naphthylene, quinoline, quinazoline, quinoxaline, 1,5-naphthyridine, 1,6-naphthyridine, 1,7-naphthyridine, 1,8-naphthyridine, isoquinoline, phthalazine, 2,6-naphthyridine and 2,7-naphthyridine.

12. The method of claim 1, wherein the substitution on Ar2 includes carboxylic acid.

13. The method of claim 1, wherein the substitution on Ar2 includes carboxamide.

14. The method of claim 1, wherein substitution on Ar2 includes trifluormethyl.

15. The method of claim 1, wherein substitution on Ar2 includes hydroxyl.

16. The method of claim 1, wherein n is 0 and m is 2, and at least one compound of Formula (I) is described by a formula selected from (III) or (IV).

(III)

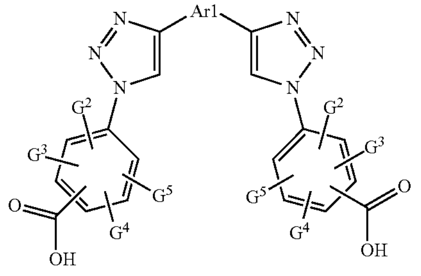

or

-continued (IV)

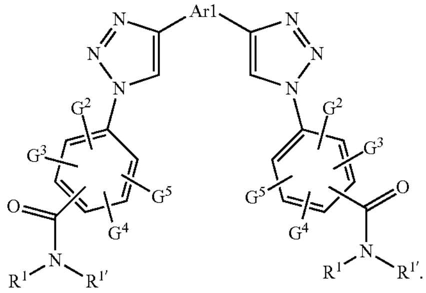

17. The method of claim 1, wherein substitution on Ar2 includes at least two of hydroxyl, carboxylic acid and trifluoromethyl.

18. The method of claim 15, wherein the at least one compound of Formula (I) is described by a formula selected from (V), (VI), (VII), (VIII), or (IX):

(V)

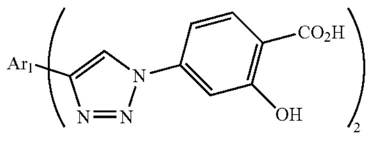

;

(VI)

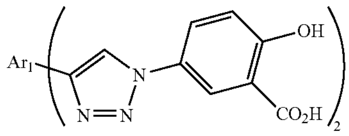

;

(VII)

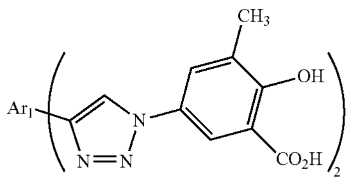

;

(VIII)

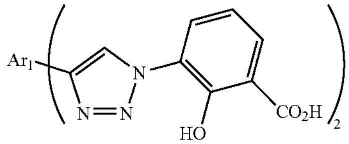

or (IX)

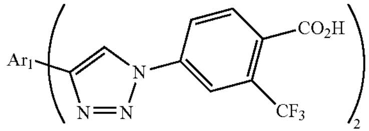

.

19. The method of claim 1, wherein the compound of Formula (I) is in a form of a chelate.

20. The method of claim 19, wherein the chelate is a copper chelate.

21. The method of claim 1, wherein the compound of Formula (I) has a log P of at least 4.9.

22. The method of claim 1, wherein the compound of Formula (I) is selected from:

4,4'-((4-(methylcarbamoyl)pyridine-2,6-diyl)bis(1H-1,2,3-triazole-4,1-diyl))bis(2-(trifluoromethyl)benzoic acid);

4,4'-((4-(morpholine-4-carbonyl)pyridine-2,6-diyl)bis(1H-1,2,3-triazole-4,1-diyl))bis(2-(trifluoromethyl)benzoic acid);

4,4'-((4-(diethylcarbamoyl)pyridine-2,6-diyl)bis(1H-1,2,3-triazole-4,1-diyl))bis(2-(trifluoromethyl)benzoic acid);

4,4'-((4-carbamoylpyridine-2,6-diyl)bis(1H-1,2,3-triazole-4,1-diyl))bis(2-(trifluoromethyl)benzoic acid);

4,4'-((4-(ethoxycarbonyl)pyridine-2,6-diyl)bis(1H-1,2,3-triazole-4,1-diyl))bis(2-(trifluoromethyl)benzoic acid);

4,4'-((4-(azetidine-1-carbonyl)pyridine-2,6-diyl)bis(1H-1,2,3-triazole-4,1-diyl))bis(2-hydroxybenzoic acid);

4,4'-((4-(ethyl(methyl)carbamoyl)pyridine-2,6-diyl)bis(1H-1,2,3-triazole-4,1-diyl))bis(2-hydroxybenzoic acid);

N-ethyl-2,6-bis(1-(4-(2,2,2-trifluoroacetyl)phenyl)-1H-1,2,3-triazol-4-yl)isonicotinamide;

4,4'-(pyridine-2,6-diylbis(1H-1,2,3-triazole-4,1-diyl))bis(2-(trifluoromethyl)benzoic acid);

4,4'-((4-(cyclopropylcarbamoyl)pyridine-2,6-diyl)bis(1H-1,2,3-triazole-4,1-diyl))bis(2-(trifluoromethyl)benzoic acid);

4,4'-((4-(butylcarbamoyl)pyridine-2,6-diyl)bis(1H-1,2,3-triazole-4,1-diyl))bis(2-(trifluoromethyl)benzoic acid);

5,5'-((4-(diethylcarbamoyl)pyridine-2,6-diyl)bis(1H-1,2,3-triazole-4,1-diyl))bis(2-(trifluoromethyl)benzoic acid);

5,5'-((4-(morpholine-4-carbonyl)pyridine-2,6-diyl)bis(1H-1,2,3-triazole-4,1-diyl))bis(2-(trifluoromethyl)benzoic acid);

4,4'-(pyridazine-3,6-diylbis(1H-1,2,3-triazole-4,1-diyl))bis(2-hydroxybenzoic acid);

5,5'-((4-(ethylcarbamoyl)pyridine-2,6-diyl)bis(1H-1,2,3-triazole-4,1-diyl))bis(3-(trifluoromethyl)benzoic acid);

3,3'-(((4-(ethylcarbamoyl)pyridine-2,6-diyl)bis(1H-1,2,3-triazole-4,1-diyl))bis(4,1-phenylene))dipropionic acid;

4,4'-(((4-(ethylcarbamoyl)pyridine-2,6-diyl)bis(1H-1,2,3-triazole-4,1-diyl))bis(4,1-phenylene))dibutyric acid;

4,4'-((4-(ethylcarbamoyl)pyridine-2,6-diyl)bis(1H-1,2,3-triazole-4,1-diyl))diphthalic acid;

4,4'-((4-(ethylcarbamoyl)pyridine-2,6-diyl)bis(1H-1,2,3-triazole-4,1-diyl))bis(2-methoxybenzoic acid);

5,5'-((4-(ethylcarbamoyl)pyridine-2,6-diyl)bis(1H-1,2,3-triazole-4,1-diyl))diisophthalic acid;

4,4'-((4-(ethylcarbamoyl)pyridine-2,6-diyl)bis(1H-1,2,3-triazole-4,1-diyl))bis(3-hydroxybenzoic acid);

diethyl (3-(4-(6-(1-(3-(diethoxyphosphoryl)propyl)-1H-1,2,3-triazol-4-yl)-4-(ethylcarbamoyl) pyridin-2-yl)-1H-1,2,3-triazol-1-yl)propyl) phosphonate;

4,4'-((4-(ethylcarbamoyl)pyridine-2,6-diyl)bis(1H-1,2,3-triazole-4,1-diyl))bis(2-methylbenzoic acid);

2,2'-((4-(ethylcarbamoyl)pyridine-2,6-diyl)bis(1H-1,2,3-triazole-4,1-diyl))bis(3-(trifluoromethyl)benzoic acid);

4,4'-((4-((2-hydroxyethyl)carbamoyl)pyridine-2,6-diyl)bis(1H-1,2,3-triazole-4,1-diyl))bis(2-(trifluoromethyl)benzoic acid);

4,4'-((4-(ethylcarbamoyl)pyridine-2,6-diyl)bis(1H-1,2,3-triazole-4,1-diyl))bis(2-nitrobenzoic acid);

4,4'-((4-((3,3,3-trifluoropropyl)carbamoyl)pyridine-2,6-diyl)bis(1H-1,2,3-triazole-4,1-diyl))bis(2-(trifluoromethyl)benzoic acid);

(4-(4-(4-(ethylcarbamoyl)-6-(1-(4-phosphonophenyl)-1H-1,2,3-triazol-4-yl)pyridin-2-yl)-1H-1,2,3-triazol-1-yl)phenyl)phosphonic acid;

4,4',4'',4'''-((((butane-1,4-diylbis(azanediyl))bis(carbonyl))bis(pyridine-4,2,6-triyl))tetrakis(1H-1,2,3-triazole-4,1-diyl))tetrakis(2-(trifluoromethyl)benzoic acid);

2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))diacetic acid;

dimethyl 2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))diacetate;

(2S,2'S)-2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))disuccinic acid;

2,2'-((2,2'-((4,4'-((4-(ethylcarbamoyl)pyridine-2,6-diyl)bis(1H-1,2,3-triazole-4,1-diyl))bis(2-(trifluoromethyl)benzoyl))bis(azanediyl))bis(acetyl))bis(azanediyl))diacetic acid;

2,6-bis(1-(4-cyano-3-(trifluoromethyl)phenyl)-1H-1,2,3-triazol-4-yl)-N-ethylisonicotinamide;

4,4'-((5-(ethylcarbamoyl)-1,3-phenylene)bis(1H-1,2,3-triazole-1,4-diyl))bis(2-(trifluoromethyl)benzoic acid);

4,4'-(thiophene-2,5-diylbis(1H-1,2,3-triazole-4,1-diyl))bis(2-(trifluoromethyl)benzoic acid);

4,4'-(furan-2,5-diylbis(1H-1,2,3-triazole-4,1-diyl))bis(2-(trifluoromethyl)benzoic acid);

3'-(4-(4-(ethylcarbamoyl)-6-(1-(3'-(trifluoromethyl)-[1,1'-biphenyl]-3-yl)-1H-1,2,3-triazol-4-yl)pyridin-2-yl)-1H-1,2,3-triazol-1-yl)-3-(trifluoromethyl)-[1,1'-biphenyl]-4-carboxylic acid;

4,4'-((4-(ethylcarbamoyl)pyridine-2,6-diyl)bis(1H-1,2,3-triazole-4,1-diyl))bis(2-cyanobenzoic acid); and 4,4'-((4-(ethylcarbamoyl)pyridine-2,6-diyl)bis(1H-1,2,3-triazole-4,1-diyl))bis(2-chlorobenzoic acid).

23. The method of claim 1, wherein the compound of Formula (I) increases the length of a resulting nucleic acid product compared to a nucleic acid polymerase reaction lacking the compound of Formula (I).

24. The method of claim 1, wherein the at least one compound of Formula (I) comprises a plurality of compounds of Formula (I).

25. The method of claim 1, wherein the nucleic acid polymerase is a DNA polymerase.

26. The method of claim 25, wherein the DNA polymerase is DPO4 or a variant thereof.

27. The method of claim 1, wherein the mixture of nucleotides or nucleotide analogs is a mixture of nucleotide analogs comprising nucleoside triphosphoramidates, wherein each of the nucleoside triphosphoramidates comprises a nucleobase selected from the group consisting of adenine, guanine, thymine, and cytosine and a polymeric tether moiety, wherein a first end of the polymeric tether moiety is attached to the nucleobase and a second end of the polymeric tether moiety is attached to the alpha phosphate of the nucleoside triphosphoramidate to provide for expansion of the nucleotide analogs by cleavage of the phosphoramidate bond.

28. The method of claim 1, wherein the nucleic acid polymerization reaction produces an expandable polymer of nucleotide analogs, wherein the expandable polymer encodes the nucleobase sequence information of the template nucleic acid.

29. The method of claim 1, wherein the conditions for allowing a nucleic acid polymerization reaction comprise a suitable polymerization buffer and an oligonucleotide primer.

30. The method of claim 1, wherein the suitable buffer comprises at least one of Tris OAc, $NH_4OAc$, PEG, a water-miscible organic solvent, polyphosphate 60, NMS, and $MnCl_2$.

31. The method of claim 1, wherein the reaction mixture further comprises a single-strand binding protein.

32. The method of claim 1, wherein the reaction mixture further comprises urea.

33. The method of claim 1, wherein the mixture of nucleotides or nucleotide analogs comprises nucleotide analogs comprising a detectable label.

34. The method of claim 31, wherein the detectable label is an optically detectable label selected from the group consisting of luminescent, chemiluminescent, fluorescent, fluorogenic, chromophoric or chromogenic labels.

* * * * *